United States Patent
Hoffman et al.

(10) Patent No.: US 11,802,128 B2
(45) Date of Patent: Oct. 31, 2023

(54) AZETIDINE AND PYRROLIDINE PARP1 INHIBITORS AND USES THEREOF

(71) Applicant: Xinthera, Inc., San Diego, CA (US)

(72) Inventors: Robert L. Hoffman, San Diego, CA (US); Qing Dong, San Diego, CA (US); Stephen W. Kaldor, San Diego, CA (US); Lynnie Trzoss, San Diego, CA (US); Porino Jinjo Va, San Diego, CA (US)

(73) Assignee: Xinthera, Inc., San Diego, CA (US)

( * ) Notice: Subject to any disclaimer, the term of this patent is extended or adjusted under 35 U.S.C. 154(b) by 0 days.

(21) Appl. No.: 18/115,314

(22) Filed: Feb. 28, 2023

(65) Prior Publication Data

US 2023/0203033 A1    Jun. 29, 2023

Related U.S. Application Data

(63) Continuation of application No. 17/957,584, filed on Sep. 30, 2022, now abandoned.

(60) Provisional application No. 63/251,469, filed on Oct. 1, 2021, provisional application No. 63/339,597, filed on May 9, 2022, provisional application No. 63/402,835, filed on Aug. 31, 2022.

(51) Int. Cl.
| | |
|---|---|
| C07D 471/04 | (2006.01) |
| A61P 35/00 | (2006.01) |
| C07D 401/14 | (2006.01) |
| C07D 487/04 | (2006.01) |
| C07D 491/048 | (2006.01) |
| C07D 491/147 | (2006.01) |
| C07D 519/00 | (2006.01) |

(52) U.S. Cl.
CPC ............ *C07D 471/04* (2013.01); *A61P 35/00* (2018.01); *C07D 401/14* (2013.01); *C07D 487/04* (2013.01); *C07D 491/048* (2013.01); *C07D 491/147* (2013.01); *C07D 519/00* (2013.01); *C07B 2200/05* (2013.01)

(58) Field of Classification Search
CPC .................................................. C07D 471/04
See application file for complete search history.

(56) References Cited

U.S. PATENT DOCUMENTS

| | | |
|---|---|---|
| 8,404,713 B2 | 3/2013 | Angibaud et al. |
| 8,541,417 B2 | 9/2013 | Brown et al. |
| 10,464,919 B2 | 11/2019 | Lee et al. |
| 11,325,906 B2 | 5/2022 | Johannes et al. |
| 11,591,331 B2 | 2/2023 | Trzoss et al. |
| 2021/0009577 A1 | 1/2021 | Lanman et al. |
| 2021/0040084 A1 | 2/2021 | Johannes et al. |
| 2022/0015338 A1 | 1/2022 | Zhang et al. |
| 2023/0128041 A1 | 4/2023 | Trzoss et al. |
| 2023/0159525 A1 | 5/2023 | Hoffman et al. |
| 2023/0234952 A1 | 7/2023 | Hoffman et al. |

FOREIGN PATENT DOCUMENTS

| | | |
|---|---|---|
| AU | 2016276806 B2 | 2/2019 |
| CN | 115232129 A | 10/2022 |
| CN | 115403595 A | 11/2022 |
| CN | 116143776 A | 5/2023 |
| CN | 116535401 A | 8/2023 |
| WO | WO-03080581 A1 | 10/2003 |
| WO | WO-2009053373 A1 | 4/2009 |
| WO | WO-2009076512 A1 | 6/2009 |
| WO | WO-2010085570 A1 | 7/2010 |
| WO | WO-2011014681 A1 | 2/2011 |
| WO | WO-2014064149 A1 | 5/2014 |
| WO | WO 2015/134973 A1 | 9/2015 |
| WO | WO 2016/107603 A1 | 7/2016 |
| WO | WO 2016/200101 A2 | 12/2016 |
| WO | WO 2020/098630 A1 | 5/2020 |
| WO | WO-2021013735 A1 | 1/2021 |
| WO | WO-2021260092 A1 | 12/2021 |
| WO | WO-2022222921 A1 | 10/2022 |
| WO | WO-2022222964 A1 | 10/2022 |
| WO | WO-2022222965 A1 | 10/2022 |
| WO | WO-2022222966 A1 | 10/2022 |
| WO | WO-2022222995 A1 | 10/2022 |
| WO | WO-2022223025 A1 | 10/2022 |
| WO | WO-2022225934 A1 | 10/2022 |

(Continued)

OTHER PUBLICATIONS

PCT/US2023/011613 International Search Report and Written Opinion dated Apr. 11, 2023.

(Continued)

*Primary Examiner* — Brian E McDowell

(74) *Attorney, Agent, or Firm* — Sheppard Mullin Richter & Hampton LLP

(57) ABSTRACT

Described herein are azetidine and pyrrolidine PARP1 inhibitors and pharmaceutical compositions comprising said inhibitors. The subject compounds and compositions are useful for the treatment of cancer and are of Formula I(b)

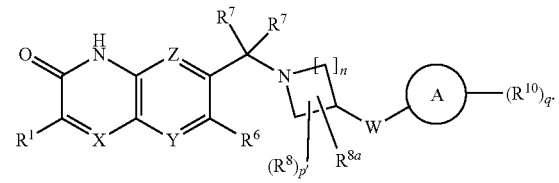

Formula (Ib)

15 Claims, No Drawings

(56) References Cited

FOREIGN PATENT DOCUMENTS

| WO | WO-2022228387 A1 | 11/2022 |
|---|---|---|
| WO | WO-2022247816 A1 | 12/2022 |
| WO | WO-2022261777 A1 | 12/2022 |
| WO | WO 2023/036285 A1 | 3/2023 |
| WO | WO-2023025307 A1 | 3/2023 |
| WO | WO-2023046034 | 3/2023 |
| WO | WO-2023046149 A1 | 3/2023 |
| WO | WO-2023046158 | 3/2023 |
| WO | WO-2023051716 A1 | 4/2023 |
| WO | WO-2023051807 A1 | 4/2023 |
| WO | WO-2023051812 A1 | 4/2023 |
| WO | WO-2023056039 A1 | 4/2023 |
| WO | WO-2023061406 A1 | 4/2023 |
| WO | WO-2023088408 A1 | 5/2023 |
| WO | WO 2023/109521 A1 | 6/2023 |
| WO | WO 2023/133413 A1 | 7/2023 |
| WO | WO 2023/138541 A1 | 7/2023 |
| WO | WO 2023/143236 A1 | 8/2023 |
| WO | WO 2023/144450 A1 | 8/2023 |
| WO | WO 2023/146294 A1 | 8/2023 |
| WO | WO 2023/146957 A1 | 8/2023 |
| WO | WO 2023/146960 A1 | 8/2023 |
| WO | WO 2023/147009 A1 | 8/2023 |
| WO | WO 2023/156386 A1 | 8/2023 |

OTHER PUBLICATIONS

U.S. Appl. No. 18/099,770 Office Action dated Apr. 26, 2023.
PCT/US2023/011268 International Search Report and Written Opinion dated Apr. 4, 2023.
PCT/US2023/011609 International Search Report and Written Opinion dated Mar. 29, 2023.
Boehler et al. Poly(ADP-ribose) polymerase 3 (PARP3), a newcomer in cellular response to DNA damage and mitotic progression. PNAS USA 108(7):2783-2788 (2011).
Co-pending U.S. Appl. No. 17/933,326, inventors Trzoss; Lynnie et al., filed Sep. 19, 2022.
Co-pending U.S. Appl. No. 17/957,584, inventors Hoffman; Robert L. et al., filed Sep. 30, 2022.
Co-pending U.S. Appl. No. 18/099,770, inventors Hoffman; Robert L. et al., filed Jan. 20, 2023.
Gill et al. The novel PARP1-selective inhibitor AZD5305 has reduced haematological toxicity when compared to PARP1/2 inhibitors in pre-clinical models. Poster # 1374 AACR 2021 Annual Apr. 10-19, 2020.
Gozgit et al. PARP7 negatively regulates the type I interferon response in cancer cells and its inhibition triggers antitumor immunity. Cancer Cell 39(9):1214-1226 (2021).
Hande et al. Structure-based and property-based drug design of AZD5305, a highly selective PARP1 inhibitor and trapper. Poster #296 AACR 2021. Apr. 10-15, 2021.
Illuzzi et al. In vitro cellular profiling of AZD5305, novel PARP1-selective inhibitor and trapper. Poster #1272 AACR2021, Apr. 10-15, 2021.
Johannes et al. Discovery and first structural disclosure of AZD5305, a next generation, highly selective PARP1 inhibitor and trapper. AstraZeneca—AZD5305—a best in class highly selective PARP1 inhibitor. Presentation at AACR 2021 Apr. 10, 2021.
Kulak et al. Disruption of Wnt/I3-Catenin Signaling and Telomeric Shortening Are Inextricable Consequences of Tankyrase Inhibition in Human Cells. Mol Cell Biol. 35(14):2425-2435 (2015).
PCT/US2022/025357 International Search Report and Written Opinion dated Jun. 30, 2022.
PCT/US2022/045415 International Search Report and Written Opinion dated Nov. 25, 2022.
Ren et al. Synthesis and in vitro biological evaluation of 3-ethyl-1, 5-naphthyridin-2 (1H)-one derivatives as potent PARP-1 selective inhibitors and PARP-1 DNA trappers. Bioorg Med Chem Lett. 129046 (2022).
Staniszewska et al. The novel PARP1-selective inhibitor, AZD5305, is efficacious as monotherapy and in combination with standard of care chemotherapy in in vivo preclinical models. Poster #1270 AACR 2021. Apr. 10-15 and May 17-21, 2021.
U.S. Appl. No. 17/957,584 Office Action dated Feb. 15, 2023.
Vermehren-Schmaedick et al. Characterization of PARP6 Function in Knockout Mice and Patients with Developmental Delay. Cells 10(6):1289 (2021).
Vyas et al. A Systematic Analysis of the PARP Protein Family Identifies New Functions Critical for Cell Physiology. Nat. Commun. 4(1):2240 (2013).
Yu et al. PARP-10, a novel Myc-interacting protein with poly(ADP-ribose) polymerase activity, inhibits transformation. Oncogene 24:1982-1993 (2005).

AZETIDINE AND PYRROLIDINE PARP1 INHIBITORS AND USES THEREOF

CROSS-REFERENCE

This application is a continuation of U.S. application Ser. No. 17/957,584 filed Sep. 30, 2022, which claims the benefit of U.S. Provisional Application Ser. No. 63/251,469 filed Oct. 1, 2021, U.S. Provisional Application Ser. No. 63/339,597 filed May 9, 2022, and U. S. Provisional Application Ser. No. 63/402,835 filed Aug. 31, 2022, which are hereby incorporated by reference in their entirety.

BACKGROUND OF THE INVENTION

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut, and skeletal muscle. Inhibitors have been efficacious in inflammatory diseases such as arthritis, gout, inflammatory bowel disease, CNS inflammation such as MS and allergic encephalitis, sepsis, septic shock, hemorrhagic shock, pulmonary fibrosis, and uveitis. PARP inhibitors have also shown benefit in several models of degenerative disease including diabetes (as well as complications) and Parkinson's disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

PARP1 and PARP2 are the most extensively studied PARPs for their role in DNA damage repair. PARP1 is activated by DNA damage breaks and functions to catalyze the addition of poly (ADP-ribose) (PAR) chains to target proteins. This post-translational modification, known as PARylation, mediates the recruitment of additional DNA repair factors to DNA lesions.

Following completion of this recruitment role, PARP auto-PARylation triggers the release of bound PARP from DNA to allow access to other DNA repair proteins to complete repair. Thus, the binding of PARP to damaged sites, its catalytic activity, and its eventual release from DNA are all important steps for a cancer cell to respond to DNA damage caused by chemotherapeutic agents and radiation therapy.

Inhibition of PARP family enzymes has been exploited as a strategy to selectively kill cancer cells by inactivating complementary DNA repair pathways. A number of pre-clinical and clinical studies have demonstrated that tumor cells bearing deleterious alterations of BRCA1 or BRCA2, key tumor suppressor proteins involved in double-strand DNA break (DSB) repair by homologous recombination (HR), are selectively sensitive to small molecule inhibitors of the PARP family of DNA repair enzymes. Such tumors have deficient homologous recombination repair (HRR) pathways and are dependent on PARP enzymes function for survival. Although PARP inhibitor therapy has predominantly targeted SRCA-mutated cancers, PARP inhibitors have been tested clinically in non-SRCA-mutant tumors, those which exhibit homologous recombination deficiency (HRD).

It is believed that PARP inhibitors having improved selectivity for PARP1 may possess improved efficacy and reduced toxicity compared to other clinical PARP1/2 inhibitors. It is believed also that selective strong inhibition of PARP1 would lead to trapping of PARP1 on DNA, resulting in DNA double strand breaks (DSBs) through collapse of replication forks in S-phase. It is believed also that PARP1-DNA trapping is an effective mechanism for selectively killing tumor cells having HRD. An unmet medical need therefore exists for effective and safe PARP inhibitors. Especially PARP inhibitors having selectivity for PARP1.

SUMMARY OF THE INVENTION

Disclosed herein is a compound of Formula (I), or a pharmaceutically acceptable salt, solvate, or stereoisomer thereof:

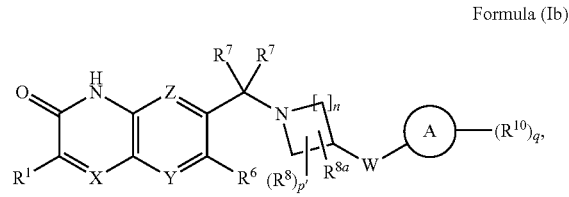

Formula (Ib)

wherein:
$R^1$ is halogen;
X is $CR^2$;
$R^2$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
Z is $CR^4$;
$R^4$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
Y is N or $CR^5$;
$R^5$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
$R^6$ is hydrogen, deuterium, halogen, —CN, —OH, —$OR^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
each $R^7$ is independently hydrogen, deuterium, fluoro, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^7$ are taken together to form a cycloalkyl or a heterocycloalkyl; each optionally substituted with one or more R;

n is 1 or 2;

each $R^8$ is independently deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

p' is 0-3;

$R^{8a}$ is deuterium, halogen, —CN, —$NO_2$, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

W is —O—;

Ring A is cycloalkyl, heterocycloalkyl, aryl, or heteroaryl;

each $R^{10}$ is independently deuterium, halogen, —CN, —$NO_2$, —OH, —$OR^a$, —OC(=O)$R^a$, —OC(=O)$OR^b$, —OC(=O)$NR^cR^d$, —SH, —$SR^a$, —S(=O)$R^a$, —S(=O)$_2R^a$, —S(O)$_2NR^cR^d$, —$NR^cR^d$, —$NR^bC(O)NR^cR^d$, —$NR^bC(=O)R^a$, —$NR^bC(=O)OR^b$, —$NR^bS(=O)_2R^a$, C(=O)$R^a$, C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently and optionally substituted with one or more R;

q is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently and optionally substituted with one or more R;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently and optionally substituted with one or more R;

each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroalyl); wherein each alkyl, alkenyl, alkynyl, cycloalkyl, heterocycloalkyl, aryl, and heteroaryl is independently and optionally substituted with one or more R;

or $R^c$ and $R^d$ are taken together with the atom to which they are attached to form a heterocycloalkyl optionally substituted with one or more R; and each R is independently deuterium, halogen, —CN, —OH, —$OC_1$-$C_6$alkyl, —S(=O)$C_1$-$C_6$alkyl, —S(=O)$_2C_1$-$C_6$alkyl, —S(=O)$_2NH_2$, —S(=O)$_2NHC_1$-$C_6$alkyl, —S(=O)$_2N(C_1$-$C_6$alkyl)$_2$, —$NH_2$, —$NHC_1$-$C_6$alkyl, —$N(C_1$-$C_6$alkyl)$_2$, —NHC(=O)$OC_1$-$C_6$alkyl, —C(=O)$C_1$-$C_6$alkyl, —C(=O)OH, —C(=O)$OC_1$-$C_6$alkyl, —C(=O)$NH_2$, —C(=O)N($C_1$-$C_6$alkyl)$_2$, —C(=O)$NHC_1$-$C_6$alkyl, $C_1$-$C_6$alkyl, $C_1$-$C_6$haloalkyl, $C_1$-$C_6$deuteroalkyl, $C_1$-$C_6$hydroxyalkyl, $C_1$-$C_6$ aminoalkyl, or $C_1$-$C_6$heteroalkyl;

or two R on the same atom form an oxo.

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treating cancer in a subject in need thereof, the method comprising administering a compound disclosed herein, or a pharmaceutically acceptable salt, solvate, or stereoisomer thereof. In some embodiments, the cancer is breast cancer, ovarian cancer, pancreatic cancer, prostate cancer, a hematological cancer, gastrointestinal cancer, or lung cancer.

Also disclosed herein is method of treating a cancer comprising a BRCA1 and/or a BRCA2 mutation in a subject in need thereof, the method comprising administering a compound disclosed herein, or a pharmaceutically acceptable salt, solvate, or stereoisomer thereof. In some embodiments, the cancer the cancer is bladder cancer, brain & CNS cancers, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Cyano" refers to —CN.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$ alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl(phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms (C$_3$-C$_{15}$ cycloalkyl or C$_3$-C$_{15}$ cycloalkenyl), from three to ten carbon atoms (C$_3$-C$_{10}$ cycloalkyl or C$_3$-C$_{10}$ cycloalkenyl), from three to eight carbon atoms (C$_3$-C$_8$ cycloalkyl or C$_3$-C$_8$ cycloalkenyl), from three to six carbon atoms (C$_3$-C$_6$ cycloalkyl or C$_3$-C$_6$ cycloalkenyl), from three to five carbon atoms (C$_3$-C$_5$ cycloalkyl or C$_3$-C$_5$ cycloalkenyl), or three to four carbon atoms (C$_3$-C$_4$ cycloalkyl or C$_3$-C$_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Cyanoalkyl" refers to an alkyl radical, as defined above, that is substituted by one or more cyano group. In some embodiments, the alkyl is substituted with one cyano. In some embodiments, the alkyl is substituted with one or two cyanos. Cyanoalkyls include, for example, cyanomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, CD$_3$, CH$_2$D, CHD$_2$, CH$_2$CD$_3$, CD$_2$CD$_3$, CHDCD$_3$, CH$_2$CH$_2$D, or CH$_2$CHD$_2$. In some embodiments, the deuteroalkyl is CD$_3$.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl or $C_2$-$C_{15}$ heterocycloalkenyl), from two to ten carbon atoms ($C_2$-$C_{10}$ heterocycloalkyl or $C_2$-$C_{10}$ heterocycloalkenyl), from two to eight carbon atoms ($C_2$-$C_8$ heterocycloalkyl or $C_2$-$C_8$ heterocycloalkenyl), from two to seven carbon atoms ($C_2$-$C_7$ heterocycloalkyl or $C_2$-$C_7$ heterocycloalkenyl), from two to six carbon atoms ($C_2$-$C_6$ heterocycloalkyl or $C_2$-$C_6$ heterocycloalkenyl), from two to five carbon atoms ($C_2$-$C_5$ heterocycloalkyl or $C_2$-$C_5$ heterocycloalkenyl), or two to four carbon atoms ($C_2$-$C_4$ heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4] dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with PARP" or, alternatively, "a PARP-mediated disease or disorder" means any disease or other deleterious condition in which PARP, or a mutant thereof, is known or suspected to play a role.

As used herein, a "disease or disorder associated with PARP1" or, alternatively, "a PARP1-mediated disease or disorder" means any disease or other deleterious condition in which PARP, or a mutant thereof, is known or suspected to play a role.

Compounds

Described herein are compounds of Formula (I), or a pharmaceutically acceptable salt, solvate, or stereoisomer thereof useful in the treatment of cancer.

Disclosed herein is a compound of Formula (I), or a pharmaceutically acceptable salt, solvate, or stereoisomer thereof:

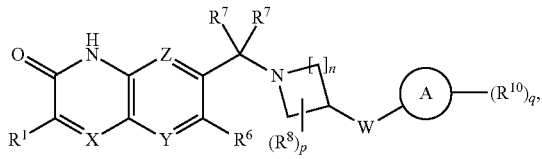

Formula (I)

wherein:
$R^1$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;
X is N or CR$^2$;
$R^2$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; or $R^1$ and $R^2$ are taken together to form a cycloalkyl, heterocycloalkyl, aryl, or heteroaryl; each optionally substituted with one or more R;
Z is N or CR$^4$;
$R^4$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; Y is N or CR$^5$;
$R^5$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
$R^6$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;
each $R^7$ is independently hydrogen, deuterium, fluoro, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
or two $R^7$ are taken together to form a cycloalkyl or a heterocycloalkyl; each optionally substituted with one or more R;
n is 1 or 2;
each $R^8$ is independently deuterium, halogen, —CN, —NO$_2$, —OH, —OR$^a$, —NR$^c$R$^d$, —C(=O)R$^a$, —C(=O)OR$^b$, —C(=O)NR$^c$R$^d$, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
or two $R^8$ on the same carbon are taken together to form an oxo;
or two $R^8$ on the same carbon or adjacent carbons are taken together to form a cycloalkyl or heterocycloalkyl; each optionally substituted with one or more R;
p is 0-4;
W is absent, —C(R$^9$)$_2$—, —O—, —S—, —S(=O)—, —S(=O)$_2$—, —S(=O)(=NR$^W$)—, or —NR$^W$—;
each $R^9$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;
or two $R^9$ are taken together to form a cycloalkyl or a heterocycloalkyl; each optionally substituted with one or more R;
$R^W$ is hydrogen, $C_1$-$C_6$alkyl, $C_1$-$C_6$haloalkyl, or $C_1$-$C_6$deuteroalkyl;
Ring A is cycloalkyl, heterocycloalkyl, aryl, or heteroaryl;
each $R^{10}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(O)$_2$NR$^c$R$^d$, —NR$^c$R$^d$, —NR$^b$C(O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently and optionally substituted with one or more R;
q is 0-4;
each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently and optionally substituted with one or more R;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently and optionally substituted with one or more R;

each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroalyl); wherein each alkyl, alkenyl, alkynyl, cycloalkyl, heterocycloalkyl, aryl, and heteroaryl is independently and optionally substituted with one or more R;

or $R^c$ and $R^d$ are taken together with the atom to which they are attached to form a heterocycloalkyl optionally substituted with one or more R; and each R is independently deuterium, halogen, —CN, —OH, —OC$_1$-C$_6$alkyl, —S(=O)C$_1$-C$_6$alkyl, —S(=O)$_2$C$_1$-C$_6$alkyl, —S(=O)$_2$NH$_2$, —S(=O)$_2$NHC$_1$-C$_6$alkyl, —S(=O)$_2$N(C$_1$-C$_6$alkyl)$_2$, —NH$_2$, —NHC$_1$-C$_6$alkyl, —N(C$_1$-C$_6$alkyl)$_2$, —NHC(=O)OC$_1$-C$_6$alkyl, —C(=O)C$_1$-C$_6$alkyl, —C(=O)OH, —C(=O)OC$_1$-C$_6$alkyl, —C(=O)NH$_2$, —C(=O)N(C$_1$-C$_6$alkyl)$_2$, —C(O)NHC$_1$-C$_6$alkyl, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or two R on the same atom form an oxo;

provided that the compound of Formula (I) is not

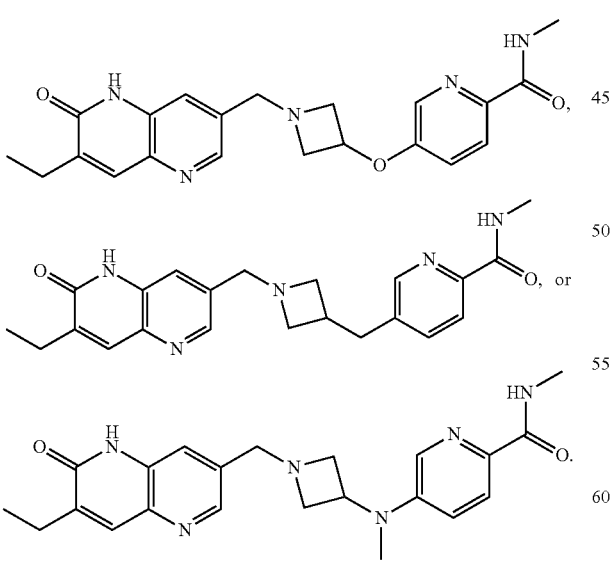

Disclosed herein is a compound of Formula (I), or a pharmaceutically acceptable salt, solvate, or stereoisomer thereof:

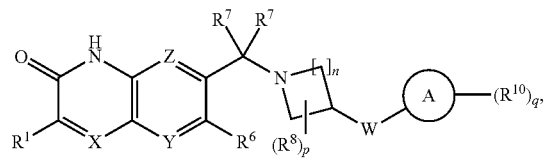

Formula (I)

wherein:
$R^1$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

X is N or CR$^2$;

$R^2$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

or $R^1$ and $R^2$ are taken together to form a cycloalkyl, heterocycloalkyl, aryl, or heteroaryl; each optionally substituted with one or more R;

Z is N or CR$^4$;

$R^4$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

Y is N or CR$^5$;

$R^5$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^6$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^7$ is independently hydrogen, deuterium, fluoro, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^7$ are taken together to form a cycloalkyl or a heterocycloalkyl; each optionally substituted with one or more R;

n is 1 or 2;

each $R^8$ is independently deuterium, halogen, —CN, —NO$_2$, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^8$ on the same carbon are taken together to form an oxo;

or two $R^8$ on the same carbon or adjacent carbons are taken together to form a cycloalkyl or heterocycloalkyl; each optionally substituted with one or more R;

p is 0-4;

W is —C(R$^9$)$_2$—, —O—, —S—, —S(=O)—, —S(=O)$_2$—, —S(=O)(=NR$^W$)—, or —NR$^W$—;

each $R^9$ is independently hydrogen, deuterium, halogen, —CN, —OH, —OR$^a$, —NR$^c$R$^d$, $C_1$-$C_6$alkyl, C₁-C₆haloalkyl, C₁-C₆deuteroalkyl, C₁-C₆hydroxyalkyl, C₁-C₆aminoalkyl, or C₁-C₆heteroalkyl;

or two $R^9$ are taken together to form a cycloalkyl or a heterocycloalkyl; each optionally substituted with one or more R;

$R^W$ is hydrogen, C₁-C₆alkyl, C₁-C₆haloalkyl, or C₁-C₆deuteroalkyl;

Ring A is cycloalkyl, heterocycloalkyl, aryl, or heteroaryl;

each $R^{10}$ is independently deuterium, halogen, —CN, —NO₂, —OH, —$OR^a$, —$OC(=O)R^a$, —$OC(=O)OR^b$, —$OC(=O)NR^cR^d$, —SH, —$SR^a$, —$S(=O)R^a$, —$S(=O)_2R^a$, —$S(=O)_2NR^cR^d$, —$NR^cR^d$, —$NR^bC(O)NR^cR^d$, —$NR^bC(=O)R^a$, —$NR^bC(=O)OR^b$, —$NR^bS(=O)_2R^a$, —$C(=O)R^a$, —$C(=O)OR^b$, —$C(=O)NR^cR^d$, C₁-C₆ alkyl, C₁-C₆haloalkyl, C₁-C₆deuteroalkyl, C₁-C₆hydroxyalkyl, C₁-C₆aminoalkyl, C₁-C₆heteroalkyl, cycloalkyl, heterocycloalkyl, aryl, or heteroaryl; wherein each alkyl, cycloalkyl, heterocycloalkyl, aryl, and heteroaryl is independently and optionally substituted with one or more R;

q is 0-4;

each $R^a$ is independently C₁-C₆alkyl, C₁-C₆haloalkyl, C₁-C₆deuteroalkyl, C₁-C₆hydroxyalkyl, C₁-C₆aminoalkyl, C₁-C₆heteroalkyl, C₂-C₆alkenyl, C₂-C₆alkynyl, cycloalkyl, heterocycloalkyl, aryl, heteroaryl, C₁-C₆alkyl(cycloalkyl), C₁-C₆alkyl(heterocycloalkyl), C₁-C₆alkyl(aryl), or C₁-C₆alkyl(heteroaryl); wherein each alkyl, alkenyl, alkynyl, cycloalkyl, heterocycloalkyl, aryl, and heteroaryl is independently and optionally substituted with one or more R;

each $R^b$ is independently hydrogen, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, C₂-C₆alkenyl, C₂-C₆alkynyl, cycloalkyl, heterocycloalkyl, aryl, heteroaryl, C₁-C₆alkyl(cycloalkyl), C₁-C₆alkyl(heterocycloalkyl), C₁-C₆alkyl(aryl), or C₁-C₆alkyl(heteroaryl); wherein each alkyl, alkenyl, alkynyl, cycloalkyl, heterocycloalkyl, aryl, and heteroaryl is independently and optionally substituted with one or more R;

each $R^c$ and $R^d$ are independently hydrogen, C₁-C₆alkyl, C₁-C₆haloalkyl, C₁-C₆deuteroalkyl, C₁-C₆hydroxyalkyl, C₁-C₆aminoalkyl, C₁-C₆heteroalkyl, C₂-C₆alkenyl, C₂-C₆alkynyl, cycloalkyl, heterocycloalkyl, aryl, heteroaryl, C₁-C₆alkyl(cycloalkyl), C₁-C₆alkyl(heterocycloalkyl), C₁-C₆alkyl(aryl), or C₁-C₆alkyl(heteroalyl); wherein each alkyl, alkenyl, alkynyl, cycloalkyl, heterocycloalkyl, aryl, and heteroaryl is independently and optionally substituted with one or more R;

or $R^c$ and $R^d$ are taken together with the atom to which they are attached to form a heterocycloalkyl optionally substituted with one or more R; and each R is independently deuterium, halogen, —CN, —OH, —OC₁-C₆alkyl, —S(=O)C₁-C₆alkyl, —S(=O)₂C₁-C₆alkyl, —S(=O)₂NH₂, —S(=O)₂NHC₁-C₆alkyl, —S(=O)₂N(C₁-C₆alkyl)₂, —NH₂, —NHC₁-C₆alkyl, —N(C₁-C₆alkyl)₂, —NHC(=O)OC₁-C₆alkyl, —C(=O)C₁-C₆alkyl, —C(=O)OH, —C(=O)OC₁-C₆alkyl, —C(=O)NH₂, —C(=O)N(C₁-C₆alkyl)₂, —C(=O)NHC₁-C₆alkyl, C₁-C₆alkyl, C₁-C₆haloalkyl, C₁-C₆ deuteroalkyl, C₁-C₆hydroxyalkyl, C₁-C₆ aminoalkyl, or C₁-C₆heteroalkyl;

or two R on the same atom form an oxo;

provided that the compound of Formula (I) is not

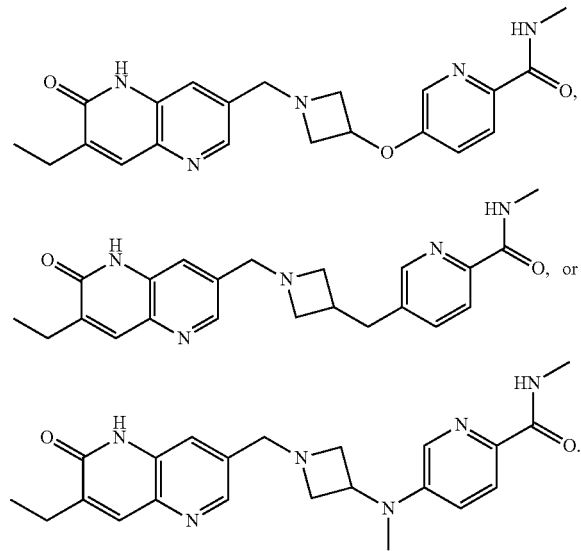

In some embodiments of a compound of Formula (I), or a pharmaceutically acceptable salt, solvate, or stereoisomer thereof, the compound is of Formula (Ia):

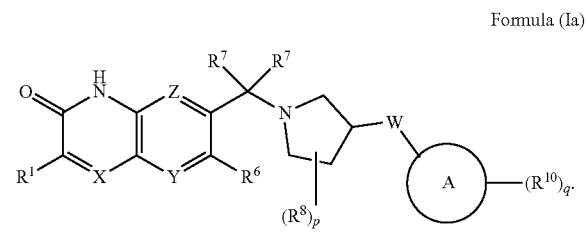

Formula (Ia)

In some embodiments of a compound of Formula (I), or a pharmaceutically acceptable salt, solvate, or stereoisomer thereof, the compound is of Formula (Ib):

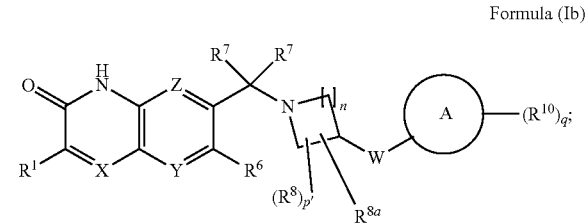

Formula (Ib)

wherein $R^{8a}$ is deuterium, halogen, —CN, —NO₂, —OH, —$OR^a$, —$NR^cR^d$, —$C(=O)R^a$, —$C(=O)OR^b$, —$C(=O)NR^cR^d$, C₁-C₆alkyl, C₁-C₆haloalkyl, C₁-C₆deuteroalkyl, C₁-C₆hydroxyalkyl, C₁-C₆aminoalkyl, or C₁-C₆heteroalkyl; and p' is 0-3.

In some embodiments of a compound of Formula (I), or a pharmaceutically acceptable salt, solvate, or stereoisomer thereof, the compound is of Formula (Ic):

Formula (Ic)

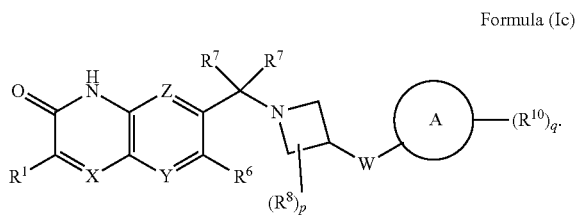

In some embodiments of a compound of Formula (I), (Ia), (Ib), or (Ic), or a pharmaceutically acceptable salt, solvate, or stereoisomer thereof, $R^1$ is hydrogen, deuterium, halogen, —CN, —OH, —$OR^a$, $C_1$-$C_6$haloalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl.

In some embodiments of a compound of Formula (I), (Ia), (Ib), or (Ic), or a pharmaceutically acceptable salt, solvate, or stereoisomer thereof, $R^1$ is halogen, —CN, —OH, $C_1$-$C_6$haloalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl.

In some embodiments of a compound of Formula (I), (Ia), (Ib), or (Ic), or a pharmaceutically acceptable salt, solvate, or stereoisomer thereof, $R^1$ is hydrogen, deuterium, halogen, —CN, —OH, —$OR^a$, $C_1$alkyl, $C_3$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl. In some embodiments of a compound of Formula (I), (Ia), (Ib), or (Ic), or a pharmaceutically acceptable salt, solvate, or stereoisomer thereof, $R^1$ is hydrogen, deuterium, $C_1$-$C_6$alkyl, $C_1$-$C_6$haloalkyl, $C_1$-$C_6$deuteroalkyl, or cycloalkyl. In some embodiments of a compound of Formula (I), (Ia), (Ib), or (Ic), or a pharmaceutically acceptable salt, solvate, or stereoisomer thereof, $R^1$ is $C_1$-$C_6$alkyl or cycloalkyl. In some embodiments of a compound of Formula (I), (Ia), (Ib), or (Ic), or a pharmaceutically acceptable salt, solvate, or stereoisomer thereof, $R^1$ is $C_1$ alkyl or $C_3$-$C_6$alkyl. In some embodiments of a compound of Formula (I), (Ia), (Ib), or (Ic), or a pharmaceutically acceptable salt, solvate, or stereoisomer thereof, $R^1$ is cycloalkyl. In some embodiments of a compound of Formula (I), (Ia), (Ib), or (Ic), or a pharmaceutically acceptable salt, solvate, or stereoisomer thereof, $R^1$ is cyclopropyl. In some embodiments of a compound of Formula (I), (Ia), (Ib), or (Ic), or a pharmaceutically acceptable salt, solvate, or stereoisomer thereof, $R^1$ is methyl or ethyl. In some embodiments of a compound of Formula (I), (Ia), (Ib), or (Ic), or a pharmaceutically acceptable salt, solvate, or stereoisomer thereof, $R^1$ is ethyl.

In some embodiments of a compound of Formula (I), (Ia), (Ib), or (Ic), or a pharmaceutically acceptable salt, solvate, or stereoisomer thereof, $R^1$ is deuterium, halogen, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, cycloalkyl, or heterocycloalkyl. In some embodiments of a compound of Formula (I), (Ia), (Ib), or (Ic), or a pharmaceutically acceptable salt, solvate, or stereoisomer thereof, $R^1$ is deuterium, halogen, $C_1$-$C_6$haloalkyl, $C_1$-$C_6$hydroxyalkyl, $C_1$-$C_6$aminoalkyl, $C_1$-$C_6$cyanoalkyl, $C_1$-$C_6$heteroalkyl, cycloalkyl, or heterocycloalkyl. In some embodiments of a compound of Formula (I), (Ia), (Ib), or (Ic), or a pharmaceutically acceptable salt, solvate, or stereoisomer thereof, $R^1$ is halogen, $C_1$-$C_6$haloalkyl, $C_1$-$C_6$deuteroalkyl, cycloalkyl, or heterocycloalkyl. In some embodiments of a compound of Formula (I), (Ia), (Ib), or (Ic), or a pharmaceutically acceptable salt, solvate, or stereoisomer thereof, $R^1$ is halogen, $C_1$-$C_6$haloalkyl, cycloalkyl, or heterocycloalkyl. In some embodiments of a compound of Formula (I), (Ia), (Ib), or (Ic), or a pharmaceutically acceptable salt, solvate, or stereoisomer thereof, $R^1$ is halogen or cycloalkyl. In some embodiments of a compound of Formula (I), (Ia), (Ib), or (Ic), or a pharmaceutically acceptable salt, solvate, or stereoisomer thereof, $R^1$ is halogen. In some embodiments of a compound of Formula (I), (Ia), (Ib), or (Ic), or a pharmaceutically acceptable salt, solvate, or stereoisomer thereof, $R^1$ is cycloalkyl. In some embodiments of a compound of Formula (I), (Ia), (Ib), or (Ic), or a pharmaceutically acceptable salt, solvate, or stereoisomer thereof, $R^1$ is cyclopropyl.

In some embodiments of a compound of Formula (I), (Ia), (Ib), or (Ic), or a pharmaceutically acceptable salt, solvate, or stereoisomer thereof, $R^1$ is halogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, cycloalkyl, or heterocycloalkyl. In some embodiments of a compound of Formula (I), (Ia), (Ib), or (Ic), or a pharmaceutically acceptable salt, solvate, or stereoisomer thereof, $R^1$ is halogen, $C_1$-$C_6$alkyl, $C_1$-$C_6$haloalkyl, $C_1$-$C_6$deuteroalkyl, cycloalkyl, or heterocycloalkyl. In some embodiments of a compound of Formula (I), (Ia), (Ib), or (Ic), or a pharmaceutically acceptable salt, solvate, or stereoisomer thereof, $R^1$ is halogen, $C_1$-$C_6$alkyl, or cycloalkyl.

In some embodiments of a compound of Formula (I), (Ia), (Ib), or (Ic), or a pharmaceutically acceptable salt, solvate, or stereoisomer thereof, X is N. In some embodiments of a compound of Formula (I), (Ia), (Ib), or (Ic), or a pharmaceutically acceptable salt, solvate, or stereoisomer thereof, X is $CR^2$.

In some embodiments of a compound of Formula (I), (Ia), (Ib), or (Ic), or a pharmaceutically acceptable salt, solvate, or stereoisomer thereof, $R^2$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), (Ia), (Ib), or (Ic), or a pharmaceutically acceptable salt, solvate, or stereoisomer thereof, $R^2$ is hydrogen, halogen, or $C_1$-$C_6$alkyl. In some embodiments of a compound of Formula (I), (Ia), (Ib), or (Ic), or a pharmaceutically acceptable salt, solvate, or stereoisomer thereof, $R^2$ is hydrogen or $C_1$-$C_6$alkyl. In some embodiments of a compound of Formula (I), (Ia), (Ib), or (Ic), or a pharmaceutically acceptable salt, solvate, or stereoisomer thereof, $R^2$ is hydrogen.

In some embodiments of a compound of Formula (I), (Ia), (Ib), or (Ic), or a pharmaceutically acceptable salt, solvate, or stereoisomer thereof, $R^1$ and $R^2$ are taken together to form a cycloalkyl, heterocycloalkyl, aryl, or heteroaryl; each optionally substituted with one or more R. In some embodiments of a compound of Formula (I), (Ia), (Ib), or (Ic), or a pharmaceutically acceptable salt, solvate, or stereoisomer thereof, $R^1$ and $R^2$ are taken together to form a cycloalkyl or heterocycloalkyl; each optionally substituted with one or more R. In some embodiments of a compound of Formula (I), (Ia), (Ib), or (Ic), or a pharmaceutically acceptable salt, solvate, or stereoisomer thereof, $R^1$ and $R^2$ are taken together to form an aryl or heteroaryl; each optionally substituted with one or more R.

Disclosed herein is a compound of Formula (II), or a pharmaceutically acceptable salt, solvate, or stereoisomer thereof:

Formula (II)

[Chemical structure diagram of Formula (II) showing: O=C-NH connected to ring B with X¹, X² substituents, (R¹¹)ₘ on ring B, Z, Y, R⁶ positions, R⁷ R⁷ groups, N linked to a ring with (R⁸)ₚ and n designation, W linker to ring A with (R¹⁰)_q]

wherein:

Ring B taken with $X^1$ and $X^2$ is a 5-membered heterocycloalkyl or a 5-membered heteroaryl;

$X^1$ is C, CH, or N;

$X^2$ is C, CH, or N;

each $R^{11}$ is independently hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$cyanoalkyl, $C_1$-$C_6$heteroalkyl, $C_2$-$C_6$alkenyl, $C_2$-$C_6$alkynyl, cycloalkyl, or heterocycloalkyl;

m is 0-3;

Z is N or $CR^4$;

$R^4$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

Y is N or $CR^5$;

$R^5$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

$R^6$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl;

each $R^7$ is independently hydrogen, deuterium, fluoro, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^7$ are taken together to form a cycloalkyl or a heterocycloalkyl; each optionally substituted with one or more R;

n is 1 or 2;

each $R^8$ is independently deuterium, halogen, —CN, —NO$_2$, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^8$ on the same carbon are taken together to form an oxo;

or two $R^8$ on the same carbon or adjacent carbons are taken together to form a cycloalkyl or heterocycloalkyl; each optionally substituted with one or more R;

p is 0-4;

W is absent, —C(R$^9$)$_2$—, —O—, —S—, —S(=O)—, —S(=O)$_2$—, —S(=O)(=NR$^W$)—, or —NR$^W$—;

each $R^9$ is independently hydrogen, deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^9$ are taken together to form a cycloalkyl or a heterocycloalkyl; each optionally substituted with one or more R;

$R^W$ is hydrogen, $C_1$-$C_6$alkyl, $C_1$-$C_6$haloalkyl, or $C_1$-$C_6$deuteroalkyl;

Ring A is cycloalkyl, heterocycloalkyl, aryl, or heteroaryl;

each $R^{10}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(O)$_2$NR$^c$R$^d$, —NR$^c$R$^d$, —NR$^b$C(O) NR$^c$R$^d$, —NR$^b$C(=O)R$^a$, —NR$^b$C(=O)OR$^b$, —NR$^b$S (=O)$_2$R$^a$, —C(=O)R$^a$, —C(=O)OR$^b$, —C(=O) NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently and optionally substituted with one or more R;

q is 0-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently and optionally substituted with one or more R;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroaryl); wherein each alkyl, alkenyl, alkynyl, cycloalkyl, heterocycloalkyl, aryl, and heteroaryl is independently and optionally substituted with one or more R;

each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkyl(cycloalkyl), $C_1$-$C_6$alkyl(heterocycloalkyl), $C_1$-$C_6$alkyl(aryl), or $C_1$-$C_6$alkyl(heteroalyl); wherein each alkyl, alkenyl, alkynyl, cycloalkyl, heterocycloalkyl, aryl, and heteroaryl is independently and optionally substituted with one or more R;

or $R^c$ and $R^d$ are taken together with the atom to which they are attached to form a heterocycloalkyl optionally substituted with one or more R; and each R is independently deuterium, halogen, —CN, —OH, —OC$_1$-$C_6$alkyl, —S(=O)C$_1$-$C_6$alkyl, —S(=O)$_2$C$_1$-$C_6$alkyl, —S(=O)$_2$NH$_2$, —S(=O)$_2$NHC$_1$-$C_6$alkyl, —S(=O)$_2$N(C$_1$-$C_6$alkyl)$_2$, —NH$_2$, —NHC$_1$-$C_6$alkyl, —N(C$_1$-$C_6$alkyl)$_2$, —NHC(=O) OC$_1$-$C_6$alkyl, —C(=O)C$_1$-$C_6$alkyl, —C(=O)OH, —C(=O)OC$_1$-$C_6$alkyl, —C(=O)NH$_2$, —C(=O)N (C$_1$-$C_6$alkyl)$_2$, —C(=O)NHC$_1$-$C_6$alkyl, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two R on the same atom form an oxo.

In some embodiments of a compound of Formula (II), or a pharmaceutically acceptable salt, solvate, or stereoisomer thereof, Ring B taken with $X^1$ and $X^2$ is a 5-membered heterocycloalkyl. In some embodiments of a compound of Formula (II), or a pharmaceutically acceptable salt, solvate, or stereoisomer thereof, Ring B taken with $X^1$ and $X^2$ is pyrrolidinyl or furanyl. In some embodiments of a compound of Formula (II), or a pharmaceutically acceptable salt, solvate, or stereoisomer thereof, Ring B taken with $X^1$ and $X^2$ is a 5-membered heteroaryl. In some embodiments of a compound of Formula (II), or a pharmaceutically acceptable salt, solvate, or stereoisomer thereof, Ring B taken with $X^1$ and $X^2$ is pyrrolyl, pyrazolyl, imidazolyl, or triazolyl. In some embodiments of a compound of Formula (II), or a pharmaceutically acceptable salt, solvate, or stereoisomer thereof, Ring B taken with $X^1$ and $X^2$ is pyrazolyl or imidazolyl. In some embodiments of a compound of Formula (II), or a pharmaceutically acceptable salt, solvate, or stereoisomer thereof, Ring B taken with $X^1$ and $X^2$ is pyrazolyl. In some embodiments of a compound of Formula (II), or a pharmaceutically acceptable salt, solvate, or stereoisomer thereof, Ring B taken with $X^1$ and $X^2$ is furanyl.

In some embodiments of a compound of Formula (II), or a pharmaceutically acceptable salt, solvate, or stereoisomer thereof, $X^1$ is C. In some embodiments of a compound of Formula (II), or a pharmaceutically acceptable salt, solvate, or stereoisomer thereof, $X^1$ is CH. In some embodiments of a compound of Formula (II), or a pharmaceutically acceptable salt, solvate, or stereoisomer thereof, $X^1$ is N. In some embodiments of a compound of Formula (II), or a pharmaceutically acceptable salt, solvate, or stereoisomer thereof, $X^2$ is C. In some embodiments of a compound of Formula (II), or a pharmaceutically acceptable salt, solvate, or stereoisomer thereof, $X^2$ is CH. In some embodiments of a compound of Formula (II), or a pharmaceutically acceptable salt, solvate, or stereoisomer thereof, $X^2$ is N.

In some embodiments of a compound of Formula (I), (Ia), (Ib), (Ic), or (II), or a pharmaceutically acceptable salt, solvate, or stereoisomer thereof, Z is N. In some embodiments of a compound of Formula (I), (Ia), (Ib), (Ic), or (II), or a pharmaceutically acceptable salt, solvate, or stereoisomer thereof, Z is $CR^4$.

In some embodiments of a compound of Formula (I), (Ia), (Ib), (Ic), or (II), or a pharmaceutically acceptable salt, solvate, or stereoisomer thereof, $R^4$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), (Ia), (Ib), (Ic), or (II), or a pharmaceutically acceptable salt, solvate, or stereoisomer thereof, $R^4$ is hydrogen, halogen, or $C_1$-$C_6$alkyl. In some embodiments of a compound of Formula (I), (Ia), (Ib), (Ic), or (II), or a pharmaceutically acceptable salt, solvate, or stereoisomer thereof, $R^4$ is hydrogen or $C_1$-$C_6$alkyl. In some embodiments of a compound of Formula (I), (Ia), (Ib), (Ic), or (II), or a pharmaceutically acceptable salt, solvate, or stereoisomer thereof, $R^4$ is hydrogen.

In some embodiments of a compound of Formula (I), (Ia), (Ib), (Ic), or (II), or a pharmaceutically acceptable salt, solvate, or stereoisomer thereof, Y is N. In some embodiments of a compound of Formula (I), (Ia), (Ib), (Ic), or (II), or a pharmaceutically acceptable salt, solvate, or stereoisomer thereof, Y is $CR^5$.

In some embodiments of a compound of Formula (I), (Ia), (Ib), (Ic), or (II), or a pharmaceutically acceptable salt, solvate, or stereoisomer thereof, $R^5$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), (Ia), (Ib), (Ic), or (II), or a pharmaceutically acceptable salt, solvate, or stereoisomer thereof, $R^5$ is hydrogen, halogen, or $C_1$-$C_6$alkyl. In some embodiments of a compound of Formula (I), (Ia), (Ib), (Ic), or (II), or a pharmaceutically acceptable salt, solvate, or stereoisomer thereof, $R^5$ is hydrogen or $C_1$-$C_6$alkyl. In some embodiments of a compound of Formula (I), (Ia), (Ib), (Ic), or (II), or a pharmaceutically acceptable salt, solvate, or stereoisomer thereof, $R^5$ is hydrogen.

In some embodiments of a compound of Formula (I), (Ia), (Ib), (Ic), or (II), or a pharmaceutically acceptable salt, solvate, or stereoisomer thereof, $R^6$ is hydrogen, deuterium, halogen, $C_1$-$C_6$alkyl, $C_1$-$C_6$haloalkyl, or $C_1$-$C_6$deuteroalkyl. In some embodiments of a compound of Formula (I), (Ia), (Ib), (Ic), or (II), or a pharmaceutically acceptable salt, solvate, or stereoisomer thereof, $R^6$ is hydrogen, halogen, or $C_1$-$C_6$alkyl. In some embodiments of a compound of Formula (I), (Ia), (Ib), (Ic), or (II), or a pharmaceutically acceptable salt, solvate, or stereoisomer thereof, $R^6$ is hydrogen or $C_1$-$C_6$alkyl. In some embodiments of a compound of Formula (I), (Ia), (Ib), (Ic), or (II), or a pharmaceutically acceptable salt, solvate, or stereoisomer thereof, $R^6$ is hydrogen.

In some embodiments of a compound of Formula (I), (Ia), (Ib), (Ic), or (II), or a pharmaceutically acceptable salt, solvate, or stereoisomer thereof, each $R^7$ is independently hydrogen, deuterium, fluoro, $C_1$-$C_6$alkyl, $C_1$-$C_6$haloalkyl, or $C_1$-$C_6$deuteroalkyl. In some embodiments of a compound of Formula (I), (Ia), (Ib), (Ic), or (II), or a pharmaceutically acceptable salt, solvate, or stereoisomer thereof, each $R^7$ is independently hydrogen, deuterium, fluoro, or $C_1$-$C_6$alkyl. In some embodiments of a compound of Formula (I), (Ia), (Ib), (Ic), or (II), or a pharmaceutically acceptable salt, solvate, or stereoisomer thereof, each $R^7$ is independently hydrogen, fluoro, or $C_1$-$C_6$alkyl. In some embodiments of a compound of Formula (I), (Ia), (Ib), (Ic), or (II), or a pharmaceutically acceptable salt, solvate, or stereoisomer thereof, each $R^7$ is independently hydrogen or $C_1$-$C_6$alkyl. In some embodiments of a compound of Formula (I), (Ia), (Ib), (Ic), or (II), or a pharmaceutically acceptable salt, solvate, or stereoisomer thereof, each $R^7$ is independently hydrogen or fluoro. In some embodiments of a compound of Formula (I), (Ia), (Ib), (Ic), or (II), or a pharmaceutically acceptable salt, solvate, or stereoisomer thereof, each $R^7$ is hydrogen. In some embodiments of a compound of Formula (I), (Ia), (Ib), (Ic), or (II), or a pharmaceutically acceptable salt, solvate, or stereoisomer thereof, one $R^7$ is hydrogen and the other $R^7$ is $C_1$-$C_6$alkyl.

In some embodiments of a compound of Formula (I), (Ia), (Ib), (Ic), or (II), or a pharmaceutically acceptable salt, solvate, or stereoisomer thereof, two $R^7$ are taken together to form a cycloalkyl or a heterocycloalkyl; each optionally substituted with one or more R. In some embodiments of a compound of Formula (I), (Ia), (Ib), (Ic), or (II), or a pharmaceutically acceptable salt, solvate, or stereoisomer thereof, two $R^7$ are taken together to form a cycloalkyl or a heterocycloalkyl. In some embodiments of a compound of Formula (I), (Ia), (Ib), (Ic), or (II), or a pharmaceutically acceptable salt, solvate, or stereoisomer thereof, two $R^7$ are taken together to form a cycloalkyl.

In some embodiments of a compound of Formula (I) or (II), or a pharmaceutically acceptable salt, solvate, or stereoisomer thereof, n is 1. In some embodiments of a compound of Formula (I) or (II), or a pharmaceutically acceptable salt, solvate, or stereoisomer thereof, n is 2.

In some embodiments of a compound of Formula (I), (Ia), (Ib), (Ic), or (II), or a pharmaceutically acceptable salt, solvate, or stereoisomer thereof, each $R^8$ is independently deuterium, halogen, —CN, —OH, —$OR^a$, —$NR^cR^d$, $C_1$-$C_6$alkyl, $C_1$-$C_6$haloalkyl, or $C_1$-$C_6$deuteroalkyl. In some embodiments of a compound of Formula (I), (Ia), (Ib), (Ic), or (II), or a pharmaceutically acceptable salt, solvate, or stereoisomer thereof, each $R^8$ is independently deuterium, halogen, —CN, $C_1$-$C_6$alkyl, $C_1$-$C_6$haloalkyl, or $C_1$-$C_6$deuteroalkyl. In some embodiments of a compound of Formula (I), (Ia), (Ib), (Ic), or (II), or a pharmaceutically acceptable salt, solvate, or stereoisomer thereof, each $R^8$ is independently deuterium, halogen, —CN, or $C_1$-$C_6$alkyl. In some embodiments of a compound of Formula (I), (Ia), (Ib), (Ic), or (II), or a pharmaceutically acceptable salt, solvate, or stereoisomer thereof, each $R^8$ is independently —CN or $C_1$-$C_6$alkyl. In some embodiments of a compound of Formula (I), (Ia), (Ib), (Ic), or (II), or a pharmaceutically acceptable salt, solvate, or stereoisomer thereof, each $R^8$ is independently $C_1$-$C_6$alkyl.

In some embodiments of a compound of Formula (I), (Ia), (Ib), (Ic), or (II), or a pharmaceutically acceptable salt, solvate, or stereoisomer thereof, two $R^8$ on the same carbon are taken together to form a cycloalkyl or heterocycloalkyl; each optionally substituted with one or more R. In some embodiments of a compound of Formula (I), (Ia), (Ib), (Ic), or (II), or a pharmaceutically acceptable salt, solvate, or stereoisomer thereof, two $R^8$ on the same carbon are taken together to form a cycloalkyl or heterocycloalkyl.

In some embodiments of a compound of Formula (I), (Ia), (Ib), (Ic), or (II), or a pharmaceutically acceptable salt, solvate, or stereoisomer thereof, two $R^8$ on adjacent carbons are taken together to form a cycloalkyl or heterocycloalkyl; each optionally substituted with one or more R. In some embodiments of a compound of Formula (I), (Ia), (Ib), (Ic), or (II), or a pharmaceutically acceptable salt, solvate, or stereoisomer thereof, two $R^8$ on adjacent carbons are taken together to form a cycloalkyl or heterocycloalkyl.

In some embodiments of a compound of Formula (I), (Ia), (Ic), or (II), or a pharmaceutically acceptable salt, solvate, or stereoisomer thereof, p is 0-3. In some embodiments of a compound of Formula (I), (Ia), (Ic), or (II), or a pharmaceutically acceptable salt, solvate, or stereoisomer thereof, p is 0-2. In some embodiments of a compound of Formula (I), (Ia), (Ic), or (II), or a pharmaceutically acceptable salt, solvate, or stereoisomer thereof, p is 0 or 1. In some embodiments of a compound of Formula (I), (Ia), (Ic), or (II), or a pharmaceutically acceptable salt, solvate, or stereoisomer thereof, p is 2-4. In some embodiments of a compound of Formula (I), (Ia), (Ic), or (II), or a pharmaceutically acceptable salt, solvate, or stereoisomer thereof, p is 2 or 3. In some embodiments of a compound of Formula (I), (Ia), (Ic), or (II), or a pharmaceutically acceptable salt, solvate, or stereoisomer thereof, p is 1-4. In some embodiments of a compound of Formula (I), (Ia), (Ic), or (II), or a pharmaceutically acceptable salt, solvate, or stereoisomer thereof, p is 1-3. In some embodiments of a compound of Formula (I), (Ia), (Ic), or (II), or a pharmaceutically acceptable salt, solvate, or stereoisomer thereof, p is 1 or 2. In some embodiments of a compound of Formula (I), (Ia), (Ic), or (II), or a pharmaceutically acceptable salt, solvate, or stereoisomer thereof, p is 0. In some embodiments of a compound of Formula (I), (Ia), (Ic), or (II), or a pharmaceutically acceptable salt, solvate, or stereoisomer thereof, p is 1. In some embodiments of a compound of Formula (I), (Ia), (Ic), or (II), or a pharmaceutically acceptable salt, solvate, or stereoisomer thereof, p is 2. In some embodiments of a compound of Formula (I), (Ia), (Ic), or (II), or a pharmaceutically acceptable salt, solvate, or stereoisomer thereof, p is 3.

In some embodiments of a compound of Formula (Ib), or a pharmaceutically acceptable salt, solvate, or stereoisomer thereof, p' is 0-2. In some embodiments of a compound of Formula (Ib), or a pharmaceutically acceptable salt, solvate, or stereoisomer thereof, p' is 0 or 1. In some embodiments of a compound of Formula (Ib), or a pharmaceutically acceptable salt, solvate, or stereoisomer thereof, p' is 2 or 3. In some embodiments of a compound of Formula (Ib), or a pharmaceutically acceptable salt, solvate, or stereoisomer thereof, p' is 1-3. In some embodiments of a compound of Formula (Ib), or a pharmaceutically acceptable salt, solvate, or stereoisomer thereof, p' is 1 or 2. In some embodiments of a compound of Formula (Ib), or a pharmaceutically acceptable salt, solvate, or stereoisomer thereof, p' is 0. In some embodiments of a compound of Formula (Ib), or a pharmaceutically acceptable salt, solvate, or stereoisomer thereof, p' is 1. In some embodiments of a compound of Formula (Ib), or a pharmaceutically acceptable salt, solvate, or stereoisomer thereof, p' is 2. In some embodiments of a compound of Formula (Ib), or a pharmaceutically acceptable salt, solvate, or stereoisomer thereof, p' is 3.

In some embodiments of a compound of Formula (Ib), or a pharmaceutically acceptable salt, solvate, or stereoisomer thereof, $R^{8a}$ is deuterium, halogen, —CN, —OH, —NR$^c$R$^d$, $C_1$-$C_6$haloalkyl, or $C_1$-$C_6$deuteroalkyl. In some embodiments of a compound of Formula (Ib), or a pharmaceutically acceptable salt, solvate, or stereoisomer thereof, $R^{8a}$ is deuterium, halogen, —CN, $C_1$-$C_6$haloalkyl, or $C_1$-$C_6$deuteroalkyl. In some embodiments of a compound of Formula (Ib), or a pharmaceutically acceptable salt, solvate, or stereoisomer thereof, $R^{8a}$ is deuterium, halogen, —CN, or $C_1$-$C_6$alkyl. In some embodiments of a compound of Formula (Ib), or a pharmaceutically acceptable salt, solvate, or stereoisomer thereof, $R^{8a}$ is —CN or $C_1$-$C_6$alkyl. In some embodiments of a compound of Formula (Ib), or a pharmaceutically acceptable salt, solvate, or stereoisomer thereof, $R^{8a}$ is $C_1$-$C_6$alkyl.

In some embodiments of a compound of Formula (I), (Ia), (Ib), (Ic), or (II), or a pharmaceutically acceptable salt, solvate, or stereoisomer thereof, W is —C($R^9$)$_2$—, —O—, —S—, —S(=O)—, —S(=O)$_2$—, —S(=O)(=NR$^W$)—, or —NR$^W$—. In some embodiments of a compound of Formula (I), (Ia), (Ib), (Ic), or (II), or a pharmaceutically acceptable salt, solvate, or stereoisomer thereof, W is absent, —C($R^9$)$_2$—, —O—, or —NR$^W$—. In some embodiments of a compound of Formula (I), (Ia), (Ib), (Ic), or (II), or a pharmaceutically acceptable salt, solvate, or stereoisomer thereof, W is —C($R^9$)$_2$—, —O—, or —NR$^W$—. In some embodiments of a compound of Formula (I), (Ia), (Ib), (Ic), or (II), or a pharmaceutically acceptable salt, solvate, or stereoisomer thereof, W is —O— or —NR$^W$—. In some embodiments of a compound of Formula (I), (Ia), (Ib), (Ic), or (II), or a pharmaceutically acceptable salt, solvate, or stereoisomer thereof, W is —S—, —S(=O)—, —S(=O)$_2$—, or —S(=O)(=NR$^W$)—. In some embodiments of a compound of Formula (I), (Ia), (Ib), (Ic), or (II), or a pharmaceutically acceptable salt, solvate, or stereoisomer thereof, W is —S—, —S(=O)—, or —S(=O)$_2$—. In some embodiments of a compound of Formula (I), (Ia), (Ib), (Ic), or (II), or a pharmaceutically acceptable salt, solvate, or stereoisomer thereof, W is —O—. In some embodiments of a compound of Formula (I), (Ia), (Ib), (Ic), or (II), or a pharmaceutically acceptable salt, solvate, or stereoisomer thereof, W is —NR$^{W2}$—. In some embodiments of a compound of Formula (I), (Ia), (Ib), (Ic), or (II), or a pharmaceutically acceptable salt, solvate, or stereoisomer thereof, W is absent.

In some embodiments of a compound of Formula (I), (Ia), (Ib), (Ic), or (II), or a pharmaceutically acceptable salt, solvate, or stereoisomer thereof, each $R^9$ is independently hydrogen, deuterium, fluoro, $C_1$-$C_6$haloalkyl, or $C_1$-$C_6$deuteroalkyl. In some embodiments of a compound of Formula (I), (Ia), (Ib), (Ic), or (II), or a pharmaceutically acceptable salt, solvate, or stereoisomer thereof, each $R^9$ is independently hydrogen, deuterium, fluoro, or $C_1$-$C_6$alkyl. In some embodiments of a compound of Formula (I), (Ia), (Ib), (Ic), or (II), or a pharmaceutically acceptable salt, solvate, or stereoisomer thereof, each $R^9$ is independently hydrogen or $C_1$-$C_6$alkyl. In some embodiments of a compound of Formula (I), (Ia), (Ib), (Ic), or (II), or a pharmaceutically acceptable salt, solvate, or stereoisomer thereof, each $R^9$ is independently hydrogen, fluoro, or $C_1$-$C_6$alkyl. In some embodiments of a compound of Formula (I), (Ia), (Ib), (Ic), or (II), or a pharmaceutically acceptable salt, solvate, or stereoisomer thereof, each $R^9$ is independently hydrogen or fluoro. In some embodiments of a compound of Formula (I), (Ia), (Ib), (Ic), or (II), or a pharmaceutically acceptable salt, solvate, or stereoisomer thereof, each $R^9$ is hydrogen. In some embodiments of a compound of Formula (I), (Ia), (Ib), (Ic), or (II), or a pharmaceutically acceptable salt, solvate, or stereoisomer thereof, one $R^9$ is hydrogen and the other $R^9$ is $C_1$-$C_6$alkyl.

In some embodiments of a compound of Formula (I), (Ia), (Ib), (Ic), or (II), or a pharmaceutically acceptable salt, solvate, or stereoisomer thereof, two $R^9$ are taken together to form a cycloalkyl or a heterocycloalkyl; each optionally substituted with one or more R. In some embodiments of a compound of Formula (I), (Ia), (Ib), (Ic), or (II), or a pharmaceutically acceptable salt, solvate, or stereoisomer thereof, two $R^9$ are taken together to form a cycloalkyl or a heterocycloalkyl. In some embodiments of a compound of Formula (I), (Ia), (Ib), (Ic), or (II), or a pharmaceutically acceptable salt, solvate, or stereoisomer thereof, two $R^9$ are taken together to form a cycloalkyl.

In some embodiments of a compound of Formula (I), (Ia), (Ib), (Ic), or (II), or a pharmaceutically acceptable salt, solvate, or stereoisomer thereof, $R^W$ is hydrogen or $C_1$-$C_6$alkyl. In some embodiments of a compound of Formula (I), (Ia), (Ib), (Ic), or (II), or a pharmaceutically acceptable salt, solvate, or stereoisomer thereof, each $R^W$ is hydrogen.

In some embodiments of a compound of Formula (I), (Ia), (Ib), (Ic), or (II), or a pharmaceutically acceptable salt, solvate, or stereoisomer thereof, Ring A is cycloalkyl or heterocycloalkyl. In some embodiments of a compound of Formula (I), (Ia), (Ib), (Ic), or (II), or a pharmaceutically acceptable salt, solvate, or stereoisomer thereof, Ring A is cycloalkyl. In some embodiments of a compound of Formula (I), (Ia), (Ib), (Ic), or (II), or a pharmaceutically acceptable salt, solvate, or stereoisomer thereof, Ring A is heterocycloalkyl.

In some embodiments of a compound of Formula (I), (Ia), (Ib), (Ic), or (II), or a pharmaceutically acceptable salt, solvate, or stereoisomer thereof, Ring A is aryl or heteroaryl. In some embodiments of a compound of Formula (I), (Ia), (Ib), (Ic), or (II), or a pharmaceutically acceptable salt, solvate, or stereoisomer thereof, Ring A is phenyl. In some embodiments of a compound of Formula (I), (Ia), (Ib), (Ic), or (II), or a pharmaceutically acceptable salt, solvate, or stereoisomer thereof, Ring A is heteroaryl.

In some embodiments of a compound of Formula (I), (Ia), (Ib), (Ic), or (II), or a pharmaceutically acceptable salt, solvate, or stereoisomer thereof, Ring A is 5- or 6-membered heteroaryl. In some embodiments of a compound of Formula (I), (Ia), (Ib), (Ic), or (II), or a pharmaceutically acceptable salt, solvate, or stereoisomer thereof, Ring A is 5-membered heteroaryl. In some embodiments of a compound of Formula (I), (Ia), (Ib), (Ic), or (II), or a pharmaceutically acceptable salt, solvate, or stereoisomer thereof, Ring A is 6-membered heteroaryl.

In some embodiments of a compound of Formula (I), (Ia), (Ib), (Ic), or (II), or a pharmaceutically acceptable salt, solvate, or stereoisomer thereof, Ring A is not pyridinyl. In some embodiments of a compound of Formula (I), (Ia), (Ib), (Ic), or (II), or a pharmaceutically acceptable salt, solvate, or stereoisomer thereof, Ring A is not In some embodiments of a compound of Formula (I), (Ia), (Ib), (Ic), or (II), or a pharmaceutically acceptable salt, solvate, or stereoisomer thereof, each $R^{10}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(O)R$^a$, —NR$^b$C(O)OR$^b$, —NR$^b$S(=O)$_2$R$^a$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; provided that one $R^{10}$ is not —C(=O)NHCH$_3$. In some embodiments of a compound of Formula (I), (Ia), (Ib), (Ic), or (II), or a pharmaceutically acceptable salt, solvate, or stereoisomer thereof, each $R^{10}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I), (Ia), (Ib), (Ic), or (II), or a pharmaceutically acceptable salt, solvate, or stereoisomer thereof, each $R^{10}$ is independently deuterium, halogen, —CN, —OH, —OR$^a$, —OC(=O)R$^a$, —OC(=O)OR$^b$, —OC(=O)NR$^c$R$^d$, —NR$^c$R$^d$, —NR$^b$C(=O)NR$^c$R$^d$, —NR$^b$C(=O)R$^a$, —NR$^b$C(=O)OR$^b$, —C(=O)R$^a$, —C(C$_0$)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl. In some embodiments of a compound of Formula (I), (Ia), (Ib), (Ic), or (II), or a pharmaceutically acceptable salt, solvate, or stereoisomer thereof, each $R^{10}$ is independently deuterium, halogen, —CN, —OC(=O)NR$^c$R$^d$, —NR$^b$C(=O)NR$^c$R$^d$, —NR$^b$C(=O)R$^a$, —NR$^b$C(=O)OR$^b$, —C(Co)R$^a$, —C(=O)OR$^b$, —C(=O)NR$^c$R$^d$, $C_1$-$C_6$alkyl, $C_1$-$C_6$haloalkyl, or $C_1$-$C_6$deuteroalkyl.

In some embodiments of a compound of Formula (I), (Ia), (Ib), (Ic), or (II), or a pharmaceutically acceptable salt, solvate, or stereoisomer thereof, each $R^{10}$ is independently deuterium, halogen, —CN, —C(=O)NR$^c$R$^d$, $C_1$-$C_6$alkyl, $C_1$-$C_6$haloalkyl, or $C_1$-$C_6$deuteroalkyl.

In some embodiments of a compound of Formula (I), (Ia), (Ib), (Ic), or (II), or a pharmaceutically acceptable salt, solvate, or stereoisomer thereof, each $R^{10}$ is independently —C(=O)NR$^c$R$^d$.

In some embodiments of a compound of Formula (I), (Ia), (Ib), (Ic), or (II), or a pharmaceutically acceptable salt, solvate, or stereoisomer thereof, q is 0-3. In some embodiments of a compound of Formula (I), (Ia), (Ib), (Ic), or (II), or a pharmaceutically acceptable salt, solvate, or stereoisomer thereof, q is 0-2. In some embodiments of a compound of Formula (I), (Ia), (Ib), (Ic), or (II), or a pharmaceutically acceptable salt, solvate, or stereoisomer thereof, q is 0 or 1. In some embodiments of a compound of Formula (I), (Ia), (Ib), (Ic), or (II), or a pharmaceutically acceptable salt, solvate, or stereoisomer thereof, q is 1-4. In some embodiments of a compound of Formula (I), (Ia), (Ib), (Ic), or (II), or a pharmaceutically acceptable salt, solvate, or stereoisomer thereof, q is 1-3. In some embodiments of a compound of Formula (I), (Ia), (Ib), (Ic), or (II), or a pharmaceutically acceptable salt, solvate, or stereoisomer thereof, q is 2-4. In some embodiments of a compound of Formula (I), (Ia), (Ib), (Ic), or (II), or a pharmaceutically acceptable salt, solvate, or stereoisomer thereof, q is 2 or 3. In some embodiments of a compound of Formula (I), (Ia), (Ib), (Ic), or (II), or a pharmaceutically acceptable salt, solvate, or stereoisomer thereof, q is 1 or 2. In some embodiments of a compound of Formula (I), (Ia), (Ib), (Ic), or (II), or a pharmaceutically acceptable salt, solvate, or stereoisomer thereof, q is 1. In some embodiments of a compound of Formula (I), (Ia), (Ib), (Ic), or (II), or a pharmaceutically acceptable salt, solvate, or stereoisomer thereof, q is 2. In some embodiments of a compound of Formula (I), (Ia), (Ib), (Ic), or (II), or a pharmaceutically acceptable salt, solvate, or stereoisomer thereof, q is 3.

In some embodiments of a compound of Formula (I), (Ia), (Ib), (Ic), or (II), or a pharmaceutically acceptable salt, solvate, or stereoisomer thereof, A—$(R^{10})_q$ is not

[structure: pyridine-2-carboxamide N-Me]

In some embodiments of a compound of Formula (I), (Ia), (Ib), (Ic), or (II), or a pharmaceutically acceptable salt, solvate, or stereoisomer thereof, A—$(R^{10})_q$ is [pyridine-2-carboxamide N-Me].

In some embodiments of a compound of Formula (I), (Ia), (Ib), (Ic), or (II), or a pharmaceutically acceptable salt, solvate, or stereoisomer thereof, A—$(R^{10})_q$ is [pyridine-2-carboxamide N-cyclopropyl].

In some embodiments of a compound of Formula (I), (Ia), (Ib), (Ic), or (II), or a pharmaceutically acceptable salt, solvate, or stereoisomer thereof, each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^a$ is independently $C_1$-$C_6$alkyl, $C_1$-$C_6$haloalkyl, $C_1$-$C_6$deuteroalkyl, cycloalkyl, or heterocycloalkyl; wherein each alkyl, cycloalkyl, and heterocycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^a$ is independently $C_1$-$C_6$alkyl, $C_1$-$C_6$haloalkyl, or cycloalkyl; wherein each alkyl and cycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^a$ is independently $C_1$-$C_6$alkyl or cycloalkyl; wherein each alkyl and cycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^a$ is independently $C_1$-$C_6$alkyl or $C_1$-$C_6$haloalkyl; wherein each alkyl is independently and optionally substituted with one or more R.

In some embodiments of a compound of Formula (I), (Ia), (Ib), (Ic), or (II), or a pharmaceutically acceptable salt, solvate, or stereoisomer thereof, each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^b$ is independently hydrogen, $C_1$-$C_6$alkyl, $C_1$-$C_6$haloalkyl, $C_1$-$C_6$deuteroalkyl, cycloalkyl, or heterocycloalkyl; wherein each alkyl, cycloalkyl, and heterocycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^b$ is independently hydrogen, $C_1$-$C_6$alkyl, $C_1$-$C_6$haloalkyl, or cycloalkyl; wherein each alkyl and cycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^b$ is independently hydrogen, $C_1$-$C_6$alkyl, or cycloalkyl; wherein each alkyl and cycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^b$ is independently hydrogen, $C_1$-$C_6$alkyl, or $C_1$-$C_6$haloalkyl; wherein each alkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^b$ is independently hydrogen or $C_1$-$C_6$alkyl independently and optionally substituted with one or more R.

In some embodiments of a compound of Formula (I), (Ia), (Ib), (Ic), or (II), or a pharmaceutically acceptable salt, solvate, or stereoisomer thereof, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl; wherein each alkyl, cycloalkyl, and heterocycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^c$ and $R^d$ are independently hydrogen, $C_1$-$C_6$alkyl, $C_1$-$C_6$haloalkyl, $C_1$-$C_6$deuteroalkyl, cycloalkyl, or heterocycloalkyl; wherein each alkyl, cycloalkyl, and heterocycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^c$ and $R^d$ are independently hydrogen, $C_1$-$C_6$alkyl, $C_1$-$C_6$haloalkyl, or cycloalkyl; wherein each alkyl and cycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^c$ and $R^d$ are independently hydrogen, $C_1$-$C_6$alkyl, or cycloalkyl; wherein each alkyl and cycloalkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^c$ and $R^d$ are independently hydrogen, $C_1$-$C_6$alkyl, or $C_1$-$C_6$haloalkyl; wherein each alkyl is independently and optionally substituted with one or more R. In some embodiments of a compound of Formula (I), (Ia), (Ib), (Ic), or (II), or a pharmaceutically acceptable salt, solvate, or stereoisomer thereof, each $R^c$ and $R^d$ are independently hydrogen or $C_1$-$C_6$alkyl independently and optionally substituted with one or more R. In some embodiments of a compound of Formula (I), (Ia), (Ib), (Ic), or (II), or a pharmaceutically acceptable salt, solvate, or stereoisomer thereof, $R^c$ is cycloalkyl and $R^d$ hydrogen.

In some embodiments of a compound of Formula (I), (Ia), (Ib), (Ic), or (II), or a pharmaceutically acceptable salt, solvate, or stereoisomer thereof, $R^c$ and $R^d$ are taken together with the atom to which they are attached to form a heterocycloalkyl optionally substituted with one or more R. In some embodiments of a compound of Formula (I), (Ia), (Ib), (Ic), or (II), or a pharmaceutically acceptable salt, solvate, or stereoisomer thereof, $R^c$ and $R^d$ are taken together with the atom to which they are attached to form a heterocycloalkyl.

In some embodiments of a compound of Formula (I), (Ia), (Ib), (Ic), or (II), or a pharmaceutically acceptable salt, solvate, or stereoisomer thereof, each R is independently deuterium, halogen, —CN, —OH, —O$C_1$-$C_6$alkyl, —NH$_2$, —NH$C_1$-$C_6$alkyl, —N($C_1$-$C_6$alkyl)$_2$, —C(O)$C_1$-$C_6$alkyl, —C(=O)OH, —C(O)O$C_1$-$C_6$alkyl, —C(=O)NH$_2$, —C(=O)N($C_1$-$C_6$alkyl)$_2$, —C(=O)NH$C_1$-$C_6$alkyl, $C_1$-$C_6$alkyl, $C_1$-$C_6$haloalkyl, or $C_1$-$C_6$deuteroalkyl; or two R on the same atom form an oxo. In some embodiments of a compound of Formula (I), (Ia), (Ib), (Ic), or (II), or a pharmaceutically acceptable salt, solvate, or stereoisomer thereof, each R is independently deuterium, halogen, —CN, —OH, —O$C_1$-$C_6$alkyl, —NH$_2$, —NH$C_1$-$C_6$alkyl, —N($C_1$-$C_6$alkyl)$_2$, $C_1$-$C_6$alkyl, $C_1$-$C_6$haloalkyl, or $C_1$-$C_6$deuteroalkyl; or two R on the same atom form an oxo. In some embodiments of a compound of Formula (I), (Ia), (Ib), (Ic), or (II), or a pharmaceutically acceptable salt, solvate, or stereoisomer thereof, each R is independently deuterium, halogen, —CN, —OH, —O$C_1$-$C_6$alkyl, —$C_1$-$C_6$alkyl, $C_1$-$C_6$haloalkyl, or $C_1$-$C_6$deuteroalkyl; or two R on the same atom form an oxo.

In some embodiments of a compound disclosed herein, each $R^a$, $R^b$, $R^c$, $R^d$, the cycloalkyl, heterocycloalkyl, aryl, or heteroaryl formed when $R^1$ and $R^2$ are taken together, the cycloalkyl and heterocycloalkyl formed when two $R^7$ are taken together, the cycloalkyl and heterocycloalkyl formed when two $R^8$ are taken together, the cycloalkyl and heterocycloalkyl formed when two $R^9$ are taken together, and the heterocycloalkyl formed when $R^c$ and $R^d$ are taken together, is independently substituted with one, two, three, or four substituents as defined herein. In some embodiments of a compound disclosed herein, each $R^a$, $R^b$, $R^c$, $R^d$, the cycloalkyl, heterocycloalkyl, aryl, or heteroaryl formed when $R^1$ and $R^2$ are taken together, the cycloalkyl and heterocycloalkyl formed when two $R^7$ are taken together, the cycloalkyl and heterocycloalkyl formed when two $R^8$ are taken together, the cycloalkyl and heterocycloalkyl formed when two $R^9$ are taken together, and the heterocycloalkyl formed when $R^c$ and $R^d$ are taken together, is independently substituted with one, two, or three substituents as defined herein. In some embodiments of a compound disclosed herein, each $R^a$, $R^b$, $R^c$, $R^d$, the cycloalkyl, heterocycloalkyl, aryl, or heteroaryl formed when $R^1$ and $R^2$ are taken together, the cycloalkyl and heterocycloalkyl formed when two $R^7$ are taken together, the cycloalkyl and heterocycloalkyl formed when two $R^8$ are taken together, the cycloalkyl and heterocycloalkyl formed when two $R^9$ are taken together, and the heterocycloalkyl formed when $R^c$ and $R^d$ are taken together, is independently substituted with one or two substituents as defined herein.

Any combination of the groups described above for the various variables is contemplated herein. Throughout the specification, groups and substituents thereof are chosen by one skilled in the field to provide stable moieties and compounds.

In some embodiments, the compound disclosed herein is a compound selected from Table 1, or a pharmaceutically acceptable salt, solvate, or stereoisomer thereof.

TABLE 1

| Example # | Structure |
|---|---|
| 1 | 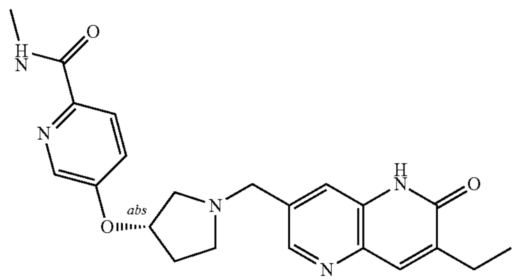 [SMILES: CCc1cc2ncc(CN3CC[C@H](Oc4ccc(C(=O)NC)nc4)C3)cc2[nH]c1=O] |
| 2 | 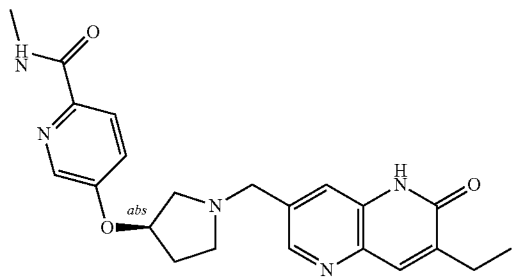 [SMILES: CCc1cc2ncc(CN3CC[C@@H](Oc4ccc(C(=O)NC)nc4)C3)cc2[nH]c1=O] |
| 3 | 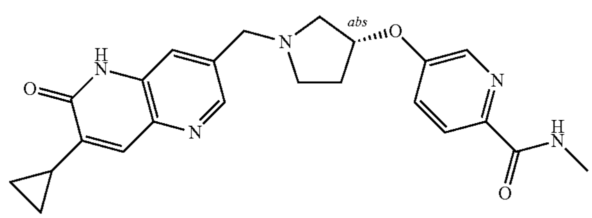 [SMILES: CNC(=O)c1ccc(O[C@@H]2CCN(Cc3cnc4cc(C5CC5)c(=O)[nH]c4c3)C2)cn1] |
| 4 | 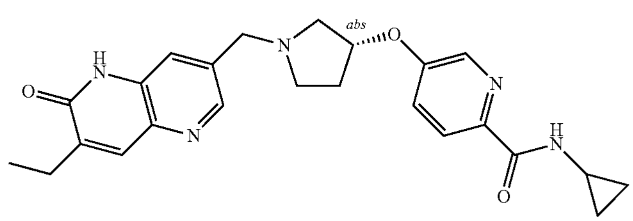 [SMILES: CCc1cc2ncc(CN3CC[C@@H](Oc4ccc(C(=O)NC5CC5)nc4)C3)cc2[nH]c1=O] |
| 5 | 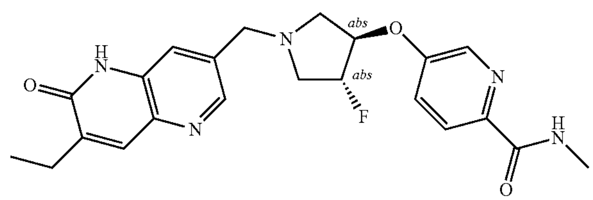 [SMILES: CCc1cc2ncc(CN3C[C@@H](F)[C@H](Oc4ccc(C(=O)NC)nc4)C3)cc2[nH]c1=O] |
| 6 | 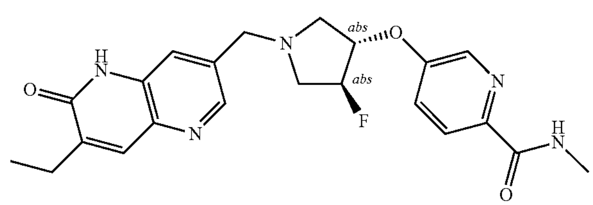 [SMILES: CCc1cc2ncc(CN3C[C@H](Oc4ccc(C(=O)NC)nc4)[C@@H](F)C3)cc2[nH]c1=O] |

TABLE 1-continued

| Example # | Structure |
|---|---|
| 7 | 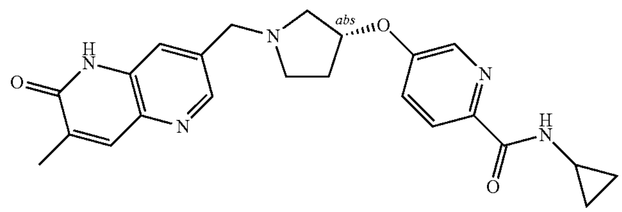 [SMILES: Cc1cc2ncc(CN3CC[C@@H](Oc4ccc(C(=O)NC5CC5)nc4)C3)cc2[nH]c1=O] |
| 8 | 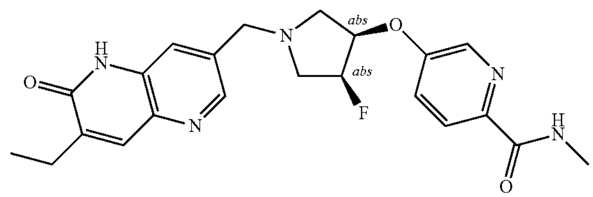 [SMILES: CCc1cc2ncc(CN3C[C@H](F)[C@H](Oc4ccc(C(=O)NC)nc4)C3)cc2[nH]c1=O] |
| 9 | 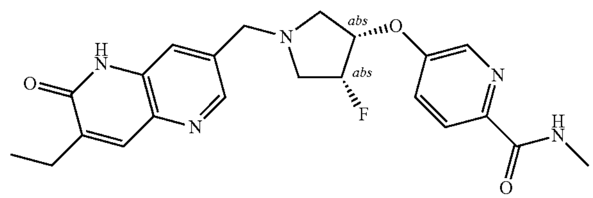 [SMILES: CCc1cc2ncc(CN3C[C@@H](F)[C@@H](Oc4ccc(C(=O)NC)nc4)C3)cc2[nH]c1=O] |
| 10 | 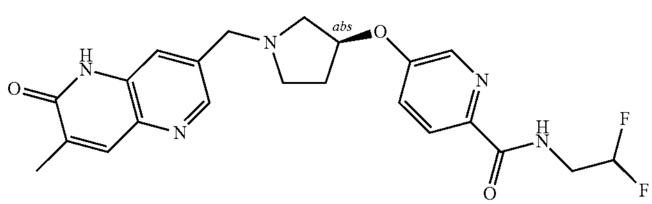 [SMILES: Cc1cc2ncc(CN3CC[C@H](Oc4ccc(C(=O)NCC(F)F)nc4)C3)cc2[nH]c1=O] |
| 11 | 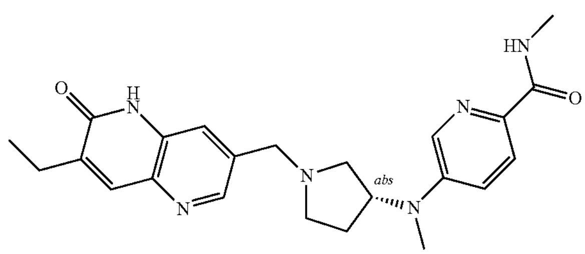 [SMILES: CCc1cc2ncc(CN3CC[C@@H](N(C)c4ccc(C(=O)NC)nc4)C3)cc2[nH]c1=O] |
| 12 | 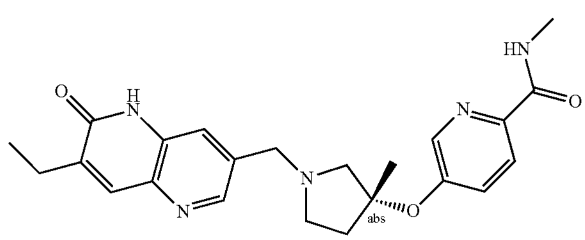 [SMILES: CCc1cc2ncc(CN3CC[C@@](C)(Oc4ccc(C(=O)NC)nc4)C3)cc2[nH]c1=O] |

TABLE 1-continued

| Example # | Structure |
|---|---|
| 13 | 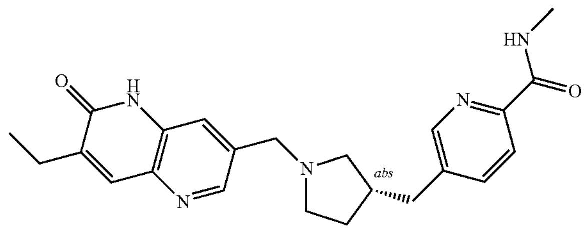 [SMILES: CCc1cc2ncc(CN3CC[C@@H](Cc4ccc(C(=O)NC)nc4)C3)cc2[nH]c1=O] |
| 14 | 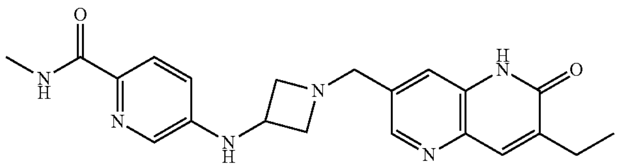 [SMILES: CCc1cc2ncc(CN3CC(Nc4ccc(C(=O)NC)nc4)C3)cc2[nH]c1=O] |
| 15 | 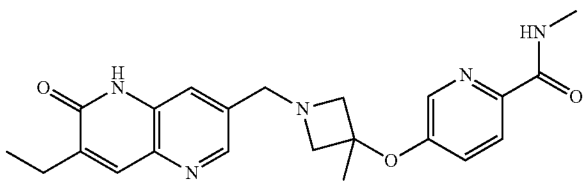 [SMILES: CCc1cc2ncc(CN3CC(C)(Oc4ccc(C(=O)NC)nc4)C3)cc2[nH]c1=O] |
| 16 | 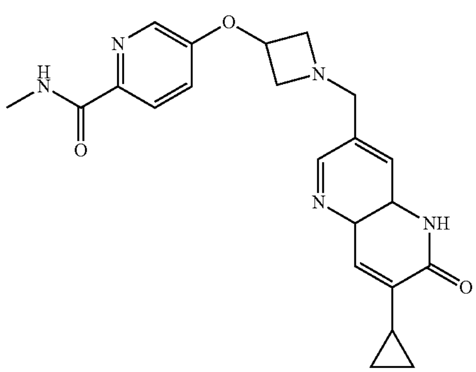 [SMILES: CNC(=O)c1ccc(OC2CN(CC3=CC4NC(=O)C(C5CC5)=CC4N=C3)C2)cn1] |
| 17 | 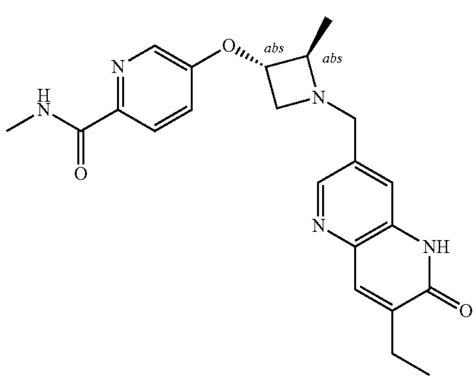 [SMILES: CCc1cc2ncc(CN3C[C@H](Oc4ccc(C(=O)NC)nc4)[C@H]3C)cc2[nH]c1=O] |

TABLE 1-continued

| Example # | Structure |
|---|---|
| 18 | 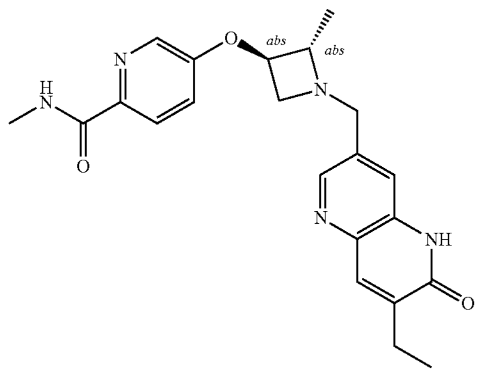 [SMILES: CCc1cc2ncc(CN3C[C@@H](Oc4ccc(C(=O)NC)nc4)[C@@H]3C)cc2[nH]c1=O] |
| 19 | 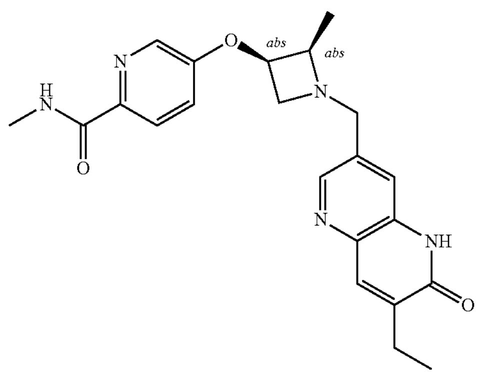 [SMILES: CCc1cc2ncc(CN3C[C@@H](Oc4ccc(C(=O)NC)nc4)[C@H]3C)cc2[nH]c1=O] |
| 20 | 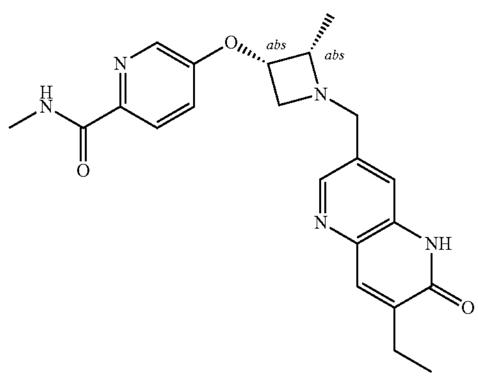 [SMILES: CCc1cc2ncc(CN3C[C@H](Oc4ccc(C(=O)NC)nc4)[C@@H]3C)cc2[nH]c1=O] |
| 21 | 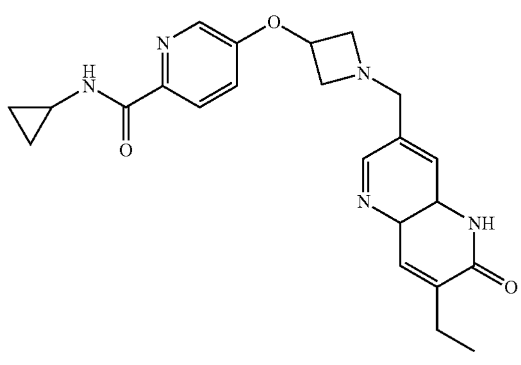 [SMILES: CCC1=CC2N=CC(CN3CC(Oc4ccc(C(=O)NC5CC5)nc4)C3)=CC2NC1=O] |

TABLE 1-continued
| Example # | Structure |
|---|---|
| 22 | 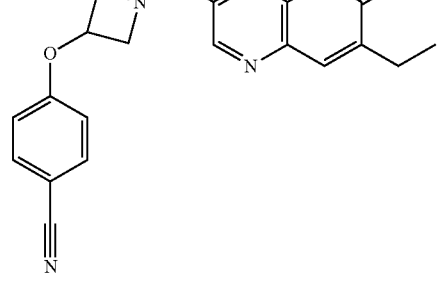 |
| 23 | 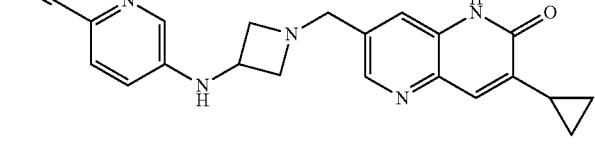 |
| 24 | 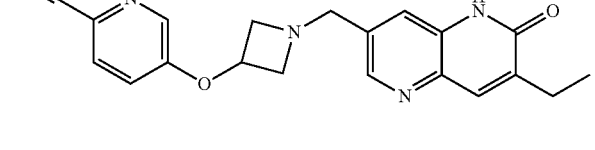 |
| 25 | 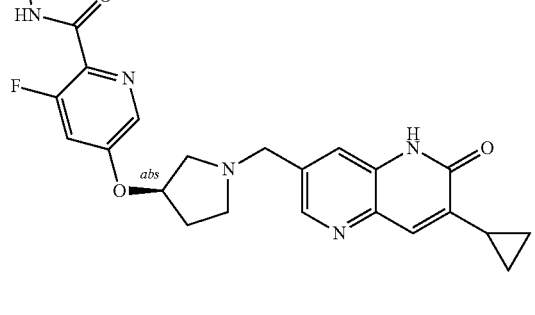 |
| 26 | 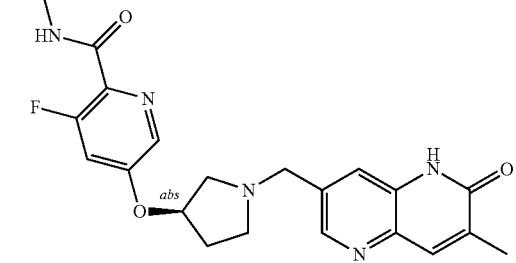 |

TABLE 1-continued
| Example # | Structure |
|---|---|
| 27 | 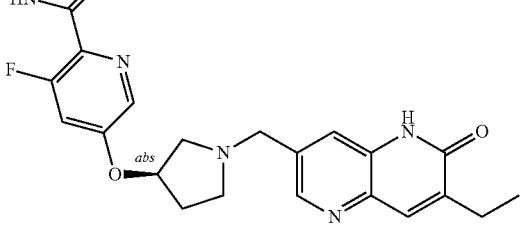 |
| 28 | 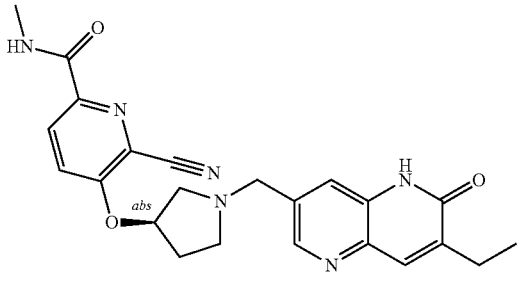 [SMILES: CCc1cc2ncc(CN3CC[C@@H](Oc4ccc(C(=O)NC)nc4C#N)C3)cc2[nH]c1=O] |
| 29 | 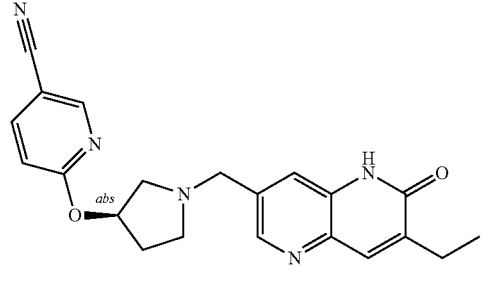 [SMILES: CCc1cc2ncc(CN3CC[C@@H](Oc4ccc(C#N)cn4)C3)cc2[nH]c1=O] |
| 30 | 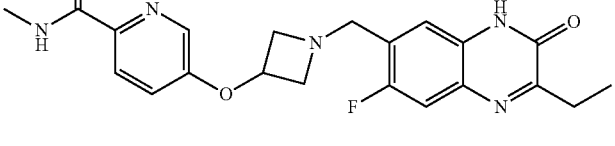 |
| 31 | 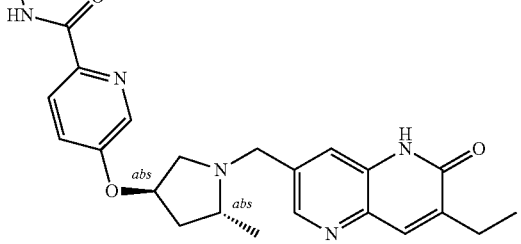 |

TABLE 1-continued

| Example # | Structure |
|---|---|
| 32 | 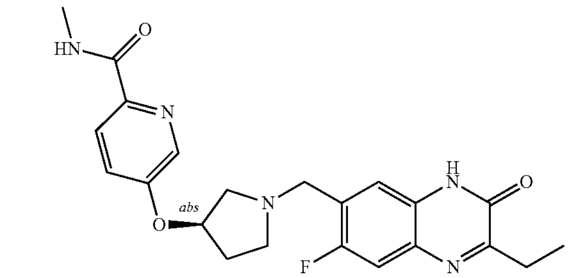 [SMILES: CCc1nc2cc(F)c(CN3CC[C@@H](Oc4ccc(C(=O)NC)nc4)C3)cc2[nH]c1=O] |
| 33 | 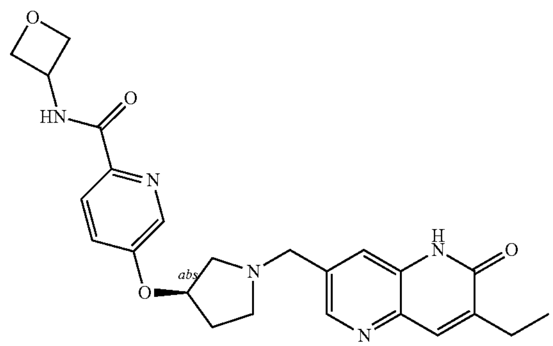 [SMILES: CCc1cc2ncc(CN3CC[C@@H](Oc4ccc(C(=O)NC5COC5)nc4)C3)cc2[nH]c1=O] |
| 34 | 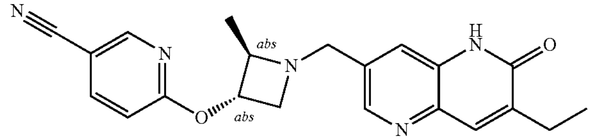 [SMILES: CCc1cc2ncc(CN3C[C@H](Oc4ccc(C#N)cn4)[C@H]3C)cc2[nH]c1=O] |
| 35 | 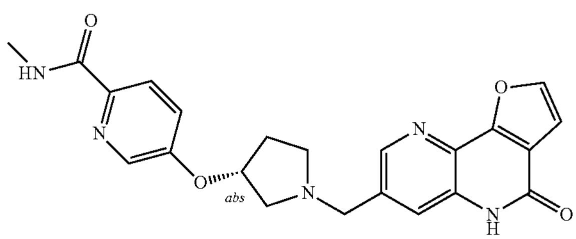 [SMILES: CNC(=O)c1ccc(O[C@@H]2CCN(Cc3cnc4c(c3)[nH]c(=O)c3ccoc34)C2)cn1] |
| 36 | 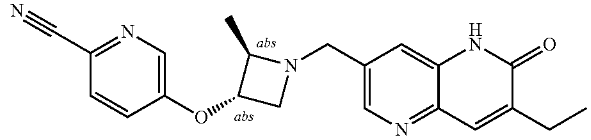 [SMILES: CCc1cc2ncc(CN3C[C@H](Oc4ccc(C#N)nc4)[C@H]3C)cc2[nH]c1=O] |
| 37 | 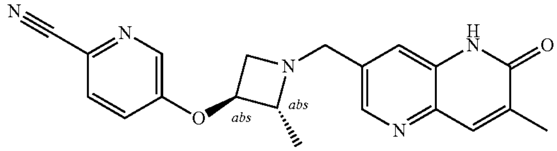 [SMILES: Cc1cc2ncc(CN3C[C@H](Oc4ccc(C#N)nc4)[C@H]3C)cc2[nH]c1=O] |
| 38 | 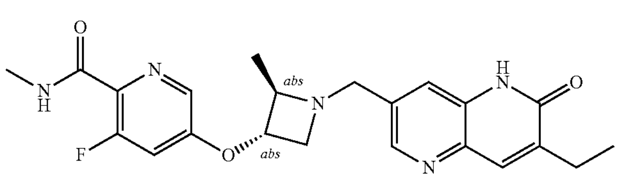 [SMILES: CCc1cc2ncc(CN3C[C@H](Oc4cnc(C(=O)NC)c(F)c4)[C@H]3C)cc2[nH]c1=O] |

TABLE 1-continued

| Example # | Structure |
|---|---|
| 39 | (chemical structure) |
| 40 | (chemical structure) |
| 41 | (chemical structure) |
| 42 | (chemical structure) |
| 43 | (chemical structure) |
| 44 | (chemical structure) |
| 45 | (chemical structure) |
| 46 | (chemical structure) |

TABLE 1-continued

| Example # | Structure |
|---|---|
| 47 | 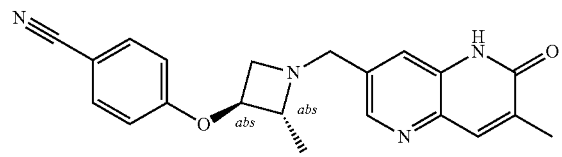 [SMILES: Cc1cc2ncc(CN3C[C@H](Oc4ccc(C#N)cc4)[C@H]3C)cc2[nH]c1=O] |
| 48 | 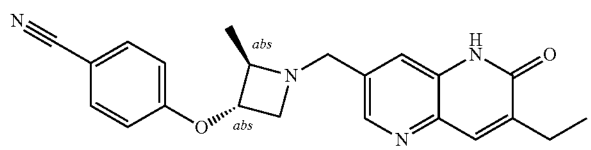 [SMILES: CCc1cc2ncc(CN3C[C@H](Oc4ccc(C#N)cc4)[C@H]3C)cc2[nH]c1=O] |
| 49 | 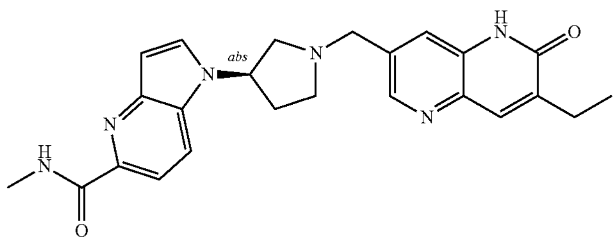 [SMILES: CCc1cc2ncc(CN3CC[C@@H](n4ccc5nc(C(=O)NC)ccc54)C3)cc2[nH]c1=O] |
| 50 | 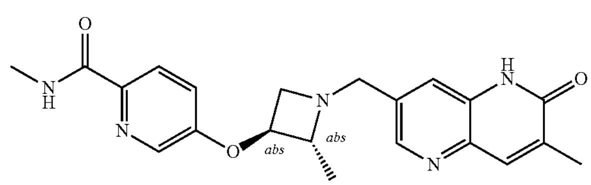 |
| 51 | 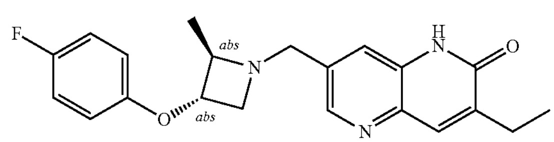 [SMILES: CCc1cc2ncc(CN3C[C@H](Oc4ccc(F)cc4)[C@H]3C)cc2[nH]c1=O] |
| 52 | 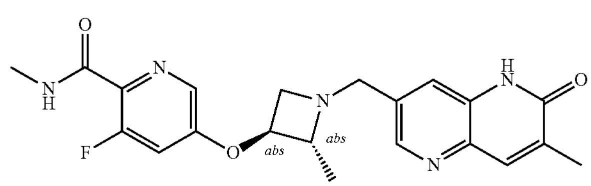 |
| 53 | 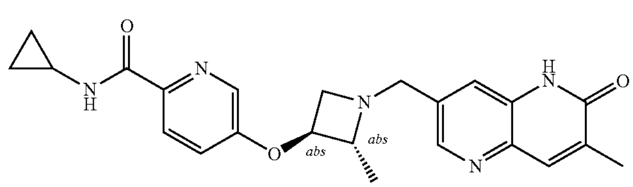 [SMILES: Cc1cc2ncc(CN3C[C@H](Oc4ccc(C(=O)NC5CC5)nc4)[C@H]3C)cc2[nH]c1=O] |
| 54 | 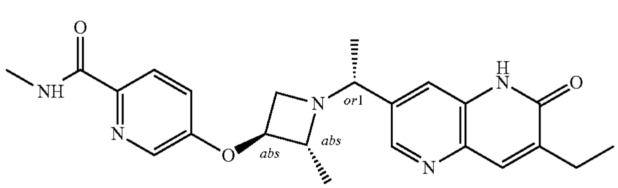 [SMILES: CCc1cc2ncc([C@@H](C)N3C[C@H](Oc4ccc(C(=O)NC)nc4)[C@H]3C)cc2[nH]c1=O] |

TABLE 1-continued

| Example # | Structure |
|---|---|
| 55 | 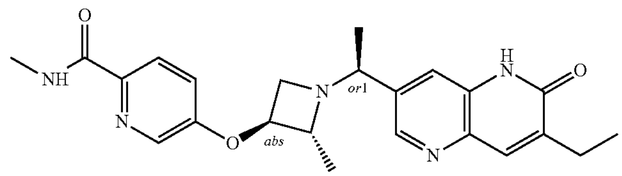 [SMILES: CCc1cc2ncc([C@H](C)N3C[C@H](Oc4ccc(C(=O)NC)nc4)[C@H]3C)cc2[nH]c1=O] |
| 56 | 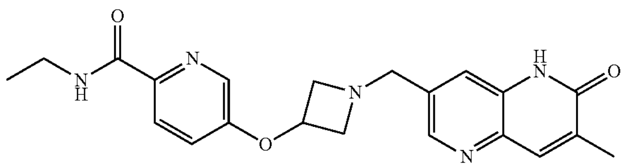 [SMILES: CCNC(=O)c1ccc(OC2CN(Cc3cnc4cc(C)c(=O)[nH]c4c3)C2)cn1] |
| 57 | 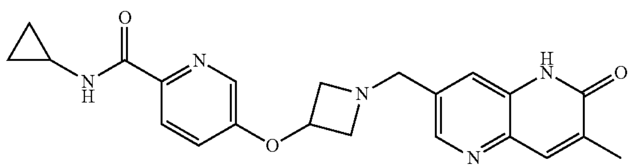 [SMILES: Cc1cc2ncc(CN3CC(Oc4ccc(C(=O)NC5CC5)nc4)C3)cc2[nH]c1=O] |
| 58 | 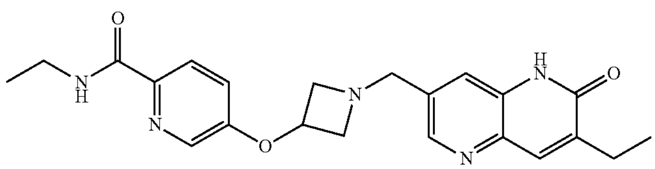 [SMILES: CCNC(=O)c1ccc(OC2CN(Cc3cnc4cc(CC)c(=O)[nH]c4c3)C2)cn1] |
| 59 | 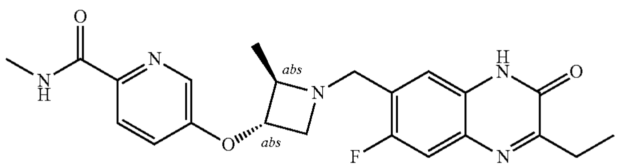 [SMILES: CCc1nc2cc(F)c(CN3C[C@H](Oc4ccc(C(=O)NC)nc4)[C@H]3C)cc2[nH]c1=O] |
| 60 | 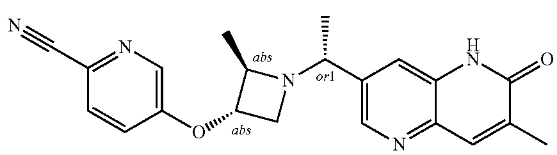 [SMILES: Cc1cc2ncc([C@@H](C)N3C[C@H](Oc4ccc(C#N)nc4)[C@H]3C)cc2[nH]c1=O] |
| 61 | 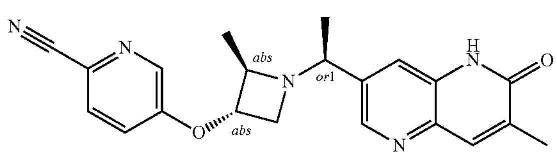 [SMILES: Cc1cc2ncc([C@H](C)N3C[C@H](Oc4ccc(C#N)nc4)[C@H]3C)cc2[nH]c1=O] |
| 62 | 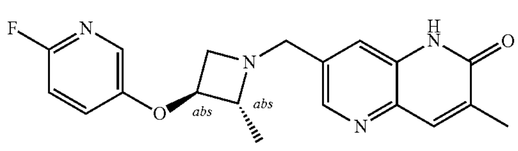 [SMILES: Cc1cc2ncc(CN3C[C@H](Oc4ccc(F)nc4)[C@H]3C)cc2[nH]c1=O] |

TABLE 1-continued

| Example # | Structure |
|---|---|
| 63 | 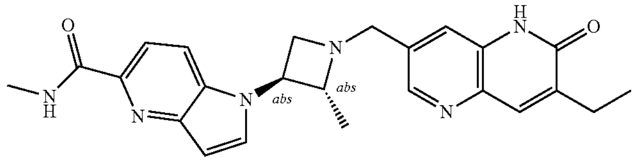 [SMILES: CCc1cc2ncc(CN3C[C@H](n4ccc5nc(C(=O)NC)ccc54)[C@H]3C)cc2[nH]c1=O] |
| 64 | 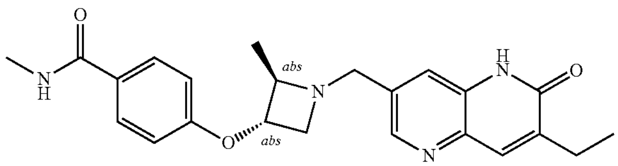 [SMILES: CCc1cc2ncc(CN3C[C@H](Oc4ccc(C(=O)NC)cc4)[C@H]3C)cc2[nH]c1=O] |
| 65 | 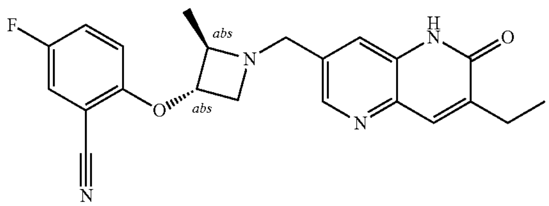 [SMILES: CCc1cc2ncc(CN3C[C@H](Oc4ccc(F)cc4C#N)[C@H]3C)cc2[nH]c1=O] |
| 66 | 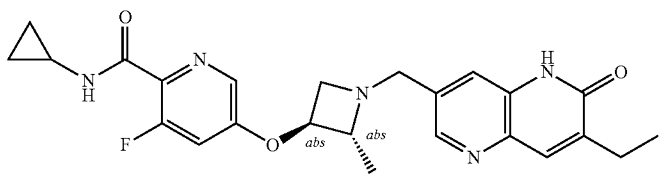 [SMILES: CCc1cc2ncc(CN3C[C@H](Oc4cnc(C(=O)NC5CC5)c(F)c4)[C@H]3C)cc2[nH]c1=O] |
| 67 | 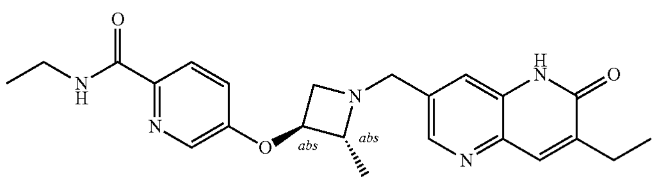 [SMILES: CCNC(=O)c1ccc(O[C@H]2CN(Cc3cnc4cc(CC)c(=O)[nH]c4c3)[C@@H]2C)cn1] |
| 68 | 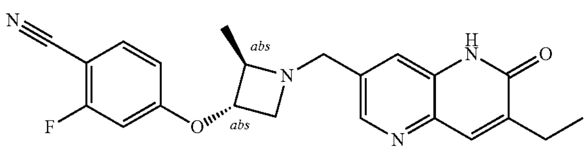 [SMILES: CCc1cc2ncc(CN3C[C@H](Oc4ccc(C#N)c(F)c4)[C@H]3C)cc2[nH]c1=O] |
| 69 | 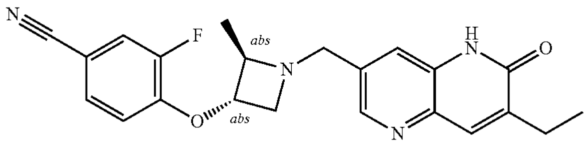 [SMILES: CCc1cc2ncc(CN3C[C@H](Oc4ccc(C#N)cc4F)[C@H]3C)cc2[nH]c1=O] |
| 70 | 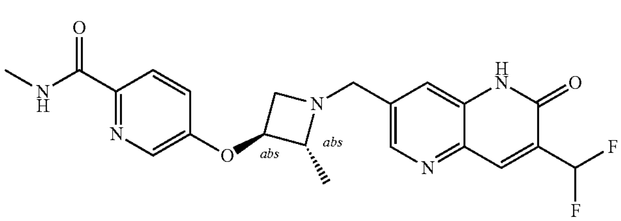 [SMILES: CNC(=O)c1ccc(O[C@H]2CN(Cc3cnc4cc(C(F)F)c(=O)[nH]c4c3)[C@@H]2C)cn1] |

TABLE 1-continued

| Example # | Structure |
|---|---|
| 71 | (structure) |
| 72 | (structure) |
| 73 | (structure) |
| 74 | (structure) |
| 75 | (structure) |
| 76 | (structure) |
| 77 | (structure) |

TABLE 1-continued

| Example # | Structure |
|---|---|
| 78 | 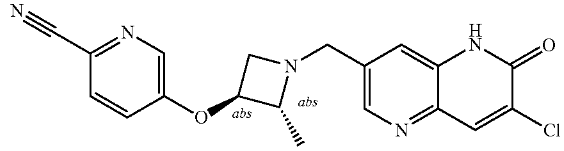 [SMILES: C[C@@H]1[C@@H](Oc2ccc(C#N)nc2)CN1Cc1cnc2cc(Cl)c(=O)[nH]c2c1] |
| 79 | 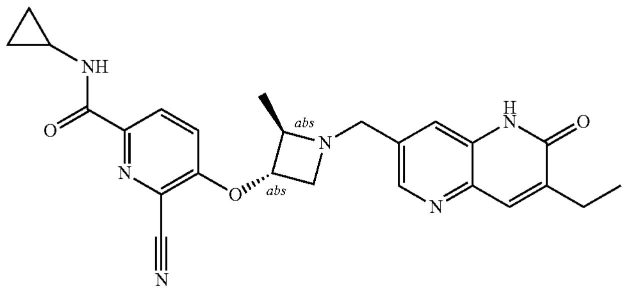 [SMILES: CCc1cc2ncc(CN3C[C@H](Oc4ccc(C(=O)NC5CC5)nc4C#N)[C@H]3C)cc2[nH]c1=O] |
| 80 | 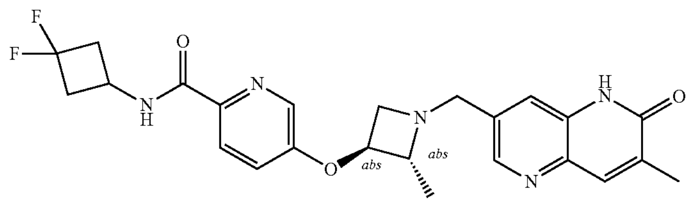 [SMILES: Cc1cc2ncc(CN3C[C@H](Oc4ccc(C(=O)NC5CC(F)(F)C5)nc4)[C@H]3C)cc2[nH]c1=O] |
| 81 | 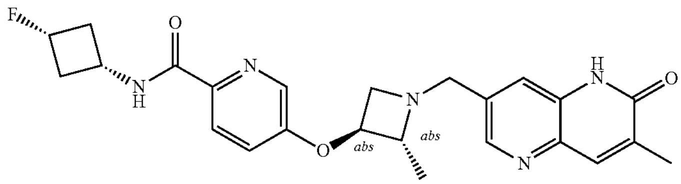 [SMILES: Cc1cc2ncc(CN3C[C@H](Oc4ccc(C(=O)N[C@H]5C[C@@H](F)C5)nc4)[C@H]3C)cc2[nH]c1=O] |
| 82 | 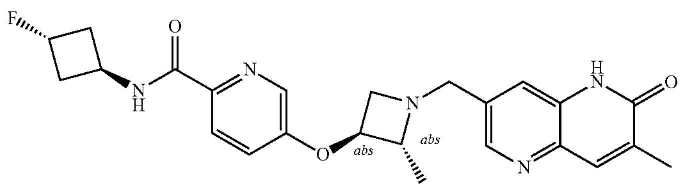 [SMILES: Cc1cc2ncc(CN3C[C@H](Oc4ccc(C(=O)N[C@H]5C[C@H](F)C5)nc4)[C@H]3C)cc2[nH]c1=O] |
| 83 | 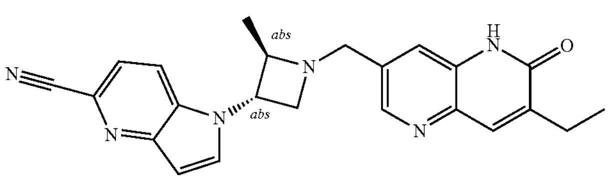 [SMILES: CCc1cc2ncc(CN3C[C@H](n4ccc5nc(C#N)ccc54)[C@H]3C)cc2[nH]c1=O] |
| 84 | 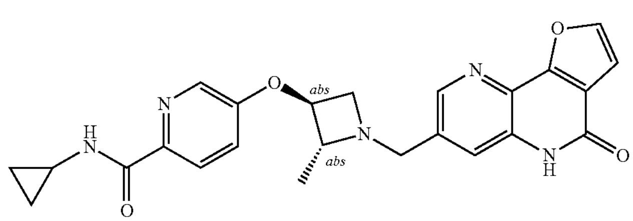 [SMILES: C[C@@H]1[C@@H](Oc2ccc(C(=O)NC3CC3)nc2)CN1Cc1cnc2c(c1)[nH]c(=O)c1ccoc12] |

TABLE 1-continued

| Example # | Structure |
|---|---|
| 85 | (structure) |
| 86 | (structure) |
| 87 | (structure) |
| 88 | (structure) |
| 89 | (structure) |
| 90 | (structure) |
| 91 | (structure) |
| 92 | (structure) |

TABLE 1-continued

| Example # | Structure |
|---|---|
| 93 | 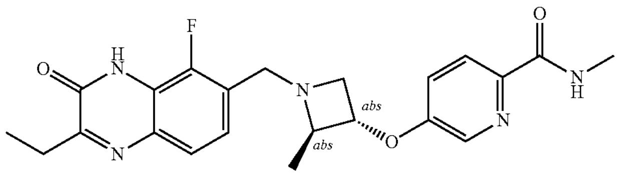 [SMILES: CCc1nc2ccc(CN3C[C@H](Oc4ccc(C(=O)NC)nc4)[C@H]3C)c(F)c2[nH]c1=O] |
| 94 | 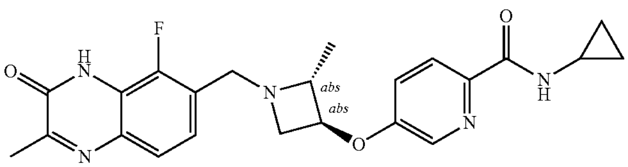 [SMILES: Cc1nc2ccc(CN3C[C@H](Oc4ccc(C(=O)NC5CC5)nc4)[C@H]3C)c(F)c2[nH]c1=O] |
| 95 | 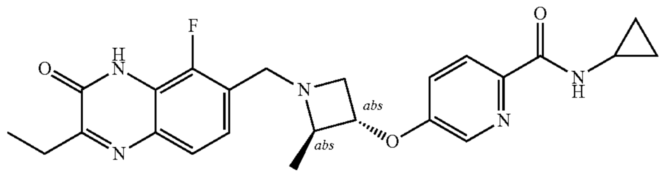 [SMILES: CCc1nc2ccc(CN3C[C@H](Oc4ccc(C(=O)NC5CC5)nc4)[C@H]3C)c(F)c2[nH]c1=O] |
| 96 | 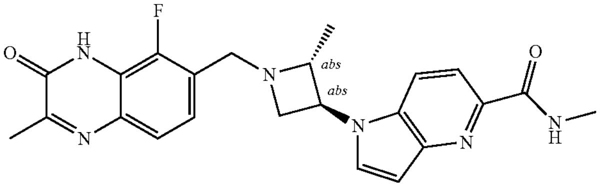 |
| 97 | 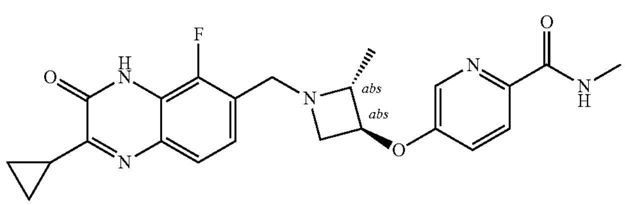 [SMILES: CNC(=O)c1ccc(O[C@H]2CN(Cc3ccc4nc(C5CC5)c(=O)[nH]c4c3F)[C@@H]2C)cn1] |
| 98 | 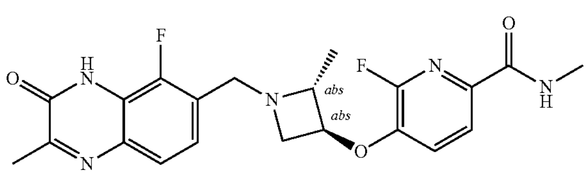 |
| 99 | 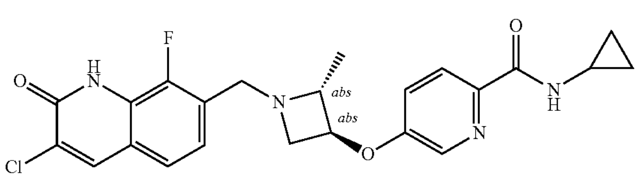 [SMILES: C[C@@H]1[C@@H](Oc2ccc(C(=O)NC3CC3)nc2)CN1Cc1ccc2cc(Cl)c(=O)[nH]c2c1F] |
| 100 | 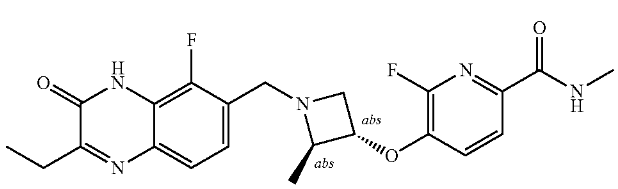 [SMILES: CCc1nc2ccc(CN3C[C@H](Oc4ccc(C(=O)NC)nc4F)[C@H]3C)c(F)c2[nH]c1=O] |

TABLE 1-continued
| Example # | Structure |
|---|---|
| 101 | 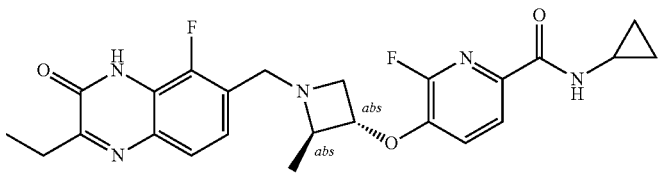 [SMILES: CCc1nc2ccc(CN3C[C@H](Oc4ccc(C(=O)NC5CC5)nc4F)[C@H]3C)c(F)c2[nH]c1=O] |
| 102 | 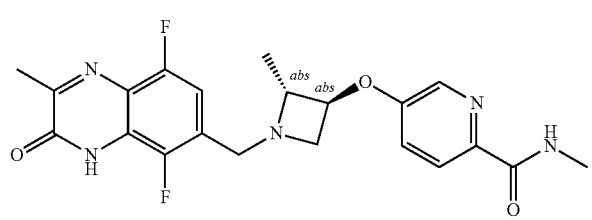 |
| 103 | 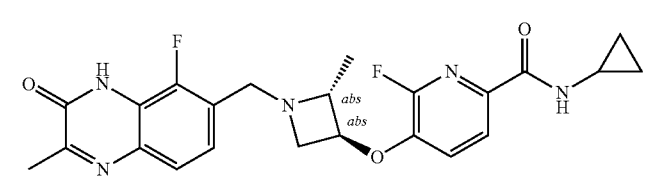 [SMILES: Cc1nc2ccc(CN3C[C@H](Oc4ccc(C(=O)NC5CC5)nc4F)[C@H]3C)c(F)c2[nH]c1=O] |
| 104 | 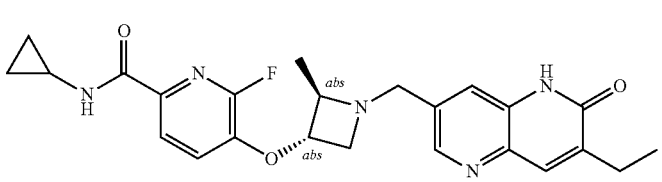 [SMILES: CCc1cc2ncc(CN3C[C@H](Oc4ccc(C(=O)NC5CC5)nc4F)[C@H]3C)cc2[nH]c1=O] |
| 105 | 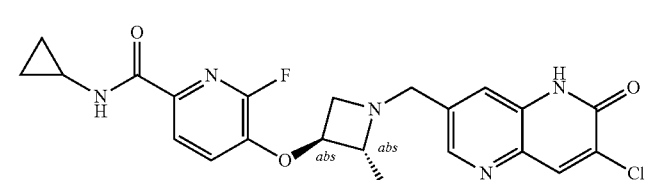 |
| 106 | 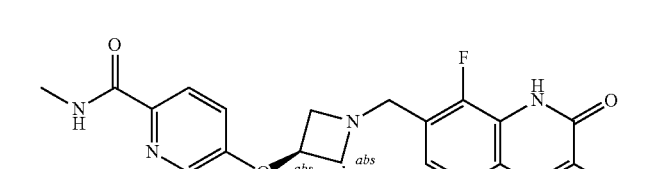 |
| 107 | 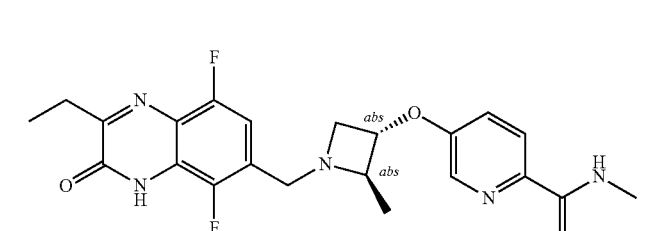 |

TABLE 1-continued

| Example # | Structure |
|---|---|
| 108 | 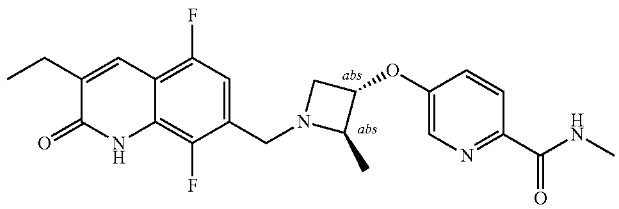 [SMILES: CCc1cc2c(F)cc(CN3C[C@H](Oc4ccc(C(=O)NC)nc4)[C@H]3C)c(F)c2[nH]c1=O] |
| 109 | 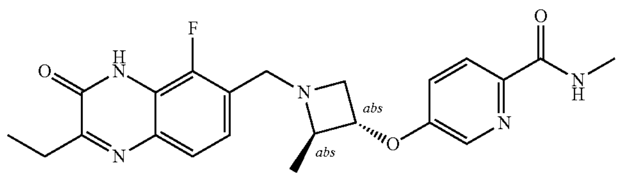 [SMILES: CCc1nc2ccc(CN3C[C@H](Oc4ccc(C(=O)NC)nc4)[C@H]3C)c(F)c2[nH]c1=O] |
| 110 | 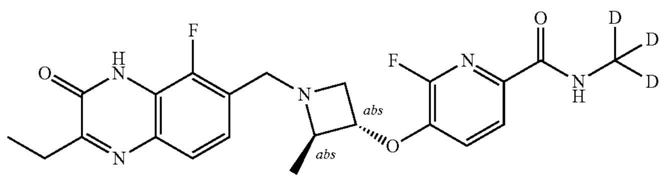 [SMILES: [2H]C([2H])([2H])NC(=O)c1ccc(O[C@H]2CN(Cc3ccc4nc(CC)c(=O)[nH]c4c3F)[C@@H]2C)c(F)n1] |
| 111 | 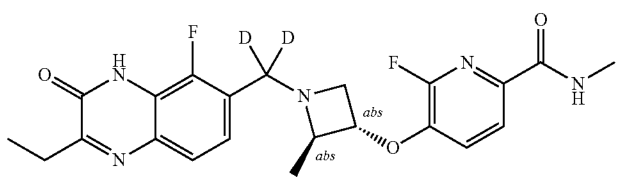 [SMILES: [2H]C([2H])(c1ccc2nc(CC)c(=O)[nH]c2c1F)N1C[C@H](Oc2ccc(C(=O)NC)nc2F)[C@H]1C] |
| 112 | 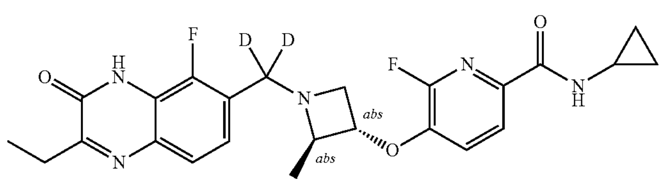 [SMILES: [2H]C([2H])(c1ccc2nc(CC)c(=O)[nH]c2c1F)N1C[C@H](Oc2ccc(C(=O)NC3CC3)nc2F)[C@H]1C] |
| 113 | 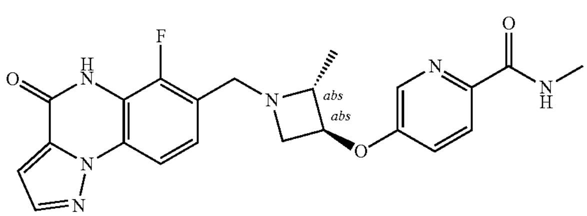 [SMILES: CNC(=O)c1ccc(O[C@H]2CN(Cc3ccc4c([nH]c(=O)c5ccnn54)c3F)[C@@H]2C)cn1] |
| 114 | 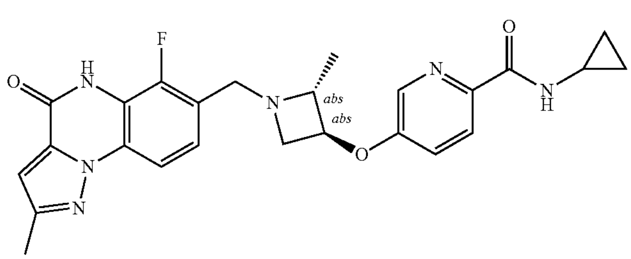 [SMILES: Cc1cc2c(=O)[nH]c3c(F)c(CN4C[C@H](Oc5ccc(C(=O)NC6CC6)nc5)[C@H]4C)ccc3n2n1] |

TABLE 1-continued
| Example # | Structure |
|---|---|
| 115 | 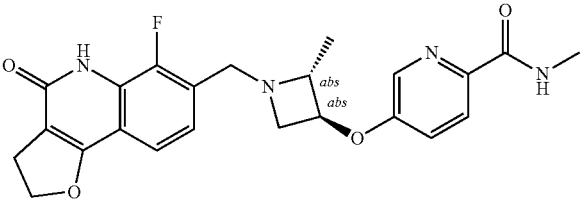 [SMILES: CNC(=O)c1ccc(O[C@H]2CN(Cc3ccc4c5c(c(=O)[nH]c4c3F)CCO5)[C@@H]2C)cn1] |
| 116 | 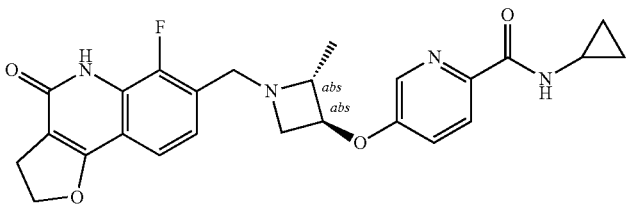 [SMILES: C[C@@H]1[C@@H](Oc2ccc(C(=O)NC3CC3)nc2)CN1Cc1ccc2c3c(c(=O)[nH]c2c1F)CCO3] |
| 117 | 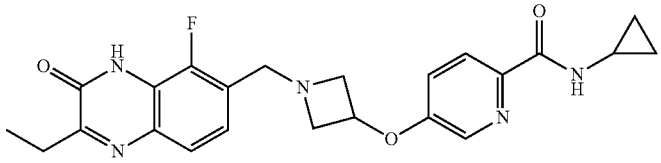 [SMILES: CCc1nc2ccc(CN3CC(Oc4ccc(C(=O)NC5CC5)nc4)C3)c(F)c2[nH]c1=O] |
| 118 | 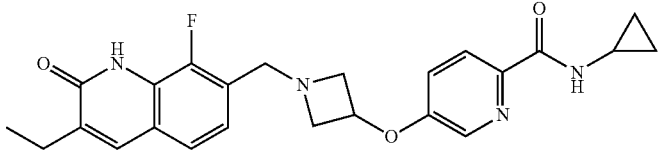 [SMILES: CCc1cc2ccc(CN3CC(Oc4ccc(C(=O)NC5CC5)nc4)C3)c(F)c2[nH]c1=O] |
| 119 | 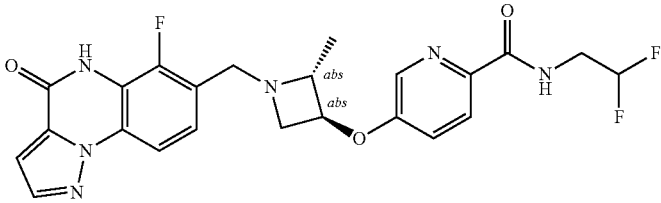 [SMILES: C[C@@H]1[C@@H](Oc2ccc(C(=O)NCC(F)F)nc2)CN1Cc1ccc2c([nH]c(=O)c3ccnn32)c1F] |
| 120 | 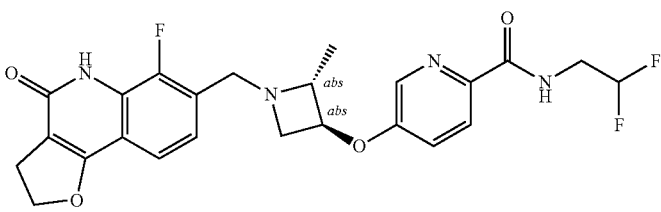 [SMILES: C[C@@H]1[C@@H](Oc2ccc(C(=O)NCC(F)F)nc2)CN1Cc1ccc2c3c(c(=O)[nH]c2c1F)CCO3] |
| 121 | 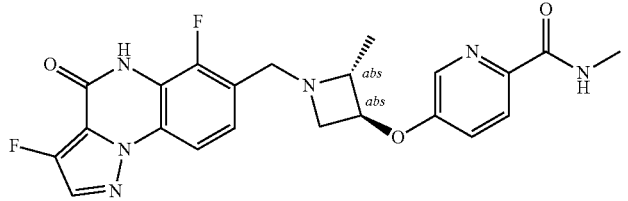 [SMILES: CNC(=O)c1ccc(O[C@H]2CN(Cc3ccc4c([nH]c(=O)c5c(F)cnn54)c3F)[C@@H]2C)cn1] |

The absolute label (abs) is added to a chiral center to denote that it is unambiguously a pure sample of the drawn stereoisomer.

The OR label (or) denotes a pure substance, but the absolute configuration of the stereochemical center is unknown. After chiral separation with pure structures isolated, multiple OR labels (OR indicates purity) with the same numerical value will indicates that a sample is one of a pair of pure enantiomers (but the absolute configuration of the stereochemical center is unknown).

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}$H and $^{14}$C are incorporated, are useful in drug and/or substrate tissue distribution assays. Tritiated, i.e., $^{3}$H and carbon-14, i.e., $^{14}$C, isotopes are particularly preferred for their ease of preparation and detectability. Further, substitution with heavy isotopes such as deuterium, i.e., $^{2}$H, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein are methods of treatment of a disease in which inhibition of PARP is beneficial, the method comprising administering a compound disclosed herein. Also disclosed herein are methods of treatment of a disease in which inhibition of PARP1 is beneficial, the method comprising administering a compound disclosed herein. In some embodiments, the disease is cancer. In some embodiments, the cancer is breast cancer, ovarian cancer, pancreatic cancer, prostate cancer, a hematological cancer, a gastrointestinal cancer such as gastric cancer and colorectal cancer, or lung cancer. In some embodiments, the cancer is breast cancer, ovarian cancer, pancreatic cancer, or prostate cancer. In some embodiment, the cancer is leukemia, colon cancer, glioblastoma, lymphoma, melanoma, or cervical cancer.

In some embodiments, the cancer comprises a BRCA1 and/or a BRCA2 mutation.

In some embodiments, the cancer comprising a BRCA1 and/or a BRCA2 mutation is bladder cancer, brain & CNS cancers, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

In some embodiments, the cancer is a cancer deficient in Flomologous Recombination (FIR) dependent DNA DSB repair activity. The FIR dependent DNA DSB repair pathway repairs double-strand breaks (DSBs) in DNA via homologous mechanisms to reform a continuous DNA helix. The components of the FIR dependent DNA DSB repair pathway include, but are not limited to, ATM (NM_000051), RAD51 (NM_002875), RAD51 L1 (NM_002877), RAD51 C (NM_002876), RAD51 L3 (NM_002878), DMC1 (NM_007068), XRCC$_2$ (NM_005431), XRCC$_3$ (NM_005432), RAD52 (NM_002879), RAD54L (NM_003579), RAD54B (NM_012415), BRCA1 (NM_007295), BRCA2 (NM_000059), RAD50 (NM_005732), MRE1 1 A (NM_005590) and NBS1 (NM_002485). Other proteins involved in the FIR dependent DNA DSB repair pathway include regulatory factors such as EMSY. In some embodiments, the cancer which is deficient in FIR dependent DNA DSB repair comprises one or more cancer cells which have a reduced or abrogated ability to repair DNA DSBs through that pathway, relative to normal cells i.e. the activity of the FIR dependent DNA DSB repair pathway may be reduced or abolished in the one or more cancer cells.

In some embodiments, the activity of one or more components of the FIR dependent DNA DSB repair pathway is abolished in the one or more cancer cells of an individual having a cancer which is deficient in FIR dependent DNA DSB repair.

In some embodiments, the cancer cells have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor. BRCA1 and BRCA2 are known tumor suppressors whose wild-type alleles are frequently lost in tumors of heterozygous carriers. Amplification of the EMSY gene, which encodes a BRCA2 binding factor, is also known to be associated with breast and ovarian cancer. Carriers of mutations in BRCA1 and/or BRCA2 are also at elevated risk of certain cancers, including breast cancer, ovarian cancer, pancreatic cancer, prostate cancer, a hematological cancer, gastrointestinal cancer, and lung cancer.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (0 administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating cancer using a compound disclosed herein, or a pharmaceutically acceptable salt, solvate, or stereoisomer thereof, in combination with an additional therapeutic agent.

In some embodiments, the additional therapeutic agent is an anticancer agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLES

Example 1

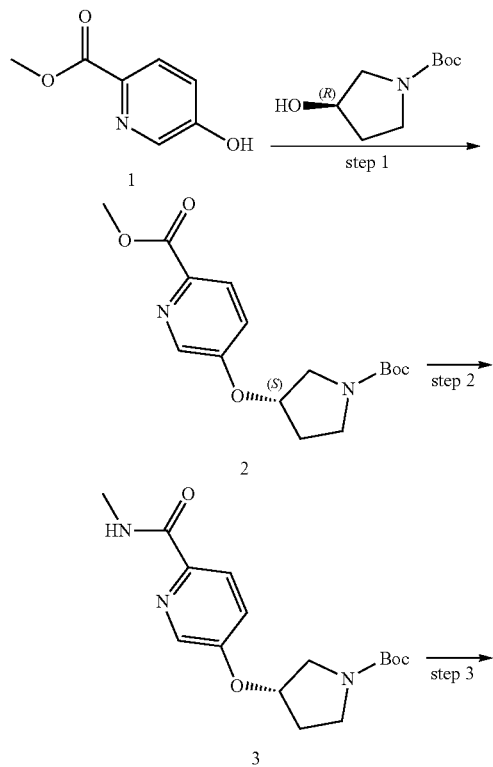

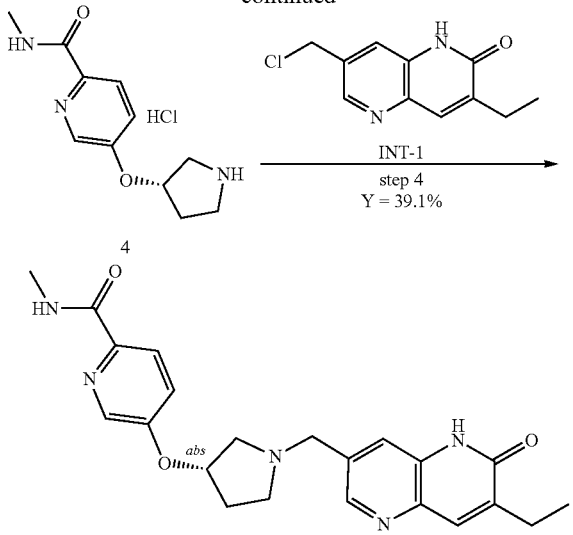

Example 1

Step 1: Preparation of methyl 5-{[(3S)-1-(tert-butoxycarbonyl)pyrrolidin-3-yl]oxy}pyridine carboxylate To a stirred solution of methyl 5-hydroxypyridine-2-carboxylate (1.00 g, 6.53 mmol, 1.00 equiv.), tert-butyl(3R)-3-hydroxypyrrolidine-1-carboxylate (1.83 g, 9.79 mmol, 1.50 equiv.) and PPh$_3$ (2.57 g, 9.79 mmol, 1.50 equiv.) in toluene (10 mL) was added DBAD (2.26 g, 9.79 mmol, 1.50 equiv.) in toluene (5 mL) dropwise at 0° C. under nitrogen atmosphere. The resulting mixture was stirred for 1 h at 0° C. The mixture was allowed to warm to room temperature and stirred for 1 h. The reaction was monitored by LCMS. The reaction mixture was poured into water (50 mL), extracted with EtOAc (50 mL×3). The combined organic layers were concentrated under reduced pressure. The residue was purified by silica gel column chromatography to afford methyl 5-{[(3S)-1-(tert-butoxycarbonyl)pyrrolidin-3-yl]oxy}pyridine-2-carboxylate (4.0 g, contain PPh$_3$ & Ph$_3$PO). The resulting mixture was used in the next step directly. LC-MS: (ES+H, m/z): [M+H]$^+$=323.1.

Step 2: Preparation of tert-butyl(3S)-3-{[6-(methylcarbamoyl)pyridin-3-yl]oxy}pyrrolidine-1-carboxylate A solution of methyl 5-{[(3S)-1-(tert-butoxycarbonyl)pyrrolidin-3-yl]oxy}pyridine-2-carboxylate (2.00 g, 6.20 mmol, 1.00 equiv.) and methylamine (8.6 mL, 25% in water) in MeOH (8.6 mL) was stirred for 2 h at room temperature under nitrogen atmosphere. The resulting mixture was concentrated under reduced pressure. The residue was purified by silica gel column chromatography to afford tert-butyl (3S)-3-{[6-(methylcarbamoyl)pyridin-3-yl]oxy}pyrrolidine-1-carboxylate (1.50 g, contain PPh$_3$&Ph$_3$PO). The crude product was used in the next step directly. LC-MS: (ES+H, m/z): [M+H]$^+$=322.1.

Step 3: Preparation of N-methyl-5-[(3S)-pyrrolidin-3-yloxy]pyridine-2-carboxamide, HCl Salt A solution of tert-butyl(3S)-3-{[6-(methyl carbamoyl)pyridin-3-yl]oxy}pyrrolidine-1-carboxylate (1.00 g, crude)

and HCl (gas) in 1,4-dioxane (8.0 mL 4M) was stirred for 2 h at room temperature under nitrogen atmosphere. The resulting mixture was concentrated under reduced pressure. The product was precipitated by the addition of EtOAc. The precipitated solids were collected by filtration and washed with PE (3×10 mL) to afford N-methyl-5-[(3S)-pyrrolidin-3-yloxy] pyridine-2-carboxamide, HCl salt (800 mg, crude). LC-MS: (ES+H, m/z): [M+H]⁺=222.2.

Step 4: Preparation of 5-{[(3S)-1-[(7-ethyl-6-oxo-5H-1,5-naphthyridin-3-yl) methyl]pyrrolidin-3-yl]oxy}-N-methylpyridine-2-carboxamide To a stirred solution of N-methyl-5-[(3S)-pyrrolidin-3-yloxy]pyridine-2-carboxamide (250 mg, crude) and DIEA (580 mg, 4.49 mmol, 5.00 equiv.) in MeCN (5 mL) ware added KI (30 mg, 0.18 mmol, 0.20 equiv.) and 7-(chloromethyl)-3-ethyl-1H-1,5-naphthyridin-2-one (200 mg, 0.90 mmol, 1.00 equiv.) at room temperature under nitrogen atmosphere. The resulting mixture was stirred for 2 h at 80° C. under nitrogen atmosphere. The mixture was allowed to cool down to room temperature. The resulting mixture was concentrated under reduced pressure. The residue was purified by silica gel column chromatography to afford 5-{[(3S)-1-[(7-ethyl-6-oxo-5H-1,5-naphthyridin-3-yl) methyl]pyrrolidin-3-yl]oxy}-N-methylpyridine-2-carboxamide (143.7 mg, 39.1%). LC-MS: (ES+H, m/z): [M+H]⁺=407.90. ¹H NMR (400 MHz, DMSO-d₆) δ 11.86 (s, 1H), 8.55 (d, 1H), 8.39 (s, 1H), 8.24 (d, 1H), 7.95 (d, 1H), 7.74 (s, 1H), 7.61 (s, 1H), 7.48 (dd, 1H), 5.10-5.04 (m, 1H), 3.73 (s, 2H), 2.91-2.64 (m, 6H), 2.55-2.52 (m, 2H), 2.49-2.30 (m, 2H), 1.89-1.77 (m, 1H), 1.18 (t, 3H).

Example 2

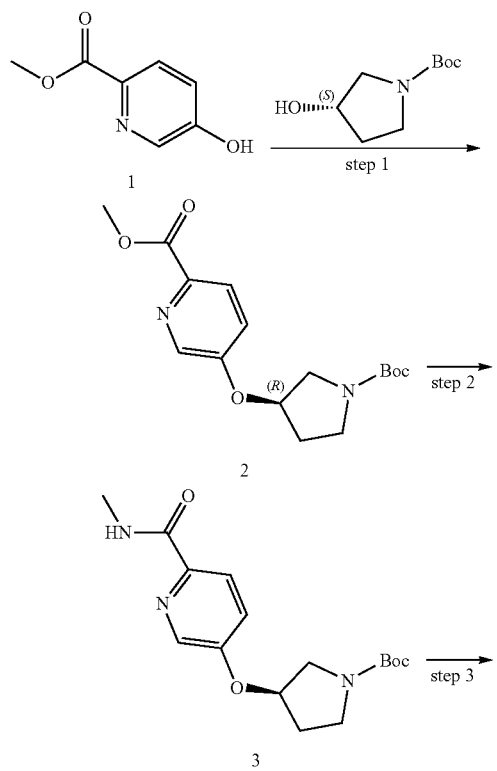

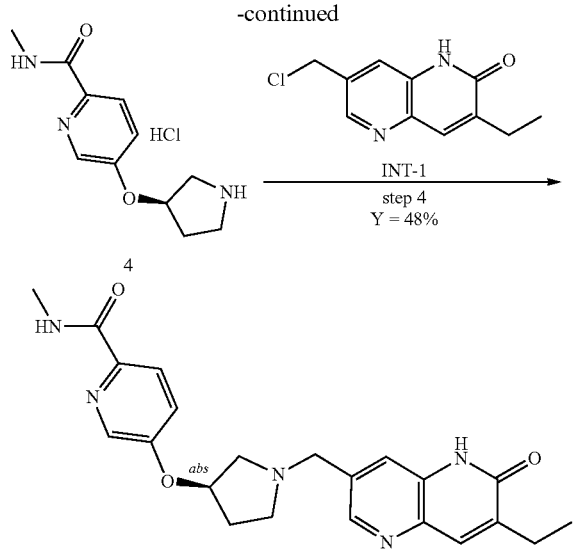

Example 2

Step 1: Preparation of methyl 5-{[(3R)-1-(tert-butoxycarbonyl)pyrrolidin-3-yl]oxy}pyridine-2-carboxylate To a stirred solution of methyl 5-hydroxypyridine-2-carboxylate (1.00 g, 6.53 mmol, 1.00 equiv.) and tert-butyl (3S)-3-hydroxypyrrolidine-1-carboxylate (1.83 g, 9.79 mmol, 1.50 equiv.) in THF (10 mL) was added PPh₃ (3.43 g, 13.06 mmol, 2.00 equiv.) at room temperature. The resulting mixture was stirred until 0° C. under nitrogen atmosphere. To the above mixture was added DEAD (2.27 g, 13.06 mmol, 2.00 equiv.) dropwise at 0° C. The resulting mixture was stirred for additional 1 h at room temperature. The reaction was quenched with Water (100 mL) at room temperature. The resulting mixture was extracted with EtOAc (3×100 mL). The combined organic layers were washed with brine (3×100 mL), dried over anhydrous Na₂SO₄. After filtration, the filtrate was concentrated under reduced pressure. The residue was purified by reversed combi-flash chromatography. This resulted in methyl 5-{[(3R)-1-(tert-butoxycarbonyl)pyrrolidin-3-yl]oxy}pyridine-2-carboxylate (4.00 g, contained TPPO). LC-MS: (ES+H, m/z): [M+H]⁺=323.2.

Step 2: Preparation of tert-butyl(3R)-3-{[6-(methylcarbamoyl)pyridin-3-yl]oxy}pyrrolidine-1-carboxylate To a stirred solution of methyl 5-{[(3R)-1-(tert-butoxycarbonyl)pyrrolidin-3-yl]oxy}pyridine-2-carboxylate (3.80 g crude contained TPPO) in MeOH (20 mL) was added Methylamine (20 mL, 25-30% wt in water) at room temperature. The resulting mixture was stirred for 2 h at room temperature under nitrogen atmosphere. Desired product could be detected by LCMS. The solvent was removed under reduced pressure. The residue was purified by reversed combi-flash chromatography. This resulted in tert-butyl(3R)-3-{[6-(methylcarbamoyl)pyridin-3-yl]oxy}pyrrolidine-1-carboxylate (3.80 g, contained TPPO). LC-MS: (ES+H, m/z): [M+H]⁺=322.1.

Step 3: Preparation of N-methyl-5-[(3R)-pyrrolidin-3-yloxy]pyridine-2-carboxamide, HCl Salt Into a 100 mL round-bottom flask were added tert-butyl (3R)-3-{[6-(methylcarbamoyl)pyridin-3-yl]oxy}pyrrolidine-1-carboxylate (3.80 g, crude contained TPPO) and HCl (gas) in 1,4-dioxane (40 mL) at room temperature. The resulting mixture was stirred for 1 h at room temperature under air atmosphere. The resulting mixture was concentrated under vacuum. The residue was purified by reversed combi-flash chromatography. This resulted in N-methyl-5-[(3R)-pyrrolidin-3-yloxy]pyridine-2-carboxamide, HCl salt (400 mg, crude). LC-MS: (ES+H, m/z): $[M+H]^+=222.0$.

Step 4: Preparation of 5-{[(3R)-1-[(7-ethyl-6-oxo-5H-1,5-naphthyridin-3-yl)methyl]pyrrolidin-3-yl]oxy}-N-methylpyridine-2-carboxamide To a stirred solution of N-methyl-5-[(3R)-pyrrolidin-3-yloxy]pyridine-2-carboxamide (200 mg, crude) and 7-(chloromethyl)-3-ethyl-1H-1,5-naphthyridin-2-one (120 mg, 0.53 mmol, 1.00 equiv.) in ACN (5 mL) was added DIEA (348 mg, 2.69 mmol, 5.00 equiv.) and KI (9 mg, 0.05 mmol, 0.10 equiv.). The resulting mixture was stirred for 2 h at 80° C. The resulting mixture was concentrated under vacuum. The crude product (700 mg) was purified by Prep-HPLC, the pure fraction was concentrated and lyophilized to afford 5-{[(3R)-1-[(7-ethyl-6-oxo-5H-1,5-naphthyridin-3-yl)methyl]pyrrolidin-3-yl]oxy}-N-methylpyridine-2-carboxamide (106.9 mg, 48.49%). LC-MS: (ES+H, m/z): $[M+H]^+$=407.85. $^1$H NMR (300 MHz, DMSO-$d_6$) δ 11.86 (s, 1H), 8.55 (d, 1H), 8.39 (d, 1H), 8.24 (d, 1H), 7.95 (d, 1H), 7.74 (s, 1H), 7.60 (d, 1H), 7.48 (dd, 1H), 5.10-5.04 (m, 1H), 3.74 (s, 2H), 2.96-2.86 (m, 1H), 2.77 (d, 3H), 2.76-2.70 (m, 2H), 2.61-2.52 (m, 1H), 2.49-2.31 (m, 3H), 1.88-1.77 (m, 1H), 1.18 (t, 3H).

The following examples were made using similar procedures as shown for example 2:

| Ex | NMR | LCMS (ESI) m/z |
|---|---|---|
| 27 | $^1$H NMR (300 MHz, DMSO-$d_6$) δ 11.86 (s, 1H), 8.50-8.33 (m, 2H), 8.14 (s, 1H), 7.74 (s, 1H), 7.60 (s, 1H), 7.46 (dd, 1H), 5.07 (s, 1H), 3.73 (s, 2H), 2.96-2.84 (m, 1H), 2.83-2.65 (m, 5H), 2.62-2.55 (m, 2H), 2.48-2.30 (m, 2H), 1.91-1.72 (m, 1H), 1.18 (t, 3H). $^{19}$F NMR (282 MHz, DMSO-$d_6$) δ-118.48. | $[M+H]^+$ = 426.2 |
| 31 | $^1$H NMR (400 MHz, DMSO-$d_6$) δ 11.80 (s, 1H), 8.53 (q, 1H), 8.38 (d, 1H), 8.20 (d, 1H), 7.92 (d, 1H), 7.74 (s, 1H), 7.58 (d, 1H), 7.44 (dd, 1H), 4.95 (q, 1H), 4.11 (d, 1H), 3.46-3.35 (m, 2H), 2.85-2.75 (m, 4H), 2.57-2.52 (m, 2H), 2.30 (dd, 1H), 2.10-2.00 (m, 1H), 1.94-1.84 (m, 1H), 1.22-1.13 (m, 6H). | $[M+H]^+$ = 422.3 |
| 32 | $^1$H NMR (300 MHz, DMSO-$d_6$) δ 12.31 (s, 1H), 8.55 (d, 1H), 8.24 (d, 1H), 7.95 (d, 1H), 7.61-7.47 (m, 2H), 7.35 (d, 1H), 5.06 (s, 1H), 3.76 (s, 2H), 2.94 (dd, 1H), 2.81-2.74 (m, 7H), 2.43-2.31 (m, 2H), 1.89-1.75 (m, 1H), 1.21 (t, 3H). $^{19}$F NMR (282 MHz, DMSO-$d_6$) δ-124.55. | $[M+H]^+$ = 426.1 |
| 33 | $^1$H NMR (300 MHz, DMSO-$d_6$) δ 11.89 (s, 1H), 9.26 (d, 1H), 8.39 (d, 1H), 8.28 (d, 1H), 7.94 (d, 1H), 7.74 (s, 1H), 7.60 (d, 1H), 7.49 (dd, 1H), 5.13-4.92 (m, 2H), 4.74-4.63 (m, 4H), 3.73 (s, 2H), 2.91 (dd, 1H), 2.81-2.70 (m, 2H), 2.60-2.54 (m, 2H), 2.49-2.30 (m, 2H), 1.90-1.75 (m, 1H), 1.18 (t, 3H). | $[M+H]^+$ = 450.3 |
| 35 | $^1$H NMR (400 MHz, DMSO-$d_6$) δ 11.85 (s, 1 H), 8.55-8.54 (m, 1 H), 8.47 (d, 1 H), 8.25 (d, 1H), 8.18 (d, 1 H), 7.95 (d, 1H), 7.77 (d, 1 H), 7.49 (dd, 1 H), 7.12 (d, 1 H), 5.07-4.90 (m, 1 H), 3.79 (s, 2H), 2.96-2.81 (m, 1 H), 2.80-2.74 (m, 6 H), 2.50-2.35 (m, 1 H), 1.86-1.81 (m, 1 H). | $[M+H]^+$ = 420.1 |

Example 3

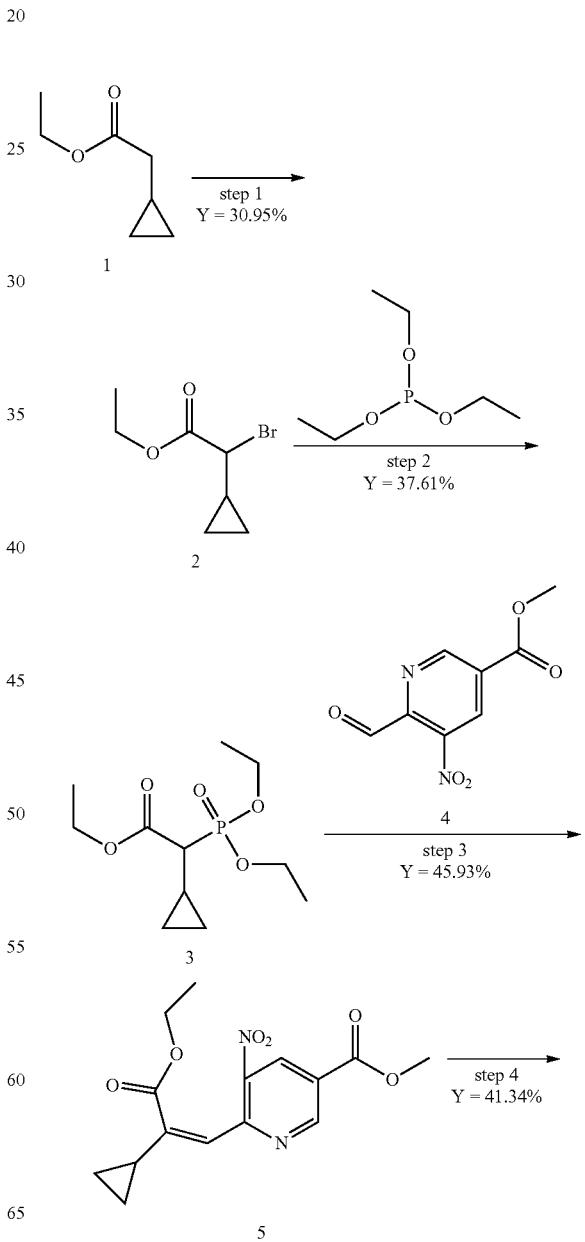

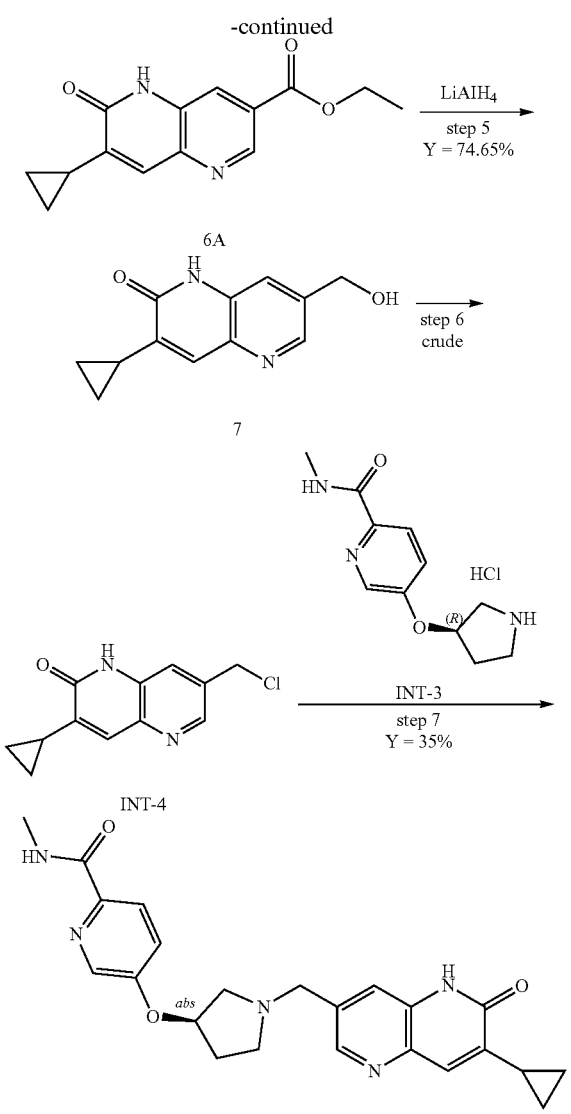

Example 3

Step 1: Preparation of ethyl 2-bromo-2-cyclopropylacetate

To a stirred solution of ethyl 2-cyclopropylacetate (10.00 g, 78.02 mmol, 1.00 equiv.) in THF (100 mL) was added LDA (42.9 mL, 85.82 mmol, 1.10 equiv., 2.0 M in THF) dropwise at −78° C. under nitrogen atmosphere. The reaction was stirred for 1 hour then TMSCl (8.48 g, 78.02 mmol, 1.00 equiv.) added dropwise and the reaction stirred for 3 hours as it warmed to room temperature. The reaction was cooled to −78° C. and NBS (15.28 g, 85.82 mmol, 1.10 equiv.) in 50 mL THF added dropwise. The reaction was then stirred for 2 hours and allowed to warm to room temperature. The reaction was monitored by LCMS. The reaction was quenched by the addition of sat. $NH_4Cl$ (aqueous.) (50 mL) at 0° C. The resulting mixture was extracted with $Et_2O$ (3×200 mL). The combined organic layers were washed with brine (3×200 mL), dried over anhydrous $Na_2SO_4$. After filtration, the filtrate was concentrated under reduced pressure. The residue was purified by reversed combi-flash chromatography to afford ethyl 2-bromo-2-cyclopropylacetate (5.00 g, 30.95%) as a yellow liquid. $^1$H NMR (300 MHz, Chloroform-d) δ 4.25 (q, 2H), 3.58 (d, 1H), 1.65-1.55 (m, 1H), 1.31 (t, 3H), 0.92-0.76 (m, 2H), 0.61-0.53 (m, 1H), 0.48-0.40 (m, 1H).

Step 2: Preparation of ethyl 2-cyclopropyl-2-(diethoxyphosphoryl)acetate

A solution of ethyl 2-bromo-2-cyclopropylacetate (5.00 g, 24.14 mmol, 1.00 equiv.) and triethyl phosphite (5.22 g, 31.39 mmol, 1.30 equiv.) was stirred for 24 hours at 130° C. under nitrogen atmosphere. The residue was purified by reversed combi-flash chromatography to afford ethyl 2-cyclopropyl-2-(diethoxyphosphoryl)acetate (2.40 g, 37.61%) as a yellow liquid. $^1$H NMR (300 MHz, Chloroform-d) δ 4.26-4.07 (m, 6H), 2.19 (dd, 1H), 1.30 (dt, 10H), 0.71 (dddd, 1H), 0.60 (ddddd, 1H), 0.47-0.37 (m, 1H), 0.24 (ddtd, 1H).

Step 3: Preparation of methyl 6-[(1Z)-2-cyclopropyl-3-ethoxy-3-oxoprop-1-en-1-yl]-5-nitropyridine-3-carboxylate To a stirred mixture of NaH (0.29 g, 7.14 mmol, 1.50 equiv., 60% wt) in THF (20 mL) was added ethyl 2-cyclopropyl-2-(diethoxyphosphoryl)acetate (1.89 g, 7.14 mmol, 1.50 equiv.) dropwise at 0° C. under nitrogen atmosphere. The resulting mixture was stirred for 10 min at 0° C. and then warmed to 40° C. stirred for 10 min under nitrogen atmosphere. The resulting mixture was cooled to −78° C. followed by the addition of methyl 6-formyl-5-nitropyridine-3-carboxylate (1.00 g, 4.76 mmol, 1.00 equiv.) in THF (20 mL) dropwise. The resulting mixture was stirred for 30 min at −78° C. under nitrogen atmosphere. The reaction was monitored by LCMS. The reaction was quenched by the addition of sat. $NH_4Cl$ (aqueous.) (5 mL) at 0° C. The resulting mixture was added 20 mL water and extracted with EtOAc (3×20 mL). The combined organic layers were washed with brine (1×50 mL), dried over anhydrous $Na_2SO_4$. After filtration, the filtrate was concentrated under reduced pressure. The residue was purified by silica gel column chromatography to afford methyl 6-[(1Z)-2-cyclopropyl-3-ethoxy-3-oxoprop-1-en-1-yl]-5-nitropyridine-3-carboxylate (700 mg, 45.93%) as a brown oil. LC-MS: (ES+H, m/z): [M+H]$^+$=320.8.

Step 4: Preparation of ethyl 7-cyclopropyl-6-oxo-5H-1,5-naphthyridine-3-carboxylate To a stirred mixture of methyl 6-[(1Z)-2-cyclopropyl-3-ethoxy-3-oxoprop-1-en-1-yl]-5-nitropyridine-3-carboxylate (600 mg, 1.87 mmol, 1.00 equiv.) and Fe (1.04 g, 18.73 mmol, 10.00 equiv.) in EtOH (10 mL) was added $CaCl_2$ (1.24 g, 11.24 mmol, 6.00 equiv.) at room temperature under nitrogen atmosphere. The resulting mixture was stirred overnight at 90° C. under nitrogen atmosphere. The reaction was monitored by LCMS. The mixture was allowed to cool down to room temperature. The resulting mixture was filtered, the filter cake was washed with EtOAc (2×50 mL). The filtrate was concentrated under reduced pressure. The resulting mixture was added 50 mL water and extracted with EtOAc (2×50 mL). The combined organic layers were washed with brine (2×50 mL), dried over anhydrous $Na_2SO_4$. After filtration, the filtrate was concentrated under reduced pressure. The residue was purified by silica gel column chromatography to afford ethyl 7-cyclopropyl-6- oxo-5H-1,5-naphthyridine-3-carboxylate (200 mg, 41.34%). LC-MS: (ES+H, m/z): [M+H]⁺=259.0.

Step 5: Preparation of 3-cyclopropyl-7-(hydroxymethyl)-1H-1,5-naphthyridin-2-one To a stirred solution of ethyl 7-cyclopropyl-6-oxo-5H-1,5-naphthyridine-3-carboxylate (160 mg, 0.62 mmol, 1.00 equiv.) was added LiAlH₄ (0.50 mL, 1.23 mmol, 2.00 equiv., 2.5M in THF) dropwise at 0° C. under nitrogen atmosphere. The resulting mixture was stirred for 1 h at 0° C. under nitrogen atmosphere. The reaction was monitored by LCMS. The reaction was quenched by the addition of 1M aqueous HCl (1 mL) at 0° C. The resulting mixture was concentrated under reduced pressure. The residue was purified by silica gel column chromatography to afford 3-cyclopropyl-7-(hydroxymethyl)-1H-1,5-naphthyridin-2-one (100 mg, 74.65%). LC-MS: (ES+H, m/z): [M+H]⁺=217.2.

Step 6: Preparation of 7-(chloromethyl)-3-cyclopropyl-1H-1,5-naphthyridin-2-one To a stirred mixture of 3-cyclopropyl-7-(hydroxymethyl)-1H-1,5-naphthyridin-2-one (80 mg, 0.37 mmol, 1.00 equiv.) and DMF (3 mg, 0.04 mmol, 0.10 equiv.) in DCM (10 mL) was added SOCl₂ (264 mg, 2.22 mmol, 6.00 equiv.) dropwise at 0° C. under nitrogen atmosphere. The resulting mixture was stirred overnight at room temperature under nitrogen atmosphere. The reaction was monitored by LCMS. The resulting mixture was concentrated under reduced pressure to afford 7-(chloromethyl)-3-cyclopropyl-1H-1,5-naphthyridin-2-one. The crude product was used in the next step directly without further purification. LC-MS: (ES+H, m/z): [M+H]⁺=235.0.

Step 7: Preparation of 5-{[(3R)-1-[(7-ethyl-6-oxo-5H-1,5-naphthyridin-3-yl)methyl]pyrrolidin-3-yl]oxy}-N-methylpyridine-2-carboxamide To a stirred solution of (R)—N-methyl-5-(pyrrolidin-3-yloxy)picolinamide. HCl salt (170 mg, crude) and 7-(chloromethyl)-3-cyclopropyl-1H-1,5-naphthyridin-2-one (120 mg, 0.51 mmol, 1.00 equiv.) in ACN (10 mL) were added KI (8 mg, 0.05 mmol, 0.10 equiv.) and DIEA (330 mg, 2.55 mmol, 5.00 equiv.) at room temperature. The resulting mixture was stirred for 2 h at 80° C. under nitrogen atmosphere. The reaction was monitored by LCMS. The mixture was allowed to cool down to room temperature. The resulting mixture was concentrated under vacuum. The crude product (900 mg) was purified by Prep-HPLC, the pure fraction was concentrated under reduced pressure then lyophilized to afford 5-{[(3R)-1-[(7-cyclopropyl-6-oxo-5H-1,5-naphthyridin-3-yl)methyl]pyrrolidin-3-yl]oxy}-N-methylpyridine-2-carboxamide (75.6 mg, 35.14%). LC-MS: (ES+H, m/z): [M+H]⁺=420.2. ¹H NMR (400 MHz, DMSO-d₆) δ 11.89 (s, 1H), 8.55 (d, 1H), 8.36 (d, 1H), 8.24 (d, 1H), 7.94 (d, 1H), 7.60-7.55 (m, 1H), 7.47 (dd, 1H), 7.41 (s, 1H), 5.05 (m, 1H), 3.78-3.66 (m, 2H), 2.90 (dd, 1H), 2.78 (d, 3H), 2.76-2.67 (m, 2H), 2.49-2.42 (m, 1H), 2.41-2.30 (m, 1H), 2.18-2.12 (m, 1H), 1.86-1.78 (m, 1H), 0.99-0.94 (m, 2H), 0.86-0.77 (m, 2H).

The following examples were made using similar procedures as shown for example 3:

| Ex | NMR | LCMS (ESI) m/z |
|---|---|---|
| 25 | ¹H NMR (300 MHz, DMSO-d₆) δ 11.89 (s, 1H), 8.52-8.30 (m, 2H), 8.14 (s, 1H), 7.58 (s, 1H), 7.52-7.37 (m, 2H), 5.17-4.93 (m, 1H), 3.72 (s, 2H), 2.95-2.84 (m, 1H), 2.83-2.67 (m, 5H), 2.47-2.35 (m, 2H), 2.14-2.12 (m, 1H), 1.90-1.71 (m, 1H), 0.99-0.94 (m, 2H), 0.79-0.84 (m, 2H). ¹⁹F NMR (282 MHz, DMSO-d₆) δ-118.485. | [M + H]⁺ = 438.05 |

Example 4

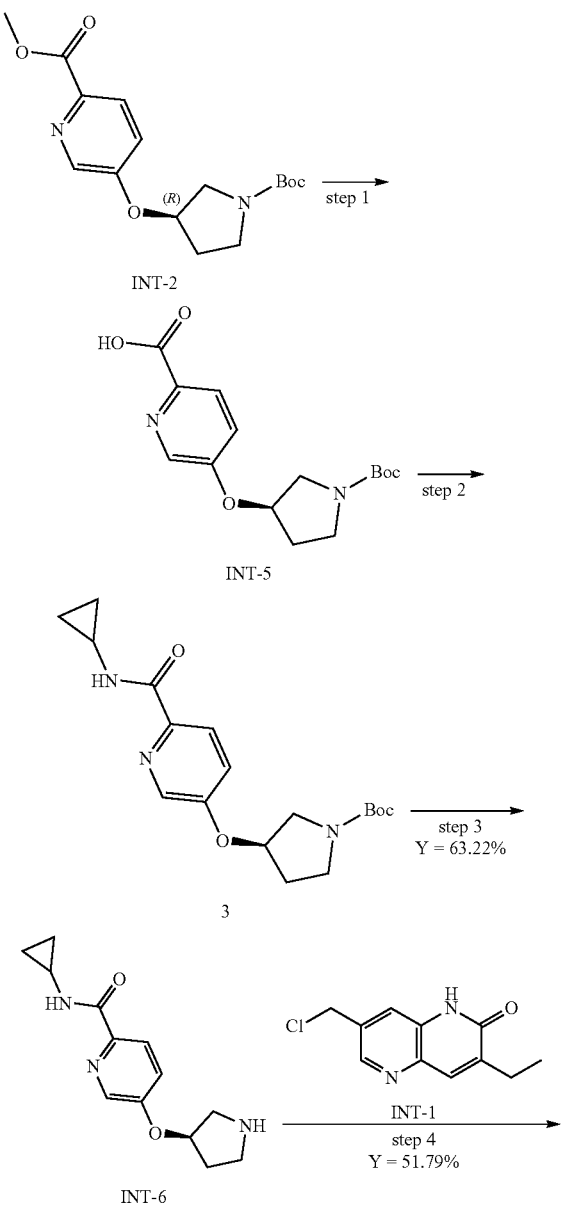

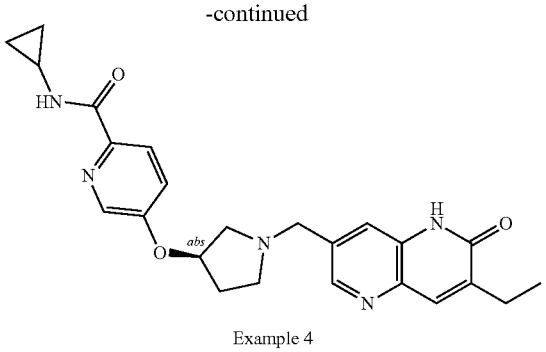

Example 4

Step 1: Preparation of 5-{[(3R)-1-(tert-butoxycarbonyl)pyrrolidin-3-yl]oxy}pyridine-2-carboxylic acid To a stirred mixture of methyl 5-{[(3R)-1-(tert-butoxycarbonyl)pyrrolidin-3-yl]oxy}pyridine carboxylate (16.00 g, 1.00 equiv., crude) in MeOH (160 mL) was added LiOH in H$_2$O (50 mL, 2 M) dropwise at 0° C. The mixture was stirred for 1 h at 25° C. under nitrogen atmosphere. The reaction was monitored by LCMS. The reaction mixture was diluted with H$_2$O (50 mL), and the aqueous phase was extracted with EA (100 mL*3). then the aqueous phase was adjusted to pH 5~6 with H$_3$PO$_4$, and extracted with EA (100 mL*3). The combined organic layers were washed with brine (100 mL), dried over sodium sulfate, filtered, and concentrated in vacuo. Concentration in vacuo resulted in 5-{[(3R)-1-(tert-butoxycarbonyl)pyrrolidin-3-yl]oxy}pyridine-2-carboxylic acid (6 g, crude) as a white oil. LC-MS: (ES+H, m/z): [M+H]$^+$=309.2.

Step 2: Preparation of tert-butyl(3R)-3-{[6-(cyclopropylcarbamoyl)pyridin-3-yl]oxy}pyrrolidine-1-carboxylate To a mixture of 5-{[(3R)-1-(tert-butoxycarbonyl)pyrrolidin-3-yl]oxy}pyridine-2-carboxylic acid (2.00 g, 6.49 mmol, 1.00 equiv.), aminocyclopropane (444 mg, 7.78 mmol, 1.20 equiv.) and DIEA (3.35 g, 25.94 mmol, 4.00 equiv.) in DCM (20 mL) was added T3P (16.52 g, 25.94 mmol, 4.00 equiv., 50% wt in EA) dropwise at 0° C. under nitrogen atmosphere. The mixture was stirred for 1 h at 25° C. The reaction was monitored by LCMS. The reaction mixture was diluted with H$_2$O (50 mL), and extracted with EA (100 mL*3). The combined organic layers were washed with brine (100 mL), dried over sodium sulfate, filtered, and concentrated in vacuo. Concentration in vacuo resulted in tert-butyl(3R)-3-{[6-(cyclopropylcarbamoyl)pyridin-3-yl]oxy}pyrrolidine-1-carboxylate (1.5 g, crude) as an orange oil. LC-MS: (ES+H, m/z): [M+H]$^+$=348.2

Step 3: Preparation of N-cyclopropyl-5-[(3R)-pyrrolidin-3-yloxy]pyridine-2-carboxamide A mixture of tert-butyl(3R)-3-{[6-(cyclopropylcarbamoyl)pyridin-3-yl]oxy}pyrrolidine-1-carboxylate (2.00 g, 5.76 mmol, 1.00 equiv.) and HCl (gas) in 1,4-dioxane (10 mL, 4M) in MeOH (10 mL) was stirred for 30 min at 25° C. under nitrogen atmosphere. The reaction was monitored by LCMS. The solvent was removed under reduced pressure. The crude product was purified by reversed combi-phase flash to afford N-cyclopropyl-5-[(3R)-pyrrolidin-3-yloxy]pyridine-2-carboxamide (900 mg, 63.22%) as an off-white oil. LC-MS: (ES+H, m/z): [M+H]$^+$=248.0

Step 4: Preparation of N-cyclopropyl-5-{[(3R)-1-[(7-ethyl-6-oxo-5H-1,5-naphthyridin-3-yl)methyl]pyrrolidin-3-yl]oxy}pyridine-2-carboxamide A mixture of 7-(chloromethyl)-3-ethyl-1H-1,5-naphthyridin-2-one (120 mg, 0.54 mmol, 1.00 equiv.), N-cyclopropyl-5-[(3R)-pyrrolidin-3-yloxy]pyridine-2-carboxamide (159 mg, 0.65 mmol, 1.20 equiv.), DIEA (208 mg, 1.62 mmol, 3.00 equiv.) and KI (9 mg, 0.05 mmol, 0.10 equiv.) in MeCN (5 mL) was stirred for 2 h at 80° C. under nitrogen atmosphere. The reaction was monitored by LCMS. The solvent was removed under reduced pressure. The crude product was purified by Prep-HPLC. The pure fractions were concentrated and lyophilized to afford N-cyclopropyl-5-{[(3R)-1-[(7-ethyl-6-oxo-5H-1,5-naphthyridin-3-yl)methyl]pyrrolidin-3-yl]oxy}pyridine-2-carboxamide (121 mg, 51.79%). LC-MS: (ES+H, m/z): [M+H]$^+$=434.2. $^1$H NMR (400 MHz, DMSO-d$_6$) δ 11.83 (s, 1H), 8.49 (d, 1H), 8.39 (d, 1H), 8.21 (d, 1H), 7.94 (d, 1H), 7.74 (s, 1H), 7.60 (d, 1H), 7.47 (dd, 1H), 5.05 (m, 1H), 3.73 (s, 2H), 2.87 (ddt, 2H), 2.74 (dd, 2H), 2.59-2.52 (m, 2H), 2.49-2.32 (m, 2H), 1.86-1.78 (m, 1H), 1.18 (t, 3H), 0.72-0.59 (m, 4H).

Example 5

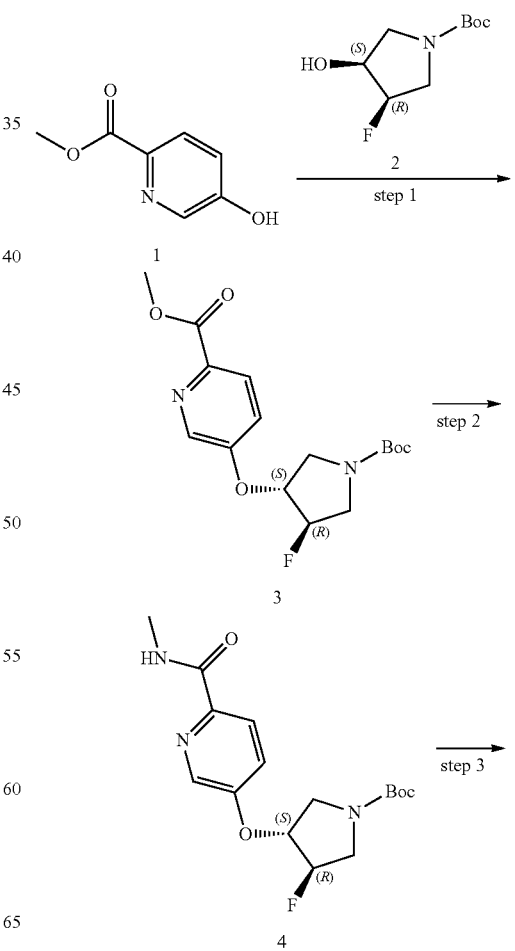

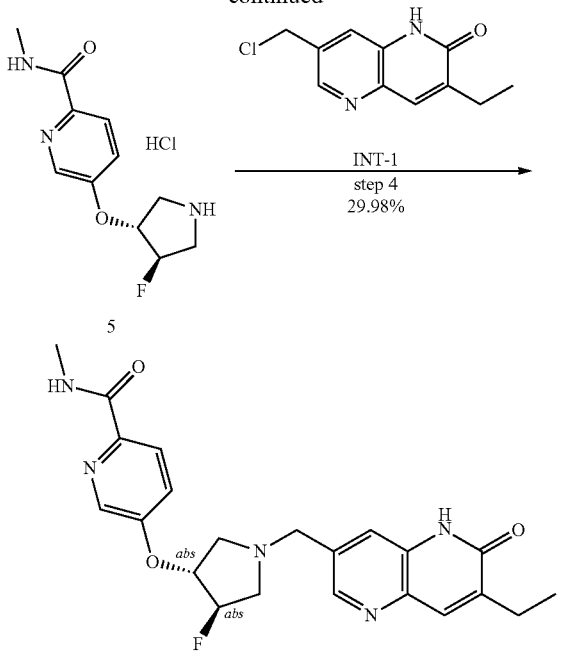

Example 5

Step 1: Preparation of methyl 5-{[(3R,4R)-1-(tert-butoxycarbonyl)-4-fluoropyrrolidin-3-yl]oxy}pyridine-2-carboxylate To a stirred solution of methyl 5-hydroxypyridine-2-carboxylate (0.30 g, 1.95 mmol, 1.00 equiv.), tert-butyl(3R,4S)-3-fluoro-4-hydroxypyrrolidine-1-carboxylate (0.40 g, 1.96 mmol, 1.00 equiv.) and PPh$_3$ (1.03 g, 3.91 mmol, 2.00 equiv.) in toluene (10 mL) was added DBAD (0.90 g, 3.91 mmol, 2.00 equiv.) in toluene (5 mL) dropwise at 0° C. under nitrogen atmosphere. The resulting mixture was stirred for 3 h at 60° C. The reaction was monitored by LCMS. The reaction mixture was poured into water (50 mL), extracted with EtOAc (3×50 mL). The combined organic layers were concentrated under reduced pressure to afford methyl 5-{[(3R,4R)-1-(tert-butoxycarbonyl)-4-fluoropyrrolidin-3-yl]oxy}pyridine-2-carboxylate (2.00 g, crude). The resulting mixture was used in the next step directly. LC-MS: (ES+H, m/z): [M+H]$^+$=341.2.

Step 2: Preparation of tert-butyl(3R,4R)-3-fluoro-4-{[6-(methylcarbamoyl)pyridin-3-yl]oxy}pyrrolidine-1-carboxylate A solution of methyl 5-{[(3R,4R)-1-(tert-butoxycarbonyl)-4-fluoropyrrolidin-3-yl]oxy}pyridine-2-carboxylate (1.00 g, crude) and methylamine (4.0 mL, 25% in water) in MeOH (4.0 mL) was stirred for 2 h at room temperature under nitrogen atmosphere. The resulting mixture was concentrated under reduced pressure to afford tert-butyl(3R,4R)-3-fluoro-4-{[6-(methylcarbamoyl)pyridin-3-yl]oxy}pyrrolidine-1-carboxylate (1.00 g, crude). The crude product was used in the next step directly. LC-MS: (ES+H, m/z): [M+H]$^+$=340.2.

Step 3: Preparation of 5-{[(3R,4R)-4-fluoropyrrolidin-3-yl]oxy}-N-methylpyridine-2-carboxamide, HCl Salt A solution of tert-butyl(3R,4R)-3-fluoro-4-{[6-(methylcarbamoyl)pyridin-3-yl]oxy}pyrrolidine-1-carboxylate (1.00 g, crude) and HCl (gas) in 1,4-dioxane (8 mL, 4M) was stirred for 2 h at room temperature under nitrogen atmosphere. The resulting mixture was concentrated under reduced pressure. The product was precipitated by the addition of EtOAc (10 mL). The precipitated solids were collected by filtration and washed with PE (3×10 mL) to afford 5-{[(3R,4R)-4-fluoropyrrolidin-3-yl]oxy}-N-methylpyridine-2-carboxamide, HCl salt (400 mg, crude). LC-MS: (ES+H, m/z): [M+H]$^+$=240.2.

Step 4: Preparation of 5-{[(3R,4R)-1-[(7-ethyl-6-oxo-5H-1,5-naphthyridin-3-yl)methyl]fluoropyrrolidin-3-yl]oxy}-N-methylpyridine-2-carboxamide To a stirred solution of 5-{[(3R,4R)-4-fluoropyrrolidin-3-yl]oxy}-N-methylpyridine-2-carboxamide, HCl salt (400 mg, crude) and DIEA (290 mg, 2.24 mmol, 5.00 equiv.) in MeCN (5 mL) ware added KI (15 mg, 0.09 mmol, 0.20 equiv.) and 7-(chloromethyl)-3-ethyl-1H-1,5-naphthyridin-2-one (100 mg, 0.44 mmol, 1.00 equiv.) at room temperature. The resulting mixture was stirred for 2 h at 80° C. under nitrogen atmosphere. The mixture was allowed to cool down to room temperature. The resulting mixture was concentrated under reduced pressure. The residue was purified by silica gel column chromatography to afford 5-{[(3R,4R)-1-[(7-ethyl-6-oxo-5H-1,5-naphthyridin-3-yl) methyl]-4-fluoropyrrolidin-3-yl]oxy}-N-methylpyridine-2-carboxamide (56.80 mg, 28.98%). LC-MS: (ES+H, m/z): [M+H]$^+$=426.1. Optical rotation [a]$^{25}_D$ (c=0.5, MeOH): +1.8°; $^1$H NMR (400 MHz, DMSO-d$_6$) δ 11.88 (s, 1H), 8.59 (d, 1H), 8.45-8.25 (m, 2H), 7.99 (d, 1H), 7.75 (s, 1H), 7.65-7.44 (m, 2H), 5.28-5.11 (m, 2H), 3.79 (t, 2H), 3.43-3.33 (m, 1H), 2.94-2.88 (m, 2H), 2.79 (d, 3H), 2.55-2.08 (m, 3H), 1.18 (t, 3H). $^{19}$F NMR (377 MHz, DMSO-d$_6$) δ−179.44.

Example 6

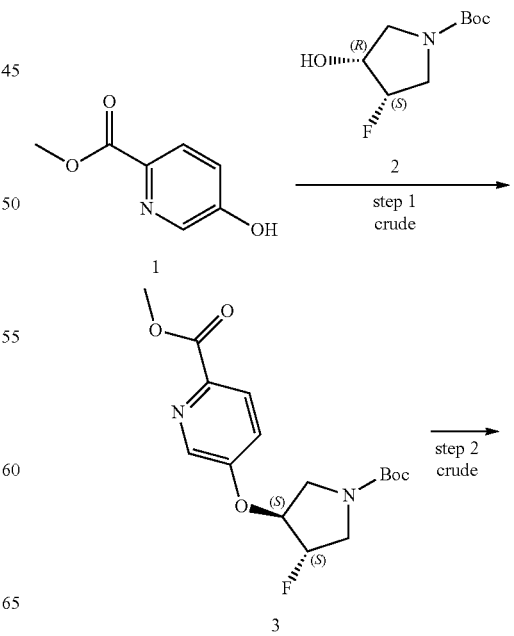

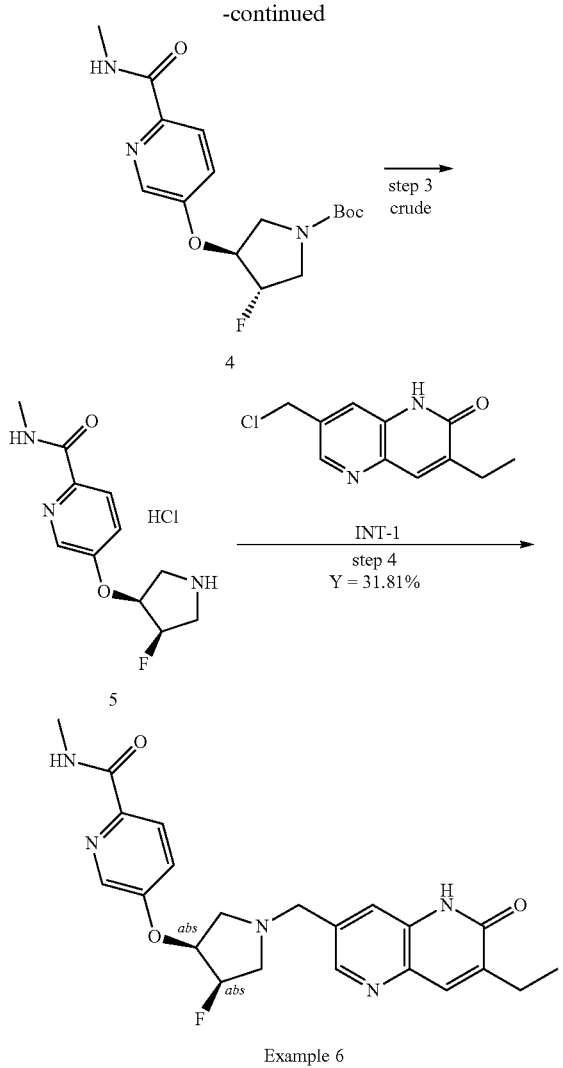

Example 6

Step 1: Preparation of methyl 5-(((3S,4S)-1-(tert-butoxycarbonyl)-4-fluoropyrrolidin-3-yl)oxy)picolinate To a stirred mixture of methyl 5-hydroxypyridine-2-carboxylate (300 mg, 1.96 mmol, 1.00 equiv.), tert-butyl(3S,4R)-3-fluoro-4-hydroxypyrrolidine-1-carboxylate (402 mg, 1.96 mmol, 1.00 equiv.) and PPh$_3$ (1.03 g, 3.92 mmol, 2.00 equiv.) in Toluene (50 mL) was added DBAD (902 mg, 3.92 mmol, 2.00 equiv.) at 0° C. under nitrogen atmosphere. The resulting mixture was stirred for 2 h at 60° C. under nitrogen atmosphere. The reaction was monitored by LCMS. The resulting mixture was concentrated under reduced pressure. The resulting mixture methyl 5-{[(3S,4S)-1-(tert-butoxycarbonyl)-4-fluoropyrrolidin-3-yl]oxy}pyridine-2-carboxylate (4 g, crude) was used in the next step directly without further purification. LC-MS: (ES+H, m/z): [M+H]$^+$=341.1.

Step 2: Preparation of tert-butyl(3S,4S)-3-fluoro-4-((6-(methylcarbamoyl)pyridin-3-yl)oxy)pyrrolidine-1-carboxylate To a stirred solution of methyl 5-{[(3S,4S)-1-(tert-butoxycarbonyl)-4-fluoropyrrolidin-3-yl]oxy}pyridine-2-carboxylate (4 g, crude) in MeOH (5 mL) was added methylamine (5 mL, 25-30% wt) dropwise at room temperature under nitrogen atmosphere. The resulting mixture was stirred for 1 h at room temperature under nitrogen atmosphere. The reaction was monitored by LCMS. The resulting mixture was diluted with sat. NH$_4$Cl (aqueous.) (100 mL). The resulting mixture was extracted with DCM (3×100 mL). The combined organic layers were washed with brine (3×100 mL), dried over anhydrous Na$_2$SO$_4$. After filtration, the filtrate was concentrated under reduced pressure to afford tert-butyl(3S,4S)-3-fluoro-4-{[6-(methylcarbamoyl)pyridin-3-yl]oxy}pyrrolidine-1-carboxylate (2.7 g, crude). LC-MS: (ES+H, m/z): [M+H]$^+$=340.2.

Step 3: Preparation of 5-(((3S,4S)-4-fluoropyrrolidin-3-yl)oxy)-N-methylpicolinamide, HCl Salt To a stirred solution of tert-butyl(3S,4S)-3-fluoro-4-{[6-(methylcarbamoyl)pyridin-3-yl]oxy}pyrrolidine-1-carboxylate (2.7 g, crude) in DCM (20 mL) was added HCl (gas) in 1,4-dioxane (5 mL, 4M) dropwise at room temperature under nitrogen atmosphere. The resulting mixture was stirred for 1 h at room temperature under nitrogen atmosphere. The reaction was monitored by LCMS. The resulting mixture was concentrated under reduced pressure. The residue was purified by trituration with EtOAc (3×20 mL). The precipitated solids were collected by filtration and washed with EtOAc (3×10 mL). This result in 5-(((3S,4S)-4-fluoropyrrolidin-3-yl)oxy)-N-methylpicolinamide, HCl salt (1 g, crude). LC-MS: (ES+H, m/z): [M+H]$^+$=240.2

Step 4: Preparation of 5-(((3S,4S)-1-((7-ethyl-6-oxo-5,6-dihydro-1,5-naphthyridin-3-yl)methyl)-4-fluoropyrrolidin-3-yl)oxy)-N-methylpicolinamide To a stirred mixture of 5-(((3S,4S)-4-fluoropyrrolidin-3-yl)oxy)-N-methylpicolinamide, HCl salt (322 mg, crude) and 7-(chloromethyl)-3-ethyl-1H-1,5-naphthyridin-2-one (150 mg, 0.67 mmol, 1.00 equiv.) in MeCN (10 mL) were added KI (22 mg, 0.14 mmol, 0.20 equiv.) and DIEA (435 mg, 3.37 mmol, 5.00 equiv.) at room temperature. The resulting mixture was stirred for 2 h at 80° C. under nitrogen atmosphere. The reaction was monitored by LCMS. The mixture was allowed to cool down to room temperature. The resulting mixture was diluted with water (50 mL). The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The crude product was purified by Prep-HPLC. The pure fractions were concentrated and lyophilized to afford 5-(((3S,4S)-14 (7-ethyl-6-oxo-5,6-dihydro-1,5-naphthyridin-3-yl)methyl)-4-fluoropyrrolidin-3-yl)oxy)-N-methylpicolinamide (91.6 mg, 31.81%). LC-MS: (ES+H, m/z): [M+H]$^+$=426.2. Optical rotation [a]$^{25}_D$ (c=0.5, MeOH): +0.4°; $^1$H NMR (400 MHz, DMSO-d$_6$) δ 11.88 (s, 1H), 8.59 (q, 1H), 8.39 (d, 1H), 8.31 (d, 1H), 7.99 (d, 1H), 7.75 (s, 1H), 7.60 (d, 1H), 7.54 (dd, 1H), 5.36-5.00 (m, 2H), 3.84-3.72 (m, 2H), 3.36 (d, 1H), 3.00-2.85 (m, 2H), 2.79 (d, 3H), 2.58-2.52 (m, 3H), 1.18 (t, 3H). $^{19}$F NMR (377 MHz, DMSO-d$_6$) δ−179.43.

Example 7

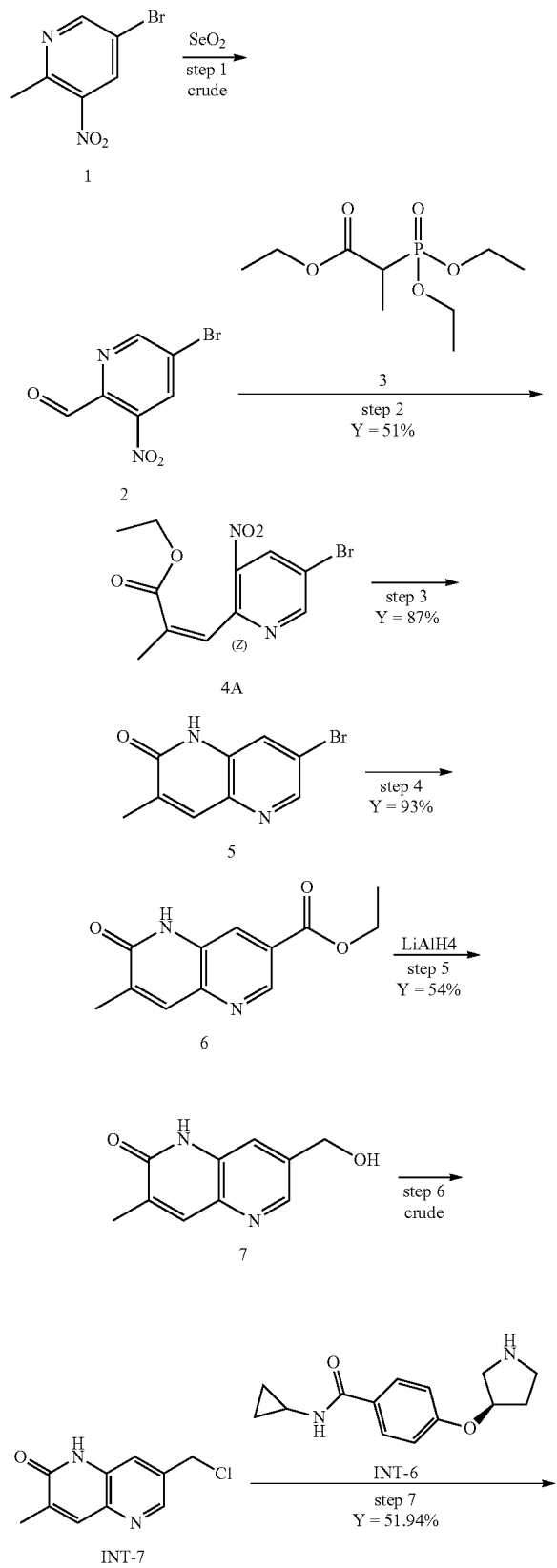

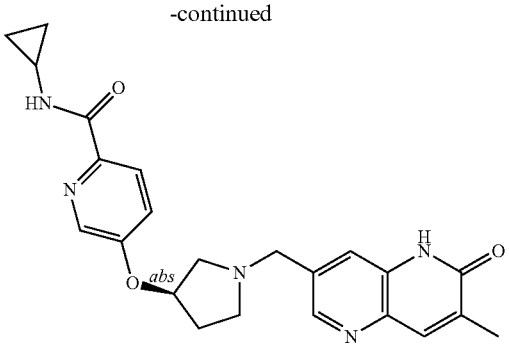

Example 7

Step 1: Preparation of 5-bromo-3-nitropicolinaldehyde

A mixture of 5-bromo-2-methyl-3-nitropyridine (20.00 g, 92.16 mmol, 1.00 equiv.) and SeO2 (51.13 g, 460.79 mmol, 5.00 equiv.) in dioxane (300 mL) was stirred overnight at 110° C. under nitrogen atmosphere. Desired product could be detected by LCMS. The mixture was allowed to cool down to room temperature. The resulting mixture was filtered, the filter cake was washed with EtOAc (3×400 mL). The filtrate was concentrated under reduced pressure. The resulting mixture was washed with THF (3×300 mL). The resulting mixture was concentrated under reduced pressure to afford 5-bromo-3-nitropicolinaldehyde (21 g, crude). $^1$H NMR (400 MHz, DMSO-$d_6$) δ 10.08 (s, 1H), 9.22 (d, 1H), 8.95 (d, 1H).

Step 2: Preparation of ethyl (2Z)-3-(5-bromo-3-nitropyridin-2-yl)-2-methylprop-2-enoate To a stirred mixture of NaH (4.93 g, 123.37 mmol, 1.50 equiv., 60% wt) in THF (250 mL) was added ethyl 2-(diethoxyphosphoryl)propanoate (29.39 g, 123.37 mmol, 1.50 equiv.) dropwise at 0° C. under nitrogen atmosphere. The resulting mixture was stirred for 15 min at 0° C. and 30 min at 40° C. under nitrogen atmosphere. To the above mixture was added 5-bromo-3-nitropyridine-2-carbaldehyde (19.00 g, 82.25 mmol, 1.00 equiv.) in THF (50 mL) dropwise over 30 min at −78° C. The resulting mixture was stirred for additional 1 h at −78° C. Desired product could be detected by LCMS. The reaction was quenched with sat. NH4Cl (aqueous.) at 0° C. The resulting mixture was added water (600 mL) and extracted with EtOAc (3×600 mL). The combined organic layers were washed with brine (2×300 mL), dried over anhydrous Na2SO4. After filtration, the filtrate was concentrated under reduced pressure. The residue was purified by flash chromatography to afford ethyl (2Z)-3-(5-bromo-3-nitropyridin-2-yl)-2-methylprop-2-enoate (13.20 g, 51%). LC-MS: (ES+H, m/z): [M+H]$^+$=315/317. $^1$H NMR (300 MHz, Chloroform-d) δ 8.96 (d, 1H), 8.50 (d, 1H), 7.85 (q, 1H), 4.32 (q, 2H), 2.17 (d, 3H), 1.38 (t, 3H).

Step 3: Preparation of 7-bromo-3-methyl-1H-1,5-naphthyridin-2-one

To a stirred mixture of ethyl (2Z)-3-(5-bromo-3-nitropyridin-2-yl)-2-methylprop-2-enoate (7.60 g, 24.12 mmol, 1.00 equiv.) and Fe (8.08 g, 144.71 mmol, 6.00 equiv.) in EtOH (200 ml) was added CaCl2 (16.06 g, 144.71 mmol, 6.00 equiv.) at room temperature under nitrogen atmosphere. The resulting mixture was stirred for 2 h at 90° C. under nitrogen atmosphere. The reaction was monitored by LCMS. The resulting mixture was concentrated under reduced pressure. The residue was purified by flash silica gel column chromatography. The resulting mixture was concentrated under reduced pressure. The precipitated solids were collected by filtration and washed with water (3×10 mL). The resulting mixture was concentrated under reduced pressure. This resulted in 7-bromo-3-methyl-1H-1,5-naphthyridin-2-one (5.00 g, 87%). LC-MS: (ES+H, m/z): [M+H]$^+$=239/241. $^1$H NMR (300 MHz, DMSO-d$_6$) δ 11.96 (s, 1H), 8.52 (d, 1H), 7.86-7.78 (m, 2H), 2.13 (d, 3H).

Step 4: Preparation of ethyl
7-methyl-6-oxo-5H-1,5-naphthyridine-3-carboxylate

To a mixture of 7-bromo-3-methyl-1H-1,5-naphthyridin-2-one (5.00 g, 20.91 mmol, 1.00 equiv.) and Pd(PPh$_3$)$_2$Cl$_2$ (1.47 g, 2.09 mmol, 0.10 equiv.) in EtOH (100 ml) was added NEt$_3$ (6.35 g, 62.74 mmol, 3.00 equiv.). The resulting mixture was stirred overnight at 100° C. under carbon monoxide atmosphere (30 atm). The reaction was monitored by LCMS. The resulting mixture was concentrated under reduced pressure. The residue was purified by silica gel column chromatography. The resulting mixture was concentrated under reduced pressure. This resulted in ethyl 7-methyl-6-oxo-5H-1,5-naphthyridine-3-carboxylate (4.5 g, 93%). LC-MS: (ES+H, m/z): [M+H]$^+$=233. $^1$H NMR (300 MHz, DMSO-d$_6$) δ 12.06 (s, 1H), 8.88 (d, 1H), 8.15 (dd, 1H), 7.94-7.87 (m, 1H), 4.38 (q, 2H), 2.18 (d, 3H), 1.35 (t, 3H).

Step 5: Preparation of 7-(hydroxymethyl)-3-methyl-1H-1,5-naphthyridin-2-one

To a stirred solution ethyl 7-methyl-6-oxo-5H-1,5-naphthyridine-3-carboxylate (4.50 g, 19.38 mmol, 1.00 equiv.) in THF (100 mL) was added LiAlH$_4$ (15.5 mL, 38.75 mmol, 2.00 equiv., 2.5M in THF) dropwise at 0° C. under nitrogen atmosphere. The resulting mixture was stirred for 1 h at 0° C. under nitrogen atmosphere. The reaction was monitored by LCMS. The reaction was quenched by the addition of HCl aqueous. (20 ml, 1 M) at 0° C. The resulting mixture was concentrated under reduced pressure. The residue was purified by silica gel column chromatography. The resulting mixture was concentrated under reduced pressure. This resulted in 7-(hydroxymethyl)-3-methyl-1H-1,5-naphthyridin-2-one (2 g, 54%). LC-MS: (ES+H, m/z): [M+H]$^+$=191.1. $^1$H NMR (300 MHz, DMSO-d$_6$) δ 11.91 (s, 1H), 8.37 (d, 1H), 7.82 (s, 1H), 7.61 (s, 1H), 5.46 (t, 1H), 4.62 (d, 2H), 2.17-2.10 (m, 3H).

Step 6: Preparation of 7-(chloromethyl)-3-methyl-1H-1,5-naphthyridin-2-one

To a stirred mixture of 7-(hydroxymethyl)-3-methyl-1H-1,5-naphthyridin-2-one (250 mg, 1.31 mmol, 1.00 equiv.) and DMF (10 mg, 0.13 mmol, 0.10 equiv.) in DCM (5 mL) was added SOCl$_2$ (0.6 mL, 7.88 mmol, 6.00 equiv.) dropwise at 0° C. under nitrogen atmosphere. The resulting mixture was stirred for 2 h at room temperature under nitrogen atmosphere. The reaction was monitored by LCMS. Desired product could be detected by LCMS. The resulting mixture was concentrated under reduced pressure. This resulted in 7-(chloromethyl)-3-methyl-1H-1,5-naphthyridin-2-one (310 mg, crude). The crude product mixture was used in the next step directly without further purification. LC-MS: (ES+H, m/z): [M+H]$^+$=209.0

Step 7: Preparation of N-cyclopropyl-5-{[(3R)-1-[(7-methyl-6-oxo-5H-1,5-naphthyridin-3-yl)methyl]pyrrolidin-3-yl]oxy}pyridine-2-carboxamide A mixture of N-cyclopropyl-5-[(3R)-pyrrolidin-3-yloxy]pyridine-2-carboxamide (170 mg, 0.69 mmol, 1.20 equiv.), 7-(chloromethyl)-3-methyl-1H-1,5-naphthyridin-2-one (120 mg, 0.58 mmol, 1.00 equiv.), DIEA (223 mg, 1.73 mmol, 3.00 equiv.) and KI (9.55 mg, 0.06 mmol, 0.10 equiv.) in MeCN (5 mL) was stirred for 2 h at 80° C. under nitrogen atmosphere. The reaction was monitored by LCMS. The solvent was removed under reduced pressure. The crude product was purified by Prep-HPLC. The pure fractions were concentrated and lyophilized to afford to afford N-cyclopropyl-5-{[(3R)-1-[(7-methyl-6-oxo-5H-1,5-naphthyridin-3-yl)methyl]pyrrolidin-3-yl]oxy}pyridine-2-carboxamide (125.3 mg, 51.94%). LC-MS: (ES+H, m/z): [M+H]$^+$=420.2. $^1$H NMR (400 MHz, DMSO-d$_6$) δ 11.70 (s, 1H), 8.49 (d, 1H), 8.38 (d, 1H), 8.21 (d, 1H), 7.94 (d, 1H), 7.84-7.79 (m, 1H), 7.59 (d, 1H), 7.47 (dd, 1H), 5.05 (m, 1H), 3.72 (d, 2H), 2.95-2.67 (m, 4H), 2.48-2.31 (m, 2H), 2.13 (d, 3H), 1.87-1.77 (m, 1H), 0.72-0.58 (m, 4H).

The following examples were made using similar procedures as shown for example 7:

| Ex | NMR | LCMS (ESI) m/z |
|---|---|---|
| 26 | $^1$H NMR (400 MHz, DMSO-d$_6$) δ 11.85 (s, 1H), 8.45-8.35 (m, 2H), 8.11 (d, 1H), 7.81 (s, 1H), 7.59 (d, 1H), 7.40 (dd, 1H), 5.10-5.02 (m, 1H), 3.72 (s, 2H), 3.00-2.66 (m, 4H), 2.49-2.31 (m, 2H), 2.22-2.06 (m, 3H), 1.88-1.74 (m, 1H), 0.72-0.63 (m, 2H), 0.62-0.54 (m, 2H). $^{19}$F NMR (282 MHz, DMSO-d$_6$) δ-118.665. | [M + H]$^+$ = 438.2 |

Example 8

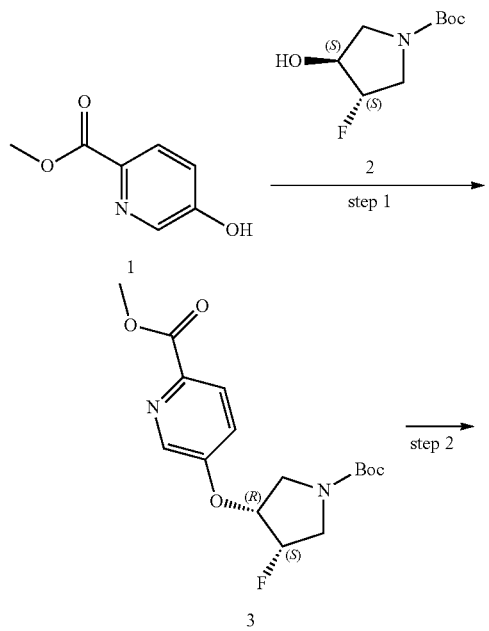

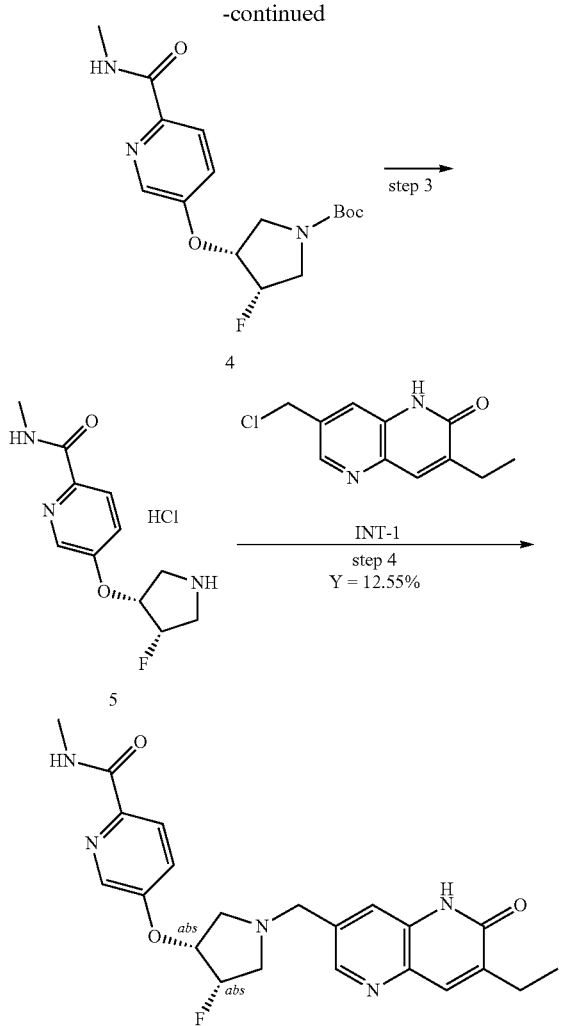

Example 8

Step 1: Preparation of methyl 5-{[(3R,4S)-1-(tert-butoxycarbonyl)-4-fluoropyrrolidin-3-yl]oxy}pyridine-2-carboxylate To a stirred mixture of tert-butyl(3S,4S)-3-fluoro-4-hydroxypyrrolidine-1-carboxylate (500 mg, 2.44 mmol, 1.00 equiv.) and methyl 5-hydroxypyridine-2-carboxylate (373 mg, 2.44 mmol, 1.00 equiv.) and PPh$_3$ (1.34 g, 5.12 mmol, 2.10 equiv.) in tetrahydrofuran (10 mL) were added DBAD (1.12 g, 4.87 mmol, 2.00 equiv.) in THF (5 mL) dropwise at 0° C. under nitrogen atmosphere. The resulting mixture was stirred for 3 h at 60° C. under nitrogen atmosphere. The reaction was monitored by LCMS. The mixture was allowed to cool down to room temperature. The resulting mixture was concentrated under reduced pressure. The resulting mixture was diluted with ethyl acetate (100 mL). The resulting mixture was washed with water (2×30 mL). The organic phase was dried over anhydrous Na$_2$SO$_4$. After filtration, the filtrate was concentrated under vacuum to afford methyl 5-{[(3R,4S)-1-(tert-butoxycarbonyl)-4-fluoropyrrolidin-3-yl]oxy}pyridine-2-carboxylate (2 g, crude). It was used in the next step directly without further purification. LC-MS: (ES+H, m/z): [M+H]$^+$=341.1.

Step 2: Preparation of tert-butyl(3S,4R)-3-fluoro-4-{[6-(methylcarbamoyl)pyridin-3-yl]oxy}pyrrolidine-1-carboxylate To a stirred solution of methyl 5-{[(3R,4S)-1-(tert-butoxycarbonyl)-4-fluoropyrrolidin-3-yl]oxy}pyridine-2-carboxylate (2 g, crude) in CH$_3$OH (7 mL) was added CH$_3$NH$_2$ in water (7 mL, 25-30% wt) dropwise at room temperature under nitrogen atmosphere. The resulting mixture was stirred overnight at room temperature under nitrogen atmosphere. The reaction was monitored by LCMS. The resulting mixture was concentrated under reduced pressure. The resulting mixture was diluted with ethyl acetate (100 mL). The residue was washed with NH$_4$Cl (aqueous)(2×30 mL). The organic phase was dried over anhydrous Na$_2$SO$_4$. After filtration, the filtrate was concentrated under vacuum. The crude product tert-butyl (3S,4R)-3-fluoro-4-{[6-(methylcarbamoyl)pyridin-3-yl]oxy}pyrrolidine-1-carboxylate (2 g; crude) was used in the next step directly without further purification. LC-MS: (ES+H, m/z): [M+H]$^+$=340.1.

Step 3: Preparation of 5-{[(3R,4S)-4-fluoropyrrolidin-3-yl]oxy}-N-methylpyridine-2-carboxamide, HCl Salt To a stirred solution of tert-butyl(3S,4R)-3-fluoro-4-{[6-(methylcarbamoyl)pyridin-3-yl]oxy}pyrrolidine-1-carboxylate (2 g, crude) in CH$_2$Cl$_2$ (5 mL) was added HCl in dioxane (8 mL, 4M) dropwise at 0° C. under nitrogen atmosphere. The resulting mixture was stirred for 2 h at room temperature under nitrogen atmosphere. The reaction was monitored by LCMS. The resulting mixture was concentrated under reduced pressure. The residue was purified by trituration with ethyl ether/n-hexane (3×10 mL). The resulting mixture was concentrated under vacuum. The crude product 5-{[(3R,4S)-4-fluoropyrrolidin-3-yl]oxy}-N-methylpyridine-2-carboxamide, HCl salt (0.8 g, crude) was used in the next step directly without further purification. LC-MS: (ES+H, m/z): [M+4]$^+$=240.2.

Step 4: Preparation of 5-{[(3R,4S)-1-[(7-ethyl-6-oxo-5H-1,5-naphthyridin-3-yl)methyl]-4-fluoropyrrolidin-3-yl]oxy}-N-methylpyridine-2-carboxamide To a stirred mixture of 5-{[(3R,4S)-4-fluoropyrrolidin-3-yl]oxy}-N-methylpyridine-2-carboxamide (160 mg, 0.67 mmol, 1.00 equiv.) and 7-(chloromethyl)-3-ethyl-1H-1,5-naphthyridin-2-one, HCl salt (300 mg, crude) in acetonitrile (6 mL) were added KI (56 mg, 0.34 mmol, 0.50 equiv.) and DIEA (432 mg, 3.35 mmol, 5.00 equiv.) dropwise at room temperature. The resulting mixture was stirred for 2 h at 80° C. under nitrogen atmosphere. The reaction was monitored by LCMS. The mixture was allowed to cool down to room temperature. The residue was purified by silica gel column chromatography. After that, the residue was purified by Prep-HPLC chromatography. The pure fractions were concentrated and lyophilized to afford 5-{[(3R,4S)-1-[(7-ethyl-6-oxo-5H-1,5-naphthyridin-3-yl)methyl]-4-fluoropyrrolidin-3-yl]oxy}-N-methylpyridine-2-carboxamide (36.0 mg, 12.55%). LC-MS: (ES+H, m/z): [M+H]$^+$=426.05. Optical rotation [a]$^{25}_D$ (c=0.5, MeOH): −17°; $^1$H NMR (300 MHz, DMSO-d$_6$) δ 11.88 (s, 1H), 8.58-8.56 (m, 1H), 8.40-8.37 (dd, 2H), 7.98-7.95 (d, 1H), 7.75 (s, 1H), 7.65-7.61 (m, 2H), 5.51-5.33 (m, 1H), 5.15-5.05 (m, 1H), 3.85-3.75 (m, 2H), 3.08-2.94 (m, 2H), 2.92-2.84 (m, 2H), 2.80-2.79 (d, 3H), 2.58-2.51 (m, 2H), 1.23-1.16 (t, 3H). $^{19}$F NMR (282 MHz, DMSO-d$_6$) δ −195.59.

Example 9

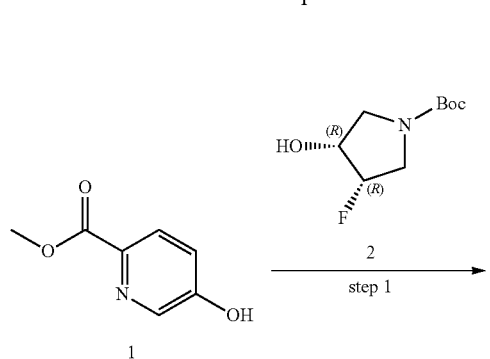

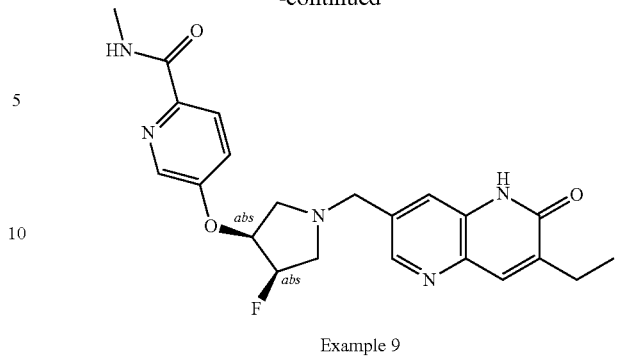

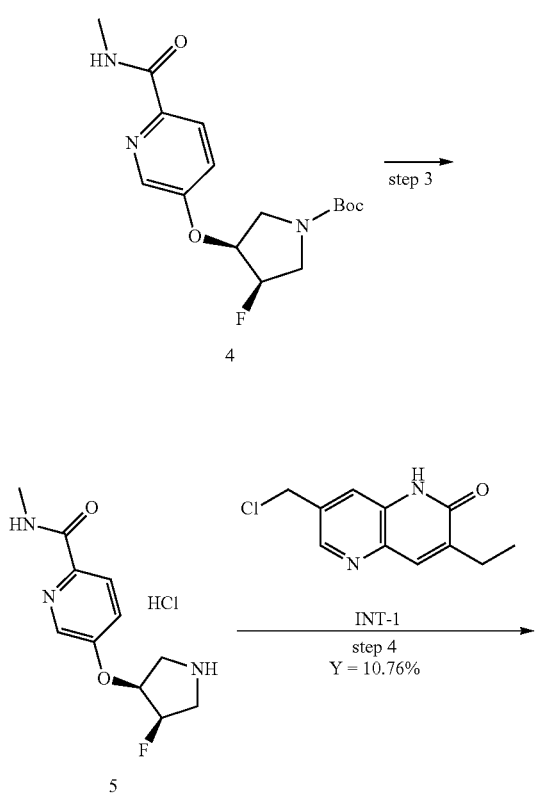

Step 1: Preparation of methyl 5-{[(3S,4R)-1-(tert-butoxycarbonyl)-4-fluoropyrrolidin-3-yl]oxy}pyridine-2-carboxylate To a stirred mixture of methyl 5-hydroxypyridine-2-carboxylate (373 mg, 2.44 mmol, 1.00 equiv.), PPh$_3$ (1.28 g, 4.87 mmol, 2.00 equiv.) and tert-butyl(3R,4R)-3-fluoro-4-hydroxypyrrolidine-1-carboxylate (500 mg, 2.44 mmol, 1.00 equiv.) in toluene (10 mL) was added DBAD (1.12 g, 4.87 mmol, 2.00 equiv.) dropwise at 0° C. under nitrogen atmosphere. The resulting mixture was stirred overnight at 60° C. under nitrogen atmosphere. The reaction was monitored by LCMS. The mixture was allowed to cool down to room temperature. The resulting mixture was concentrated under reduced pressure. The residue was dissolved in EtOAc (30 mL). The mixture was washed with saturated NaHCO$_3$ (1×20 mL), dried over anhydrous Na$_2$SO$_4$. After filtration, the filtrate was concentrated under reduced pressure to afford methyl 5-{[(3S,4R)-1-(tert-butoxycarbonyl)-4-fluoropyrrolidin-3-yl]oxy}pyridine-2-carboxylate (3.5 g, crude). LC-MS: (ES+H, m/z): [M+H]$^+$=341.2.

Step 2: Preparation of tert-butyl(3R,4S)-3-fluoro-4-((6-(methylcarbamoyl)pyridin-3-yl)oxy)pyrrolidine-1-carboxylate To a stirred mixture of methyl 5-(((3S,4R)-1-(tert-butoxycarbonyl)-4-fluoropyrrolidin-3-yl)oxy)picolinate (3.5 g, crude) in MeOH (30 mL) was added methylamine (10 mL, 25-30% wt in water) at room temperature. The resulting mixture was stirred overnight at room temperature under nitrogen atmosphere. The reaction was monitored by LCMS. The resulting mixture was concentrated under reduced pressure. The resulting mixture was added saturated NH$_4$Cl (50 mL) and extracted with EtOAc (3×50 mL). The combined organic layers were washed with brine (1×50 mL), and dried over anhydrous Na$_2$SO$_4$. After filtration, the filtrate was concentrated under reduced pressure to afford tert-butyl(3R,4S)-3-fluoro-4-((6-(methylcarbamoyl)pyridin-3-yl)oxy)pyrrolidine-1-carboxylate (2.2 g, crude). LC-MS: (ES+H, m/z): [M+H]$^+$=340.2.

Step 3: Preparation of 5-(((3S,4R)-4-fluoropyrrolidin-3-yl)oxy)-N-methylpicolinamide, HCl Salt To a stirred solution of tert-butyl(3R,4S)-3-fluoro-4-((6-(methylcarbamoyl)pyridin-3-yl)oxy)pyrrolidine-1-carboxylate (2.2 g, crude) in DCM (20 mL) were added HCl (gas) in 1,4-dioxane (10 mL, 4M) dropwise at room temperature. The resulting mixture was stirred for 30 min at room temperature. The reaction was monitored by LCMS. The resulting mixture was concentrated under reduced pressure. The residue was purified by trituration with DCM (20 mL). The precipitated solid was collected by filtration and washed with hexane (3×5 mL). The precipitated solid was concentrated under reduced pressure to afford 5-(((3S,4R)-4-fluoropyrrolidin-3-yl)oxy)-N-methylpicolinamide, HCl salt (750 mg, 82.98%). LC-MS: (ES+H, m/z): [M+H]⁺=240.0.

Step 4: Preparation of 5-(3S,4R)-1-((7-ethyl-6-oxo-5,6-dihydro-1,5-naphthyridin-3-yl)methyl)-4-fluoropyrrolidin-3-yl)oxy)-N-methylpicolinamide To a stirred mixture of 5-(((3S,4R)-4-fluoropyrrolidin-3-yl)oxy)-N-methylpicolinamide, HCl salt (300 mg, crude) and 7-(chloromethyl)-3-ethyl-1H-1,5-naphthyridin-2-one (200 mg, 0.90 mmol, 1.00 equiv.) in ACN (6 mL) were added DIEA (580 mg, 4.49 mmol, 5.00 equiv.) and KI (15 mg, 0.09 mmol, 0.10 equiv.) at room temperature. The resulting mixture was stirred for 2 h at 80° C. under nitrogen atmosphere. The reaction was monitored by LCMS. The mixture was allowed to cool down to room temperature. The reaction mixture was poured into water (50 mL) at room temperature. The resulting mixture was extracted with $CH_2Cl_2$/i-PrOH (3/1, 3×50 mL). The combined organic layers were washed with brine (1×50 mL), dried over anhydrous $Na_2SO_4$. After filtration, the filtrate was concentrated under reduced pressure. The crude product was purified by PREP-HPLC, the pure fractions was concentrated then lyophilized to afford 5-(((3S,4R)-1-((7-ethyl-6-oxo-5,6-dihydro-1,5-naphthyridin-3-yl)methyl)-4-fluoropyrrolidin-3-yl)oxy)-N-methylpicolinamide (49.5 mg, 10.76%). LC-MS: (ES+H, m/z): [M+H]⁺=426.1. Optical rotation [a]$^{25}_D$ (c=0.5, MeOH): +19°; ¹H NMR (300 MHz, DMSO-d₆) δ 11.88 (s, 1H), 8.57 (q, 1H), 8.41 (d, 1H), 8.34 (d, 1H), 7.96 (d, 1H), 7.75 (d, 1H), 7.63 (dd, 2H), 5.57-5.26 (m, 1H), 5.18-5.03 (m, 1H), 3.88-3.71 (m, 2H), 3.10-2.95 (m, 2H), 2.94-2.83 (m, 2H), 2.79 (d, 3H), 2.61-2.52 (m, 2H), 1.18 (t, 3H). ¹⁹F NMR (282 MHz, DMSO-d₆) δ−195.59.

Example 10

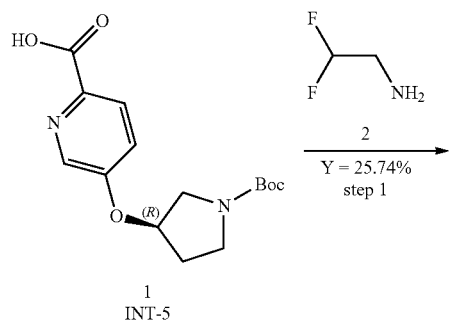

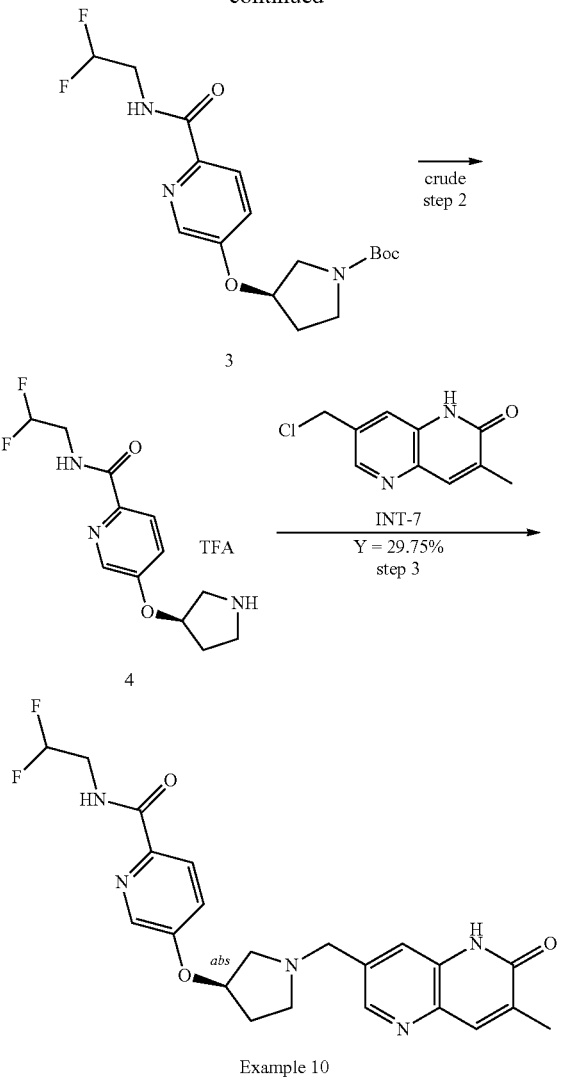

Example 10

Step 1: Preparation of tert-butyl(3R)-3-({6-[(2,2-difluoroethyl)carbamoyl]pyridin-3-yl}oxy)pyrrolidine-1-carboxylate To a stirred mixture of 5-{[(3R)-1-(tert-butoxycarbonyl)pyrrolidin-3-yl]oxy}pyridine-2-carboxylic acid (1.00 g, 3.24 mmol, 1.00 equiv.), 2,2-difluoroethanamine (0.29 g, 3.57 mmol, 1.10 equiv.) and DIEA (2.10 g, 16.22 mmol, 5.00 equiv.) in DCM (28 mL) was added T3P (6.19 g, 9.73 mmol, 3.00 equiv., 50% wt in EA) dropwise at room temperature under nitrogen atmosphere. The resulting mixture was stirred overnight at room temperature under nitrogen atmosphere. The reaction was monitored by LCMS. The resulting mixture was diluted with water (50 mL). The resulting mixture was extracted with $CH_2Cl_2$ (3×50 mL). The combined organic layers were washed with brine (1×100 mL), dried over anhydrous $Na_2SO_4$. After filtration, the filtrate was concentrated under reduced pressure. The residue was purified by silica gel column chromatography to afford tert-butyl(3R)-3-({6-[(2,2-difluoroethyl)carbamoyl]pyridin-3-yl}oxy)pyrrolidine-1-carboxylate (310 mg, 25.74%) as an off-white oil. LC-MS: (ES+H, m/z): [M+H-t-Bu]⁺=316.0. ¹H NMR (300 MHz, DMSO-d₆) δ 8.97-8.84

(t, 1H), 8.39-8.27 (m, 1H), 8.02 (d, 1H), 7.62-7.58 (m, 1H), 6.29-5.78 (m, 1H), 3.74-3.34 (m, 8H), 2.20-2.03 (m, 1H), 1.40 (d, 9H).

Step 2: Preparation of N-(2,2-difluoroethyl)-5-[(3R)-pyrrolidin-3-yloxy]pyridine-2-carboxamide, TFA Salt To a stirred solution of tert-butyl(3R)-3-({6-[(2,2-difluoroethyl)carbamoyl]pyridin-3-yl}oxy)pyrrolidine-1-carboxylate (230 mg, 0.62 mmol, 1.00 equiv.) in DCM (6 mL) was added TFA (2 mL) dropwise at 0° C. under nitrogen atmosphere. The resulting mixture was stirred for 1 h at room temperature under nitrogen atmosphere. The reaction was monitored by LCMS. The resulting mixture was concentrated under reduced pressure. The crude product was used in the next step directly without further purification. LC-MS: (ES+H, m/z): [M+H]$^+$=272.2.

Step 3: Preparation of N-(2,2-difluoroethyl)-5-[(3R)-1-[(7-methyl-6-oxo-5H-1,5-naphthyridin-3-yl)methyl]pyrrolidin-3-yl]oxy)pyridine-2-carboxamide To a stirred solution of N-(2,2-difluoroethyl)-5-[(3R)-pyrrolidin-3-yloxy]pyridine-2-carboxamide, TFA slat (168 mg, crude) and 7-(chloromethyl)-3-methyl-1H-1,5-naphthyridin-2-one (142 mg, 0.68 mmol, 1.0 equiv.) in MeCN (10 mL) was added KI (22 mg, 0.14 mmol, 0.20 equiv.) and DIEA (440 mg, 3.40 mmol, 5.00 equiv.) at room temperature. The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography, the pure fraction was concentrated then lyophilized to afford N-(2,2-difluoroethyl)-5-{[(3R)-1-[(7-methyl-6-oxo-5H-1,5-naphthyridin-3-yl)methyl]pyrrolidin-3-yl]oxy}pyridine-2-carboxamide (82.1 mg, 29.75%). LC-MS: (ES+H, m/z): [M+H]$^+$=444.0. $^1$H NMR (300 MHz, DMSO-d$_6$) δ 11.87 (s, 1H), 8.86 (t, 1H), 8.39 (d, 1H), 8.29 (d, 1H), 7.98 (d, 1H), 7.85-7.79 (m, 1H), 7.62-7.55 (m, 1H), 7.51 (dd, 1H), 6.40-5.85 (m, 1H), 5.08 (s, 1H), 3.81-3.58 (m, 4H), 2.92 (dd, 1H), 2.83-2.68 (q, 2H), 2.48-2.25 (m, 2H), 2.14 (d, 3H), 1.74-1.88 (m, 1H). $^{19}$F NMR (282 MHz, DMSO-d$_6$) δ-122.05

Example 11

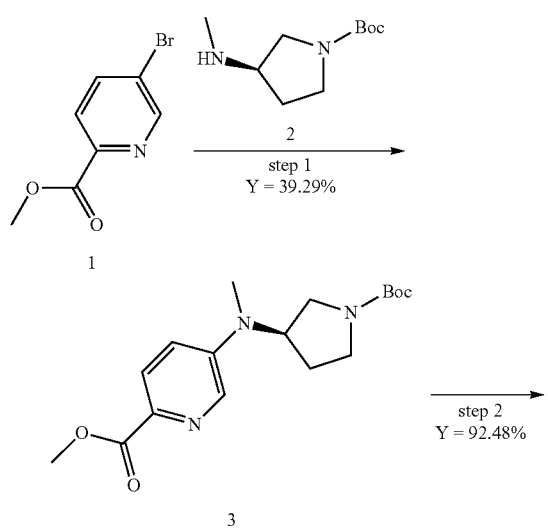

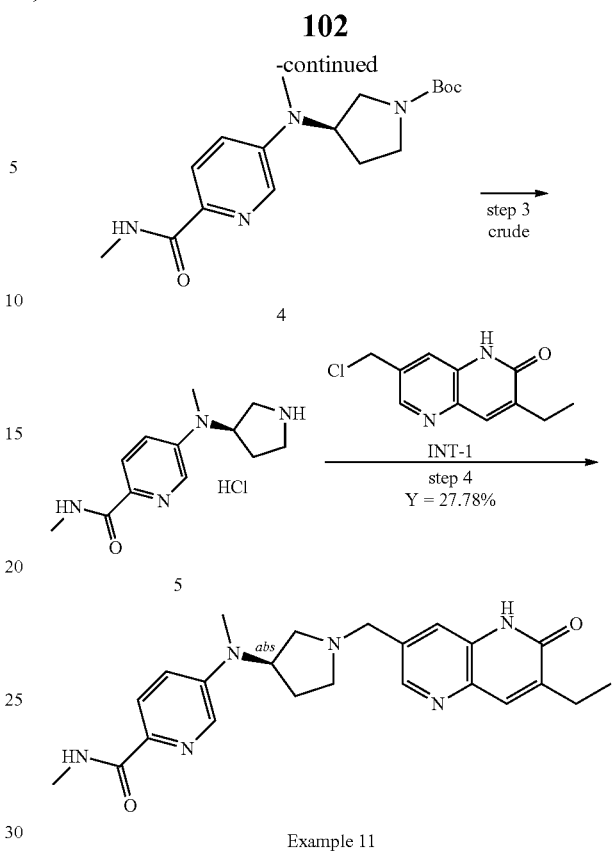

Example 11

Step 1: Preparation of methyl 5-{[(3R)-1-(tert-butoxycarbonyl)pyrrolidin-3-yl](methyl)amino}pyridine-2-carboxylate A mixture of methyl 5-bromopyridine-2-carboxylate (800 mg, 3.70 mmol, 1.00 equiv.), tert-butyl (3R)-3-(methylamino)pyrrolidine-1-carboxylate (890 mg, 4.44 mmol, 1.20 equiv.), Cs$_2$CO$_3$ (2.41 g, 7.41 mmol, 2.00 equiv.), RuPhos Palladacycle Gen.3 (310 mg, 0.37 mmol, 0.10 equiv.) in 1,4-dioxane (10 mL) was stirred overnight at 110° C. under nitrogen atmosphere. The mixture was allowed to cool down to room temperature. The reaction was monitored by LCMS. The resulting mixture was diluted with water (20 mL). The resulting mixture was filtered, the filter cake was washed with EtOAc (3×20 mL). The filtrate was concentrated under reduced pressure. The residue was purified by silica gel column chromatography to afford methyl 5-{[(3R)-1-(tert-butoxycarbonyl)pyrrolidin-3-yl](methyl)amino}pyridine-2-carboxylate (488 mg, 39.29%). LC-MS: (ES+H, m/z): [M+H]$^+$=336.25. $^1$H NMR (400 MHz, DMSO-d$_6$) δ 8.30 (d, 1H), 7.86 (d, 1H), 7.26 (dd, 1H), 4.79-4.6 (m, 1H), 3.80 (s, 3H), 3.58-3.40 (m, 2H), 3.24-3.20 (m, 2H), 2.89 (s, 3H), 2.04 (d, 2H), 1.41 (s, 9H).

Step 2: Preparation of tert-butyl(3R)-3-{methyl-[6-(methylcarbamoyl)pyridin-3-yl]amino}pyrrolidine-1-carboxylate A mixture of methyl 5-{[(3R)-1-(tert-butoxycarbonyl)pyrrolidin-3-yl](methyl)amino}pyridine-2-carboxylate (488 mg, 1.46 mmol, 1.00 equiv.) in MeOH (6 mL) and methylamine water solution (3 mL, 25-30% wt) was stirred for 4 h at room temperature. The reaction was monitored by LCMS. The resulting mixture was concentrated under vacuum to afford tert-butyl(3R)-3-{methyl-[(6-(methylcarbamoyl)pyridin-3-yl]amino}pyrrolidine-1-carboxylate (450 mg, 92.48%). LC-MS: (ES+H, m/z): [M+H]$^+$=335.2. $^1$H NMR (400 MHz, DMSO-d$_6$) δ8.34 (d, 1H), 8.18 (d, 1H), 7.81 (d, 1H), 7.31 (dd, 1H), 4.70-4.62 (m, 1H) 3.57-3.39 (m, 3H), 3.24-3.20 (m, 1H), 2.87 (d, 3H), 2.78 (d. 3H), 2.05-2.02 (m, 2H), 1.41 (s, 9H).

Step 3: Preparation of N-methyl-5-[methyl((3R)-pyrrolidin-3-yl)amino]pyridine-2-carboxamide, HCl Salt A mixture of tert-butyl(3R)-3-{methyl-[(6-(methylcarbamoyl)pyridin-3-yl]amino}pyrrolidine-1-carboxylate (450 mg, 1.35 mmol, 1.00 equiv.) in HCl (gas) in 1,4-dioxane (5 mL, 4M) was stirred for 1 h at room temperature. The reaction was monitored by LCMS. The resulting mixture was concentrated under vacuum to afford N-methyl-5-[methyl((3R)-pyrrolidin-3-yl)amino]pyridine-2-carboxamide, HCl salt (300 mg, crude). LC-MS: (ES+H, m/z): [M+H]$^+$=235.2.

Step 4: Preparation of 5-{[(3R)-1-[(7-ethyl-6-oxo-5H-1,5-naphthyridin-3-yl)methyl]pyrrolidin-3-yl](methyl)amino}-N-methylpyridine-2-carboxamide A mixture of N-methyl-5-[methyl((3R)-pyrrolidin-3-yl)amino]pyridine-2-carboxamide (237 mg, 1.01 mmol, 1.5 equiv.), 7-(chloromethyl)-3-ethyl-1H-1,5-naphthyridin-2-one (150 mg, 0.67 mmol, 1.00 equiv.), KI (20 mg, 0.12 mmol, 0.18 equiv.) and DIEA (261 mg, 2.02 mmol, 3.00 equiv.) in ACN (6 mL) was stirred for 1 h at 80° C. under nitrogen atmosphere. The mixture was allowed to cool down to room temperature. The reaction was monitored by LCMS. The resulting mixture was diluted with water (15 mL). The aqueous layer was extracted with EtOAc (3×20 mL). The resulting mixture was concentrated under vacuum. The crude product was purified by Prep-HPLC, the pure fraction was concentrated under reduced pressure then lyophilized to afford 5-{[(3R)-1-[(7-ethyl-6-oxo-5H-1,5-naphthyridin-3-yl)methyl]pyrrolidin-3-yl](methyl)amino}-N-methylpyridine-2-carboxamide (78.7 mg, 27.78%). LC-MS: (ES+H, m/z): [M+H]$^+$=421.15. Optical rotation [a]$^{25}_D$ (c=0.5, MeOH): +6.6°; $^1$H NMR (300 MHz, DMSO-d$_6$) δ 11.90 (s, 1H), 8.41 (d, 1H), 8.30 (d, 1H), 8.11 (d, 1H), 7.88-7.71 (m, 2H), 7.63 (d, 1H), 7.23 (dd, 1H), 4.63-4.61 (m, 1H), 3.79 (d, 1H), 3.64 (d, 1H), 2.96 (s, 3H), 2.93-2.85 (m, 1H), 2.77 (d, 3H), 2.74-2.68 (m, 1H), 2.61-2.52 (m, 3H), 2.43-2.13 (m, 2H), 1.92-1.60 (m, 1H), 1.18 (t, 3H).

Example 12

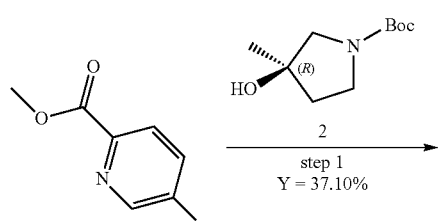

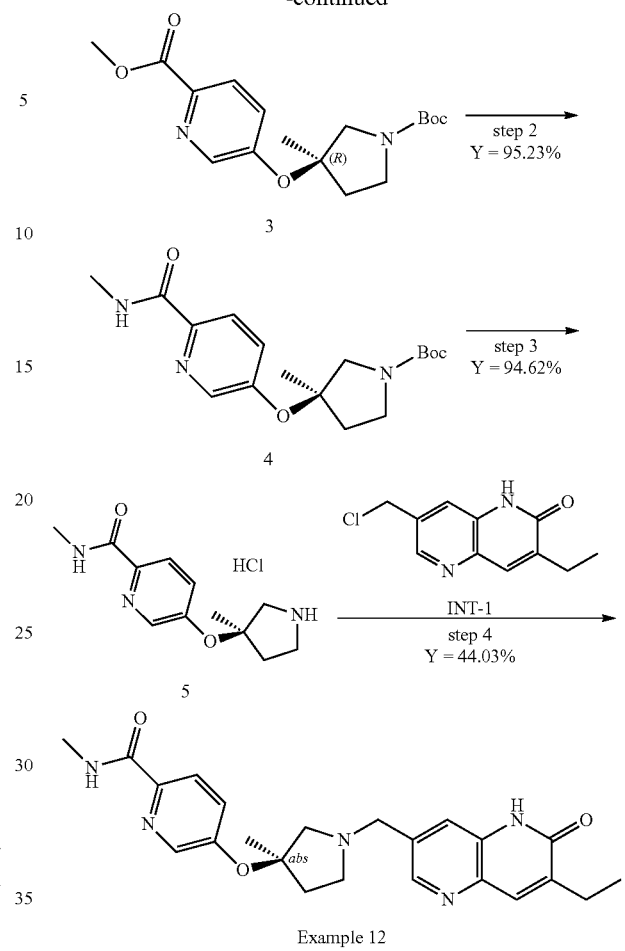

Example 12

Step 1: Preparation of methyl 5-{[(3R)-1-(tert-butoxycarbonyl)-3-methylpyrrolidin-3-yl]oxy}pyridine-2-carboxylate To a stirred mixture of NaH (139 mg, 3.47 mmol, 1.4 equiv., 60% wt) in DMF (10 mL) was added tert-butyl(3R)-3-hydroxy-3-methylpyrrolidine-1-carboxylate (500 mg, 2.48 mmol, 1.00 equiv.) in DMF (1 mL) dropwise at room temperature under nitrogen atmosphere. The resulting mixture was stirred for 30 min at room temperature under nitrogen atmosphere. To the above mixture was added methyl 5-fluoropyridine-2-carboxylate (462 mg, 2.98 mmol, 1.20 equiv.) dropwise at room temperature. The resulting mixture was stirred for 2 h at room temperature under nitrogen atmosphere. The reaction was monitored by LCMS. The reaction was quenched with MeOH at 0° C. The residue was purified by reversed combi-flash chromatography to afford methyl 5-{[(3R)-1-(tert-butoxycarbonyl)-3-methylpyrrolidin-3-yl]oxy}pyridine-2-carboxylate (310 mg, 37.10%). LC-MS: (ES+H, m/z): [M+H]$^+$=337.2. Optical rotation [a]$^{25}_D$ (c=0.5, MeOH): −23.9°; $^1$H NMR (400 MHz, DMSO-d$_6$) δ8.35 (d, 1H), 8.01 (dd, 1H), 7.62 (dd, 1H), 3.85 (s, 3H), 3.68 (dd, 1H), 3.33 (m, 2H), 2.32-2.28 (m, 1H), 2.14-1.99 (m, 2H), 1.55 (s, 3H), 1.38 (d, 9H).

Step 2: Preparation of tert-butyl(3R)-3-methyl-3-{ [6-(methylcarbamoyl)pyridin-3-yl]oxy}pyrrolidine-1-carboxylate A mixture of methyl 5-{[(3R)-1-(tert-butoxycarbonyl)-3-methylpyrrolidin-3-yl]oxy}pyridine-2-carboxylate (337 mg, 1.00 mmol, 1.00 equiv.) and $CH_3NH_2$ (5 mL, 25-30% wt in water) in $CH_3OH$ (5 mL) was stirred for 2 h at room temperature under nitrogen atmosphere. The reaction was monitored by LCMS. The resulting mixture was extracted with $CH_2Cl_2$ (3×30 mL). The combined organic layers were washed with brine (3×30 mL), dried over anhydrous $Na_2SO_4$. After filtration, the filtrate was concentrated under reduced pressure to afford tert-butyl(3R)-3-methyl-3-{[6-(methylcarbamoyl)pyridin-3-yl]oxy}pyrrolidine-1-carboxylate (319 mg, 95.23%). LC-MS: (ES+H, m/z): $[M+H]^+$ =336.2.

Step 3: Preparation of N-methyl-5-{[(3R)-3-methylpyrrolidin-3-yl]oxy}pyridine-2-carboxamide, HCl Salt To a stirred solution of tert-butyl(3R)-3-methyl-3-{[6-(methylcarbamoyl)pyridin-3-yl]oxy}pyrrolidine-1-carboxylate (300 mg, 0.89 mmol, 1.00 equiv.) in DCM (5 mL) was added HCl (gas) in 1,4-dioxane (2.5 mL, 4M) dropwise at 0° C. under nitrogen atmosphere. The resulting mixture was stirred for 30 min at room temperature under nitrogen atmosphere. The reaction was monitored by LCMS. The resulting mixture was concentrated under reduced pressure. The residue was purified by trituration with ethyl ether (20 mL) to afford N-methyl-5-{[(3R)-3-methylpyrrolidin-3-yl]oxy}pyridine-2-carboxamide, HCl salt (230 mg, 94.62%). LC-MS: (ES+H, m/z): $[M+H]^+$=236.2.

Step 4: Preparation of 5-{[(3R)-1-[(7-ethyl-6-oxo-5H-1,5-naphthyridin-3-yl)methyl]-3-methylpyrrolidin-3-yl]oxy}-N-methylpyridine-2-carboxamide A mixture of N-methyl-5-{[(3R)-3-methylpyrrolidin-3-yl]oxy}pyridine-2-carboxamide, HCl salt (205 mg, 0.75 mmol, 1.00 equiv.), 7-(chloromethyl)-3-ethyl-1H-1,5-naphthyridin-2-one (218 mg, 0.98 mmol, 1.30 equiv.), DIEA (488 mg, 3.77 mmol, 5.00 equiv.) and KI (25 mg, 0.15 mmol, 0.20 equiv.) in ACN (5 mL) was stirred for 2 h at 80° C. under nitrogen atmosphere. The reaction was monitored by LCMS. The resulting mixture was diluted with water (30 mL). The resulting mixture was concentrated under reduced pressure. The residue was purified by silica gel column chromatography, the pure fraction was concentrated then lyophilized to afford 5-{[(3R)-1-[(7-ethyl-6-oxo-5H-1,5-naphthyridin-3-yl)methyl]-3-methylpyrrolidin-3-yl]oxy}-N-methylpyridine-2-carboxamide (140 mg, 44.03%). LC-MS: (ES+H, m/z): $[M+H]^+$=422.10. Optical rotation $[a]^{25}_D$ (c=0.5, MeOH): −21.6°; $^1H$ NMR (300 MHz, DMSO-$d_6$) δ 11.88 (s, 1H), 8.55 (d, 1H), 8.39 (d, 1H), 8.22 (dd, 1H), 7.95 (dd, 1H), 7.75 (s, 1H), 7.65-7.54 (m, 2H), 3.73 (s, 2H), 2.96 (d, 1H), 2.82-2.76 (m, 4H), 2.75-2.67 (m, 1H), 2.68-2.53 (m, 3H), 2.33-2.21 (m, 1H), 2.13-1.99 (m, 1H), 1.55 (s, 3H), 1.19 (t, 3H).

The following examples were made using similar procedures as shown for example 12:

| Ex | NMR | LCMS (ESI) m/z |
|---|---|---|
| 28 | $^1H$ NMR (400 MHz, DMSO-$d_6$) δ 11.85 (s, 1H), 8.66 (q, 1H), 8.40 (d, 1H), 8.20 (d, 1H), 7.85 (d, 1H), 7.74 (d, 1H), 7.60 (d, 1H), 5.19-5.17 (m, 1H), 3.84-3.69 (m, 2H), 2.99-2.95 (m, 1H), 2.82-2.76 (m, 5H), 2.56-2.50 (m, 3H), 2.40-2.37 (m, 1H), 1.97-1.84 (m, 1H), 1.18 (t, 3H). | $[M + H]^+$ = 433.15 |
| 29 | $^1H$ NMR (300 MHz, DMSO-$d_6$) δ 11.84 (s, 1H), 8.66 (dd, 1H), 8.38 (d, 1H), 8.14 (dd, 1H), 7.74 (d, 1H), 7.60 (d, 1H), 7.00 (dd, 1H), 5.44 (d, 1H), 3.72 (s, 2H), 2.91-2.67 (m, 3H), 2.59-2.52 (m, 2H), 2.47-2.26 (m, 2H), 1.93-1.76 (m, 1H), 1.18 (t, 3H). | $[M + H]^+$ = 376.05 |

Example 13

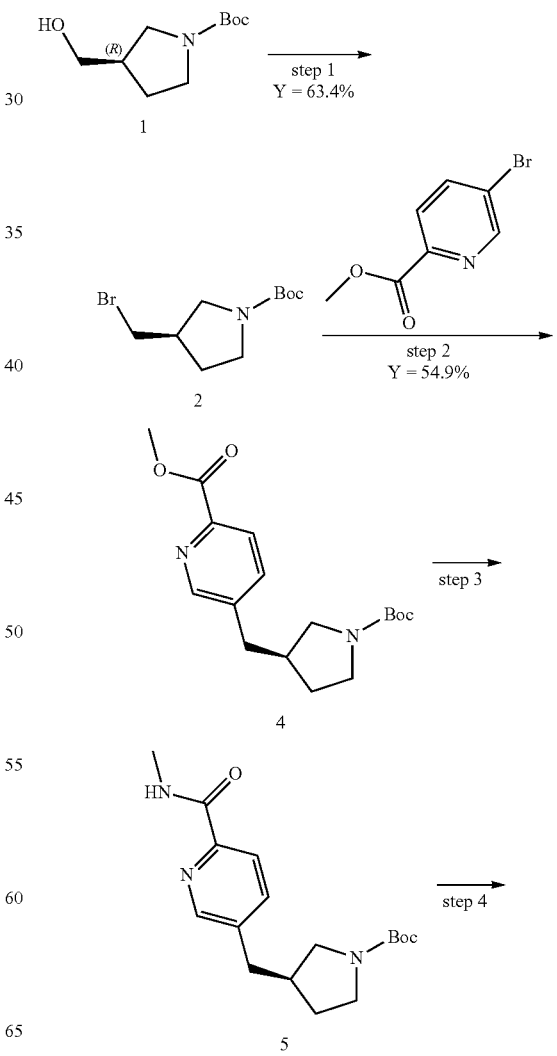

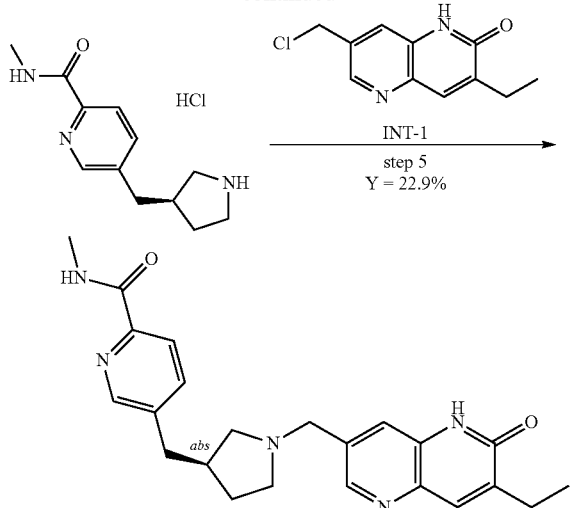

Example 13

Step 1: Preparation of tert-butyl(3R)-3-(bromomethyl)pyrrolidine-1-carboxylate To a stirred mixture of tert-butyl(3R)-3-(hydroxymethyl)pyrrolidine-1-carboxylate (3.00 g, 14.91 mmol, 1.00 equiv.) and CBr$_4$ (7.41 g, 22.34 mmol, 1.50 equiv.) in DCM (20 mL) was added a solution of PPh$_3$ (3.91 g, 14.91 mmol, 1.00 equiv.) in DCM (5 mL) dropwise at 0° C. under nitrogen atmosphere. The resulting mixture was stirred for 1 h at room temperature under nitrogen atmosphere. The reaction was monitored by TLC (PE:EA=3:1, R$_f$=0.4). The resulting mixture was concentrated under reduced pressure. The residue was purified by silica gel column chromatography to afford tert-butyl(3R)-3-(bromomethyl)pyrrolidine-1-carboxylate (2.5 g, 63.4%). $^1$H NMR (300 MHz, Chloroform-d) δ 3.70-3.66 (m, 1H), 3.59-3.52 (m, 1H), 3.49-3.48 (m, 1H), 3.48-3.34 (m, 2H), 3.21-3.14 (m, 1H), 2.75-2.60 (m, 1H), 2.18-2.10 (m, 1H), 1.90-1.70 (m, 1H), 1.54 (s, 9H).

Step 2: Preparation of methyl 5-{[(3R)-1-(tert-butoxycarbonyl)pyrrolidin-3-yl]methyl}pyridine-2-carboxylate A mixture of 1,2-dimethoxyethane dihydrochloride nickel (25 mg, 0.11 mmol, 0.10 equiv.) and 4-tert-butyl-2-(4-tert-butylpyridin-2-yl)pyridine (31 mg, 0.11 mmol, 0.10 equiv.) in DME (3 mL) was stirred for 1 h at room temperature under nitrogen atmosphere. The nickel mixture was added to a mixture of tert-butyl(3R)-3-(bromomethyl)pyrrolidine-1-carboxylate (300 mg, 1.14 mmol, 1.00 equiv.), methyl 5-bromopyridine-2-carboxylate (245 mg, 1.14 mmol, 1.00 equiv.), tris(trimethylsilyl)silane (282 mg, 1.14 mmol, 1.00 equiv.), Cs$_2$CO$_3$ (740 mg, 2.27 mmol, 2.00 equiv.) and Ir[dF(CF$_3$)ppy]$_2$(dtpby)PF$_6$ (38 mg, 0.03 mmol, 0.03 equiv.) at room temperature under nitrogen atmosphere. The reaction was stirred for 2 days and irradiated with blue LEDS (30 watts). The reaction was monitored by LCMS. The reaction was poured into water (20 mL). The aqueous layer was extracted with EtOAc (3×10 mL). The combined organic layers were concentrated under reduced pressure. The residue was purified by silica gel column chromatography to afford methyl 5-{[(3R)-1-(tert-butoxycarbonyl)pyrrolidin-3-yl]methyl}pyridine-2-carboxylate (200 mg, 54.9%). LC-MS: (ES+H, m/z): [M+H]$^+$=321.1. Optical rotation [a]$^{25}_D$ (c=0.5, MeOH): +17.6°; $^1$H NMR (400 MHz, DMSO-d$_6$) δ8.59 (dd, 1H), 8.07-7.95 (m, 1H), 7.85 (dd, 1H), 3.87 (s, 3H), 3.39-3.34 (m, 1H), 3.31-3.22 (m, 1H), 3.20-3.12 (m, 1H), 2.95-2.86 (m, 1H), 2.77 (t, 2H), 2.50-2.40 (m, 1H), 1.88-1.53 (m, 1H), 1.63-1.47 (m, 1H), 1.38 (s, 9H).

Step 3: Preparation of tert-butyl(3R)-3-{[6-(methylcarbamoyl)pyridin-3-yl]methyl}pyrrolidine-1-carboxylate To a stirred mixture of methyl 5-{[(3R)-1-(tert-butoxycarbonyl)pyrrolidin-3-yl]methyl}pyridine-2-carboxylate (190 mg, 0.66 mmol, 1.00 equiv.) in MeOH (2 mL) was added methylamine (2 mL, 25-30% wt in water) at room temperature under nitrogen atmosphere. The resulting mixture was stirred 1 h at room temperature under nitrogen atmosphere. The reaction was monitored by LCMS. The resulting mixture was concentrated under reduced pressure to afford tert-butyl(3R)-3-{[6-(methylcarbamoyl)pyridin-3-yl]methyl}pyrrolidine-1-carboxylate (190 mg, crude). LC-MS: (ES+H, m/z): [M+H]$^+$=320.3.

Step 4: Preparation of N-methyl-5-[(3R)-pyrrolidin-3-ylmethyl]pyridine-2-carboxamide, HCl Salt A mixture of tert-butyl(3R)-3-{[6-(methylcarbamoyl)pyridin-3-yl]methyl}pyrrolidine-1-carboxylate (190 mg, crude) in HCl(gas) in 1,4-dioxane (4M, 2 mL) was stirred for 0.5 h at room temperature. The reaction was monitored by LCMS. The mixture was concentrated under reduced pressure to afford N-methyl-5-[(3R)-pyrrolidin-3-ylmethyl]pyridine-2-carboxamide, HCl salt (190 mg, crude). LC-MS: (ES+H, m/z): [M+H]$^+$=220.1

Step 5: Preparation of 5-{[(3R)-1-[(7-ethyl-6-oxo-5H-1,5-naphthyridin-3-yl)methyl]pyrrolidin-3-yl]methyl}-N-methylpyridine-2-carboxamide A mixture of N-methyl-5-[(3R)-pyrrolidin-3-ylmethyl]pyridine-2-carboxamide, HCl salt (150 mg, crude), 7-(chloromethyl)-3-ethyl-1H-1,5-naphthyridin-2-one (150 mg, 0.68 mmol, 1.00 equiv.), DIEA (436 mg, 3.38 mmol, 5.00 equiv.) and KI (22 mg, 0.14 mmol, 0.20 equiv.) in ACN (5 mL) was stirred for 1 h at 80° C. under nitrogen atmosphere. The reaction was monitored by LCMS. The mixture was allowed to cool down to room temperature. The reaction was poured into water (30 mL). The aqueous layer was extracted with EtOAc (4×20 mL). The combined organic layers were concentrated under reduced pressure. The crude product (200 mg) was purified by Prep-HPLC, the pure fraction was concentrated then lyophilized to afford 5-{[(3R)-1-[(7-ethyl-6-oxo-5H-1,5-naphthyridin-3-yl)methyl]pyrrolidin-3-yl]methyl}-N-methylpyridine-2-carboxamide (62.6 mg, 22.9%). LC-MS: (ES+H, m/z): [M+H]$^+$=406.10. Optical rotation [a]$^{25}_D$ (c=0.5, MeOH): +18.4°; $^1$H NMR (400 MHz, DMSO-d$_6$) δ 11.83 (s, 1H), 8.69-8.66 (m, 1H), 8.47 (d, 1H), 8.36 (d, 1H), 7.92 (d, 1H), 7.81 (dd, 1H), 7.73 (s, 1H), 7.58 (d, 1H), 3.74-3.58 (m, 2H), 2.85-2.77 (m, 5H), 2.62-2.52 (m, 4H), 2.50-2.46 (m, 2H), 2.22-2.16 (m, 1H), 1.93-1.80 (m, 1H), 1.51-1.38 (m, 1H), 1.18 (t, 3H).

Example 14

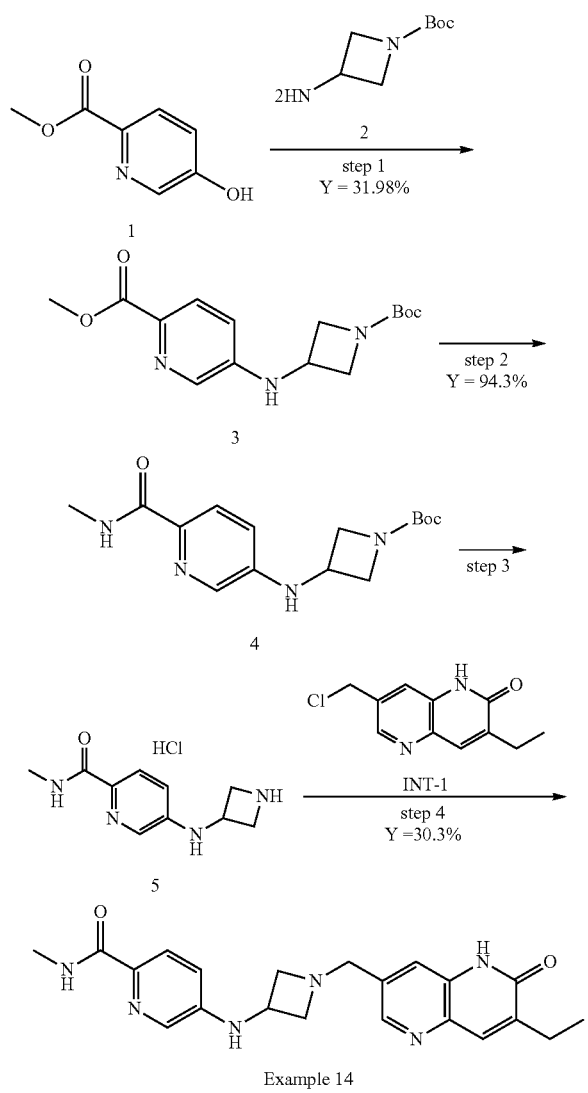

Example 14

Step 1: Preparation of methyl 5-{[1-(tert-butoxycarbonyl)azetidin-3-yl]amino}pyridine-2-carboxylate To a stirred solution of methyl 5-bromopyridine-2-carboxylate (2.00 g, 9.25 mmol, 1.00 equiv.) and tert-butyl 3-aminoazetidine-1-carboxylate (1.75 g, 10.18 mmol, 1.10 equiv.) in Toluene (20 mL) were added XantPhos (1.07 g, 1.85 mmol, 0.20 equiv.), $Pd_2(dba)_3$ (0.84 g, 0.90 mmol, 0.10 equiv.) and $Cs_2CO_3$ (9.05 g, 27.77 mmol, 3.00 equiv.) at room temperature. The resulting mixture was stirred for 2 h at 110° C. under nitrogen atmosphere. The resulting mixture was diluted with water (50 mL). The resulting mixture was extracted with EtOAc (3×50 mL). The combined organic layers were washed with brine (1×50 mL), dried over anhydrous $Na_2SO_4$. After filtration, the filtrate was concentrated under reduced pressure. The residue was purified by reversed combi-flash chromatography. This resulted in methyl 5-{[1-(tert-butoxycarbonyl)azetidin-3-yl]amino}pyridine-2-carboxylate (1.00 g, 31.98%). LC-MS: (ES+H, m/z): [M+H]$^+$=308.1. $^1$H NMR (400 MHz, DMSO-$d_6$) δ 8.00 (d, 1H), 7.83 (d, 1H), 7.37 (d, 1H), 6.87 (dd, 1H), 4.30-4.23 (m, 3H), 3.79 (m, 3H), 3.68 (m, 2H), 1.39 (s, 9H).

Step 2: Preparation of tert-butyl 3-{[6-(methylcarbamoyl)pyridin-3-yl]amino}azetidine-1-carboxylate To a stirred solution of methyl 5-{[1-(tert-butoxycarbonyl)azetidin-3-yl]amino}pyridine-2-carboxylate (500 mg, 1.62 mmol, 1.00 equiv.) in MeOH (5 mL) was added Methylamine (5 mL, 25-30% wt in water) at room temperature. The resulting mixture was stirred for 2 h at room temperature under nitrogen atmosphere. Desired product could be detected by LCMS. The solvent was removed under reduced pressure. The residue was purified by reversed combi-flash chromatography. This resulted in tert-butyl 3-{[6-(methylcarbamoyl)pyridin-3-yl]amino}azetidine-1-carboxylate (500 mg, 94.30%). LC-MS: (ES+H, m/z): [M+H]$^+$=307.1.

Step 3: Preparation of 5-(azetidin-3-ylamino)-N-methylpyridine-2-carboxamide, HCl Salt Into a 100 mL round-bottom flask were added tert-butyl 3-{[6-(methylcarbamoyl)pyridin-3-yl]amino}azetidine-1-carboxylate (500 mg, 1.63 mmol, 1.00 equiv.) and HCl (gas) in 1,4-dioxane (10 mL) at room temperature. The resulting mixture was stirred for 1 h at room temperature under nitrogen atmosphere. Desired product could be detected by LCMS. The resulting mixture was concentrated under vacuum. This resulted in 5-(azetidin-3-ylamino)-N-methylpyridine-2-carboxamide, HCl salt (400 mg, crude). The crude resulting mixture was used in the next step directly without further purification. LC-MS: (ES+H, m/z): [M+H]$^+$=207.2.

Step 4: Preparation of 5-({1-[(7-ethyl-6-oxo-5H-1,5-naphthyridin-3-yl)methyl]azetidin-3-yl}amino)-N-methylpyridine-2-carboxamide To a stirred solution of 5-(azetidin-3-ylamino)-N-methylpyridine-2-carboxamide, HCl salt (200 mg, crude) and 7-(chloromethyl)-3-ethyl-1H-1,5-naphthyridin-2-one (120 mg, 0.53 mmol, 1.00 equiv.) in ACN (5 mL) was added DIEA (348 mg, 2.69 mmol, 5.00 equiv.) and KI (9 mg, 0.05 mmol, 0.10 equiv.) at room temperature. The resulting mixture was stirred for additional 2 h at 80° C. Desired product could be detected by LCMS. The resulting mixture was concentrated under vacuum. The crude product was purified by Prep-HPLC, the pure fraction was concentrated under reduced pressure and lyophilized to afford 5-({1-[(7-ethyl-6-oxo-5H-1,5-naphthyridin-3-yl)methyl]azetidin-3-yl}amino)-N-methylpyridine-2-carboxamide (65.6 mg, 30.30%). LC-MS: (ES+H, m/z): [M+H]$^+$=393.2. $^1$H NMR (300 MHz, DMSO-$d_6$) δ 11.87 (s, 1H), 8.36 (d, 1H), 8.30 (d, 1H), 7.89 (d, 1H), 7.78-7.69 (t, 2H), 7.56 (s, 1H), 7.00-6.87 (m, 2H), 4.11 (q, 1H), 3.75-3.64 (m, 4H), 2.95 (t, 2H), 2.76 (d, 3H), 2.60-2.52 (m, 2H), 1.18 (t, 3H).

Example 15

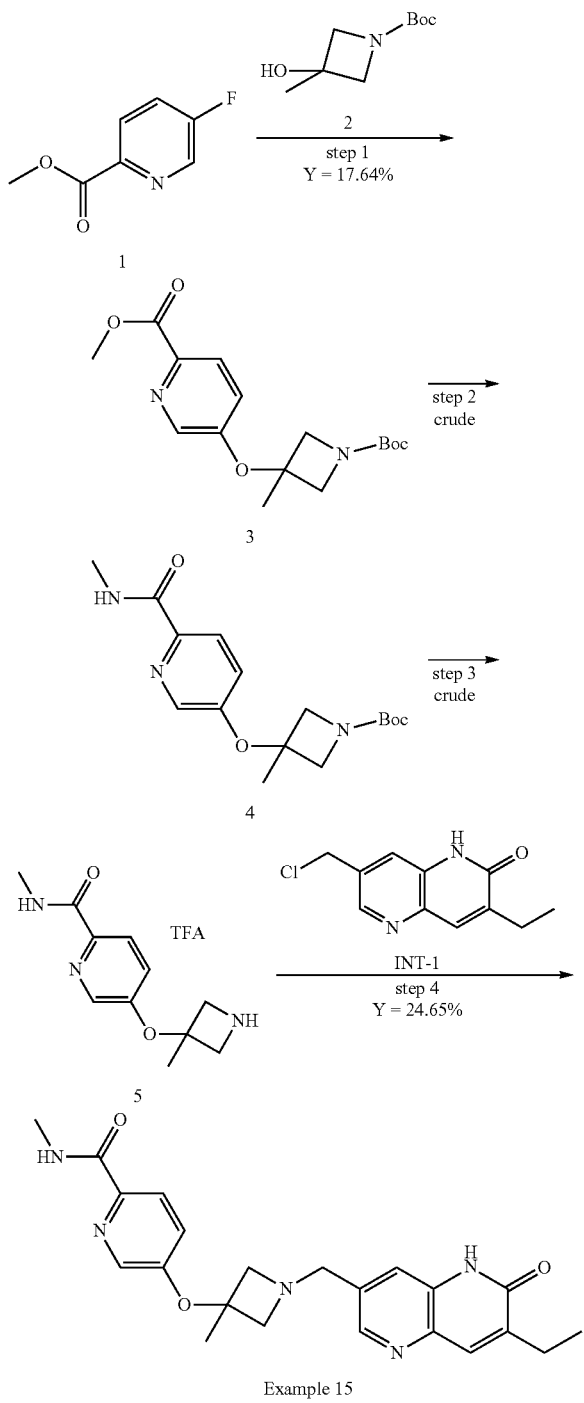

Example 15

Step 1: Preparation of methyl 5-{[1-(tert-butoxycarbonyl)-3-methylazetidin-3-yl]oxy}pyridine-2-carboxylate To a stirred solution of NaH (1.08 g, 27.08 mmol, 1.40 equiv., 60% wt) in DMF (40 mL) was added tert-butyl 3-hydroxy-3-methylazetidine-1-carboxylate (4.71 g, 25.14 mmol, 1.30 equiv.) in DMF (5 mL) dropwise at room temperature under nitrogen atmosphere. The above mixture was stirred for 30 min at room temperature under nitrogen atmosphere. Then to the resulting mixture was added methyl 5-fluoropyridine-2-carboxylate (3.00 g, 19.34 mmol, 1.00 equiv.) in DMF (5 mL) dropwise at room temperature. The resulting mixture was stirred for additional 2 h at room temperature. The reaction was monitored by LCMS. Desired product could be detected by LCMS. The reaction was quenched by the addition of MeOH (20 mL) at 0° C. The resulting mixture was diluted with EA (100 mL) and washed with water (3×30 mL). The organic layer was concentrated under vacuum. The residue was purified by reversed combiflash chromatography to afford methyl 5-{[1-(tert-butoxycarbonyl)-3-methylazetidin-3-yl]oxy}pyridine-2-carboxylate (1.1 g, 17.64%) as a white oil. LC-MS: (ES+H, m/z): [M+H]$^+$=323.2. $^1$H NMR (400 MHz, DMSO-d$_6$) δ 8.28 (d, 1H), 8.00 (d, 1H), 7.33 (dd, 1H), 4.10-4.02 (m, 4H), 3.85 (s, 3H), 1.65 (s, 3H), 1.39 (s, 9H).

Step 2: Preparation of tert-butyl 3-methyl-3-{[6-(methylcarbamoyl)pyridin-3-yl]oxy}azetidine-1-carboxylate To a stirred solution of methyl 5-{[1-(tert-butoxycarbonyl)-3-methylazetidin-3-yl]oxy}pyridine-2-carboxylate (500 mg, 1.55 mmol, 1.00 equiv.) in MeOH (5 mL) was added CH$_3$NH$_2$ (5 mL, 25.0-30.0% wt in water) dropwise at room temperature. The resulting mixture was stirred for 1 h at room temperature under nitrogen atmosphere. The reaction was monitored by LCMS. Desired product could be detected by LCMS. The resulting mixture was concentrated under vacuum to afford tert-butyl 3-methyl-3-((6-(methylcarbamoyl)pyridin-3-yl)oxy)azetidine-1-carboxylate (508 mg, crude). The crude product was used in the next step directly without further purification. LC-MS: (ES+H, m/z): [M+H]$^+$=322.2.

Step 3: Preparation of N-methyl-5-[(3-methylazetidin-3-yl)oxy]pyridine-2-carboxamide, TFA Salt To a stirred solution of tert-butyl 3-methyl-3-{[6-(methylcarbamoyl)pyridin-3-yl]oxy}azetidine-1-carboxylate (468 mg, 1.46 mmol, 1.00 equiv.) in DCM (6 mL) was added TFA (2 mL) dropwise at room temperature. The resulting mixture was stirred for 1 h at room temperature under nitrogen atmosphere. The reaction was monitored by LCMS. Desired product could be detected by LCMS. The resulting mixture was concentrated under vacuum to afford N-methyl-5-[(3-methylazetidin-3-yl)oxy]pyridine-2-carboxamide, TFA salt (396 mg, crude). The crude product was used in the next step directly without further purification. LC-MS: (ES+H, m/z): [M+H]$^+$=222.2.

Step 4: Preparation of 5-({1-[(7-ethyl-6-oxo-5H-1,5-naphthyridin-3-yl)methyl]-3-methylazetidin-3-yl}oxy)-N-methylpyridine-2-carboxamide To a stirred solution of N-methyl-5-[(3-methylazetidin-3-yl)oxy]pyridine-2-carboxamide, TFA salt (250 mg, crude) and 7-(chloromethyl)-3-ethyl-1H-1,5-naphthyridin-2-one (201 mg, 0.90 mmol, 1.00 equiv.) in MeCN (5 mL) were added DIEA (467 mg, 3.62 mmol, 4.00 equiv.) and KI (30 mg, 0.18 mmol, 0.20 equiv.) in portions at room temperature. The resulting mixture was stirred for 2 h at 80° C. under nitrogen atmosphere. The reaction was monitored by LCMS. Desired product could be detected by LCMS. The mixture was allowed to cool down to room temperature. The resulting mixture was filtered, the filter cake was washed with CH₂Cl₂/MeOH(10:1) (150 mL). The filtrate was concentrated under reduced pressure. The crude product (300 mg) was purified by Prep-HPLC, the pure fraction was concentrated then lyophilized to afford 5-({1-[(7-ethyl-6-oxo-5H-1,5-naphthyridin-3-yl)methyl]-3-methylazetidin-3-yl}oxy)-N-methylpyridine-2-carboxamide (90.8 mg, 24.65%). LC-MS: (ES+H, m/z): [M+H]⁺=408.15. ¹H NMR (400 MHz, DMSO-d₆) δ 11.85 (s, 1H), 8.54 (q, 1H), 8.37 (d, 1H), 8.13 (d, 1H), 7.92 (d, 1H), 7.73 (s, 1H), 7.56 (s, 1H), 7.28 (dd, 1H), 3.77 (s, 2H), 3.59-3.57 (m, 2H), 3.29-3.32 (m, 2H), 2.79 (d, 3H), 2.56-2.50 (m, 2H), 1.64 (s, 3H), 1.18-1.12 (t, 3H).

Example 16

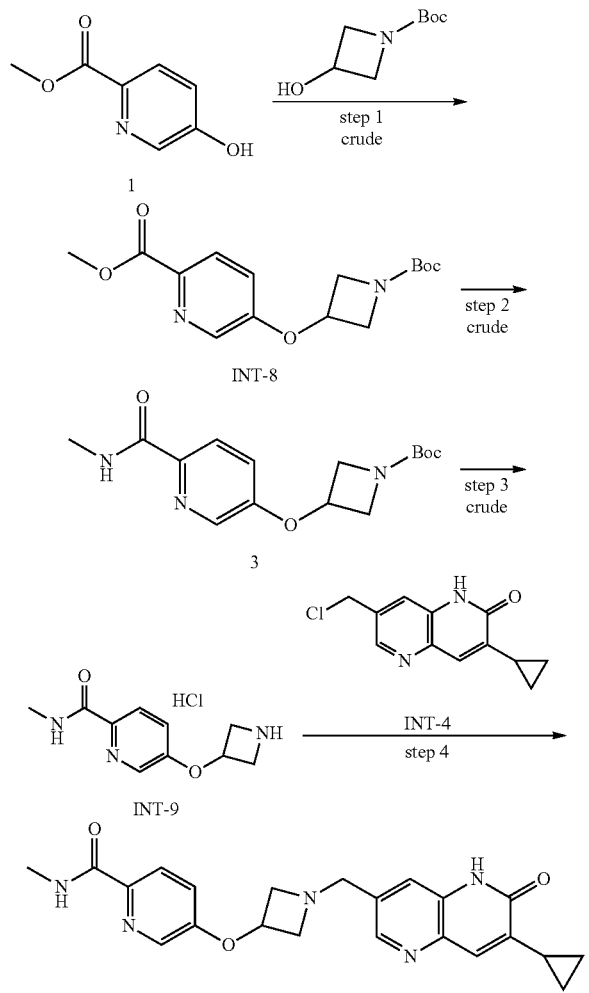

Example 16

Step 1: Preparation of methyl 5-{[1-(tert-butoxycarbonyl)azetidin-3-yl]oxy}pyridine-2-carboxylate A mixture of DEAD (5.69 g, 32.65 mmol, 5.00 equiv.) and PPh₃ (10.90 g, 39.18 mmol, 6.00 equiv.) in THF (100 ml) was stirred for 1 h at 0° C. under nitrogen atmosphere. The mixture was added to methyl 5-hydroxypyridine-2-carboxylate (1.00 g, 6.53 mmol, 1.00 equiv.) and tert-butyl 3-hydroxyazetidine-1-carboxylate (1.70 g, 9.79 mmol, 1.50 equiv.) in THF (100 ml) dropwise at 0° C. under nitrogen atmosphere. The resulting mixture was stirred for additional 2 h at room temperature under nitrogen atmosphere. The reaction was monitored by LCMS. The resulting mixture was concentrated under reduced pressure. The residue was purified by silica gel column chromatography to afford methyl 5-{[1-(tert-butoxycarbonyl)azetidin-3-yl]oxy}pyridine-2-carboxylate (4.5 g, crude, contained TPPO). LC-MS: (ES+H, m/z): [M+H]⁺=309.1.

Step 2: Preparation of tert-butyl 3-{[6-(methylcarbamoyl)pyridin-3-yl]oxy}azetidine-1-carboxylate A mixture of methyl 5-{[1-(tert-butoxycarbonyl)azetidin-3-yl]oxy}pyridine-2-carboxylate (3.50 g crude, contained TPPO) and CH₃NH₂ (20 mL, 25-30% wt in water) in MeOH (20 mL) was stirred for 2 h at room temperature under nitrogen atmosphere. The reaction was monitored by LCMS. The resulting mixture was concentrated under reduced pressure. The resulting mixture was added saturated NH₄Cl (100 mL), and extracted with DCM (3×100 mL). The combined organic layers were washed with brine (1×100 mL), and dried over anhydrous Na₂SO₄. After filtration, the filtrate was concentrated under reduced pressure. This result in tert-butyl 3-{[6-(methylcarbamoyl)pyridin-3-yl]oxy}azetidine-1-carboxylate (3.3 g, crude, contained TPPO). LC-MS: (ES+H, m/z): [M+H]⁺=308.1

Step 3: Preparation of 5-(azetidin-3-yloxy)-N-methylpyridine-2-carboxamide, HCl Salt A mixture of tert-butyl 3-{[6-(methylcarbamoyl)pyridin-3-yl]oxy}azetidine-1-carboxylate (3.30 g crude, contained TPPO) in DCM (10 mL) was added HCl (gas) in 1,4-dioxane (10 mL, 4M in dioxane) in portions at room temperature under nitrogen atmosphere. The resulting mixture was stirred for 2 h at room temperature under nitrogen atmosphere. The reaction was monitored by LCMS. The resulting mixture was concentrated under reduced pressure. The residue was purified by trituration with EtOAc (3×20 mL). The precipitated solids were collected by filtration and concentrated under reduced pressure. This result in 5-(azetidin-3-yloxy)-N-methylpyridine-2-carboxamide, HCl salt (600 mg, crude). LC-MS: (ES+H, m/z): [M+H]⁺=208.2.

Step 4: Preparation of 5-({1-[(7-cyclopropyl-6-oxo-5H-1,5-naphthyridin-3-yl)methyl]azetidin-3-yl}oxy)-N-methylpyridine-2-carboxamide A mixture of 7-(chloromethyl)-3-cyclopropyl-1H-1,5-naphthyridin-2-one (200 mg, 0.85 mmol, 1.00 equiv.), 5-(azetidin-3-yloxy)-N-methylpyridine-2-carboxamide, HCl salt (249 mg, crude), DIEA (550 mg, 4.26 mmol, 5.00 equiv.) and KI (28 mg, 0.17 mmol, 0.20 equiv.) in ACN (10 mL) was stirred for 2 h at 80° C. under nitrogen atmosphere. The reaction was monitored by LCMS. The resulting mixture was diluted with water (100 mL). The resulting mixture was extracted with EtOAc (3×100 mL). The combined organic layers was concentrated under reduced pressure. The residue was purified by flash chromatography. The resulting mixture was concentrated under reduced pressure. The residue was purified by trituration with MeOH (5 mL) at 50° C. The precipitated solids were collected by filtration and washed with MeOH (2×1 mL). The pure fractions were concentrated and lyophilized to afford 5-({1-[(7-cyclopropyl-6-oxo-5H-1,5-naphthyridin-3-yl)methyl]azetidin- 3yl}oxy)-N-methylpyridine-2-carboxamide (35.9 mg, 10.24%). LC-MS: (ES+H, m/z): [M+H]+=406.25. ¹H NMR (400 MHz, DMSO-d₆) δ 11.88 (s, 1H), 8.56 (q, 1H), 8.34 (d, 1H), 8.22 (d, 1H), 7.94 (d, 1H), 7.54 (d, 1H), 7.40 (q, 2H), 5.01 (p, 1H), 3.79-3.75 (m, 4H), 3.17-3.14 (m, 2H), 2.78 (d, 3H), 2.16-2.10 (m, 1H), 0.98-0.95 (m, 2H), 0.88-0.77 (m, 2H).

The following examples were made using similar procedures as shown for example 16:

| Ex | NMR | LCMS (ESI) m/z |
|---|---|---|
| 73 | ¹H NMR (400 MHz, DMSO-d₆) δ 11.90 (s, 1H), 8.53 (d, 1H), 8.34 (d, 1H), 8.20 (d, 1H), 7.95 (d, 1H), 7.55 (s, 1H), 7.41 (q, 2H), 5.02-4.91 (m, 1H), 3.84-3.70 (m, 4H), 3.16 (dd, 2H), 2.86 (qd, 1H), 2.08 (s, 1H), 0.97-0.96 (m, 2H) 0.82-0.81 (m, 2H), 0.70-0.61 (m, 4H). | [M + H]⁺ = 432.25 |

Example 17

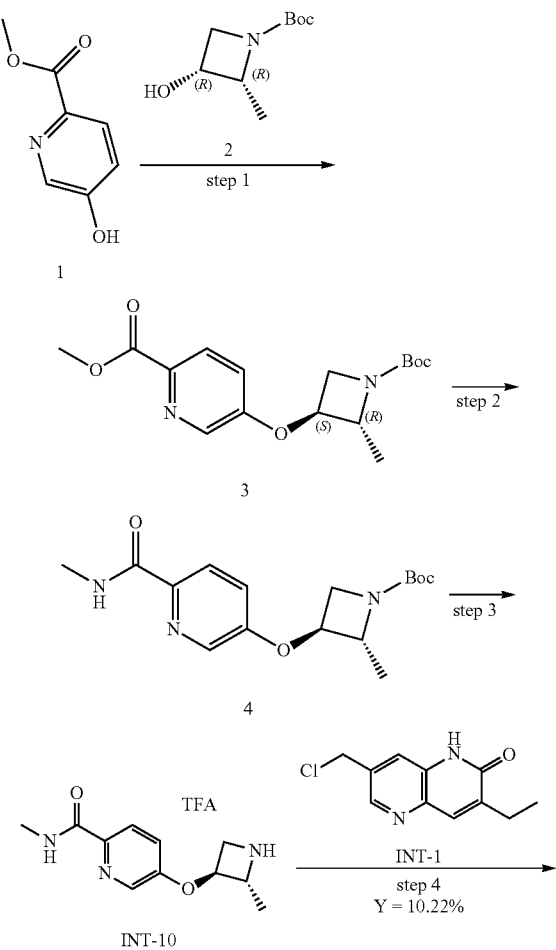

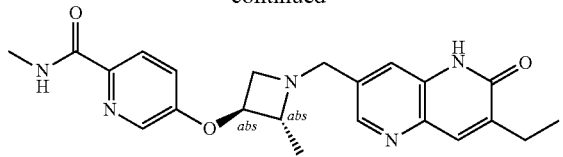

Example 17

Step 1: Preparation of methyl 5-{[(2R,3S)-1-(tert-butoxycarbonyl)-2-methylazetidin-3-yl]oxy}pyridine-2-carboxylate To a stirred mixture of tert-butyl(2R,3R)-3-hydroxy-2-methylazetidine-1-carboxylate (300 mg, 1.60 mmol, 1.00 equiv.) and methyl 5-hydroxypyridine-2-carboxylate (245 mg, 1.60 mmol, 1.00 equiv.) and PPh₃ (882 mg, 3.36 mmol, 2.10 equiv.) in THF (15 mL) were added DBAD (738 mg, 3.20 mmol, 2.00 equiv.) in THF (5 mL) dropwise at 0° C. under nitrogen atmosphere. The resulting mixture was stirred for 3 h at 60° C. under nitrogen atmosphere. The reaction was monitored by LCMS. The mixture was allowed to cool down to room temperature. The resulting mixture was concentrated under reduced pressure. The resulting mixture was diluted with EtOAc (100 mL). The residue was washed with H₂O (2×30 mL). dried over anhydrous Na₂SO₄. After filtration, the filtrate was concentrated under reduced pressure. The crude product methyl 5-{[(2R,3S)-1-(tert-butoxy carbonyl)-2-methylazetidin-3-yl]oxy}pyridine-2-carboxylate (1.5 g, crude) was used in the next step directly without further purification. LC-MS: (ES+H, m/z): [M+H]+=323.1.

Step 2: Preparation of tert-butyl(2R,3S)-2-methyl-3-{[6-(methylcarbamoyl)pyridin-3-yl]oxy}azetidine-1-carboxylate A solution of methyl 5-{[(2R,3S)-1-(tert-butoxycarbonyl)-2-methylazetidin-3-yl]oxy}pyridine-2-carboxylate (1.5 g, crude) and CH₃NH₂ (7 mL, 25%-30% wt in water) in CH₃CN (7 mL) was stirred overnight at room temperature under nitrogen atmosphere. The reaction was monitored by LCMS. The resulting mixture was concentrated under reduced pressure. The resulting mixture was diluted with ethyl acetate (100 mL). The residue was washed with NH₄Cl (aqueous) (2×30 mL), dried over anhydrous Na₂SO₄. After filtration, the filtrate was concentrated under reduced pressure. The crude product tert-butyl(2R,3S)-2-methyl-3-{[6-(methylcarbamoyl)pyridin-3-yl]oxy}azetidine-1-carboxylate (1.5 g, crude) was used in the next step directly without further purification. LC-MS: (ES+H, m/z): [M+H]+=322.1.

Step 3: Preparation of N-methyl-5-{[(2R,3S)-2-methylazetidin-3-yl]oxy}pyridine-2-carboxamide, TFA Salt To a stirred solution of tert-butyl(2R,3S)-2-methyl-3-{[6-(methylcarbamoyl)pyridin-3-yl]oxy}azetidine-1-carboxylate (1.5 g, crude) in DCM (10 mL) was added TFA (7 mL) dropwise at 0° C. under nitrogen atmosphere. The resulting mixture was stirred for 2 h at room temperature under nitrogen atmosphere. The reaction was monitored by LCMS. The resulting mixture was concentrated under reduced pressure. The residue was purified by trituration with ethyl ether/n-hexane (3×10 mL). The resulting mixture was concentrated under vacuum. The crude product N-methyl-5-{[(2R,3S)-2-methylazetidin-3-yl]oxy}pyridine-2-carboxamide, TFA salt (0.6 g, crude) was used in the next step directly without further purification.
LC-MS: (ES+H, m/z): [M+H]+=222.2.

Step 4: Preparation of 5-{[(2R,3S)-1-[(7-ethyl-6-oxo-5H-1,5-naphthyridin-3-yl)methyl]-2-methylazetidin-3-yl]oxy}-N-methylpyridine-2-carboxamide To a stirred mixture of N-methyl-5-{[(2R,3S)-2-methylazetidin-3-yl]oxy}pyridine-2-carboxamide, TFA salt (300 mg, 1.36 mmol, 1.00 equiv.) and 7-(chloromethyl)-3-ethyl-1H-1,5-naphthyridin-2-one (332 mg, 1.49 mmol, 1.10 equiv.) in $CH_3CN$ (10 mL) were added KI (45 mg, 0.27 mmol, 0.20 equiv.) and DIEA (700 mg, 5.42 mmol, 4.00 equiv.) dropwise at room temperature. The mixture was stirred for 2 h at 80° C. under nitrogen atmosphere. The reaction was monitored by LCMS. The mixture was allowed to cool down to RT. The resulting mixture was concentrated under reduced pressure. The residue was purified by silica gel column chromatography. The residue was purified by reversed combi-flash. The pure fraction was concentrated under vacuum then lyophilized to afford 5-{[(2R,3S)-1-[(7-ethyl-6-oxo-5H-1,5-naphthyridin-3-yl)methyl]-2-methylazetidin-3-yl]oxy}-N-methylpyridine-2-carboxamide (56.8 mg, 10.22%). LC-MS: (ES+H, m/z): [M+H]+=408.2. Optical rotation $[a]^{25}_D$ (c=0.5, MeOH): $^1H$ NMR (300 MHz, DMSO-$d_6$) δ 11.86 (s, 1H), 8.58-8.57 (q, 1H), 8.39 (d, 1H), 8.24 (d, 1H), 7.94 (d, 1H), 7.74 (s, 1H), 7.59 (s, 1H), 7.43 (dd, 1H), 4.65-4.59 (m, 1H), 3.95-3.90 (m, 1H), 3.84-3.80 (m, 1H), 3.66-3.62 (m, 1H), 3.39-3.34 (m, 1H), 2.80-2.78 (m, 4H), 2.58-2.51 (m, 2H), 1.21-1.16 (m, 6H).

The following examples were made using similar procedures as shown for example 17:

| Ex | NMR | LCMS (ESI) m/z |
|---|---|---|
| 38 | $^1H$ NMR (300 MHz, DMSO-$d_6$) δ 11.87 (s, 1H), 8.51-41 (m, 1H), 8.39 (d, 1H), 8.17-8.10 (m, 1H), 7.75 (s, 1H), 7.58 (d, 1H), 7.46-7.36 (m, 1H), 4.71-4.60 (m, 1H), 3.93 (d, 1H), 3.84 (t, 1H), 3.64 (d, 1H), 3.43-3.35 (m, 1H), 2.82-2.70 (m, 4H), 2.59-2.51 (m, 2H), 1.30-1.04 (m, 6H). 19F NMR (282 MHz, DMSO-$d_6$) δ-118.37. | [M + H]+ = 426.05 |
| 39 | $^1H$ NMR (300 MHz, DMSO-$d_6$) δ 11.86 (s, 1H), 8.55 (s, 1H), 8.39 (d, 1H), 8.24 (d, 1H), 7.95 (d, 1H), 7.74 (s, 1H), 7.59 (d, 1H), 7.43 (dd, 1H), 4.64-4.59 (m, 1H), 3.97-3.87 (m, 1H), 3.81 (t, 1H), 3.68-3.60 (m, 1H), 3.43-3.36 (m, 1H), 2.79 (t, 1H), 2.59-2.52 (m, 2H), 1.24-1.13 (m, 6H). | [M + H]+ = 411.20 |
| 41 | $^1H$ NMR (300 MHz, DMSO-$d_6$) δ 11.88 (s, 1H), 8.57 (d, 1H), 8.36 (d, 1H), 8.24 (d, 1H), 7.94 (d, 1H), 7.57 (s, 1H), 7.48-7.38 (m, 2H), 4.74-4.62 (m, 1H), 3.92 (d, 1H), 3.81 (t, 1H), 3.63 (d, 1H), 3.38 (d, 1H), 2.83-2.74 (m, 4H), 2.18-2.10 (m, 1H), 1.20 (d, 3H), 1.12-0.92 (m, 2H), 0.87-0.79 (m, 2H). | [M + H]+ = 420.2 |
| 42 | $^1H$ NMR (300 MHz, DMSO-$d_6$) δ 11.89 (s, 1H), 8.54-8.52 (d, 1H), 8.36 (d, 1H), 8.21-8.20 (m, 1H), 7.96-7.93 (m, 1H), 7.57 (d, 1H), 7.45-7.41 (m, 2H), 4.64-4.58 (m, 1H), 3.93-3.89 (d, 1H), 3.82-3.78 (t, 1H), 3.65-3.60 (d, 1H), 3.38-3.33 (m, 1H), 2.90-2.84 (m, 1H), 2.80-2.75 (t, 1H), 2.17-2.11 (m, 1H), 1.23-1.18 (m, 3H), 1.00-0.94 (m, 2H), 0.85-0.80 (m, 2H), 0.68-0.64 (m, 4H). | [M + H]+ = 446.20 |
| 45 | $^1H$ NMR (300 MHz, DMSO-$d_6$) δ 11.86 (s, 1H), 8.54 (s, 1H), 8.38 (d, 1H), 8.23 (d, 1H), 7.95 (d, 1H), 7.76-7.72 (m, 1H), 7.62-7.54 (m, 1H), 7.45-7.42 (m, 1H), 4.61 (q, 1H), 3.83-3.78 (m, 1H), 3.41-3.37 (m, 1H), 2.79 (t, 1H), 2.58-2.52 (m, 2H), 1.23-1.16 (m, 6H). | [M + H]+ = 413.25 |
| 46 | $^1H$ NMR (400 MHz, DMSO-$d_6$) δ 12.05 (s, 1H), 8.58 (q, 1H), 8.27 (s, 1H), 8.22 (d, 1H), 7.94 (d, 1H), 7.42 (dd, 1H), 5.80-5.76 (m, 1H), 4.62-4.52 (m, 1H), 3.84-3.79 (m, 1H), 3.78-3.72 (m, 1H), 3.58-3.47 (m, 1H), 3.35-3.31 (m, 1H), 2.83-2.76 (m, 4H), 2.40-2.30 (m, 2H), 1.21 (d, 3H), 1.10 (t, 3H). | [M + H]+ = 397.15 |
| 50 | $^1H$ NMR (300 MHz, DMSO-$d_6$) δ 11.86 (s, 1H), 8.57 (d, 1H), 8.38 (s, 1H), 8.24 (d, 1H), 7.94 (d, 1H), 7.82 (d, 1H), 7.58 (s, 1H), 7.43 (dd, 1H), 4.61 (q, 1H), 3.92 (d, 1H), 3.81 (t, 1H), 3.64 (d, 1H), 3.41-3.37 (m, 1H), 2.86 (d, 4H), 2.14 (s, 3H), 1.27 (d, 3H). | [M + H]+ = 394.20 |
| 51 | $^1H$ NMR (300 MHz, DMSO-$d_6$) δ 11.85 (s, 1H), 8.38 (s, 1H), 7.74 (s, 1H), 7.58 (s, 1H), 7.10 (t, 2H), 6.86-6.81 (m, 2H), 4.38 (q, 1H), 3.90 (d, 1H), 3.76 (t, 1H), 3.62 (d, 1H), 3.34-3.25 (m, 1H), 2.72 (t, 1H), 2.54 (d, 2H), 1.20-1.15 (m, 6H). $^{19}F$ NMR (282 MHz, DMSO-$d_6$) δ-123.37. | [M + H]+ = 368.20 |
| 52 | $^1H$ NMR (400 MHz, DMSO-$d_6$) δ 11.89 (s, 1H), 8.51-8.33 (m, 2H), 8.16-8.10 (m, 1H), 7.84-7.81 (m, 1H), 7.58 (d, 1H), 7.41 (dd, 1H), 4.65 (q, 1H), 3.97-3.79 (m, 2H), 3.67-3.60 (m, 1H), 3.41-3.35 (m, 1H), 2.80-2.73 (m, 4H), 2.15-2.12 (m, 3H), 1.19 (d, 3H). $^{19}F$ NMR (282 MHz, DMSO-$d_6$) δ-118.356. | [M + H]+ = 412.15 |
| 53 | $^1H$ NMR (300 MHz, DMSO-$d_6$) δ 11.87 (s, 1H), 8.53 (d, 1H), 8.38 (d, 1H), 8.21 (d, 1H), 7.94 (d, 1H), 7.83 (d, 1H), 7.58 (s, 1H), 7.44 (dd, 1H), 4.61 (q, 1H), 3.92 (d, 1H), 3.81 (t, 1H), 3.64 (d, 1H), 3.37 (t, 1H), 2.90-2.76 (m, 2H), 2.14 (d, 3H), 1.20 (d, 3H), 0.72-0.59 (m, 4H). | [M + H]+ = 420.2 |
| 59 | $^1H$ NMR (400 MHz, DMSO-$d_6$) δ 12.30 (s, 1H), 8.57 (d, 1H), 8.23 (s, 1H), 7.95 (d, 1H), 7.51-7.31 (m, 3H), 4.77-4.53 (m, 1H), 3.88-3.69 (m, 3H), 3.39 (d, 1H), 2.80 (m, 6H), 1.22 (m, 6H). $^{19}F$ NMR (282 MHz, DMSO-$d_6$) δ-124.64. | [M + H]+ = 426.15 |
| 62 | $^1H$ NMR (300 MHz, DMSO-$d_6$) δ 11.86 (s, 1H), 8.37 (d, 1H), 7.83-7.82 (m, 2H), 7.58 (d, 1H), 7.56-7.50 (m, 1H), 7.11 (dd, 1H), 4.53-4.47 (m, 1H), 3.91 (d, 1H), 3.78 (t, 1H), 3.62 (d, 1H), 3.34 (d, 1H), 2.75 (t, 1H), 2.14 (s, 3H), 1.17 (d, 3H). $^{19}F$ NMR (282 MHz, DMSO-$d_6$) δ-77.81. | [M + H]+ = 355.15 |
| 64 | $^1H$ NMR (400 MHz, DMSO-$d_6$) δ 11.85 (s, 1H), 8.43-8.23 (m, 2H), 7.80-7.56 (m, 4H), 6.90 (d, 2H), 4.54-4.41 (d, 1H), 3.99-3.74 (m, 2H), 3.63 (d, 1H), 3.38-3.31 (m, 1H), 2.79-2.66 (m, 4H), 2.58-2.51 (m, 2H), 2.19-2.03 (m, 6H). | [M + H]+ = 407.30 |
| 65 | $^1H$ NMR (300 MHz, DMSO-$d_6$) δ 11.86 (s, 1H), 8.40 (d, 1H), 7.84-7.72 (m, 2H), 7.59 (d, 1H), 7.57-7.46 (m, 1H), 7.11 (dd, 1H), 4.65-4.55 (m, 1H), 3.98-3.88 (m, 1H), 3.79 (t, 1H), 3.66 (d, 1H), 3.39 (d, 1H), 2.80 (t, 1H), 2.61-2.52 (m, 2H), 1.28-1.17 (m, 6H). $^{19}F$ NMR (377 MHz, DMSO-$d_6$) δ-121.31. | [M + H]+ = 393.05 |
| 67 | $^1H$ NMR (300 MHz, DMSO-$d_6$) δ 11.85 (s, 1H), 8.59 (t, 1H), 8.39 (d, 1H), 8.24 (d, 1H), 7.95 (d, 1H), 7.74 (s, 1H), 7.59 (d, 1H), 7.44 (dd, 1H), 4.62 (q, 1H), 3.93 (d, 1H), 3.82 (t, 1H), 3.65 (d, 1H), 3.39 (q, 1H), 3.32-3.24 (m, 2H), 2.79 (t, 1H), 2.61-2.52 (m, 2H), 1.24-1.15 (m, 6H), 1.10 (t, 3H). | [M-H]+ = 420.05 |

-continued

| Ex | NMR | LCMS (ESI) m/z |
|---|---|---|
| 68 | $^1$H NMR (300 MHz, DMSO-d$_6$) δ 11.85 (s, 1H), 8.38 (s, 1H), 7.83 (t, 1H), 7.74 (s, 1H), 7.58 (d, 1H), 7.07 (d, 1H), 6.91 (d, 1H), 4.60 (s, 1H), 3.94-3.83 (m, 2H), 3.66-3.62 (m, 1H), 3.45-3.35 (m, 1H), 2.78-2.76 (m, 1H), 2.57-2.55 (m, 2H), 1.21-1.16 (m, 6H). $^{19}$F NMR (282 MHz, DMSO-d$_6$) δ-105.92. | [M + H]$^+$ = 393.05 |
| 70 | $^1$H NMR (300 MHz, DMSO-d$_6$) δ 12.32 (s, 1H), 8.62-8.55 (m, 1H), 8.52 (d, 1H), 8.24 (d, 1H), 8.16 (s, 1H), 7.95 (d, 1H), 7.68 (d, 1H), 7.44 (dd, 1H), 6.98 (t, 1H), 4.68-4.60 (m, 1H), 4.03-3.95 (m, 1H), 3.88-3.81 (m, 1H), 3.75-3.66 (m, 1H), 3.46-3.38 (m, 1H), 2.87-2.81 (m, 1H), 2.79 (d, 3H), 1.22 (d, 3H). $^{19}$F NMR (282 MHz, DMSO-d$_6$) δ-119.33. | [M + H]$^+$ = 430.20 |
| 71 | $^1$H NMR (400 MHz, DMSO-d$_6$) δ 11.87 (s, 1H), 8.54 (d, 1H), 8.38 (d, 1H), 8.21 (d, 1H), 7.94 (d, 1H), 7.74 (s, 1H), 7.58 (d, 1H), 7.43 (dd, 1H), 4.61 (q, 1H), 3.80 (t, 1H), 3.41-3.34 (m, 1H), 2.90-2.82 (m, 1H), 2.78 (t, 1H), 2.55 (q, 2H), 1.22-1.15 (m, 6H), 0.70-0.60 (m, 4H). | [M + H]$^+$ = 436.25 |
| 74 | $^1$H NMR (300 MHz, DMSO-d$_6$) δ 11.86 (s, 1H), 8.63 (s, 1H), 8.37 (d, 1H), 8.20 (d, 1H), 7.93 (d, 1H), 7.82 (d, 1H), 7.58 (d, 1H), 7.42 (dd, 1H), 4.60 (q, 1H), 3.91 (d, 1H), 3.81 (t, 1H), 3.64 (d, 1H), 3.48-3.40 (m, 1H), 2.78 (t, 1H), 2.13 (d, 3H), 1.34 (s, 3H), 1.19 (d, 3H), 0.74 (q, 2H), 0.60 (q, 2H). | [M + H]$^+$ = 434.25 |
| 77 | $^1$H NMR (400 MHz, DMSO-d$_6$) δ 12.45 (s, 1H), 8.56 (d, 1H), 8.47 (d, 1H), 8.28 (d, 1H), 8.23 (d, 1H), 7.94 (d, 1H), 7.65 (d, 1H), 7.43 (dd, 1H), 4.62 (q, 1H), 3.96 (d, 1H), 3.83 (t, 1H), 3.67 (d, 1H), 3.39 (t, 1H), 2.80 (dd, 4H), 1.21 (d, 3H). | [M + H]$^+$ = 414.10 |
| 79 | $^1$H NMR (400 MHz, DMSO-d$_6$) δ 11.84 (s, 1H), 8.65 (d, 1H), 8.39 (d, 1H), 8.19 (d, 1H), 7.73 (d, 2H), 7.59 (s, 1H), 4.75 (q, 1H), 3.94 (d, 1H), 3.82 (t, 1H), 3.67 (d, 1H), 3.45 (p, 1H), 2.92-2.82 (m, 2H), 2.54 (dd, 2H), 1.25-1.14 (m, 6H), 0.68 (d, 4H). | [M + H]$^+$ = 459.10 |
| 80 | $^1$H NMR (400 MHz, DMSO-d$_6$) δ 11.87 (s, 1H), 9.12 (d, 1H), 8.38 (s, 1H), 8.27 (d, 1H), 7.96 (d, 1H), 7.82 (s, 1H), 7.59 (s, 1H), 7.46 (dd, 1H), 4.63 (d, 1H), 4.35-4.25 (m, 1H), 3.92 (d, 1H), 3.82 (d, 1H), 3.64 (d, 1H), 3.38-3.36 (m, 1H), 2.95-2.85 (m, 4H), 2.83-2.79 (m, 1H), 2.68 (s, 3H), 1.21 (d, 3H). $^{19}$F NMR (377 MHz, DMSO-d$_6$) δ-82.21, -97.78. | [M + H]$^+$ = 470.10 |
| 81 | $^1$H NMR (400 MHz, DMSO-d$_6$): δ 11.85 (s, 1H), 8.91 (d, 1H), 8.38 (d, 1H), 8.25 (d, 1H), 7.94 (d, 1H), 7.82 (d, 1H), 7.61-7.56 (m, 1H), 7.44 (dd, 1H), 4.90-4.76 (m, 1H), 4.62 (q, 1H), 4.06-3.86 (m, 2H), 3.81 (t, 1H), 3.64 (d, 1H), 3.39-3.31 (m, 1H), 2.79 (t, 1H), 2.59-2.70 (m, 2H), 2.30-2.47 (m, 2H), 2.13 (d, 3H), 1.20 (d, 3H). 19F NMR (377 MHz, DMSO-d$_6$) δ-167.17. | [M + H]$^+$ = 452.20 |
| 82 | $^1$H NMR (300 MHz, DMSO-d$_6$) δ 11.86 (s, 1H), 8.95 (d, 1H), 8.37 (d, 1H), 8.25 (d, 1H), 7.94 (d, 1H), 7.82 (s, 1H), 7.58 (s, 1H), 7.42 (d, 1H), 5.44-5.22 (m, 1H), 4.62 (q, 2H), 3.94 (d, 1H), 3.82 (t, 1H), 3.64 (d, 1H), 3.37 (t, 1H), 2.79 (t, 1H), 2.55-2.51 (m, 1H), 2.48 (s, 2H), 2.14 (d, 3H), 1.20 (d, 3H). | [M + H]$^+$ = 452.20 |
| 84 | $^1$H NMR (400 MHz, DMSO-d$_6$) δ 11.83 (s, 1H), 8.53 (dd, J = 5.0 Hz, 1H), 8.46 (d, J = 1.7 Hz, 1H), 8.20 (dd, J = 13.2, 2.4 Hz, 2H), 7.94 (d, J = 8.7 Hz, 1H), 7.75 (d, J = 1.8 Hz, 1H), 7.44 (dd, J = 8.7, 2.9 Hz, 1H), 7.12 (d, J = 2.0 Hz, 1H), 4.62 (q, J = 5.9 Hz, 1H), 3.96 (d, J = 13.5 Hz, 1H), 3.83 (t, J = 6.5 Hz, 1H), 3.68 (d, J = 13.5 Hz, 1H), 3.40 (q, J = 6.0 Hz, 1H), 2.88-2.82 (m, 1H), 2.81 (t, J = 6.8 Hz, 1H), 1.21 (d, J = 6.1 Hz, 3H), 0.70-0.61 (m, 4H). | [M + H]$^+$ = 446.20 |
| 85 | $^1$H NMR (400 MHz, DMSO-d$_6$) δ 11.86 (s, 1H), 8.72 (d, J = 8.5 Hz, 1H), 8.37 (d, J = 1.9 Hz, 1H), 8.24 (d, J = 2.8 Hz, 1H), 7.93 (d, J = 8.7 Hz, 1H), 7.82 (s, 1H), 7.58 (d, J = 1.8 Hz, 1H), 7.43 (dd, J = 8.7, 2.9 Hz, 1H), 4.61 (q, 1H), 4.43 (p, 1H), 3.92 (d, J = 13.5 Hz, 1H), 3.81 (t, J = 6.4 Hz, 1H), 3.64 (d, J = 13.5 Hz, 1H), 3.35-3.42 (m, 1H), 2.79 (t, J = 6.7 Hz, 1H), 2.23-2.06 (m, 7H), 1.61-1.66 (m, 2H), 1.20 (d, J = 6.1 Hz, 3H). | [M + H]$^+$ = 434.25 |
| 89 | $^1$H NMR (400 MHz, DMSO-d$_6$) δ 11.86 (s, 1H), 8.94 (t, J = 3.6 Hz, 1H), 8.38 (d, J = 1.9 Hz, 1H), 8.26 (d, J = 2.8 Hz, 1H), 7.97 (d, J = 8.7 Hz, 1H), 7.82 (t, J = 1.0 Hz, 1H), 7.58 (d, J = 1.9 Hz, 1H), 7.46 (dd, J = 8.7, 2.9 Hz, 1H), 4.64 (q, J = 5.9 Hz, 1H), 3.92 (d, J = 13.5 Hz, 1H), 3.81 (t, J = 6.5 Hz, 1H), 3.64 (d, J = 13.5 Hz, 1H), 3.48-3.34 (m, 2H), 2.79 (t, J = 6.7 Hz, 1H), 2.13 (d, J = 1.3 Hz, 3H), 1.96-1.84 (m, 2H), 1.20 (d, J = 6.2 Hz, 3H). $^{19}$F NMR (282 MHz, DMSO-d$_6$) δ-131.08, -131.64, -143.89, -144.45. | [M + H]$^+$ = 456.10 |
| 90 | $^1$H NMR (400 MHz, DMSO-d$_6$) δ 11.87 (s, 1H), 8.94 (t, J = 3.7 Hz, 1H), 8.38 (d, J = 1.8 Hz, 1H), 8.26 (d, J = 2.8 Hz, 1H), 7.98 (d, J = 8.7 Hz, 1H), 7.82 (d, J = 1.7 Hz, 1H), 7.58 (d, J = 1.9 Hz, 1H), 7.46 (dd, J = 8.7, 2.9 Hz, 1H), 4.63 (q, J = 5.9 Hz, 1H), 3.92 (d, J = 13.5 Hz, 1H), 3.82 (t, J = 6.4 Hz, 1H), 3.64 (d, J = 13.5 Hz, 1H), 3.48-3.34 (m, 2H), 2.79 (t, J = 6.7 Hz, 1H), 2.13 (d, J = 1.3 Hz, 3H), 1.96-1.84 (m, 2H), 1.20 (d, J = 6.2 Hz, 3H). $^{19}$F NMR (282 MHz, DMSO-d$_6$) δ-131.09, -131.64, -143.88, -144.44. | [M + H]$^+$ = 456.20 |
| 91 | $^1$H NMR (300 MHz, DMSO-d$_6$): δ 12.44 (s, 1H), 8.56 (q, J = 4.7 Hz, 1H), 8.23 (d, J = 2.8 Hz, 1H), 7.94 (d, J = 8.7 Hz, 1H), 7.50 (d, J = 8.3 Hz, 1H), 7.43 (dd, J = 8.7, 2.9 Hz, 1H), 7.26 (t, J = 7.7 Hz, 1H), 4.58 (d, J = 6.0 Hz, 1H), 3.99-3.76 (m, 2H), 3.69 (d, J = 13.4 Hz, 1H), 3.41-3.35 (m, 1H), 2.79 (d, J = 4.9 Hz, 4H), 2.41 (s, 3H), 1.20 (d, J = 6.2 Hz, 3H). $^{19}$F NMR (377 MHz, DMSO-d$_6$) δ-136.10. | [M + H]$^+$ = 412.20 |
| 92 | $^1$H NMR (300 MHz, DMSO-d$_6$) δ 12.32 (s, 1H), 8.71 (d, J = 8.5 Hz, 1H), 8.51 (d, J = 1.8 Hz, 1H), 8.25 (d, J = 2.8 Hz, 1H), 8.15 (d, J = 8.7 Hz, 1H), 7.93 (d, J = 8.7 Hz, 1H), 7.67 (s, 1H), 7.44 (dd, J = 8.7, 2.9 Hz, 1H), 7.17-6.80 (m, 1H), 4.67-4.57 (m, 1H), 4.42 (q, J = 8.4 Hz, 1H), 3.98 (d, J = 13.9 Hz, 1H), 3.84 (t, J = 6.5 Hz, 1H), 3.70 (d, J = 13.9 Hz, 1H), 3.46-3.36 (m, 1H), 2.82 (t, J = 6.7 Hz, 1H), 2.14-2.50 (m, 4H), 1.64-1.60 (m, 2H), 1.22 (d, J = 6.2 Hz, 3H). $^{19}$F NMR (282 MHz, DMSO-d$_6$) δ-119.33. | [M + H]$^+$ = 470.10 |
| 93 | $^1$H NMR (400 MHz, DMSO-d$_6$) δ 12.43 (s, 1H), 8.57 (q, J = 4.8 Hz, 1H), 8.22 (d, J = 2.8 Hz, 1H), 7.94 (d, J = 8.6 Hz, 1H), 7.52 (d, J = 8.3 Hz, 1H), 7.43 (dd, J = 8.7, 2.9 Hz, 1H), 7.26 (t, J = 8.3 Hz, 1H), 4.58 (q, J = 5.9 Hz, 1H), 3.90 (d, J = 13.3 Hz, 1H), 3.82 (t, J = 6.3 Hz, 1H), 3.69 (d, J = 13.3 Hz, 1H), 3.37 (m, 1H), 2.86-2.75 (m, 6H), 1.27-1.14 (m, 6H). $^{19}$F NMR (377 MHz, DMSO-d$_6$) δ-136.10. | [M + H]$^+$ = 426.20 |
| 94 | $^1$H NMR (300 MHz, DMSO-d$_6$) δ 12.44 (s, 1H), 8.52 (d, J = 5.0 Hz, 1H), | [M + H]$^+$ = 438.15 |

| Ex | NMR | LCMS (ESI) m/z |
|---|---|---|
|  | 8.20 (d, J = 2.8 Hz, 1H), 7.94 (d, J = 8.7 Hz, 1H), 7.57-7.36 (m, 2H), 7.25 (t, J = 9.0 Hz, 1H), 4.58 (q, J = 5.9 Hz, 1H), 3.91 (d, J = 13.3 Hz, 1H), 3.81 (t, J = 6.4 Hz, 1H), 3.69 (d, J = 13.3 Hz, 1H), 3.38-3.32 (m, 1H), 2.92-2.70 (m, 2H), 2.41 (s, 3H), 1.20 (d, J = 6.2 Hz, 3H), 0.80-0.42 (m, 4H). $^{19}$F NMR (282 MHz, DMSO-d$_6$) δ-136.10. |  |
| 95 | $^1$H NMR (400 MHz, DMSO-d$_6$) δ 12.43 (s, 1H), 8.52 (d, J = 5.0 Hz, 1H), 8.19 (d, J = 2.8 Hz, 1H), 7.93 (d, J = 8.7 Hz, 1H), 7.50 (d, J = 8.3 Hz, 1H), 7.43 (dd, J = 8.7, 2.9 Hz, 1H), 7.22 (t, J = 7.6 Hz, 1H), 4.57 (q, J = 5.9 Hz, 1H), 3.80 (t, J = 6.3 Hz, 1H), 3.69 (d, J = 13.2 Hz, 1H), 3.38-3.33 (m, 1H), 2.94-2.74 (m, 4H), 1.36-1.05 (m, 6H), 0.69-0.61 (m, 4H). $^{19}$F NMR (377 MHz, DMSO-d$_6$) δ-136.09. | [M + H]$^+$ = 452.15 |
| 97 | $^1$H NMR (300 MHz, DMSO-d$_6$) δ 12.44 (s, 1H), 8.56 (d, J = 4.9 Hz, 1H), 8.22 (d, J = 2.8 Hz, 1H), 7.94 (d, J = 8.7 Hz, 1H), 7.46-7.37 (m, 2H), 7.22 (dd, J = 8.3, 7.1 Hz, 1H), 4.57 (q, J = 6.1 Hz, 1H), 3.89 (d, J = 13.3 Hz, 1H), 3.80 (t, J = 6.4 Hz, 1H), 3.67 (d, J = 13.2 Hz, 1H), 3.36-3.33 (m, 1H), 2.78-2.70 (m, 5H), 1.19 (d, J = 6.1 Hz, 3H), 1.12-1.02 (m, 4H). $^{19}$F NMR (282 MHz, DMSO-d$_6$) δ-136.11. | [M + H]$^+$ = 438.20 |
| 98 | $^1$H NMR (300 MHz, DMSO-d$_6$) δ 12.43 (s, 1H), 8.46 (q, J = 4.6 Hz, 1H), 7.85 (d, J = 8.2, 2.6 Hz, 1H), 7.68-7.56 (m, 1H), 7.49 (d, J = 8.3 Hz, 1H), 7.26 (t, J = 7.7 Hz, 1H), 4.59 (q, J = 5.9 Hz, 1H), 3.94-3.66 (m, 3H), 3.43-3.37 (m, 1H), 2.85-2.75 (m, 4H), 2.41 (s, 3H), 1.20 (d, J = 6.2 Hz, 3H). $^{19}$F NMR (300 MHz, DMSO-d$_6$) δ-84.70, −136.08. | [M + H]$^+$ = 430.15 |
| 100 | $^1$H NMR (300 MHz, DMSO-d$_6$) δ 12.43 (s, 1H), 8.47 (q, J = 4.9 Hz, 1H), 7.85 (d, J = 8.2 Hz, 1H), 7.63-7.51 (m, 2H), 7.26 (t, J = 8.3, 7.0 Hz, 1H), 4.60 (q, J = 5.9 Hz, 1H), 3.93-3.67 (m, 3H), 3.40 (q, J = 6.0 Hz, 1H), 2.85-2.75 (m, 6H), 1.24-1.19 (m, 6H). $^{19}$F NMR (300 MHz, DMSO-d$_6$) δ-84.70, −136.09. | [M + H]$^+$ = 444.15 |
| 101 | $^1$H NMR (300 MHz, DMSO-d$_6$) δ 12.43 (s, 1H), 8.43 (d, J = 4.9 Hz, 1H), 7.85 (d, J = 8.1 Hz, 1H), 7.63-7.50 (m, 2H), 7.25 (t, J = 8.3, 7.1 Hz, 1H), 4.60 (q, J = 5.9 Hz, 1H), 3.88-3.79 (m, 2H), 3.70 (d, J = 13.2 Hz, 1H), 3.39 (t, J = 6.0 Hz, 1H), 2.89-2.73 (m, 4H), 1.23-1.18 (m, 6H), 0.66-0.64 (m, 4H). $^{19}$F NMR (300 MHz, DMSO-d$_6$) δ-84.59, −136.08. | [M + H]$^+$ = 470.15 |
| 102 | $^1$H NMR (300 MHz, DMSO-d$_6$) δ 12.60 (s, 1H), 8.56 (q, J = 4.7 Hz, 1H), 8.23 (d, J = 2.8 Hz, 1H), 7.94 (d, J = 8.7 Hz, 1H), 7.43 (dd, J = 8.7, 2.9 Hz, 1H), 7.15 (dd, J = 10.7, 5.4 Hz, 1H), 4.59 (q, J = 5.9 Hz, 1H), 3.95-3.80 (m, 2H), 3.67 (d, J = 13.5 Hz, 1H), 3.40 (q, J = 6.1 Hz, 1H), 2.85-2.75 (m, 4H), 2.43 (s, 3H), 1.22 (d, J = 6.1 Hz, 3H). $^{19}$F NMR (282 MHz, DMSO-d$_6$) δ-130.04, −139.93. | [M + H]$^+$ = 430.15 |
| 103 | $^1$H NMR (300 MHz, DMSO-d$_6$) δ 12.40 (bus, 1H), 8.43 (d, J = 4.9 Hz, 1H), 7.85 (d, J = 8.1 Hz, 1H), 7.61 (dd, J = 10.2, 8.2 Hz, 1H), 7.49 (d, J = 8.3 Hz, 1H), 7.25 (t, J = 7.6 Hz, 1H), 4.58 (q, J = 6.0 Hz, 1H), 3.93-3.79 (m, 2H), 3.69 (d, J = 13.2 Hz, 1H), 3.42-3.38 (m, 1H), 2.85-2.79 (m, 2H), 2.50 (s, 3H), 1.23-1.18 (m, 3H), 0.85-0.83 (m, 4H). $^{19}$F NMR (300 MHz, DMSO-d$_6$) δ-84.59, −136.10. | [M + H]$^+$ = 456.20 |
| 104 | $^1$H NMR (300 MHz, DMSO-d$_6$) δ 11.84 (s, 1H), 8.44-8.38 (m, 2H), 7.86 (d, J = 8.1 Hz, 1H), 7.74 (s, 1H), 7.63-7.59 (m, 2H), 4.63 (q, 1H), 3.93 (d, J = 13.4 Hz, 1H), 3.81 (t, J = 6.5 Hz, 1H), 3.65 (d, J = 13.4 Hz, 1H), 3.42-3.38 (m, 1H), 2.93-2.77 (m, 2H), 2.60-2.53 (m, 2H), 1.27-1.13 (m, 6H), 0.75-0.57 (m, 4H). $^{19}$F NMR (300 MHz, DMSO-d$_6$) δ-84.59. | [M + H]$^+$ = 452.20 |
| 105 | $^1$H NMR (400 MHz, DMSO-d$_6$) δ 12.46 (bus, 1H), 8.49-8.42 (m, 2H), 8.27 (s, 1H), 7.86 (d, J = 8.2 Hz, 1H), 7.65 (d, J = 1.9 Hz, 1H), 7.61 (dd, J = 10.2, 8.2 Hz, 1H), 4.64 (q, J = 5.9 Hz, 1H), 3.96 (d, J = 13.7 Hz, 1H), 3.82 (t, J = 6.5 Hz, 1H), 3.67 (d, J = 13.7 Hz, 1H), 3.46-3.41 (m, 1H), 2.89-2.78 (m, 2H), 1.21 (d, J = 6.2 Hz, 3H), 0.69-0.61 (m, 4H). $^{19}$F NMR (400 MHz, DMSO-d$_6$) δ-84.595. | [M + H]$^+$ = 458.15 |
| 107 | $^1$H NMR (300 MHz, DMSO-d$_6$) δ 12.60 (s, 1H), 8.57 (d, J = 5.0 Hz, 1H), 8.23 (d, J = 2.8 Hz, 1H), 7.94 (d, J = 8.6 Hz, 1H), 7.43 (dd, J = 8.7, 2.9 Hz, 1H), 7.16 (dd, J = 10.6, 5.4 Hz, 1H), 4.59 (q, J = 5.9 Hz, 1H), 3.90 (d, J = 13.5 Hz, 1H), 3.85 (t, J = 6.4 Hz, 1H), 3.68 (d, J = 13.6 Hz, 1H), 3.41-3.35 (m, 1H), 2.87-2.76 (m, 6H), 1.25-1.19 (m, 6H). $^{19}$F NMR (377 MHz, DMSO-d$_6$) δ-129.927, −129.975, −139.922, −139.970 | [M + H]$^+$ = 444.10 |
| 108 | $^1$H NMR (300 MHz, DMSO-d$_6$) δ 11.97 (s, 1H), 8.57 (q, J = 4.7 Hz, 1H), 8.23 (d, J = 2.8 Hz, 1H), 7.94 (d, J = 8.7 Hz, 1H), 7.75 (d, J = 1.5 Hz, 1H), 7.43 (dd, J = 8.7, 2.9 Hz, 1H), 7.04 (dd, J = 10.2, 4.8 Hz, 1H), 4.58 (q, J = 5.9 Hz, 1H), 3.95-3.77 (m, 2H), 3.66 (dd, J = 13.3, 1.7 Hz, 1H), 3.43-3.34 (m, 1H), 2.80-2.75 (m, 4H), 2.57-2.53 (m, 2H), 1.29-1.11 (m, 6H). $^{19}$F NMR (282 MHz, DMSO-d$_6$) δ-127.13, −140.00. | [M + H]$^+$ = 443.2 |
| 109 | $^1$H NMR (300 MHz, DMSO-d$_6$) δ 11.72 (s, 1H), 8.56 (q, J = 4.7 Hz, 1H), 8.22 (d, J = 2.8 Hz, 1H), 7.94 (d, J = 8.7 Hz, 1H), 7.74 (d, J = 1.6 Hz, 1H), 7.48-7.34 (m, 2H), 7.15 (dd, J = 8.0, 6.4 Hz, 1H), 4.57 (q, J = 5.9 Hz, 1H), 3.94-3.84 (m, 2H), 3.80 (t, J = 6.4 Hz, 1H), 3.67 (dd, J = 13.0, 1.6 Hz, 1H), 3.38-3.33 (m, 1H), 2.78-2.75 (m, 4H), 2.49-2.46 (m, 2H), 1.25-1.11 (m, 6H). $^{19}$F NMR (282 MHz, DMSO-d$_6$) δ-136.56. | [M + H]$^+$ = 425.10 |
| 111 | $^1$H NMR (300 MHz, DMSO-d$_6$) δ 12.43 (s, 1H), 8.47 (d, J = 5.3 Hz, 1H), 7.86 (d, J = 8.1 Hz, 1H), 7.58 (d, J = 8.1 Hz, 1H), 7.26 (t, J = 7.7 Hz, 1H), 4.66-4.53 (m, 1H), 3.81 (t, J = 6.4 Hz, 1H), 3.39 (t, J = 6.2 Hz, 1H), 2.91-2.70 (m, 6H), 1.22 (m, 6H). $^{19}$F NMR (300 MHz, DMSO-d$_6$) δ-84.71, −136.14. | [M + H]$^+$ = 446.1 |
| 112 | $^1$H NMR (300 MHz, DMSO-d$_6$) δ 12.43 (s, 1H), 8.44 (d, J = 4.9 Hz, 1H), 7.85 (d, J = 8.2 Hz, 1H), 7.65-7.49 (m, 2H), 7.25 (t, J = 7.7 Hz, 1H), 4.62-4.58 (m, 1H), 3.81 (t, J = 6.4 Hz, 1H), 3.44-3.34 (m, 1H), 2.91-2.74 (m, 4H), 1.27-1.13 (m, 6H), 0.71-0.59 (m, 4H). $^{19}$F NMR (282 MHz, DMSO-d$_6$) δ-84.59, −136.14. | [M + H]$^+$ = 472.2 |

Example 18

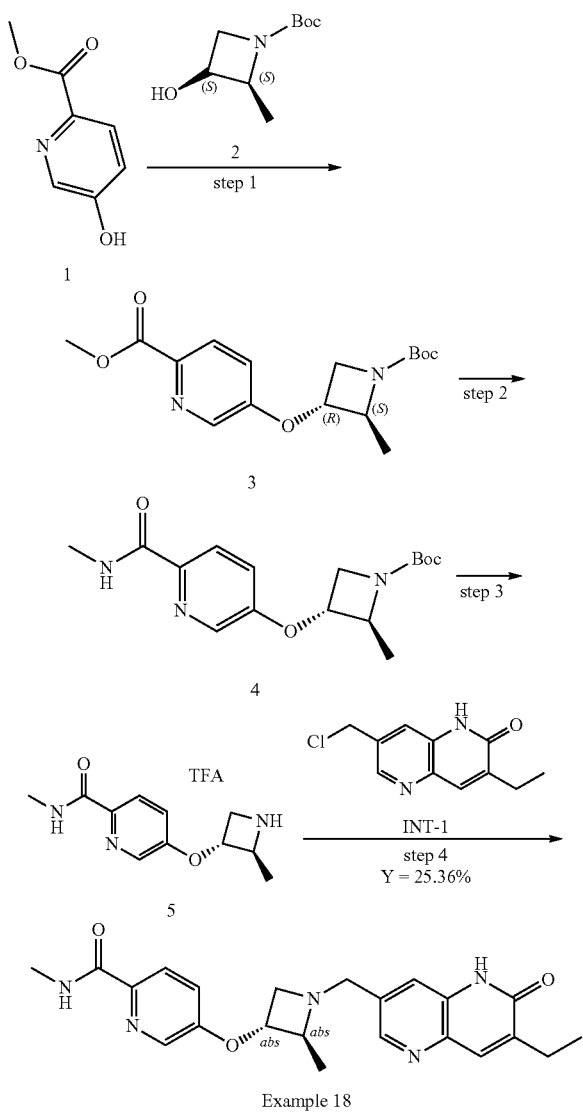

Step 1: Preparation of methyl 5-{[(2S,3R)-1-(tert-butoxycarbonyl)-2-methylazetidin-3-yl]oxy}pyridine-2-carboxylate To a stirred solution of methyl 5-hydroxypyridine-2-carboxylate (0.35 g, 2.28 mmol, 1.00 equiv.), tert-butyl(2S,3S)-3-hydroxy-2-methylazetidine-1-carboxylate (0.43 g, 2.28 mmol, 1.00 equiv.) and PPh$_3$ (1.20 g, 4.57 mmol, 2.00 equiv.) in toluene (10 mL) was added DBAD (1.05 g, 4.57 mmol, 2.00 equiv.) in toluene (5 mL) dropwise at 0° C. under nitrogen atmosphere. The resulting mixture was stirred for 2 h at 80° C. The reaction was monitored by LCMS. The mixture was allowed to cool down to room temperature. The reaction mixture was poured into water (50 mL), extracted with EtOAc (3×50 mL). The combined organic layers were concentrated under reduced pressure to afford methyl 5-{[(2S,3R)-1-(tert-butoxycarbonyl)-2-methylazetidin-3-yl]oxy}pyridine-2-carboxylate (2.00 g, crude). The crude product was used in the next step directly. LC-MS: (ES+H, m/z): [M+H]$^+$=323.1.

Step 2: Preparation of tert-butyl(2S,3R)-2-methyl-3-{[6-(methylcarbamoyl)pyridin-3-yl]oxy}azetidine-1-carboxylate A solution of methyl 5-{[(2S,3R)-1-(tert-butoxycarbonyl)-2-methylazetidin-3-yl]oxy}pyridine-2-carboxylate (1.00 g, crude) and Methylamine (2 mL, 25-30% wt in water) in MeOH (2 mL) was stirred for 2 h at room temperature under nitrogen atmosphere. The resulting mixture was concentrated under reduced pressure to afford tert-butyl(2S,3R)-2-methyl-3-{[6-(methylcarbamoyl) pyridin-3-yl]oxy}azetidine-1-carboxylate (1.00 g, crude) as a brown oil. The crude product was used in the next step directly. LC-MS: (ES+H, m/z): [M+H]$^+$=322.1.

Step 3: Preparation of N-methyl-5-{[(2S,3R)-2-methylazetidin-3-yl]oxy}pyridine-2-carboxamide, HCl Salt A solution of tert-butyl(2S,3R)-2-methyl-3-{[6-(methylcarbamoyl)pyridin-3-yl]oxy}azetidine-1-carboxylate (1.00 g, crude) in HCl (gas) in 1,4-dioxane (4 mL, 4M) was stirred for 2 h at room temperature under nitrogen atmosphere. The reaction was monitored by LCMS. The resulting mixture was concentrated under reduced pressure. The product was precipitated by the addition of EtOAc. The precipitated solids were collected by filtration and washed with PE (3×10 mL) to afford N-methyl-5-{[(2S,3R)-2-methylazetidin-3-yl]oxy}pyridine-2-carboxamide, HCl salt (200 mg, 67.95%, 3 steps). LC-MS: (ES+H, m/z): [M+H]$^+$=222.2.

Step 4: Preparation of 5-{[(2S,3R)-1-[(7-ethyl-6-oxo-5H-1,5-naphthyridin-3-yl)methyl]-2-methylazetidin-3-yl]oxy}-N-methylpyridine-2-carboxamide To a stirred solution of N-methyl-5-{[(2S,3R)-2-methylazetidin-3-yl]oxy}pyridine-2-carboxamide, HCl salt (200 mg, 0.90 mmol, 1.10 equiv.) and DIEA (531 mg, 4.11 mmol, 5.00 equiv.) in MeCN (10 mL) ware added KI (27 mg, 0.16 mmol, 0.20 equiv.) and 7-(chloromethyl)-3-ethyl-1H-1,5-naphthyridin-2-one (157 mg, 0.82 mmol, 1.00 equiv.) at room temperature. The resulting mixture was stirred for 2 h at 80° C. under nitrogen atmosphere. The mixture was allowed to cool down to room temperature. The resulting mixture was concentrated under reduced pressure. The residue was purified by silica gel column chromatography, the pure fraction was concentrated then lyophilized to afford 5-{[(2S,3R)-1-[(7-ethyl-6-oxo-5H-1,5-naphthyridin-3-yl)methyl]-2-methylazetidin-3-yl]oxy}-N-methylpyridine-2-carboxamide (73.6 mg, 25.36%). LC-MS: (ES+H, m/z): [M+H]$^+$=408.2. Optical rotation [a]$^{25}_D$ (c=0.5, MeOH): +8°; $^1$H NMR (400 MHz, DMSO-d$_6$) δ 11.86 (s, 1H), 8.57 (d, 1H), 8.38 (s, 1H), 8.23 (d, 1H), 7.94 (d, 1H), 7.74 (s, 1H), 7.59 (s, 1H), 7.43 (dd, 1H), 4.62 (q, 1H), 3.92 (d, 1H), 3.82 (t, 1H), 3.65-3.62 (m, 1H), 3.38-3.35 (m, 1H), 2.80-2.75 (m, 4H), 2.55-2.52 (m, 2H), 1.27-1.08 (m, 6H).

Example 19

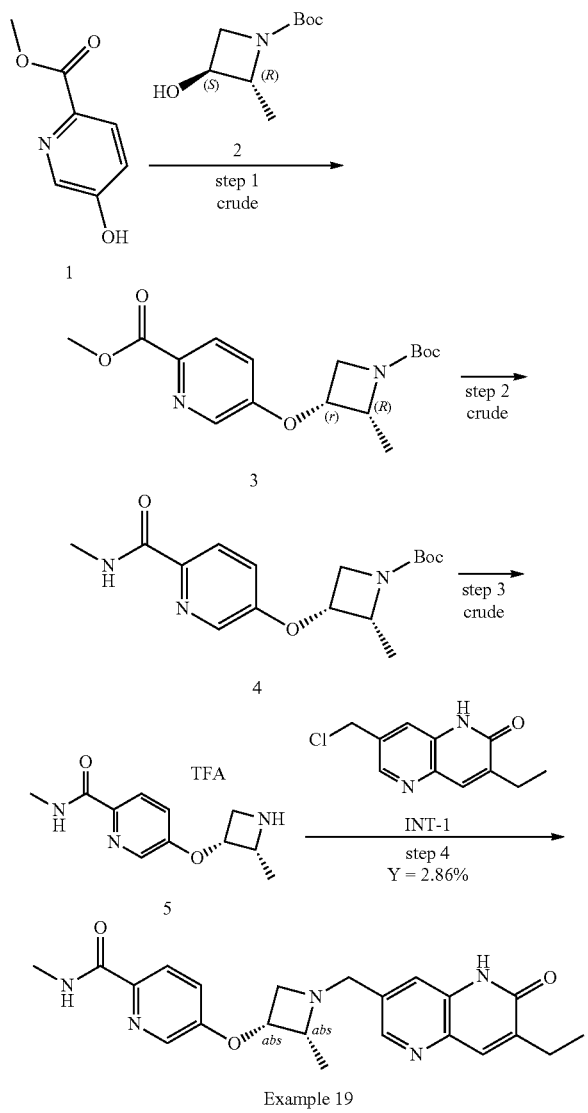

Step 1: Preparation of methyl 5-{[(2R,3R)-1-(tert-butoxycarbonyl)-2-methylazetidin-3-yl]oxy}pyridine-2-carboxylate To a stirred solution of methyl 5-hydroxypyridine-2-carboxylate (245 mg, 1.60 mmol, 1.00 equiv.) and tert-butyl (2R,3S)-3-hydroxy-2-methylazetidine-1-carboxylate (300 mg, 1.60 mmol, 1.00 equiv.) and Ph₃P (840 mg, 3.20 mmol, 2.00 equiv.) in THF (5 mL) was added DBAD (738 mg, 3.20 mmol, 2.00 equiv.) in THF (2 mL) dropwise at 0° C. under nitrogen atmosphere. The resulting mixture was stirred for 1 h at 0° C. The resulting mixture was stirred overnight at 80° C. under nitrogen atmosphere. The reaction was monitored by LCMS. The reaction mixture was poured into water (50 mL), extracted with EtOAc (50 mL×3). The combined organic layers were concentrated under reduced pressure to afford methyl 5-{[(2R,3R)-1-(tert-butoxycarbonyl)-2-methylazetidin-3-yl]oxy}pyridine-2-carboxylate (1.6 g, contain Ph₃PO) as a grey oil. The resulting mixture was used in the next step directly. LC-MS: (ES+H, m/z): [M+H]⁺=323.2.

Step 2: Preparation of tert-butyl(2R,3R)-2-methyl-3-{[6-(methylcarbamoyl)pyridin-3-yl]oxy}azetidine-1-carboxylate A solution of methyl 5-{[(2R,3R)-1-(tert-butoxycarbonyl)-2-methylazetidin-3-yl]oxy}pyridine-2-carboxylate (1.60 g, 4.96 mmol, 1.00 equiv.) and methylamine (4 mL, 25-30% wt in water) in MeOH (4 mL) was stirred overnight at room temperature under nitrogen atmosphere. The resulting mixture was concentrated under reduced pressure to afford tert-butyl(2R,3R)-2-methyl-3-{[6-(methylcarbamoyl)pyridin-3-yl]oxy}azetidine-1-carboxylate (1.53 g, contain Ph₃PO) as a grey oil. The crude product was used in the next step directly. LC-MS: (ES+H, m/z): [M+H]⁺=322.2

Step 3: Preparation of N-methyl-5-{[(2R,3R)-2-methylazetidin-3-yl]oxy}pyridine-2-carboxamide, TFA Salt A solution of tert-butyl(2R,3R)-2-methyl-3-{[6-(methylcarbamoyl)pyridin-3-yl]oxy}azetidine-1-carboxylate (1.53 g, contain Ph₃PO) and TFA (3 ml) in DCM (3 mL) was stirred for 30 min at room temperature under nitrogen atmosphere. The resulting mixture was concentrated under reduced pressure. The precipitated solids were collected by filtration and washed with ether (3×10 mL) to afford N-methyl-5-{[(2R,3R)-2-methylazetidin-3-yl]oxy}pyridine-2-carboxamide, TFA salt (810 mg, contain Ph₃PO). LC-MS: (ES+H, m/z): [M+H]⁺=222.1.

Step 4: Preparation of 5-{[(2R,3R)-1-[(7-ethyl-6-oxo-5H-1,5-naphthyridin-3-yl)methyl]-2-methylazetidin-3-yl]oxy}-N-methylpyridine-2-carboxamide To a stirred solution of N-methyl-5-{[(2R,3R)-2-methylazetidin-3-yl]oxy}pyridine-2-carboxamide (546 mg, 2.47 mmol, 1.10 equiv.) and 7-(chloromethyl)-3-ethyl-1H-1,5-naphthyridin-2-one (500 mg, 2.24 mmol, 1.00 equiv.) in MeCN (5 mL) was added KI (74 mg, 0.45 mmol, 0.20 equiv.) and DIEA (1.45 g, 11.22 mmol, 5.00 equiv.) at room temperature under nitrogen atmosphere. The resulting mixture was stirred for 2 h at 80° C. under nitrogen atmosphere. The mixture was allowed to cool down to room temperature. The resulting mixture was concentrated under reduced pressure. The residue was purified by silica gel column chromatography to afford 5-{[(2R,3R)-1-[(7-ethyl-6-oxo-5H-1,5-naphthyridin-3-yl)methyl]-2-methylazetidin-3-yl]oxy}-N-methylpyridine-2-carboxamide (26.2 mg, 2.86%). LC-MS: (ES+H, m/z): [M+H]⁺=408.20. ¹H NMR (300 MHz, DMSO-d₆) δ 11.80 (s, 1H), 8.56 (d, 1H), 8.37 (d, 1H), 8.26 (d, 1H), 7.95 (d, 1H), 7.74 (s, 1H), 7.59 (d, 1H), 7.42 (dd, 1H), 5.05-4.95 (m, 1H), 3.88 (d, 1H), 3.76 (q, 1H), 3.66 (d, 1H), 3.37-3.35 (m, 2H), 2.79 (d, 3H), 2.60-2.51 (m, 2H), 1.18 (t, 3H), 1.04 (d, 3H).

Example 20

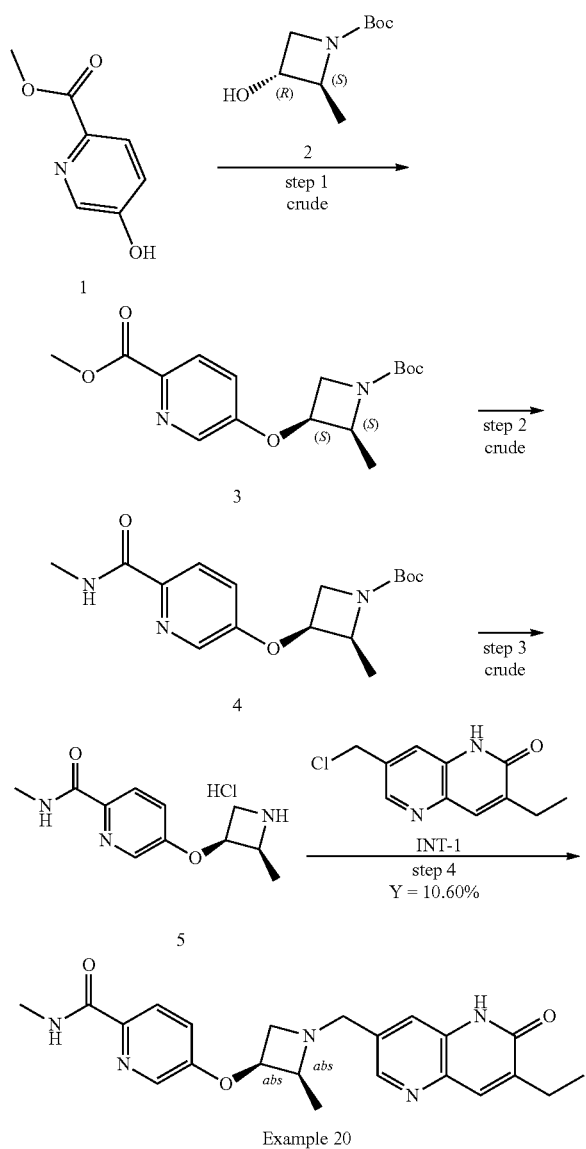

Example 20

Step 1: Preparation of methyl 5-(((2S,3S)-1-(tert-butoxycarbonyl)-2-methylazetidin-3-yl)oxy)picolinate To a stirred mixture of methyl 5-hydroxypyridine-2-carboxylate (400 mg, 2.61 mmol, 1.00 equiv.) and tert-butyl (2S,3R)-3-hydroxy-2-methylazetidine-1-carboxylate (489 mg, 2.61 mmol, 1.00 equiv.) and PPh$_3$ (1.40 g, 5.22 mmol, 2.00 equiv.) in methylbenzene (10 mL) were added DBAD (1.20 g, 5.22 mmol, 2.00 equiv.) dropwise at 0° C. under nitrogen atmosphere. The resulting mixture was stirred overnight at 80° C. under nitrogen atmosphere. The reaction was monitored by LCMS. The resulting mixture was diluted with water (50 mL). The resulting mixture was extracted with EtOAc (3×50 mL). The combined organic layers were washed with brine (3×50 mL), dried over anhydrous Na$_2$SO$_4$. After filtration, the filtrate was concentrated under reduced pressure to afford crude product (3.6 g, crude). The crude product was used in the next step directly without further purification. LC-MS: (ES+H, m/z): [M+H]$^+$=323.1.

Step 2: Preparation of tert-butyl(2S,3S)-2-methyl-3-((6-(methylcarbamoyl)pyridin-3-yl)oxy)azetidine-1-carboxylate To a stirred solution of methyl 5-(((2S,3S)-1-(tert-butoxycarbonyl)-2-methylazetidin-3-yl)oxy)picolinate (3.6 g, crude) in MeOH (10 mL) was added CH3NH2 (10 mL, 25-30% wt in water) at room temperature. The resulting mixture was stirred for 1 h at room temperature under nitrogen atmosphere. The reaction was monitored by LCMS. The resulting mixture was diluted with saturated NH$_4$Cl (100 mL). The resulting mixture was extracted with DCM (3×100 mL). The combined organic layers were washed with brine (3×100 mL), dried over anhydrous Na$_2$SO$_4$. After filtration, the filtrate was concentrated under reduced pressure to afford crude product (3.5 g, crude). The crude product was used in the next step directly without further purification. LC-MS: (ES+H, m/z): [M+H]$^+$=322.2

Step 3: Preparation of N-methyl-5-(((2S,3S)-2-methylazetidin-3-yl)oxy)picolinamide, HCl Salt To a stirred solution of tert-butyl(2S,3S)-2-methyl-3-((6-(methylcarbamoyl)pyridin-3-yl)oxy)azetidine-1-carboxylate (3.5 g, crude) in DCM (10 mL) was added HCl (gas) in 1,4-dioxane (10 mL, 4 M) dropwise at room temperature under nitrogen atmosphere. The resulting mixture was stirred for 1 h at room temperature under nitrogen atmosphere. The reaction was monitored by LCMS. The resulting mixture was concentrated under reduced pressure and was purified by trituration with ethyl acetate (20 mL) to afford crude product (1.6 g, crude). LC-MS: (ES+H, m/z): [M+H]$^+$=222.0

Step 4: Preparation of 5-(((2S,3S)-1-((7-ethyl-6-oxo-5,6-dihydro-1,5-naphthyridin-3-yl)methyl)-2-methylazetidin-3-yl)oxy)-N-methylpicolinamide To a stirred mixture of N-methyl-5-(((2S,3S)-2-methylazetidin-3-yl)oxy)picolinamide (298 mg, assumed 100% yield, 1.35 mmol, 2.00 equiv.) and 7-(chloromethyl)-3-ethyl-1H-1,5-naphthyridin-2-one (150 mg, 0.67 mmol, 1.00 equiv.) in MeCN (10 mL) were added KI (22 mg, 0.14 mmol, 0.20 equiv.) and DIEA (435 mg, 3.37 mmol, 5.00 equiv.) at room temperature. The resulting mixture was stirred for 2 h at 80° C. under nitrogen atmosphere. The reaction was monitored by LCMS. The mixture was allowed to cool down to room temperature. The resulting mixture was diluted with water (50 mL). The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The crude product was purified by Prep-HPLC. The pure fractions were concentrated and lyophilized to afford 5-(((2S,3S)-1-((7-ethyl-6-oxo-5,6-dihydro-1,5-naphthyridin-3-yl)methyl)-2-methylazetidin-3-yl)oxy)-N-methylpicolinamide (29.1 mg, 10.60%). LC-MS: (ES+H, m/z): [M+H]$^+$=408.2. $^1$H NMR (300 MHz, DMSO-d$_6$) δ 11.80 (s, 1H), 8.57 (d, 1H), 8.37 (d, 1H), 8.26 (d, 1H), 7.96 (d, 1H), 7.74 (s, 1H), 7.59 (s, 1H), 7.44 (dd, 1H), 5.08-5.03 (m, 1H), 3.88 (d, 1H), 3.80-3.74 (m, 1H), 3.66 (d, 1H), 3.34 (s, 2H), 2.79 (d, 3H), 2.56 (d, 2H), 1.18 (t, 3H), 1.04 (d, 3H).

Example 21

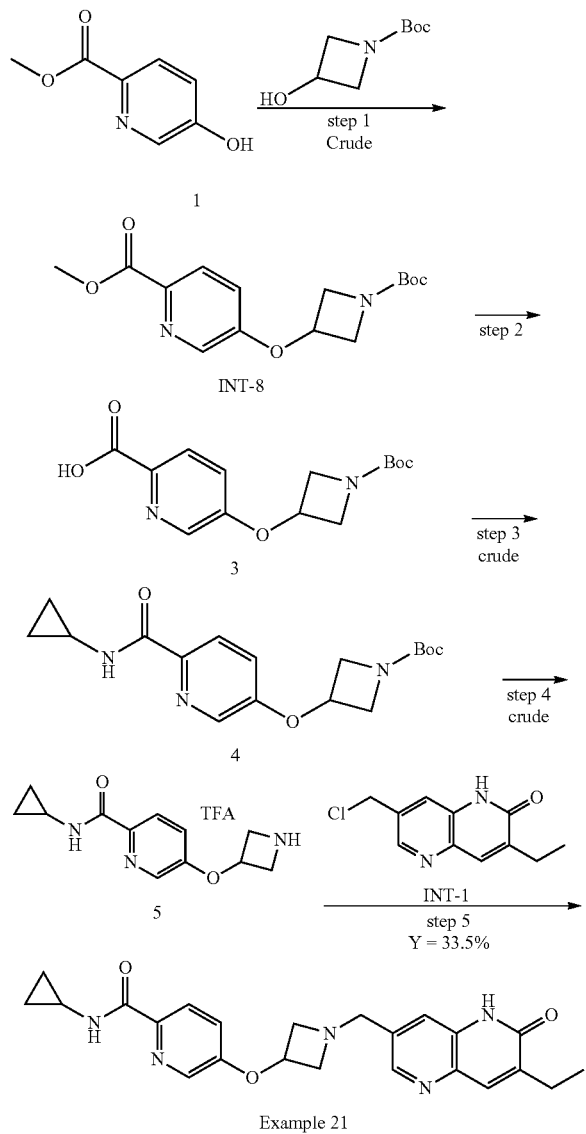

Example 21

Step 1: Preparation of methyl 5-{[1-(tert-butoxycarbonyl)azetidin-3-yl]oxy}pyridine-2-carboxylate To a stirred mixture of methyl 5-hydroxypyridine-2-carboxylate (5.00 g, 32.65 mmol, 1.00 equiv.), PPh$_3$ (17.13 g, 65.30 mmol, 2.00 equiv.) and tert-butyl 3-hydroxyazetidine-1-carboxylate (5.66 g, 32.65 mmol, 1.00 equiv.) in Toluene (80 mL) was added DBAD (15.04 g, 65.30 mmol, 2.00 equiv.) in Toluene (40 mL) dropwise at 0° C. under nitrogen atmosphere. The resulting mixture was stirred for 2 h at 60° C. under nitrogen atmosphere. Desired product could be detected by LCMS. The mixture was allowed to cool down to room temperature. The resulting mixture was poured into water (400 mL), extracted with EtOAc (3×200 mL). The combined organic layers were washed with brine (2×100 mL), dried over anhydrous Na$_2$SO$_4$. The resulting mixture was concentrated under reduced pressure to afford methyl 5-{[1-(tert-butoxycarbonyl)azetidin-3-yl]oxy}pyridine-2-carboxylate (45 g, crude) as a grey oil. The crude product was used in the next step directly without further purification. LC-MS: (ES+H, m/z): [M+H]$^+$=309.1

Step 2: Preparation of 5-{[1-(tert-butoxycarbonyl)azetidin-3-yl]oxy}pyridine-2-carboxylic Acid A mixture of methyl 5-{[1-(tert-butoxycarbonyl)azetidin-3-yl]oxy}pyridine-2-carboxylate (9.00 g 8.76 mmol, 1.00 equiv., assumed 30% yield) and LiOH (0.84 g, 35.03 mmol, 4.00 equiv.) in THF (40 mL) and H$_2$O (10 mL) was stirred for 3 h at room temperature under nitrogen atmosphere. Desired product could be detected by LCMS. The resulting mixture was poured into water (200 mL), extracted with EtOAc (1×200 mL). The aqueous layer was acidified to pH 4-6 with HCl (aqueous.). The resulting mixture was extracted with EtOAc (3×200 mL). The combined organic layers were washed with brine (1×100 mL), dried over anhydrous Na$_2$SO$_4$. The resulting mixture was concentrated under reduced pressure to afford 5-{[1-(tert-butoxycarbonyl)azetidin-3-yl]oxy}pyridine-2-carboxylic acid (2.3 g, 89.25%). LC-MS: (ES+H, m/z): [M+H]$^+$=295.1. $^1$H NMR (300 MHz, DMSO-d$_6$) δ 12.92 (s, 1H), 8.33 (dd, 1H), 8.02 (dd, 1H), 7.38 (dd, 1H), 5.20-5.17 (m, 1H), 4.41-4.28 (m, 2H), 3.91-3.80 (m, 2H), 1.39 (s, 9H).

Step 3: Preparation of tert-butyl 3-{[6-(cyclopropylcarbamoyl)pyridin-3-yl]oxy}azetidine-1-Carboxylate To a stirred mixture of 5-{[1-(tert-butoxycarbonyl)azetidin-3-yl]oxy}pyridine-2-carboxylic acid (500 mg, 1.70 mmol, 1.00 equiv.) and DIEA (1.10 g, 8.50 mmol, 5.00 equiv.) in DCM (15 mL) were added aminocyclopropane (107 mg, 1.87 mmol, 1.10 equiv.) and T3P (4.32 g, 6.80 mmol, 4.00 equiv., 50% wt in EA) at room temperature. The resulting mixture was stirred for 3 h at room temperature under nitrogen atmosphere. Desired product could be detected by LCMS. The resulting mixture was poured into water (150 mL), and extracted with EtOAc (3×200 mL). The combined organic layers were washed with brine (1×80 mL), dried over anhydrous Na$_2$SO$_4$. The resulting mixture was concentrated under reduced pressure to afford tert-butyl 3-{[6-(cyclopropylcarbamoyl)pyridin-3-yl]oxy}azetidine-1-carboxylate (780 mg, crude). LC-MS: (ES+H, m/z): [M+H]$^+$=334.0. $^1$H NMR (300 MHz, DMSO-d$_6$) δ 8.55 (d, 1H), 8.21 (d, 1H), 7.97 (d, 1H), 7.40 (dd, 1H), 5.17-5.12 (m, 1H), 4.34 (dd, 2H), 3.84 (dd, 2H), 2.94-2.82 (m, 1H), 1.39 (s, 9H), 0.78-0.61 (m, 4H).

Step 4: Preparation of 5-(azetidin-3-yloxy)-N-cyclopropylpyridine-2-carboxamide, TFA Salt A solution of tert-butyl 3-{[6-(cyclopropylcarbamoyl)pyridin-3-yl]oxy}azetidine-1-carboxylate (700 mg, 2.10 mmol, 1.00 equiv.) and TFA (7.20 g, 63.00 mmol, 30.00 equiv.) in DCM (20 mL) was stirred for 2 h at room temperature under nitrogen atmosphere. The resulting mixture was concentrated under reduced pressure. The resulting mixture was concentrated under reduced pressure. This resulted in 5-(azetidin-3-yloxy)-N-cyclopropylpyridine-2-carboxamide, TFA salt (1.2 g, crude) as a brown crude oil. LC-MS: (ES+H, m/z): [M+H]+=234.2

Step 5: Preparation of N-cyclopropyl-5-({1-[(7-ethyl-6-oxo-5H-1,5-naphthyridin-3-yl)methyl]azetidin-3-yl}oxy)pyridine-2-carboxamide To a solution of 5-(azetidin-3-yloxy)-N-cyclopropylpyridine-2-carboxamide, TFA salt (300 mg, crude) and DIEA (871 mg, 6.74 mmol, 10.00 equiv.) in MeCN (2 mL) were added 7-(chloromethyl)-3-ethyl-1H-1,5-naphthyridin-2-one (150 mg, 0.67 mmol, 1.00 equiv.) and KI (22 mg, 0.14 mmol, 0.20 equiv.). The mixture was stirred for 2 h at 50° C. under nitrogen atmosphere. The reaction was monitored by LCMS. After cooled to rt, the resulting mixture was diluted with water (100 mL). The resulting mixture was extracted with EtOAc (3×100 mL). The combined organic layers were washed with brine (1×100 mL), dried over anhydrous $Na_2SO_4$. After filtration, the filtrate was concentrated under reduced pressure. The crude product was purified by reversed combi-flash, the pure fraction was concentrated then lyophilized to afford N-cyclopropyl-5-({1-[7-ethyl-6-oxo-5H-1,5-naphthyridin-3-yl)methyl]azetidin-3-yl}oxy)pyridine-2-carboxamide (96.2 mg, 33.50%). LC-MS: (ES+H, m/z): [M+H]$^+$=420.3. $^1$H NMR (300 MHz, DMSO-$d_6$) δ 11.86 (s, 1H), 8.52 (d, 1H), 8.37 (d, 1H), 8.20 (d, 1H), 7.95 (d, 1H), 7.74 (s, 1H), 7.57 (d, 1H), 7.41 (dd, 1H), 5.02 (p, 1H), 3.83-3.75 (m, 4H), 3.24-3.12 (m, 2H), 2.87 (td, 1H), 2.57-2.52 (m, 2H), 1.18 (t, 3H), 0.68-0.65 (m, 4H).

The following examples were made using similar procedures as shown for example 21:

| Ex | NMR | LCMS (ESI) m/z |
|---|---|---|
| 30 | $^1$H NMR (300 MHz, DMSO-$d_6$) δ 12.30 (s, 1H), 8.58-8.56 (m, 1H), 8.23 (d, 1H), 7.96 (d, 1H), 7.53 (d, 1H), 7.41 (dd, 1H), 7.31 (d, 1H), 5.06-5.00 (m, 1H), 3.84-3.79 (m, 4H), 3.25-3.20 (m, 2H), 2.84-2.73 (m, 5H), 1.21 (t, 3H). $^{19}$F NMR (282 MHz, DMSO-$d_6$) δ-124.65. | [M + H]$^+$ = 412.05 |
| 56 | $^1$H NMR (400 MHz, DMSO-$d_6$) δ 11.87 (s, 1H), 8.60 (t, 1H), 8.36 (d, 1H), 8.23 (d, 1H), 7.95 (d, 1H), 7.82 (s, 1H), 7.56 (d, 1H), 7.41 (dd, 1H), 5.05-3.71 (m, 1H), 3.83-3.71 (m, 4H), 3.32-3.23 (m, 2H), 3.17 (dd, 2H), 2.13 (d, 3H), 1.10 (t, 3H). | [M + H]$^+$ = 394.15 |
| 57 | $^1$H NMR (300 MHz, DMSO-$d_6$) δ 11.87 (s, 1H), 8.52 (d, 1H), 8.35 (d, 1H), 8.20 (d, 1H), 7.94 (d, 1H), 7.81 (s, 1H), 7.57 (d, 1H), 7.41 (dd, 1H), 5.04-4.97 (m, 1H), 3.78 (dd, 4H), 3.19-3.14 (m, 2H), 2.88-2.85 (m, 1H), 2.13 (d, 3H), 0.74-0.56 (m, 4H). | [M + H]$^+$ = 406.15 |
| 58 | $^1$H NMR (400 MHz, DMSO-$d_6$) δ 11.86 (s, 1H), 8.60 (t, 1H), 8.37 (d, 1H), 8.23 (d, 1H), 7.95 (d, 1H), 7.74 (d, 1H), 7.57 (d, 1H), 7.41 (dd, 1H), 5.03-5.00 (m, 1H), 3.83-3.70 (m, 4H), 3.30 (td, 2H), 3.20-3.14 (m, 2H), 2.55 (td, 2H), 1.18 (t, 3H), 1.10 (t, 3H). | [M + H]$^+$ = 408.20 |
| 117 | $^1$H NMR (300 MHz, DMSO-$d_6$) δ 12.44 (s, 1H), 8.52 (d, J = 5.0 Hz, 1H), 8.20 (d, J = 2.8 Hz, 1H), 7.94 (d, J = 8.7 Hz, 1H), 7.53 (d, J = 8.3 Hz, 1H), 7.41 (dd, J = 8.7, 2.9 Hz, 1H), 7.25 (t, J = 8.1 Hz, 1H), 5.00-4.96 (m, 1H), 3.84-3.73 (m, 4H), 3.24-3.12 (m, 2H), 2.90-2.80 (m, 3H), 1.22 (t, J = 7.4 Hz, 3H), 0.70-0.65 (m, 4H). $^{19}$F NMR (282 MHz, DMSO-$d_6$) δ-135.97 | [M + H]$^+$ = 438.20 |
| 118 | $^1$H NMR (300 MHz, DMSO-$d_6$) δ 11.73 (s, 1H), 8.52 (d, J = 5.0 Hz, 1H), 8.19 (d, J = 2.8 Hz, 1H), 7.94 (d, J = 8.8 Hz, 1H), 7.74 (d, J = 1.5 Hz, 1H), 7.45-7.35 (m, 2H), 7.14 (dd, J = 8.1, 6.4 Hz, 1H), 4.97 (p, J = 5.5 Hz, 1H), 3.82-3.72 (m, 4H), 3.15 (dd, J = 8.2, 5.2 Hz, 2H), 2.90-2.82 (m, 1H), 2.53-2.48 (m, 2H), 1.17 (t, J = 7.4 Hz, 3H), 0.73-0.58 (m, 4H). $^{19}$F NMR (282 MHz, DMSO-$d_6$) δ-136.40. | [M + H]$^+$ = 437.15 |

Example 22

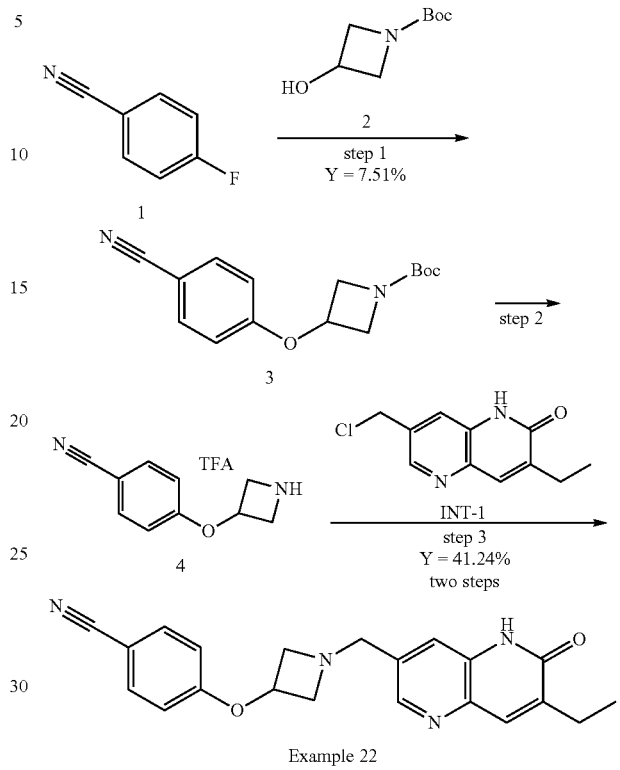

Example 22

Step 1: Preparation of tert-butyl 3-(4-cyanophenoxy)azetidine-1-carboxylate

To a stirred solution of benzonitrile, 4-fluoro- (1.00 g, 8.26 mmol, 1.00 equiv.) and tert-butyl 3-hydroxyazetidine-1-carboxylate (2.15 g, 12.39 mmol, 1.50 equiv.) in DMF (20 mL) was added $K_2CO_3$ (3.42 g, 24.77 mmol, 3.00 equiv.) at room temperature under nitrogen atmosphere. The resulting mixture was stirred for 2 h at 80° C. under nitrogen atmosphere. The reaction was monitored by LCMS. The mixture was allowed to cool down to room temperature. The reaction was poured into water (80 mL) at room temperature. The resulting mixture was extracted with EtOAc (3×80 mL). The combined organic layers were washed with brine (3×10 mL), dried over anhydrous $Na_2SO_4$. After filtration, the filtrate was concentrated under reduced pressure. The residue was purified by silica gel column chromatography, the filtrate was concentrated under reduced pressure to afford tert-butyl 3-(4-cyanophenoxy)azetidine-1-carboxylate (170 mg, 7.51%). LC-MS: (ES+H, m/z): [M-tBu+ACN]$^+$=260.0. $^1$H NMR (300 MHz, DMSO-$d_6$) δ 7.84-7.75 (m, 2H), 7.05-6.98 (m, 2H), 5.17-5.05 (m, 1H), 4.49-4.24 (m, 2H), 3.86-3.76 (m, 2H), 1.39 (s, 9H).

Step 2: Preparation of 4-(azetidin-3-yloxy)benzonitrile, TFA Salt

To a stirred solution of tert-butyl 3-(4-cyanophenoxy) azetidine-1-carboxylate (160 mg, 0.58 mmol, 1.00 equiv.) in DCM (3 mL) was added TFA (1 mL) at room temperature under nitrogen atmosphere. The resulting mixture was stirred for 30 min at room temperature under nitrogen atmosphere. The reaction was monitored by LCMS. The resulting mixture was concentrated under reduced pressure to afford 4-(azetidin-3-yloxy)benzonitrile, TFA salt (232 mg, crude) as a brown oil. LC-MS: (ES+H, m/z): [M+H]$^+$=175.0

Step 3: Preparation of 4-({1-[(7-ethyl-6-oxo-5H-1,5-naphthyridin-3-yl)methyl]azetidin-3-yl}oxy)benzonitrile To a stirred solution of 4-(azetidin-3-yloxy)benzonitrile (221 mg, 0.58 mmol, 1.00 equiv., 46% wt) and DIEA (377 mg, 2.92 mmol, 5.00 equiv.) in MeCN (5 mL) were added 7-(chloromethyl)-3-ethyl-1H-1,5-naphthyridin-2-one (130 mg, 0.58 mmol, 1.00 equiv.) and KI (4 mg, 0.02 mmol, 0.04 equiv.) at room temperature under nitrogen atmosphere. The resulting mixture was stirred for 1 h at 80° C. under nitrogen atmosphere. The reaction was monitored by LCMS. The resulting mixture was poured into water (60 mL). The resulting mixture was extracted with EtOAc (3×80 mL). The combined organic layers were washed with brine (3×10 mL), dried over anhydrous Na$_2$SO$_4$. After filtration, the filtrate was concentrated under reduced pressure. The crude product (200 mg) was purified by Prep-HPLC, the pure fractions was concentrated under reduced pressure then lyophilized to afford 4-({1-[(7-ethyl-6-oxo-5H-1,5-naphthyridin-3-yl)methyl]azetidin-3-yl}oxy)benzonitrile (86.7 mg, 41.24%, two steps). LC-MS: (ES+H, m/z): [M+H]$^+$=361.10. $^1$H NMR (400 MHz, DMSO-d$_6$) δ 11.84 (s, 1H), 8.36 (d, 1H), 7.82-7.66 (m, 3H), 7.56 (s, 1H), 7.02 (d, 2H), 5.01-4.90 (m, 1H), 3.85-3.65 (m, 4H), 3.21-3.04 (m, 2H), 2.59-2.52 (m, 2H), 1.18 (t, 3H). The following examples were made using similar procedures as shown for example 22:

| Ex | NMR | LCMS (ESI) m/z |
|---|---|---|
| 23 | $^1$H NMR (300 MHz, DMSO-d$_6$) δ 11.88 (s, 1H), 8.36 (dd, 2H), 7.98 (d, 1H), 7.54 (d, 1H), 7.47 (dd, 1H), 7.39 (s, 1H), 5.15-4.96 (m, 1H), 3.81-3.71 (m, 4H), 3.21-3.10 (m, 2H), 2.20-2.05 (m, 1H), 1.01-0.90 (m, 2H), 0.85-0.76 (m, 2H). | [M + H]$^+$ = 374.3 |
| 24 | $^1$H NMR (400 MHz, DMSO-d$_6$) δ 11.84 (s, 1H), 8.40 (d, 1H), 8.36 (d, 1H), 7.99 (d, 1H), 7.73 (s, 1H), 7.56 (d, 1H), 7.52-7.43 (m, 1H), 5.10-5.01 (m, 1H), 3.84-2.69 (m, 4H), 3.22-3.14 (m, 2H), 2.58-2.51 (m, 2H), 1.18 (t, 3H). | [M + H]$^+$ = 362.1 |
| 34 | $^1$H NMR (300 MHz, DMSO-d$_6$) δ11.83 (s, 1H), 8.67 (d, 1H), 8.38 (d, 1H), 8.18 (dd, 1H), 7.74 (s, 1H), 7.59 (d, 1H), 7.04 (d, 1H), 4.87 (q, 1H), 3.91 (d, 1H), 3.75 (t, 1H), 3.65 (d, 1H), 3.33-3.26 (m, 1H), 2.84 (t, 1H), 2.59-2.52 (m, 2H), 1.24-1.17 (m, 6H). | [M + H]$^+$ = 376.05 |
| 36 | $^1$H NMR (300 MHz, DMSO-d$_6$) δ 11.86 (s, 1H), 8.40 (dd, 2H), 7.98 (d, 1H), 7.74 (s, 1H), 7.58 (s, 1H), 7.51-7.48 (m, 1H), 4.69-4.63 (m, 1H), 3.95-3.90 (m, 1H), 3.82 (t, 1H), 3.64 (d, 1H), 3.43-3.34 (m, 1H), 2.78 (t, 1H), 2.58-2.50 (m, 2H), 1.23-1.16 (m, 6H). | [M + H]$^+$ = 376.1 |
| 37 | $^1$H NMR (300 MHz, DMSO-d$_6$) δ 11.87 (s, 1H), 8.40-8.39 (m, 2H), 8.04 (d, 1H), 7.82 (s, 1H), 7.51-7.47 (m, 1H), 4.66-4.56 (m, 1H), 3.94-3.90 (m, 1H), 3.82 (t, 1H), 3.63 (d, 1H), 3.51-3.49 (m, 1H), 2.78 (t, 1H), 2.12 (s, 3H), 1.20 (d, 3H). | [M + H]$^+$ = 362.00 |
| 47 | $^1$H NMR (400 MHz, DMSO-d$_6$) δ 11.86 (s, 1H), 8.37 (d, 1H), 7.84-7.72 (m, 3H), 7.58 (d, 1H), 7.06-7.00 (m, 2H), 4.55 (q, 1H), 3.91 (d, 1H), 3.84-3.75 (m, 1H), 3.63 (d, 1H), 3.36-3.32 (m, 1H), 2.75 (t, 1H), 2.13 (d, 3H), 1.19 (d, 3H). | [M + H]$^+$ = 361.20 |
| 48 | $^1$H NMR (400 MHz, DMSO-d$_6$) δ 11.85 (s, 1H), 8.38 (s, 1H), 7.80-7.70 (m, 3H), 7.61-7.55 (m, 1H), 7.03 (d, 2H), 4.55 (q, 1H), 3.91 (d, 1H), 3.80 (t, 1H), 3.63 (d, 1H), 3.39-3.34 (m, 1H), 2.75 (t, 1H), 2.59-2.52 (m, 2H), 1.33-1.03 (m, 6H). | [M + H]$^+$ = 375.20 |
| 69 | $^1$H NMR (300 MHz, DMSO-d$_6$) δ 11.85 (s, 1H), 8.39 (s, 1H), 7.89 (d, 1H), 7.74 (s, 1H), 7.64 (d, 1H), 7.59 (s, 1H), 7.18 (t, 1H), 4.64 (d, 1H), 3.92 (d, 1H), 3.82-3.78 (m, 1H), 3.65 (d, 1H), 3.43-3.32 (m, 1H), 2.83-2.80 (m, 1H), 2.59-2.54 (m, 2H), 1.22-1.20 (m, 6H). $^{19}$F NMR (282 MHz, DMSO-d$_6$) δ-132.07. | [M + H]$^+$ = 393.05 |
| 72 | $^1$H NMR (400 MHz, DMSO-d$_6$) δ 11.87 (s, 1H), 8.43 (s, 2H), 8.10 (d, 1H), 7.75 (s, 1H), 7.60 (s, 1H), 7.25 (d, 1H), 4.76 (s, 1H), 3.94 (d, 2H), 3.83 (s, 1H), 3.67 (s, 1H), 2.83 (s, 1H), 2.58-2.51 (m, 2H), 1.21-1.16 (m, 6H). | [M + H]$^+$ = 400.20 |
| 78 | $^1$H NMR (400 MHz, DMSO-d$_6$) δ 12.44 (s, 1H), 8.46 (d, 1H), 8.40 (d, 1H), 8.27 (s, 1H), 7.98 (d, 1H), 7.65 (d, 1H), 7.49 (m, 1H), 4.67 (q, 1H), 3.95 (d, 1H), 3.83 (t, 1H), 3.67 (d, 1H), 3.40 (q, 1H), 2.80 (t, 1H), 1.20 (d, 3H). | [M-H]$^+$ = 380.10 |

Example 43

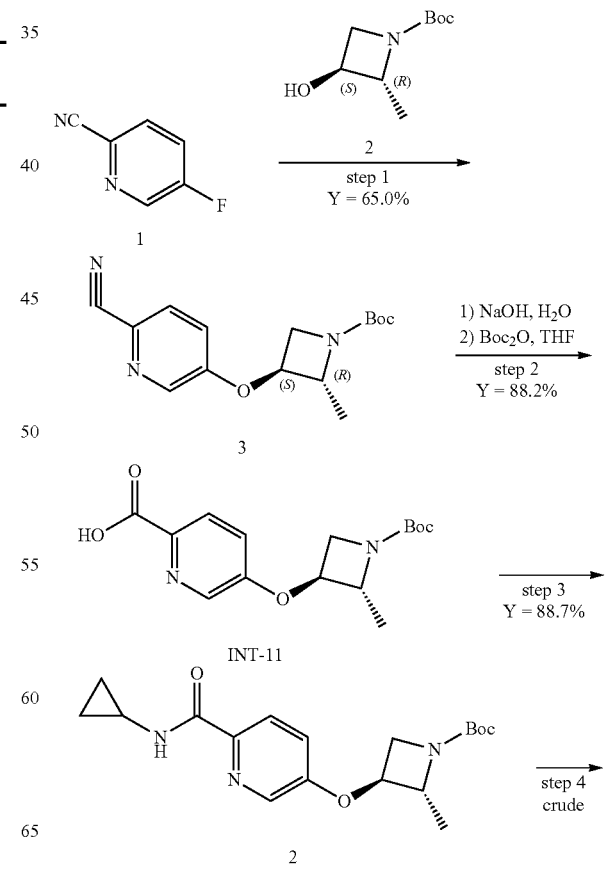

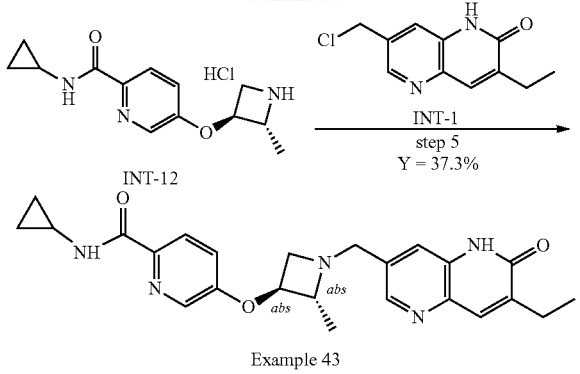

Example 43

Step 1: Preparation of tert-butyl(2R,3S)-3-((6-cyanopyridin-3-yl)oxy)-2-methylazetidine-1-carboxylate To a stirred mixture of NaH (1.49 g, 37.37 mmol, 1.20 equiv., 60% in oil) in THF (30 mL) was added tert-butyl (2R,3S)-3-hydroxy-2-methylazetidine-1-carboxylate (6.99 g, 37.35 mmol, 1.20 equiv.) in THF (30 mL) dropwise at 0° C. under nitrogen atmosphere. The resulting mixture was stirred for 1 h at room temperature under nitrogen atmosphere. To the above mixture was added 5-fluoropyridine-2-carbonitrile (3.8 g, 31.12 mmol, 1.00 equiv.) in THF (30 mL) dropwise over 15 min at 0° C. The resulting mixture was stirred for additional 1 h at room temperature. The reaction was monitored by LCMS. The reaction was quenched by the addition of water (10 mL) at 0° C. The resulting mixture was diluted with water (50 mL). The resulting mixture was extracted with CH$_2$Cl$_2$ (3×50 mL). The combined organic layers were dried over anhydrous Na$_2$SO$_4$. After filtration, the filtrate was concentrated under reduced pressure. The residue was purified by silica gel column chromatography to afford tert-butyl(2R,3S)-3-((6-cyanopyridin-3-yl)oxy)-2-methylazetidine-1-carboxylate (6.24 g, 65.0%). LC-MS: (ES+H, m/z): [M+H-tBu]$^+$=234.1.

Step 2: Preparation of 5-(((2R,3S)-1-(tert-butoxycarbonyl)-2-methylazetidin-3-yl)oxy)picolinic acid To a stirred mixture of tert-butyl(2R,3S)-3-[(6-cyanopyridin-3-yl)oxy]-2-methylazetidine-1-carboxylate (6.6 g, 22.81 mmol, 1.00 equiv.) in water (40 mL) was added NaOH (20 mL, 2N in water) in portions at room temperature. The resulting mixture was stirred for 2 h at 100° C. under nitrogen atmosphere. The reaction was monitored by TLC. The mixture was allowed to cool down to room temperature. To the above mixture was added THF (40 mL) and Boc2O (9.96 g, 45.62 mmol, 2.00 equiv.) in portions over 10 min at 0° C. The resulting mixture was stirred for additional 6 h at room temperature. The reaction was monitored by LCMS. The mixture was acidified to pH 3-4 with citric acid. The resulting mixture was extracted with CH$_2$Cl$_2$ (3×50 mL). The combined organic layers were dried over anhydrous Na$_2$SO$_4$. After filtration, the filtrate was concentrated under reduced pressure. The residue was purified by silica gel column chromatography to afford 5-(((2R,3S)-1-(tert-butoxycarbonyl)-2-methylazetidin-3-yl)oxy)picolinic acid (6.2 g, 88.2%). LC-MS: (ES+H, m/z): [M+H]$^+$=309.2. $^1$H NMR (300 MHz, DMSO-d$_6$) δ 8.33 (d, 1H), 8.02 (d, 1H), 7.38 (dd, 1H), 4.82-4.65 (m, 1H), 4.30-4.21 (m, 2H), 3.72-3.56 (m, 1H), 1.45 (s, 3H), 1.37 (s, 9H).

Step 3: Preparation of tert-butyl(2R,3S)-3-{[6-(cyclopropylcarbamoyl)pyridin-3-yl]oxy}-2-methylazetidine-1-carboxylate To a stirred solution of 5-{[(2R,3S)-1-(tert-butoxycarbonyl)-2-methylazetidin-3-yl]oxy}pyridine-2-carboxylic acid (600 mg, 1.95 mmol, 1.00 equiv.) and HATU (1.11 g, 2.92 mmol, 1.50 equiv.) and DIEA (503 mg, 3.89 mmol, 2.00 equiv.) in DCM (5 mL) were added aminocyclopropane (133 mg, 2.33 mmol, 1.20 equiv.) at 0° C. The resulting mixture was stirred for 1.5 h at room temperature under nitrogen atmosphere. The reaction was monitored by LCMS. The resulting mixture was diluted with CH$_2$Cl$_2$ (100 mL). The resulting mixture was washed with water (3×20 mL). The resulting mixture was concentrated under reduced pressure. The residue was purified by silica gel column chromatography to afford tert-butyl (2R,3S)-3-{[6-(cyclopropylcarbamoyl)pyridin-3-yl]oxy}-2-methylazetidine-1-carboxylate (600 mg, 88.7%). LC-MS: (ES+H, m/z): [M+H]$^+$=348.1

Step 4: Preparation of N-cyclopropyl-5-{[(2R,3S)-2-methylazetidin-3-yl]oxy}pyridine-2-carboxamide HCl Salt To a stirred solution of tert-butyl(2R,3S)-3-{[6-(cyclopropylcarbamoyl)pyridin-3-yl]oxy}-2-methylazetidine-1-carboxylate (500 mg, 1.44 mmol, 1.00 equiv.) in DCM (3 mL) were added HCl (gas) in 1,4-dioxane (5 mL, 4 mol/L) dropwise at 0° C. under nitrogen atmosphere. The resulting mixture was stirred for 1 h at room temperature under nitrogen atmosphere. The reaction was monitored by LCMS. The resulting mixture was concentrated under reduced pressure. The residue was purified by trituration with Et$_2$O (2×10 mL). The resulting mixture was concentrated under reduced pressure to afford N-cyclopropyl-5-{[(2R,3S)-2-methylazetidin-3-yl]oxy}pyridine-2-carboxamide, HCl salt (400 mg, crude). LC-MS: (ES+H, m/z): [M+H]$^+$=248.2.

Step 5: Preparation of N-cyclopropyl-5-{[(2R,3S)-1-[(7-ethyl-6-oxo-5H-1,5-naphthyridin-3-yl)methyl]-2-methylazetidin-3-yl]oxy}pyridine-2-carboxamide To a stirred mixture of N-cyclopropyl-5-{[(2R,3S)-2-methylazetidin-3-yl]oxy}pyridine-2-carboxamide HCl salt (200 mg, crude) and 7-(chloromethyl)-3-ethyl-1H-1,5-naphthyridin-2-one (150 mg, 0.67 mmol, 1.00 equiv.) in CH$_3$CN (8 mL) were added KI (56 mg, 0.34 mmol, 0.5 equiv.) and DIEA (697 mg, 5.39 mmol, 8 equiv.) dropwise at room temperature. The resulting mixture was stirred for 2 h at 60° C. under nitrogen atmosphere. The reaction was monitored by LCMS. The mixture was allowed to cool down to room temperature. The resulting mixture was concentrated under reduced pressure. The residue was purified by silica gel column chromatography. After that The residue was purified by reversed combi-flash chromatography. the pure fraction was concentrated under vacuum to afford N-cyclopropyl-5-{[(2R,3S)-1-[(7-ethyl-6-oxo-5H-1,5-naphthyridin-3-yl)methyl]-2-methylazetidin-3-yl]oxy}pyridine-2-carboxamide (109.3 mg, 37.3%). LC-MS: (ES+H, m/z): [M-H]+=434.25, Optical rotation [a]$^{25}$$_D$ (c=0.25, DCM/MeOH=10/1): −12°; $^1$H NMR (300 MHz, DMSO-d$_6$) δ 11.86 (s, 1H), 8.54-8.52 (d, 1H), 8.39-8.38 (d, 1H), 8.22-8.21 (d, 1H), 7.96-7.93 (d, 1H), 7.74 (s, 1H), 7.59-7.58 (d, 1H), 7.45-7.42 (dd, 1H), 4.64-4.58 (q, 1H), 3.94-3.90 (d, 1H), 3.83-3.79 (t, 1H), 3.66-3.62 (d, 1H), 3.39-3.34 (q, 1H), 2.91-2.76 (m, 2H), 2.58-2.50 (m, 2H), 1.21-1.16 (m, 6H), 0.71-0.60 (m, 4H).

Example 44

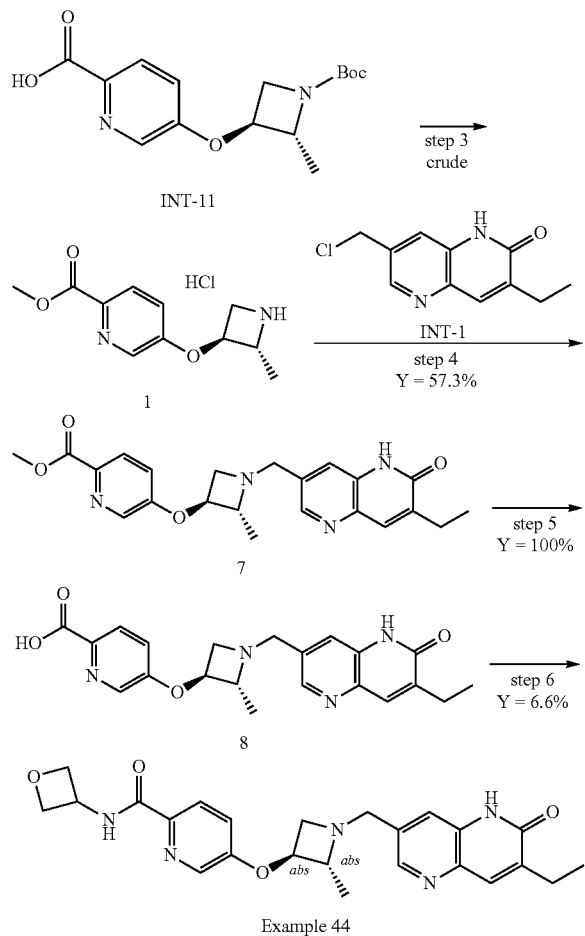

Example 44

Step 1: Preparation of methyl 5-(((2R,3S)-2-methylazetidin-3-yl)oxy)picolinate, HCl Salt To a stirred mixture of tert-butyl 3-{[6-(dihydroxymethyl) piperidin-3-yl]oxy}-2-methylazetidine-1-carboxylate (600 mg, 1.90 mmol, 1.00 equiv.) in MeOH (10 mL) was added SOCl$_2$ (1.13 g, 9.48 mmol, 5.00 equiv.) dropwise at room temperature. The resulting mixture was stirred for 2 h at 80° C. under nitrogen atmosphere. The reaction was monitored by LCMS. The mixture was allowed to cool down to room temperature. The resulting mixture was concentrated under vacuum and the crude product was used in the next step directly without further purification. LC-MS: (ES+H, m/z): [M+H]$^+$=223.2.

Step 2: Preparation of methyl 5-(((2R,3S)-1-((7-ethyl-6-oxo-5,6-dihydro-1,5-naphthyridin-3-yl)methyl)-2-methylazetidin-3-yl)oxy)picolinate To a stirred mixture of methyl 5-{[(2R,3S)-2-methylazetidin-3-yl]oxy}pyridine-2-carboxylate (380 mg, 1.71 mmol, 1.00 equiv.), KI (28 mg, 0.17 mmol, 0.10 equiv.) and 7-(chloromethyl)-3-ethyl-1H-1,5-naphthyridin-2-one (456 mg, 2.05 mmol, 1.20 equiv.) in CH$_3$CN (5 mL) was added DIEA (884 mg, 6.84 mmol, 4.00 equiv.) at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was diluted with water (40 mL). The resulting mixture was extracted with CH$_2$Cl$_2$ (3×30 mL). The combined organic layers were dried over anhydrous Na$_2$SO$_4$. After filtration, the filtrate was concentrated under reduced pressure. The residue was purified by silica gel column chromatography to afford methyl 5-{[(2R,3S)-1-[(7-ethyl-6-oxo-5H-1,5-naphthyridin-3-yl)methyl]-2-methylazetidin-3-yl]oxy}pyridine-2-carboxylate (400 mg, 57.3%) as a brown oil. LC-MS: (ES+H, m/z): [M+H]$^+$=409.2

Step 3: Preparation of 5-(((2R,3S)-1-((7-ethyl-6-oxo-5,6-dihydro-1,5-naphthyridin-3-yl)methyl)-2-methylazetidin-3-yl)oxy)picolinic Acid To a stirred solution of methyl 5-{[(2R,3S)-1-[(7-ethyl-6-oxo-5H-1,5-naphthyridin-3-yl)methyl]-2-methylazetidin-3-yl]oxy}pyridine-2-carboxylate (300 mg, 0.73 mmol, 1.00 equiv.) in MeOH (3 mL) was added NaOH (aqueous., 3 mL, 2N in H$_2$O) in portions at room temperature under nitrogen atmosphere. The resulting mixture was stirred for 1 h at room temperature under nitrogen atmosphere. The reaction was monitored by LCMS. The aqueous layer was extracted with CH$_2$Cl$_2$(2×30 mL). The mixture was acidified to pH 6-7 with HCl (aqueous.). The aqueous layer was concentrated under vacuum. The residue was purified by trituration with MeOH (40 mL). The resulting mixture was filtered, the filter cake was washed with MeOH (1×20 mL). The filtrate was concentrated under reduced pressure. The crude product was used in the next step directly without further purification. LC-MS: (ES+H, m/z): [M+H]$^+$=395.2.

Step 4: Preparation of 5-(((2R,3S)-1-((7-ethyl-6-oxo-5,6-dihydro-1,5-naphthyridin-3-yl)methyl)-2-methylazetidin-3-yl)oxy)-N-(oxetan-3-yl)picolinamide To a stirred mixture of 5-{[(2R,3S)-1-[(7-ethyl-6-oxo-5H-1,5-naphthyridin-3-yl)methyl]-2-methylazetidin-3-yl]oxy}pyridine-2-carboxylic acid (200 mg, 0.51 mmol, 1.00 equiv.), DIEA (262 mg, 2.03 mmol, 4.00 equiv.) and oxetan-3-amine (45 mg, 0.61 mmol, 1.20 equiv.) in DMF (5 mL) was added HATU (289 mg, 0.76 mmol, 1.50 equiv.) in portions at room temperature under nitrogen atmosphere. The resulting mixture was stirred for 2 h at room temperature under nitrogen atmosphere. The reaction was monitored by LCMS. The resulting mixture was diluted with water (30 mL). The resulting mixture was extracted with CH$_2$Cl$_2$ (3×20 mL). The combined organic layers were washed with water (1×30 mL), dried over anhydrous Na$_2$SO$_4$. After filtration, the filtrate was concentrated under reduced pressure. The crude product (130 mg) was purified by Prep-HPLC to afford 5-(((2R,3S)-1-((7-ethyl-6-oxo-5,6-dihydro-1,5-naphthyridin-3-yl)methyl)-2-methylazetidin-3-yl)oxy)-N-(oxetan-3-yl)picolinamide (15.6 mg, 6.6%). LC-MS: (ES+H, m/z): [M+H]$^+$=450.2. $^1$H NMR (300 MHz, DMSO-d$_6$) δ 11.86 (s, 1H), 9.29 (d, 1H), 8.39 (d, 1H), 8.28 (d, 1H), 7.94 (d, 1H), 7.75 (s, 1H), 7.59 (s, 1H), 7.45 (dd, 1H), 5.01

(q, 1H), 4.75-4.61 (m, 5H), 3.93 (d, 1H), 3.82 (t, 1H), 3.65 (d, 1H), 2.80 (t, 1H), 2.57 (d, 2H), 1.24-1.14 (m, 6H).

Example 54 and 55

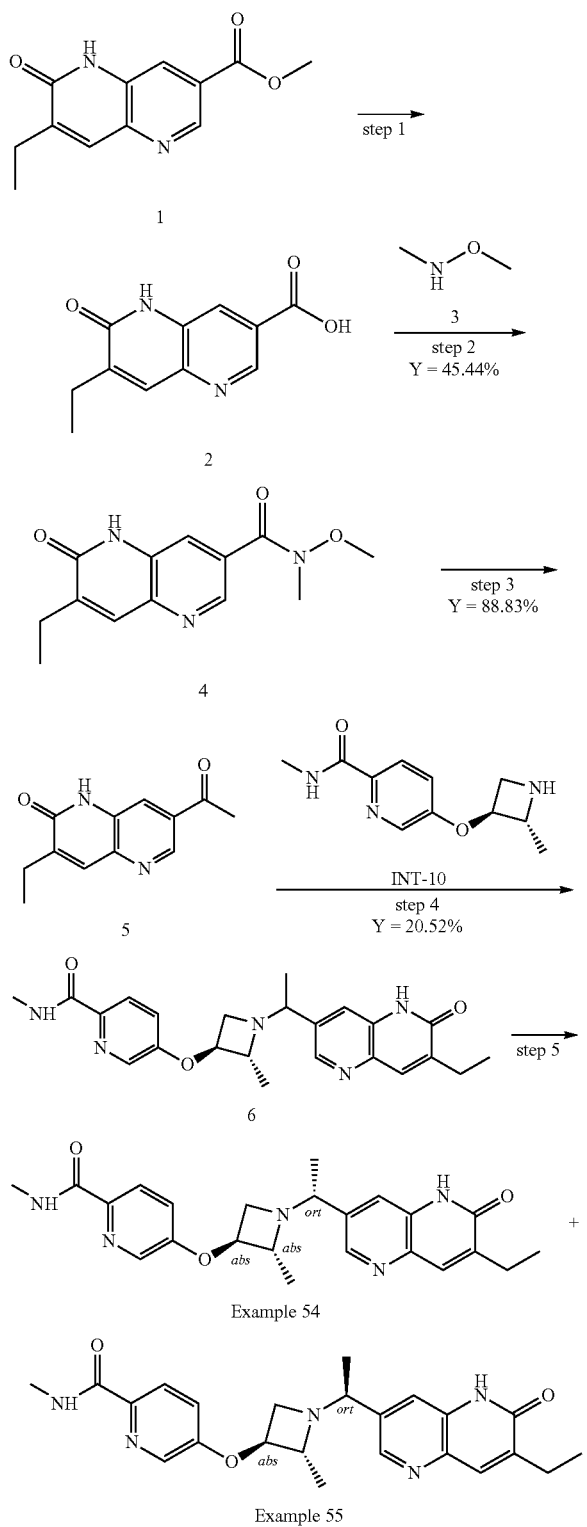

Step 1: Preparation of 7-ethyl-6-oxo-5H-1,5-naphthyridine-3-carboxylic Acid

To a solution of methyl 7-ethyl-6-oxo-5H-1,5-naphthyridine-3-carboxylate (1.15 g, 4.95 mmol, 1.00 equiv.) in MeOH (15 mL) and H$_2$O (3 mL) was added NaOH (0.59 g, 14.86 mmol, 3.00 equiv.) in portions at room temperature. The resulting mixture was stirred for 1 h at room temperature. The reaction was monitored by LCMS. The resulting mixture was diluted with water (10 mL). The residue was acidified to pH 4 with 6N HCl (aqueous.). The resulting mixture was filtered, the solid was concentrated under reduced pressure to afford 7-ethyl-6-oxo-5H-1,5-naphthyridine-3-carboxylic acid (800.0 mg, crude). LC-MS: (ES+H, m/z): [M+H]$^+$=218.9. $^1$H NMR (400 MHz, DMSO-d$_6$) δ 13.43 (s, 1H), 12.08 (s, 1H), 8.89 (d, 1H), 8.15 (d, 1H), 7.82 (s, 1H), 2.62-2.54 (m, 2H), 1.20 (t, 3H).

Step 2: Preparation of 7-ethyl-N-methoxy-N-methyl-6-oxo-5H-1,5-naphthyridine-3-carboxamide To a solution of 7-ethyl-6-oxo-5H-1,5-naphthyridine-3-carboxylic acid (800 mg, crude) and N,O-dimethylhydroxylamine (336 mg, 5.50 mmol, 1.50 equiv.) in DMF (8 mL) was added EDCI (2.10 g, 11.00 mmol, 3.00 equiv.) in portions at room temperature under nitrogen atmosphere. The resulting mixture was stirred for 2 h at room temperature under nitrogen atmosphere. The reaction was monitored by LCMS. The resulting mixture was diluted with water (20 mL). The resulting mixture was extracted with EtOAc (3×25 mL). The combined organic layers were washed with brine (3×50 mL), dried over anhydrous Na$_2$SO$_4$. After filtration, the filtrate was concentrated under reduced pressure. The residue was purified by silica gel column chromatography to afford 7-ethyl-N-methoxy-N-methyl-6-oxo-5H-1,5-naphthyridine-3-carboxamide (540 mg, 45.44%). LC-MS: (ES+H, m/z): [M+H]$^+$=262.1. $^1$H NMR (400 MHz, DMSO-d$_6$) δ 12.02 (s, 1H), 8.64 (d, 1H), 7.89 (dd, 1H), 7.80 (s, 1H), 3.58 (s, 3H), 3.31 (s, 3H), 2.57 (q, 2H), 1.20 (t, 3H).

Step 3: Preparation of 7-acetyl-3-ethyl-1H-1,5-naphthyridin-2-one

To a solution of 7-ethyl-N-methoxy-N-methyl-6-oxo-5H-1,5-naphthyridine-3-carboxamide (540 mg, 2.07 mmol, 1.00 equiv.) in THF (5 mL) was added CH$_3$MgBr (1.4 mL, 4.13 mmol, 2.00 equiv., 3M in THF) dropwise at 0° C. under nitrogen atmosphere. The resulting mixture was stirred for 1.5 h at room temperature under nitrogen atmosphere. The reaction was monitored by LCMS. The reaction was quenched with water at 0° C. The resulting mixture was diluted with water (15 mL). The resulting mixture was extracted with EtOAc (3×20 mL). The combined organic layers were washed with brine (2×60 mL), dried over anhydrous Na$_2$SO$_4$. After filtration, the filtrate was concentrated under reduced pressure. The residue was purified by silica gel column chromatography to afford 7-acetyl-3-ethyl-1H-1,5-naphthyridin-2-one (397 mg, 88.83%). LC-MS: (ES+H, m/z): [M+H]$^+$=217.1. $^1$H NMR (400 MHz, DMSO-d$_6$) δ 12.06 (s, 1H), 8.98 (s, 1H), 8.09 (d, 1H), 7.84 (d, 1H), 2.67 (s, 3H), 2.58 (q, 2H), 1.20 (t, 3H).

Step 4: Preparation of 5-{[(2R,3S)-1-[1-(7-ethyl-6-oxo-5H-1,5-naphthyridin-3-yl)ethyl]-2-methylazetidin-3-yl]oxy}-N-methylpyridine-2-carboxamide A mixture of 7-acetyl-3-ethyl-1H-1,5-naphthyridin-2-one (400 mg, 1.85 mmol, 1.00 equiv.) and N-methyl-5-{[(2R, 3S)-2-methylazetidin-3-yl]oxy}pyridine-2-carboxamide (614 mg, 2.78 mmol, 1.50 equiv.) in DCM (5 mL) was stirred for 15 min at room temperature under nitrogen atmosphere. The resulting mixture was concentrated under reduced pressure. To the above mixture was added tetrakis (propan-2-yloxy)titanium (1.58 g, 5.55 mmol, 3.00 equiv.). The resulting mixture was stirred for 4 h at 80° C. under nitrogen atmosphere. The residue was dissolved in EtOH (10 mL). To the above mixture was added NaBH$_3$CN (233 mg, 3.70 mmol, 2.00 equiv.). The resulting mixture was stirred for 4 h at 80° C. under nitrogen atmosphere. The reaction was monitored by LCMS. The mixture was allowed to cool down to room temperature. The reaction was quenched by the addition of Water (20 mL) at room temperature. The resulting mixture was filtered, the filter cake was washed with CH$_2$Cl$_2$/MeOH=1:1 (3×40 mL). The filtrate was concentrated under reduced pressure. The crude product (350 mg) was purified by Prep-HPLC to afford 5-{[(2R,3S)-1-[1-(7-ethyl-6-oxo-5H-1,5-naphthyridin-3-yl)ethyl]-2-methylazetidin-3-yl]oxy}-N-methylpyridine-2-carboxamide (160 mg, 20.52%).

Step 5: Preparation of 5-{[(2R,3S)-1-[(1R*)-1-(7-ethyl-6-oxo-5H-1,5-naphthyridin-3-yl)ethyl]-2-methylazetidin-3-yl]oxy}-N-methylpyridine-2-carboxamide and 5-{[(2R,3S)-1-[(1R*)-1-(7-ethyl-6-oxo-5H-1,5-naphthyridin-3-yl)ethyl]-2-methylazetidin-3-yl]oxy}-N-methylpyridine-2-carboxamide The racemate 5-{[(2R,3S)-1-[1-(7-ethyl-6-oxo-5H-1,5-naphthyridin-3-yl)ethyl]-2-methylazetidin-3-yl]oxy}-N-methylpyridine-2-carboxamide (160 mg) was separated by Prep-Chiral-HPLC to afford 5-{[(2R,3S)-1-[(1R*)-1-(7-ethyl-6-oxo-5H-1,5-naphthyridin-3-yl)ethyl]-2-methylazetidin-3-yl]oxy}-N-methylpyridine-2-carboxamide (66.6 mg, ee=100%). and 5-{[(2R,3S)-1-[(1R*)-1-(7-ethyl-6-oxo-5H-1,5-naphthyridin-3-yl)ethyl]-2-methylazetidin-3-yl]oxy}-N-methylpyridine-2-carboxamide (48.6 mg, ee=100%).

Example 54: LC-MS: (ES+H, m/z): [M+H]$^+$=422.15. $^1$H NMR (300 MHz, DMSO-d$_6$) δ 11.81 (s, 1H), 8.55 (d, 1H), 8.39 (s, 1H), 8.21 (d, 1H), 7.91 (d, 1H), 7.73 (s, 1H), 7.58 (s, 1H), 7.41-7.35 (m, 1H), 4.55 (d, 1H), 3.72-3.40 (m, 4H), 2.77 (d, 3H), 2.56 (m, 2H), 1.43 (d, 3H), 1.28 (d, 3H), 1.17 (t, 3H).

Example 55: LC-MS: (ES+H, m/z): [M+H]$^+$=422.15. $^1$H NMR (300 MHz, DMSO-d$_6$) δ 11.89 (s, 1H), 8.58 (q, 1H), 8.45 (d, 1H), 8.24 (d, 1H), 7.96 (d, 1H), 7.74 (s, 1H), 7.63 (d, 1H), 7.45 (dd, 1H), 4.55 (q, 1H), 4.02 (t, 1H), 3.60-3.49 (m, 1H), 3.25 (t, 1H), 2.92-2.73 (m, 4H), 2.60-2.52 (m, 2H), 1.19 (q, 6H), 0.70 (d, 3H).

The following examples were made using similar procedures as shown for example 54 and 55:

| Ex | NMR | LCMS (ESI) m/z |
|---|---|---|
| 60 | $^1$H NMR (400 MHz, DMSO-d$_6$) δ 11.89 (s, 1H), 8.42 (dd, 2H), 8.00 (d, 1H), 7.82 (d, 1H), 7.61 (d, 1H), 7.51 (dd, 1H), 4.60 (q, 1H), 4.02 (t, 1H), 3.60-3.49 (m, 1H), 3.27 (t, 1H), 2.85 (t, 1H), 2.13 (d, 3H), 1.22 (d, 3H), 0.69 (d, 3H). | [M + H]$^+$ = 376.15 |
| 61 | $^1$H NMR (400 MHz, DMSO-d$_6$) δ 11.82 (s, 1H), 8.40-8.34 (m, 2H), 7.94 (d, 1H), 7.81 (d, 1H), 7.56 (d, 1H), 7.44 (dd, 1H), 4.59 (q, 1H), 3.65 (q, 1H), 3.57 (t, 1H), 3.48 (p, 1H), 2.57 (dd, 1H), 2.13 (d, 3H), 1.42 (d, 3H), 1.27 (d, 3H). | [M + H]$^+$ = 376.2 |

Example 63

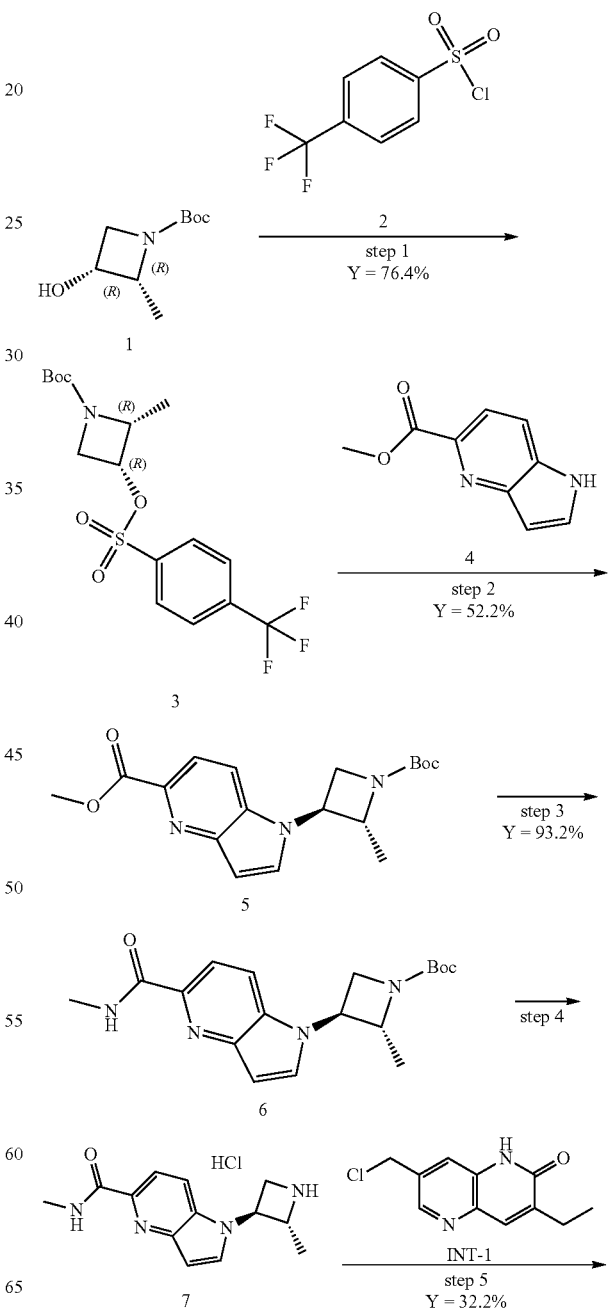

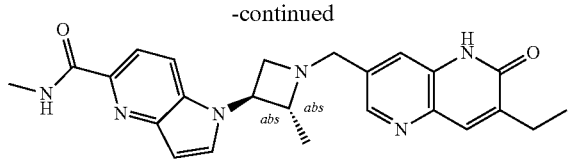

Example 63

Step 1: Preparation of tert-butyl(2R,3R)-2-methyl-3-{[4-(trifluoromethyl)benzenesulfonyl]oxy}azetidine-1-carboxylate To a stirred solution of tert-butyl(2R,3R)-3-hydroxy-2-methylazetidine-1-carboxylate (1.00 g, 5.34 mmol, 1.00 equiv.) and Et$_3$N (1.62 g, 16.02 mmol, 3.00 equiv.) and DMAP (0.03 g, 0.26 mmol, 0.05 equiv.) in DCM (20 mL) was added 4-(trifluoromethyl)benzenesulfonyl chloride (1.44 g, 5.87 mmol, 1.10 equiv.) in DCM (10 mL) at 0° C. under nitrogen atmosphere. The resulting mixture was stirred for 2 h at 0° C. under nitrogen atmosphere. The reaction was monitored by TLC (PE/EA=2/1, KMnO4). The resulting mixture was concentrated under reduced pressure. The residue was purified by silica gel column chromatography to afford tert-butyl(2R,3R)-2-methyl-3-{[4-(trifluoromethyl)benzenesulfonyl]oxy}azetidine-1-carboxylate (1.7 g, 76.4%). $^1$H NMR (300 MHz, Chloroform-d) δ 8.08-8.04 (m, 2H), 7.88-7.85 (m, 2H), 5.13-5.12 (m, 1H), 4.52-4.50 (m, 1H), 4.13 (dd, 1H), 3.86 (dd, 1H), 1.43 (s, 9H), 1.36 (d, 3H).

Step 2: Preparation of tert-butyl(2R,3S)-3-[5-(methoxycarbonyl)pyrrolo[3,2-b]pyridin-1-yl]-2-methylazetidine-1-carboxylate To a stirred solution of tert-butyl(2R,3R)-2-methyl-3-{[4-(trifluoromethyl)benzenesulfonyl]oxy}azetidine-1-carboxylate (1.00 g, 2.52 mmol, 1.00 equiv.) and methyl 1H-pyrrolo[3,2-b]pyridine-5-carboxylate (445 mg, 2.52 mmol, 1.00 equiv.) in DMF (20 mL) was added Cs$_2$CO$_3$ (1.65 g, 5.05 mmol, 2.00 equiv.) at room temperature. The resulting mixture was stirred for 2 h at 110° C. under nitrogen atmosphere. The reaction was monitored by LCMS. The mixture was allowed to cool down to room temperature. The resulting mixture was diluted with EtOAc (200 mL). The resulting mixture was washed with H$_2$O (3×100 mL). The organic layers were washed with brine (50 mL), dried over anhydrous Na$_2$SO$_4$. After filtration, the filtrate was concentrated under reduced pressure. The residue was purified by silica gel column chromatography to afford tert-butyl(2R,3S)-3-[5-(methoxycarbonyl)pyrrolo[3,2-b]pyridin-1-yl]-2-methylazetidine-1-carboxylate (460 mg, 52.2%). LC-MS: (ES+H, m/z): [M+H]$^+$=346.1

$^1$H NMR (300 MHz, DMSO-d$_6$) δ 8.24 (d, 1H), 8.07 (d, 1H), 7.92 (d, 1H), 6.83 (d, 1H), 5.08-5.06 (m, 1H), 4.53-4.50 (m, 1H), 4.27-4.25 (m, 1H), 4.21-4.10 (m, 1H), 3.89 (s, 3H), 1.47 (d, 3H), 1.43 (s, 9H).

Step 3: Preparation of tert-butyl(2R,3S)-2-methyl-3-[5-(methylcarbamoyl)pyrrolo[3,2-b]pyridin-1-yl]azetidine-1-carboxylate To a stirred solution of tert-butyl(2R,3S)-3-[5-(methoxycarbonyl)pyrrolo[3,2-b]pyridin-1-yl]-2-methylazetidine-1-carboxylate (460 mg, 1.39 mmol, 1.00 equiv.) and ACN (3 mL) was added CH$_3$NH$_2$ in water (3 mL, 30% wt) dropwise at room temperature under nitrogen atmosphere. The resulting mixture was stirred for 6 h at room temperature under nitrogen atmosphere. The reaction was monitored by LCMS. The resulting mixture was diluted with sat. NH$_4$Cl (aqueous. 50 mL). The resulting mixture was extracted with CH$_2$Cl$_2$ (3×100 mL). The combined organic layers were washed with brine (3×50 mL), dried over anhydrous Na$_2$SO$_4$. After filtration, the filtrate was concentrated under reduced pressure. The residue was purified by silica gel column chromatography to afford tert-butyl(2R,3S)-2-methyl-3-[5-(methylcarbamoyl)pyrrolo[3,2-b]pyridin-1-yl]azetidine-1-carboxylate (450 mg, 93.2%). LC-MS: (ES+H, m/z): [M+H]$^+$=345.2. $^1$H NMR (300 MHz, DMSO-d$_6$) δ 8.66-8.64 (m, 1H), 8.18 (d, 1H), 8.09-8.03 (m, 1H), 7.90 (d, 1H), 6.75 (d, 1H), 5.07-5.03 (m, 1H), 4.53-4.51 (m, 1H), 4.27 (t, 1H), 4.14 (dd, 1H), 2.84 (d, 3H), 1.47 (d, 3H), 1.43 (s, 9H).

Step 4: Preparation of N-methyl-1-[(2R,3S)-2-methylazetidin-3-yl]pyrrolo[3,2-b]pyridine-5-carboxamide Hydrochloride To a stirred mixture of tert-butyl(2R,3S)-2-methyl-3-[5-(methylcarbamoyl)pyrrolo[3,2-b]pyridin-1-yl]azetidine-1-carboxylate (450 mg, 1.30 mmol, 1.00 equiv.) and HCl (gas) in 1,4-dioxane (5 mL, 4 M/L in dioxane). The resulting mixture was stirred for 1 h at room temperature. The reaction was monitored by LCMS. The resulting mixture was concentrated under reduced pressure. The residue was purified by trituration with hexane/Et$_2$O=1:1 (50 mL). The crude product N-methyl-1-[(2R,3S)-2-methylazetidin-3-yl]pyrrolo[3,2-b]pyridine-5-carboxamide hydrochloride (320 mg) was used in the next step directly without further purification. LC-MS: (ES+H, m/z): [M+H]$^+$=245.1

Step 5: Preparation of 1-[(2R,3S)-1-[(7-ethyl-6-oxo-5H-1,5-naphthyridin-3-yl)methyl]-2-methylazetidin-3-yl]-N-methylpyrrolo[3,2-b]pyridine-5-carboxamide To a stirred solution of 7-(chloromethyl)-3-ethyl-1H-1,5-naphthyridin-2-one (200 mg, 0.89 mmol, 1.00 equiv.) and N-methyl-1-[(2R,3S)-2-methylazetidin-3-yl]pyrrolo[3,2-b]pyridine-5-carboxamide hydrochloride (241 mg, assumed 100% yield, 0.98 mmol, 1.10 equiv.) and KI (29 mg, 0.18 mmol, 0.20 equiv.) in ACN (5 mL) was added DIEA (580 mg, 4.49 mmol, 5.00 equiv.) dropwise at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford crude product. The residue was dissolved in DMSO (3 mL). The residue was purified by Prep-HPLC. The pure fraction was concentrated under vacuum then lyophilized to afford 1-[(2R,3S)-1-[(7-ethyl-6-oxo-5H-1,5-naphthyridin-3-yl)methyl]-2-methylazetidin-3-yl]-N-methylpyrrolo[3,2-b]pyridine-5-carboxamide (126.2 mg, 32.2%). LC-MS: (ES+H, m/z): [M+H]$^+$=431.15. Optical rotation [a]$^{25}_D$ (c=0.5, MeOH): −26.4°; $^1$H NMR (300 MHz, DMSO-d$_6$) δ 11.91 (s, 1H), 8.65 (d, 1H), 8.45 (d, 1H), 8.18-8.11 (m, 2H), 7.87 (d, 1H), 7.76 (s, 1H), 7.65 (d, 1H), 6.75 (d, 1H), 4.86 (d, 1H), 4.1 (d, 1H), 3.82-3.76 (m, 2H), 3.68-3.63 (m, 1H), 3.31-3.29 (m, 1H), 2.84 (d, 3H), 2.56-2.51 (m, 2H), 1.2-1.16 (m, 6H).

The following examples were made using similar procedures as shown for example 63:

| Ex | NMR | LCMS (ESI) m/z |
|---|---|---|
| 40 | $^1$H NMR (300 MHz, DMSO-$d_6$) δ 11.91 (s, 1H), 8.65 (d, 1H), 8.43 (d, 1H), 8.17 (dd, 2H), 7.89 (d, 1H), 7.75 (s, 1H), 7.64 (d, 1H), 6.75 (d, 1H), 5.35-5.23 (m, 1H), 3.91-3.78 (m, 4H), 3.58-3.48 (m, 2H), 2.84 (d, 3H), 2.56 (q, 2H), 1.18 (t, 3H). | [M + H]$^+$ = 417.2 |
| 49 | $^1$H NMR (300 MHz, Methanol-d4) δ 8.53 (d, 1H), 8.12 (dd, 1H), 7.98-7.91 (m, 2H), 7.86-7.76 (m, 2H), 6.71 (dd, 1H), 5.30-5.15 (m, 1H), 3.89 (s, 2H), 3.26-3.14 (m, 1H), 3.00 (s, 4H), 2.96-2.90 (m, 1H), 2.74-2.48 (m, 4H), 2.23-2.02 (m, 1H), 1.29 (t, 3H). | [M + H]$^+$ = 431.25 |
| 83 | $^1$H NMR (400 MHz, DMSO-$d_6$) δ 11.95 (s, 1H), 8.46 (s, 1H), 8.39 (s, 1H), 8.26 (d, J = 8.5 Hz, 1H), 7.84-7.71 (m, 2H), 7.67 (s, 1H), 6.87 (d, J = 3.4 Hz, 1H), 4.96 (brs, 1H), 4.04 (brs, 1H), 3.81-3.68 (m, 3H), 3.38-3.33 (m, 1H), 2.63-2.53 (m, 2H), 1.23-1.16 (m, 6H). | [M + H]$^+$ = 399.20 |
| 86 | $^1$H NMR (400 MHz, DMSO-$d_6$) δ 11.91 (s, 1H), 8.57 (d, J = 4.9 Hz, 1H), 8.44 (d, J = 1.8 Hz, 1H), 8.17 (d, J = 4.2 Hz, 1H), 8.13 (d, J = 8.8 Hz, 1H), 7.88 (d, J = 8.6 Hz, 1H), 7.75 (s, 1H), 7.64 (d, J = 1.9 Hz, 1H), 6.75 (d, J = 3.4 Hz, 1H), 4.86 (q, J = 7.5 Hz, 1H), 4.03 (d, J = 13.4 Hz, 1H), 3.83-3.73 (m, 2H), 3.65 (p, J = 6.2 Hz, 1H), 3.32 (t, J = 7.4 Hz, 1H), 2.95-2.87 (m, 1H), 2.54 (q, J = 7.56 Hz, 2H), 1.21-1.17 (m, 6H), 0.72-0.66 (m, 4H). | [M + H]$^+$ = 457.20 |
| 87 | $^1$H NMR (300 MHz, DMSO-$d_6$) δ 11.92 (s, 1H), 8.63 (q, J = 5.0 Hz, 1H), 8.42 (d, J = 1.8 Hz, 1H), 8.14-8.11 (m, 2H), 7.86 (d, J = 8.6 Hz, 1H), 7.63 (d, J = 1.8 Hz, 1H), 7.42 (s, 1H), 6.75 (d, J = 3.4 Hz, 1H), 4.85 (q, J = 7.5 Hz, 1H), 4.00 (d, J = 13.5 Hz, 1H), 3.80-3.76 (m, 2H), 3.65-3.61 (m, 1H), 3.30-3.29 (m, 1H), 2.84 (d, J = 4.8 Hz, 3H), 2.18-2.10 (m, 1H), 1.19 (d, J = 6.0 Hz, 3H), 0.98-0.96 (m, 2H), 0.84-0.82 (m, 2H). | [M + H]$^+$ = 443.20 |
| 88 | $^1$H NMR (400 MHz, DMSO-$d_6$) δ 11.91 (s, 1H), 8.67 (t, J = 6.1 Hz, 1H), 8.45 (d, J = 1.8 Hz, 1H), 8.18 (d, J = 3.4 Hz, 1H), 8.13 (d, J = 8.6 Hz, 1H), 7.88 (d, J = 8.5 Hz, 1H), 7.76 (s, 1H), 7.65 (d, J = 1.8 Hz, 1H), 6.76 (d, J = 3.5 Hz, 1H), 4.86 (q, J = 7.5 Hz, 1H), 4.02 (d, J = 13.5 Hz, 1H), 3.83-3.75 (m, 2H), 3.65-3.62 (m, 1H), 3.38-3.35 (m, 1H), 3.34-3.29 (m, 2H), 2.57-2.51 (m, 2H), 1.20-1.12 (m, 9H). | [M + H]$^+$ = 445.15 |
| 96 | $^1$H NMR (300 MHz, DMSO-$d_6$) δ 12.46 (s, 1H), 8.64 (q, J = 4.8 Hz, 1H), 8.13-8.05 (m, 2H), 7.85 (d, J = 8.6 Hz, 1H), 7.52 (d, J = 8.3 Hz, 1H), 7.33 (t, J = 7.6 Hz, 1H), 6.74 (d, J = 3.4 Hz, 1H), 4.83 (q, J = 7.5 Hz, 1H), 4.00 (d, J = 13.4 Hz, 1H), 3.86-3.79 (m, 2H), 3.66 (p, J = 5.9 Hz, 1H), 3.30-3.29 (m, 1H), 2.84 (d, J = 4.8 Hz, 3H), 2.42 (s, 3H), 1.20 (d, J = 5.9 Hz, 3H). | [M + H]$^+$ = 435.10 |

Example 66

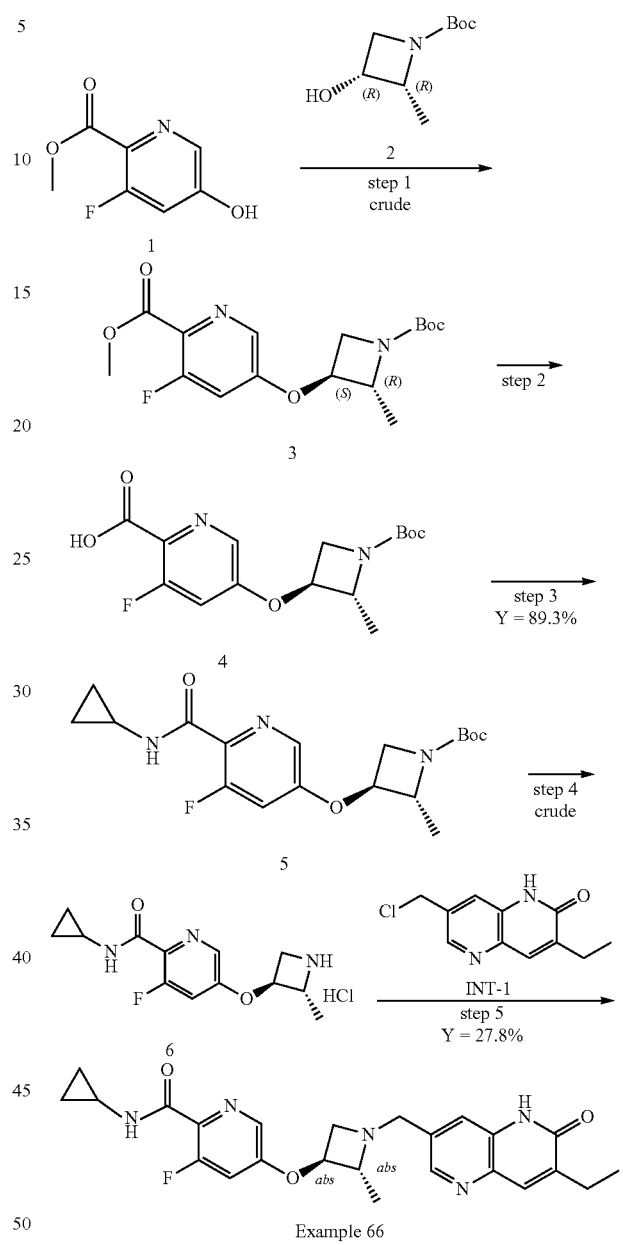

Example 66

Step 1: Preparation of methyl 5-{[(2R,3S)-1-(tert-butoxycarbonyl)-2-methylazetidin-3-yl]oxy}-3-fluoropyridine-2-carboxylate A solution of methyl 3-fluoro-5-hydroxypyridine-2-carboxylate (500 mg, 2.92 mmol, 1.00 equiv.), tert-butyl(2R,3R)-3-hydroxy-2-methylazetidine-1-carboxylate (547 mg, 2.92 mmol, 1.00 equiv.) and PPh$_3$ (1.53 g, 5.84 mmol, 2.00 equiv.) in PhMe (20 mL) was treated with DBAD (1.35 g, 5.84 mmol, 2.00 equiv.) in PhCH$_3$ (5 mL) at 0° C. The resulting mixture was stirred for 2 h at 60° C. The mixture was allowed to cool down to room temperature. The reaction was monitored by LCMS. The resulting mixture was concentrated under reduced pressure. The resulting mixture was diluted with water (30 mL). The resulting mixture was extracted with EtOAc (3×40 mL). The combined organic layers were washed with brine (1×40 mL), dried over anhydrous Na$_2$SO$_4$. After filtration, the filtrate was concentrated under reduced pressure. This resulted in methyl 5-{[(2R,3S)-1-(tert-butoxycarbonyl)-2-methylazetidin-3-yl]oxy}-3-fluoropyridine-2-carboxylate (4.2 g, crude) as a black oil. The crude resulting mixture was used in the next step directly without further purification. LC-MS: (ES+H, m/z): [M+H]$^+$=341.05.

Step 2: Preparation of 5-{[(2R,3S)-1-(tert-butoxycarbonyl)-2-methylazetidin-3-yl]oxy}-3-fluoropyridine-2-carboxylic Acid A solution of methyl 5-{[(2R,3S)-1-(tert-butoxycarbonyl)-2-methylazetidin-3-yl]oxy}-3-fluoropyridine-2-carboxylate (4.00 g, Crude) in THF (14 mL) was treated with NaOH (0.94 g, 23.50 mmol, 2.00 equiv.) in H$_2$O (7 mL) at 0° C. The resulting mixture was stirred for 1 h at room temperature. The reaction was monitored by LCMS. The resulting mixture was diluted with water (40 ml). The resulting mixture was extracted with EtOAc (3×70 mL). The aqueous layer was acidified to pH 4 with HCl (aqueous. 1 mol/L). The resulting mixture was extracted with EtOAc (3×70 mL). The combined organic layers were washed with brine (1×60 mL), dried over anhydrous Na$_2$SO$_4$. After filtration, the filtrate was concentrated under reduced pressure. This resulted in 5-{[(2R,3S)-1-(tert-butoxycarbonyl)-2-methylazetidin-3-yl]oxy}-3-fluoropyridine-2-carboxylic acid (900 mg, 94.2%, over two steps). LC-MS: (ES+H, m/z): [M+H]$^+$=327.1.

Step 3: Preparation of tert-butyl(2R,3S)-3-{[6-(cyclopropylcarbamoyl)-5-fluoropyridin-3-yl]oxy}methylazetidine-1-carboxylate A solution of 5-{[(2R,3S)-1-(tert-butoxycarbonyl)-2-methylazetidin-3-yl]oxy}-3-fluoropyridine-2-carboxylic acid (600 mg, 1.83 mmol, 1.00 equiv.) in DMF (10 mL) was treated with HATU (1.05 g, 2.75 mmol, 1.50 equiv.) for 10 min at room temperature followed by the addition of aminocyclopropane (524 mg, 9.19 mmol, 5.00 equiv.) and DIEA (950. mg, 7.35 mmol, 4.00 equiv.) at room temperature. The resulting mixture was stirred for additional 1.5 h at room temperature. The reaction was monitored by LCMS. The resulting mixture was diluted with water (50 mL). The resulting mixture was extracted with EtOAc (3×80 mL). The combined organic layers were washed with brine (1×80 mL), dried over anhydrous Na$_2$SO$_4$. After filtration, the filtrate was concentrated under reduced pressure. The residue was purified by silica gel column chromatography to afford tert-butyl(2R,3S)-3-{[6-(cyclopropylcarbamoyl)-5-fluoropyridin-3-yl]oxy}-2-methylazetidine-1-carboxylate (600 mg, 89.3%). LC-MS: (ES+H, m/z): [M+H]$^+$=366.10. $^1$H NMR (300 MHz, DMSO-d$_6$): δ 8.48 (d, 1H), 8.12 (dd, 1H), 7.40 (dd, 1H), 4.83-4.78 (m, 1H), 4.31-4.22 (m, 2H), 3.64 (dd, 1H), 2.87-2.81 (m, 1H), 1.39 (s, 9H), 1.43 (d, 3H), 0.71-0.65 (m, 2H), 0.62-0.57 (m, 2H).

Step 4: Preparation of N-cyclopropyl-3-fluoro-5-{[(2R,3S)-2-methylazetidin-3-yl]oxy}pyridine-2-carboxamide Hydrochloride A solution of tert-butyl(2R,3S)-3-{[6-(cyclopropylcarbamoyl)-5-fluoropyridin-3-yl]oxy}-2-methylazetidine-1-carboxylate (600 mg, 1.64 mmol, 1.00 equiv.) in EA (20 mL) was treated with HCl (gas) in 1,4-dioxane (10 mL, 4M) at 0° C. The resulting mixture was stirred for 1.5 h at room temperature. The reaction was monitored by LCMS. The resulting mixture was concentrated under reduced pressure. This resulted in N-cyclopropyl-3-fluoro-5-[(2R,3S)-2-methylazetidin-3-yl]oxy)pyridine-2-carboxamide hydrochloride (600 mg, Crude). LC-MS: (ES+H, m/z): [M+H]$^+$=266.05.

Step 5: Preparation of N-cyclopropyl-5-{[(2R,3S)-1-[(7-ethyl-6-oxo-5H-1,5-naphthyridin-3-yl)methyl]-2-methylazetidin-3-yl]oxy}-3-fluoropyridine-2-carboxamide To a stirred mixture of N-cyclopropyl-3-fluoro-5-{[(2R,3S)-2-methylazetidin-3-yl]oxy}pyridine-2-carboxamide hydrochloride (285 mg, assumed 100% yield, 1.07 mmol, 1.20 equiv.) and DIEA (464 mg, 3.59 mmol, 4.00 equiv.) in MeCN (10 mL) were added 7-(chloromethyl)-3-ethyl-1H-1,5-naphthyridin-2-one (200 mg, 0.89 mmol, 1.00 equiv.) and KI (29.82 mg, 0.18 mmol, 0.20 equiv.) at room temperature. The resulting mixture was stirred for additional 2 h at 80° C. The mixture was allowed to cool down to room temperature. The reaction was monitored by LCMS. The resulting mixture was diluted with water (30 mL). The resulting mixture was extracted with CH$_2$Cl$_2$ (3×40 mL). The combined organic layers were washed with brine (1×30 mL), dried over anhydrous Na$_2$SO$_4$. After filtration, the filtrate was concentrated under reduced pressure. The residue was purified by reversed combi-flash chromatography. The resulting mixture was concentrated under reduced pressure. This resulted in N-cyclopropyl-5-{[(2R,3S)-1-[(7-ethyl-6-oxo-5H-1,5-naphthyridin-3-yl)methyl]-2-methylazetidin-3-yl]oxy}-3-fluoropyridine-2-carboxamide (112.9 mg, 27.8%). LC-MS: (ES+H, m/z): [M+H]$^+$=452.20. Optical rotation [a]$^{25}_D$ (c=0.1, MeOH): −6.0°; $^1$H NMR (400 MHz, DMSO-d$_6$): δ 11.86 (s, 1H), 8.46 (d, 1H), 8.38 (d, 1H), 8.15 (d, 1H), 7.74 (s, 1H), 7.58 (d, 1H), 7.41 (dd, 1H), 4.64 (q, 1H), 3.91 (d, 1H), 3.82 (t, 1H), 3.64 (d, 1H), 3.38 (t, 1H), 2.85-2.75 (m, 2H), 2.56-2.53 (m, 2H), 1.28 (m, 6H), 0.69-0.63 (m, 2H), 0.61-0.56 (m, 2H). $^{19}$F NMR (377 MHz, DMSO-d$_6$) δ−118.55.

Example 75

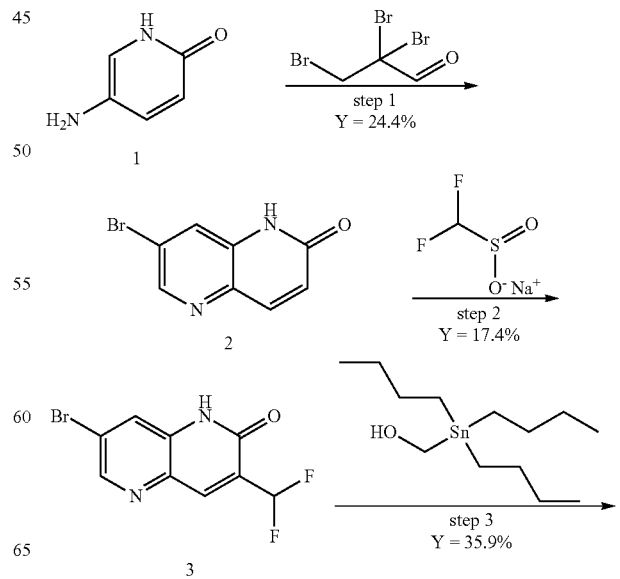

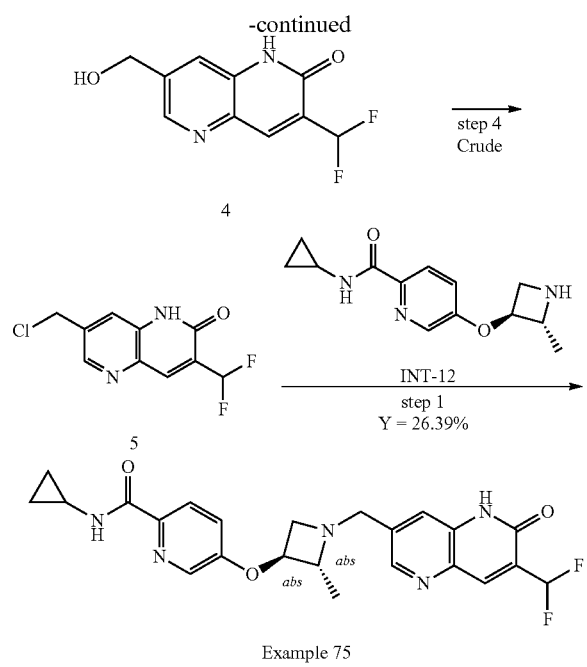

Example 75

Step 1: Preparation of 7-bromo-1H-1,5-naphthyridin-2-one

To a stirred mixture of 5-aminopyridin-2-ol (5.00 g, 45.41 mmol, 1.00 equiv.) in AcOH (60 mL) was added 2,2,3-tribromopropanal (13.38 g, 45.40 mmol, 1.00 equiv.) at room temperature under nitrogen atmosphere. The resulting mixture was stirred for 2 h at 70° C. under nitrogen atmosphere. The reaction was monitored by LCMS. The resulting mixture was concentrated under reduced pressure. The resulting mixture was diluted with water (200 mL). The resulting mixture was extracted with EtOAc (3×200 mL). The combined organic layers were washed with brine (2×100 mL), dried over anhydrous $Na_2SO_4$. After filtration, the filtrate was concentrated under reduced pressure. The residue was purified by silica gel column chromatography to afford 7-bromo-1H-1,5-naphthyridin-2-one (2.50 g, 24.4%). LC-MS: (ES+H, m/z): $[M+H]^+$=225.00/227.00. $^1$H NMR (400 MHz, DMSO-$d_6$) δ 11.95 (s, 1H), 8.55 (d, J=2.1 Hz, 1H), 7.92 (d, J=9.8 Hz, 1H), 7.85 (d, J=2.1 Hz, 1H), 6.78 (d, J=9.8 Hz, 1H).

Step 2: Preparation of 7-bromo-3-(difluoromethyl)-1H-1,5-naphthyridin-2-one

To a stirred mixture of 7-bromo-1H-1,5-naphthyridin-2-one (2.30 g, 10.22 mmol, 1.00 equiv.) in MeCN (20 mL) and $H_2O$ (6 mL) were added sodium difluoromethanesulfinate (3.53 g, 20.44 mmol, 2.00 equiv., 80% wt) and potassium peroxydisulfate (11.05 g, 40.88 mmol, 4.00 equiv.) at room temperature under nitrogen atmosphere. The resulting mixture was stirred overnight at 80° C. under nitrogen atmosphere. The reaction was monitored by LCMS. The mixture was allowed to cool down to room temperature. The resulting mixture was filtered; the filter cake was washed with DCM/MeOH (10:1) (3×100 mL). The filtrate was concentrated under reduced pressure. The residue was purified by silica gel column chromatography to afford 7-bromo-3-(difluoromethyl)-1H-1,5-naphthyridin-2-one (490 mg, 17.4%). LC-MS: (ES+H, m/z): $[M+H]^+$=275.00/277.00. $^1$H NMR (300 MHz, DMSO-$d_6$) δ 12.40 (s, 1H), 8.66 (d, J=2.1 Hz, 1H), 8.16 (d, J=1.8 Hz, 1H), 7.91 (d, J=2.1 Hz, 1H), 7.17-6.76 (m, 1H). $^{19}$F NMR (282 MHz, DMSO-$d_6$) δ −119.76.

Step 3: Preparation of 3-(difluoromethyl)-7-(hydroxymethyl)-1H-1,5-naphthyridin-2-one To a stirred solution of 7-bromo-3-(difluoromethyl)-1H-1,5-naphthyridin-2-one (2.20 g, 7.99 mmol, 1.00 equiv.) in 1,4-dioxane (30 mL) were added (tributylstannyl)methanol (2.83 g, 8.79 mmol, 1.10 equiv.) and 2nd Generation XPhos Precatalyst (314 mg, 0.40 mmol, 0.05 equiv.) at room temperature under nitrogen atmosphere. The resulting mixture was stirred overnight at 80° C. under nitrogen atmosphere. The reaction was monitored by LCMS. The resulting mixture was concentrated under reduced pressure. The residue was purified by silica gel column chromatography to afford 3-(difluoromethyl)-7-(hydroxymethyl)-1H-1,5-naphthyridin-2-one (650 mg, 35.9%). LC-MS: (ES+H, m/z): $[M+H]^+$=227.1. $^1$H NMR (300 MHz, DMSO-$d_6$) δ 12.36 (s, 1H), 8.50 (d, J=1.8 Hz, 1H), 8.16 (d, J=1.8 Hz, 1H), 7.70 (d, J=1.9 Hz, 1H), 7.18-6.78 (m, 1H), 5.57 (t, J=5.6 Hz, 1H), 4.67 (d, J=5.6 Hz, 2H). $^{19}$F NMR (282 MHz, DMSO-$d_6$) δ −119.24.

Step 4: Preparation of 7-(chloromethyl)-3-(difluoromethyl)-1H-1,5-naphthyridin-2-one To a stirred mixture of 3-(difluoromethyl)-7-(hydroxymethyl)-1H-1,5-naphthyridin-2-one (290 mg, 1.28 mmol, 1.00 equiv.) in DCM (5 mL) were added DMF (9 mg, 0.12 mmol, 0.10 equiv.) and $SOCl_2$ (0.93 mL, 12.82 mmol, 10.00 equiv.) dropwise at 0° C. under nitrogen atmosphere. The resulting mixture was stirred overnight at room temperature under nitrogen atmosphere. The reaction was monitored by LCMS. The resulting mixture was concentrated under reduced pressure to afford 7-(chloromethyl)-3-(difluoromethyl)-1H-1,5-naphthyridin-2-one (310 mg, crude). LC-MS: (ES+H, m/z): $[M+H]^+$=245.1.

Step 5: Preparation of N-cyclopropyl-5-{[(2R,3S)-1-{[7-(difluoromethyl)-6-oxo-5H-1,5-naphthyridin-3-yl]methyl}-2-methylazetidin-3-yl]oxy}pyridine-2-carboxamide To a stirred solution of 7-(chloromethyl)-3-(difluoromethyl)-1H-1,5-naphthyridin-2-one (110 mg, 0.45 mmol, 1.00 equiv.), N-cyclopropyl-5-{[(2R,3S)-2-methylazetidin-3-yl]oxy}pyridine-2-carboxamide (144 mg, 0.58 mmol, 1.30 equiv.) and KI (14 mg, 0.09 mmol, 0.20 equiv.) in ACN (5 mL) was added DIEA (290 mg, 2.25 mmol, 5.00 equiv.) dropwise at room temperature under nitrogen atmosphere. The resulting mixture was stirred for 1 h at 80° C. The reaction was monitored by LCMS. The mixture was allowed to cool down to room temperature. The residue was dissolved in water (50 mL). The solution was extracted with EtOAc (3×100 mL). The combined organic layers were dried over anhydrous $Na_2SO_4$. After filtration, the filtrate was concentrated under reduced pressure. The residue was purified by silica gel column chromatography to afford crude product (90 mg). The crude product was isolated by PRE-P_HPLC to afford N-cyclopropyl-5-{[(2R,3S)-1-{[7-(difluoromethyl)-6-oxo-5H-1,5-naphthyridin-3-yl]methyl}-2-methylazetidin-3-yl]oxy}pyridine-2-carboxamide (54.6 mg, 26.39%, 99.0% purity, $[α]_D^{25}$=−9.800 (C=1, MeOH:

DCM=1:1) test in PHA). LC-MS: (ES+H, m/z): [M+H]⁺ =456.15. ¹H NMR (300 MHz, DMSO-d₆) δ 12.30 (s, 1H), 8.54-8.47 (m, 2H), 8.22 (d, 1H), 8.16 (s, 1H), 7.95 (d, 1H), 7.68 (d, 1H), 7.44 (dd, 1H), 6.98 (t, 1H), 4.72-4.51 (m, 1H), 3.98 (d, 1H), 3.89-3.78 (m, 1H), 3.71 (d, 1H), 3.45-3.35 (m, 1H), 2.95-2.74 (m, 2H), 1.22 (d, 3H), 0.73-0.55 (m, 4H). ¹⁹F NMR (282 MHz, DMSO-d₆) δ−119.30.

Example 76

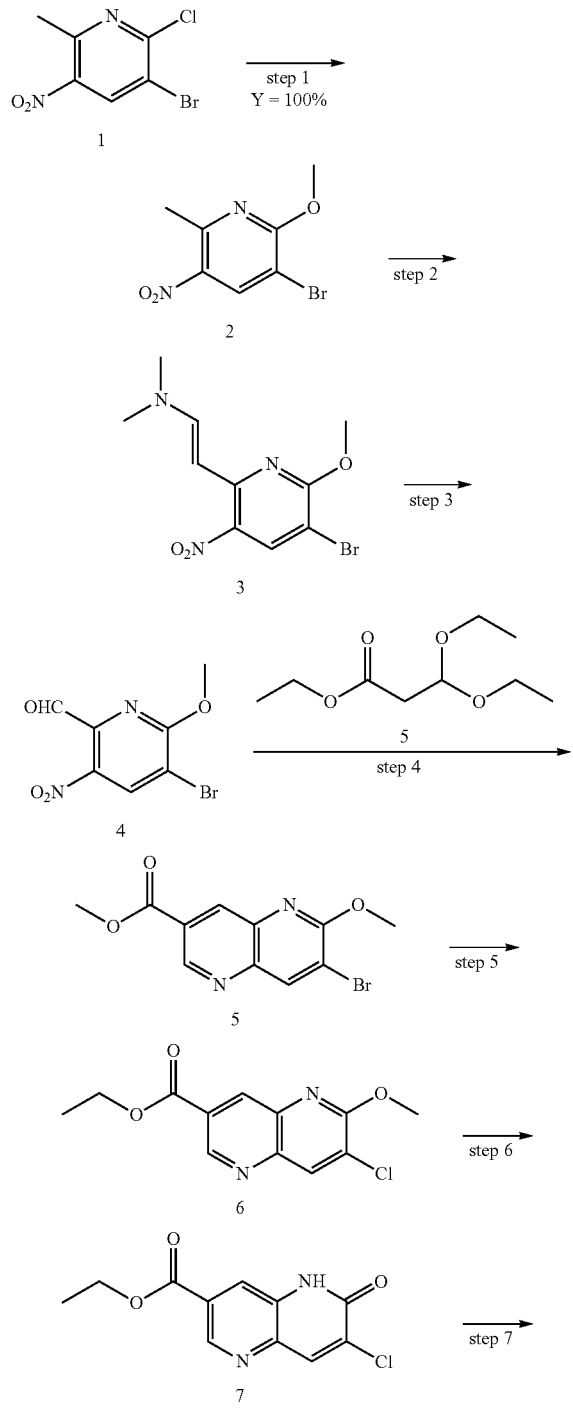

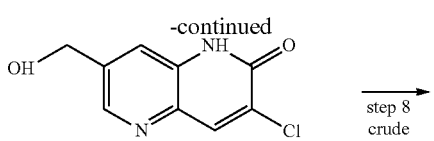

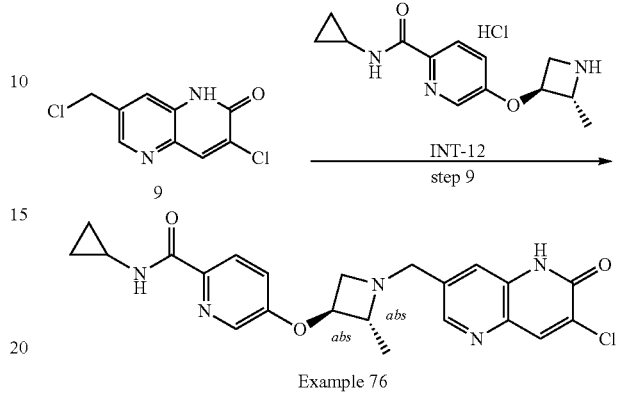

Example 76

Step 1: Preparation of 3-bromo-2-methoxy-6-methyl-5-nitropyridine

To a stirred mixture of 3-bromo-2-chloro-6-methyl-5-nitropyridine (20.00 g, 79.54 mmol, 1.00 equiv.) in MeOH (50 mL) was added NaOMe (15.76 g, 87.49 mmol, 1.10 equiv., 30% wt) dropwise at 0° C. under nitrogen atmosphere. The resulting mixture was stirred overnight at room temperature under nitrogen atmosphere. The reaction was monitored by TLC (PE:EA=1:1, R_f=0.4). The resulting mixture was concentrated under reduced pressure and water (100 mL) was added. The resulting mixture was extracted with EtOAc (3×100 mL). The combined organic layers were washed with brine (1×200 mL), dried over anhydrous Na₂SO₄. After filtration, the filtrate was concentrated under reduced pressure to afford 3-bromo-2-methoxy-6-methyl-5-nitropyridine (20 g, 99%). ¹H NMR (400 MHz, DMSO-d₆) δ 8.66 (s, 1H), 4.04 (s, 3H), 2.70 (s, 3H).

Step 2: Preparation of (E)-2-(5-bromo-6-methoxy-3-nitropyridin-2-yl)-N,N-dimethylethen-1-amine A mixture of 3-bromo-2-methoxy-6-methyl-5-nitropyridine (15.00 g, 60.72 mmol, 1.00 equiv.) in DMF-DMA (100 mL) and DMF (100 mL) was stirred overnight at 100° C. under nitrogen atmosphere. The reaction was monitored by TLC. The mixture was allowed to cool down to room temperature. The resulting mixture was concentrated under reduced pressure. The crude product was used in the next step directly without further purification.

Step 3: Preparation of 5-bromo-6-methoxy-3-nitropicolinaldehyde

To a stirred mixture of (E)-2-(5-bromo-6-methoxy-3-nitropyridin-2-yl)ethenyl)dimethylamine (18.01 g, crude) in THF (100 mL) and H₂O (100 mL) was added NaIO₄ (28.00 g, 131.07 mmol, 2.20 equiv.) in portions at 0° C. under nitrogen atmosphere. The resulting mixture was stirred for 2h at room temperature under nitrogen atmosphere. The reaction was monitored by TLC. The reaction was quenched by the addition of sat. sodium hyposulfite (aqueous.) (100 mL) at room temperature. The resulting mixture was extracted with EtOAc (3×100 mL). The combined organic layers were washed with brine (2×100 mL), dried over anhydrous $Na_2SO_4$. After filtration, the filtrate was concentrated under reduced pressure. The crude product was used in the next step directly without further purification $^1$H NMR (400 MHz, DMSO-$d_6$) δ 10.16 (s, 1H), 8.87 (s, 1H), 4.10 (s, 3H).

Step 4: Preparation of ethyl 7-bromo-6-methoxy-1,5-naphthyridine-3-carboxylate To a stirred mixture of 5-bromo-6-methoxy-3-nitropyridine-2-carbaldehyde (7.00 g, crude) and ethyl 3,3-diethoxypropanoate (20.40 g, 107.27 mmol, 4.00 equiv.) in EtOH (100 mL) were added $SnCl_2$ (26.25 g, 134.09 mmol, 5.00 equiv.) in portions at room temperature under nitrogen atmosphere. The resulting mixture was stirred overnight at 90° C. under nitrogen atmosphere. The reaction was monitored by LCMS. The mixture was allowed to cool down to room temperature. The resulting mixture was concentrated under reduced pressure. The crude mixture was poured into saturated sodium bicarbonate (100 mL). The resulting mixture was extracted with EtOAc (3×100 mL). The combined organic layers were concentrated under reduced pressure. The residue was purified by silica gel column chromatography to afford crude product. The crude product was purified by trituration with hexane (50 mL) to afford ethyl 7-bromo-6-methoxy-1,5-naphthyridine-3-carboxylate (3.50 g, 18.5%, over three steps). LC-MS: (ES+H, m/z): $[M+H]^+$=311.0/313.0. $^1$H NMR (400 MHz, DMSO-$d_6$) δ 9.22 (s, 1H), 8.78 (s, 1H), 8.58 (s, 1H), 4.42 (q, 2H), 4.12 (s, 3H), 1.39 (t, 3H).

Step 5: Preparation of ethyl 7-chloro-6-methoxy-1,5-naphthyridine-3-carboxylate To a stirred mixture of ethyl 7-bromo-6-methoxy-1,5-naphthyridine-3-carboxylate (1.20 g, 3.85 mmol, 1.00 equiv.) in DMF (10 mL) was added CuCl (0.57 g, 5.78 mmol, 1.50 equiv.) at room temperature under nitrogen atmosphere. The resulting mixture was stirred overnight at 120° C. The reaction was monitored by LCMS. The mixture was allowed to cool down to room temperature. The resulting mixture was diluted with EtOAc (20 mL). The resulting mixture was washed with 3×30 mL of Water (10% $NH_3·H_2O$). The resulting mixture was concentrated under reduced pressure. The residue was purified by silica gel column chromatography to afford ethyl 7-chloro-6-methoxy-1,5-naphthyridine-3-carboxylate (800 mg, 77.78%). LC-MS: (ES+H, m/z): $[M+H]^+$=267.0. $^1$H NMR (300 MHz, DMSO-$d_6$) δ 9.27 (d, 1H), 8.63 (d, 1H), 8.57 (s, 1H), 4.41 (q, 2H), 4.12 (s, 3H), 1.37 (t, 3H).

Step 6: Preparation of ethyl 7-chloro-6-oxo-5H-1,5-naphthyridine-3-carboxylate To a stirred mixture of ethyl 7-chloro-6-methoxy-1,5-naphthyridine-3-carboxylate (800 mg, 3.00 mmol, 1.00 equiv.) in $CH_3CN$ (8 mL) was added TMSI (1.80 g, 9.00 mmol, 3.00 equiv.) at room temperature under nitrogen atmosphere. The resulting mixture was stirred for 2 h at 50° C. The reaction was monitored by LCMS. The mixture was allowed to cool down to room temperature. The resulting mixture was diluted with EtOAc (50 mL). The aqueous layer was washed with 3×50 mL of water (10% $Et_3N$). The combined organic layers were washed with brine (50 mL), dried over anhydrous $Na_2SO_4$. After filtration, the filtrate was concentrated under reduced pressure. The residue was purified by silica gel column chromatography to afford ethyl 7-chloro-6-oxo-5H-1,5-naphthyridine-3-carboxylate (740 mg, 97.64%). LC-MS: (ES+H, m/z): $[M+H]^+$=252.9. $^1$H NMR (300 MHz, DMSO-$d_6$) δ12.61 (s, 1H), 8.94 (d, 1H), 8.37 (d, 1H), 8.20 (s, 1H), 4.39 (q, 2H), 1.36 (t, 3H).

Step 7: Preparation of 3-chloro-7-(hydroxymethyl)-1H-1,5-naphthyridin-2-one

To a stirred mixture of ethyl 7-chloro-6-oxo-5H-1,5-naphthyridine-3-carboxylate (740 mg, 2.92 mmol, 1.00 equiv.) in THF (6 mL) was added $LiAlH_4$ (2.5 mL, 5.85 mmol, 2.00 equiv.) dropwise at 0° C. under nitrogen atmosphere. The resulting mixture was stirred for additional 2 h at 0° C. The reaction was monitored by LCMS. The mixture was acidified to pH 5 with 1 M HCl. The resulting mixture was concentrated under reduced pressure. The residue was purified by silica gel column chromatography to afford 3-chloro-7-(hydroxymethyl)-1H-1,5-naphthyridin-2-one (250 mg, 40.53%). LC-MS: (ES+H, m/z): $[M+H]^+$=211.00. $^1$H NMR (400 MHz, DMSO-$d_6$) δ0.491 (s, 1H), 8.45 (d, 1H), 8.28 (s, 1H), 7.69 (d, 1H), 5.53 (t, 1H), 4.64 (d, 2H).

Step 8: Preparation of 3-chloro-7-(chloromethyl)-1H-1,5-naphthyridin-2-one

To a stirred mixture of 3-chloro-7-(hydroxymethyl)-1H-1,5-naphthyridin-2-one (250 mg, 1.18 mmol, 1.00 equiv.) in $CH_2Cl_2$ (5 mL) was added $SOCl_2$ (423 mg, 3.56 mmol, 3.00 equiv.) and DMF (8 mg, 0.11 mmol, 0.10 equiv.) dropwise at room temperature under nitrogen atmosphere. The resulting mixture was stirred for 3 h at room temperature. The reaction was monitored by LCMS. The resulting mixture was concentrated under reduced pressure. This resulted in 3-chloro-7-(chloromethyl)-1H-1,5-naphthyridin-2-one (280 mg, crude). The crude product was used in the next step directly without further purification. LC-MS: (ES+H, m/z): $[M+H]^+$=228.95.

Preparation of 5-{[(2R,3S)-1-[7-chloro-6-oxo-5H-1,5-naphthyridin-3-yl)methyl]-2-metylazetidin-3-yl]oxy}-N-clopropylpyridine-2-carboxamide A mixture of N-cyclopropyl-5-{[(2R,3S)-2-methylazetidin-3-yl]oxy}pyridine-2-carboxamide hydrochloride (178 mg, 0.72 mmol, 1.10 equiv.), 3-chloro-7-(chloromethyl)-1H-1,5-naphthyridin-2-one (150 mg, 0.65 mmol, 1.00 equiv.), KI (21 mg, 0.13 mmol, 0.20 equiv.) and DIEA (423 mg, 3.27 mmol, 5.00 equiv.) in ACN (3 mL) was stirred for 8 h at 50° C. under nitrogen atmosphere. The reaction was monitored by LCMS. The resulting mixture was cooled down to r.t. and poured into 50 mL of water. The resulting mixture was extracted with EtOAc (3×33 mL). The combined organic layers were washed with brine (100 mL), dried over anhydrous $Na_2SO_4$. After filtration, the filtrate was concentrated under reduced pressure. The crude product was purified by Prep-HPLC to afford 5-{[(2R,3S)-1-[(7-chloro-6-oxo-5H-1,5-naphthyridin-3-yl)methyl]-2-methylazetidin-3-yl]oxy}-N-cyclopropylpyridine-2-carboxamide (82.1 mg, 27.93%). LC-MS: (ES+H, m/z): $[M+H]^+$=415. $^1$H NMR (300 MHz, DMSO-$d_6$) δ 12.45 (s, 1H), 8.52 (d, 1H), 8.46 (d, 1H), 8.27 (s, 1H), 8.21 (d, 1H), 7.95 (d, 1H), 7.66 (d, 1H), 7.44 (dd, 1H), 4.62 (q, 1H), 3.95 (d, 1H), 3.82 (t, 1H), 3.67 (d, 1H), 3.40 (q, 1H), 2.93-2.74 (m, 2H), 1.21 (d, 3H), 0.76-0.57 (m, 4H).

Example 106

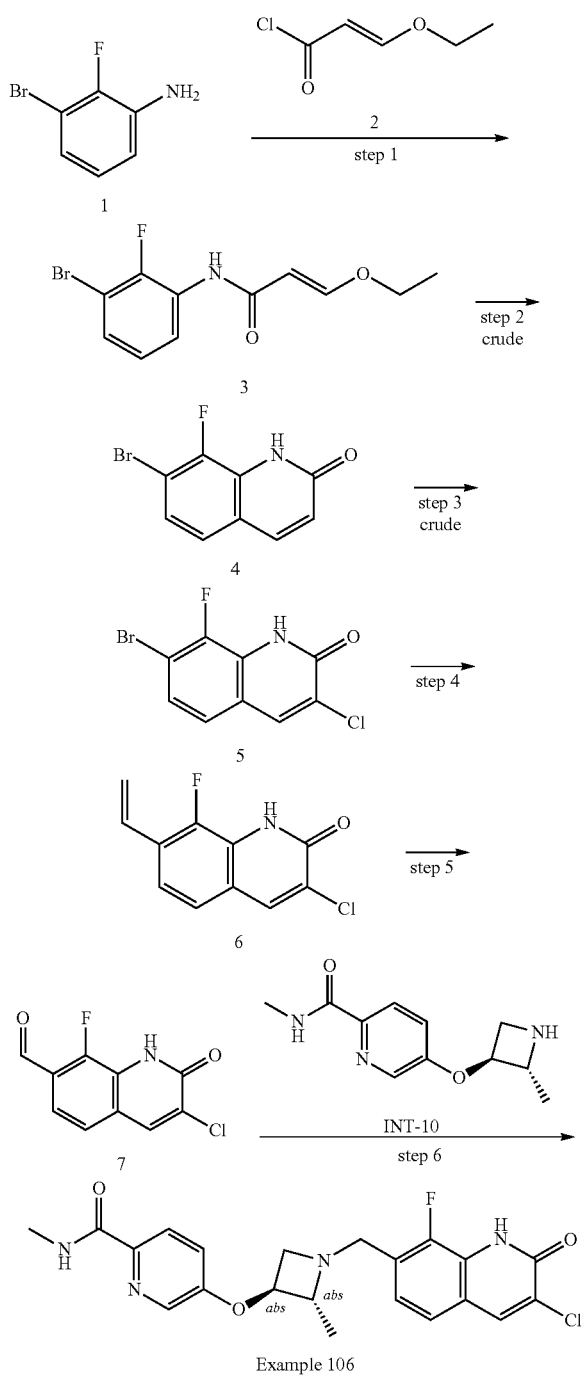

Example 106

Step 1: Preparation of (2E)-N-(3-bromo-2-fluorophenyl)-3-ethoxyprop-2-enamide To a stirred mixture of 3-bromo-2-fluoroaniline (20.00 g, 105.25 mmol, 1.00 equiv.) in DCM (300 mL) was added Pyridine (14.99 g, 189.45 mmol, 1.80 equiv.) dropwise at room temperature under nitrogen atmosphere. The resulting mixture was stirred for 5 min at room temperature under nitrogen atmosphere. To the above mixture was added (2E)-3-ethoxyprop-2-enoyl chloride (21.24 g, 157.88 mmol, 1.50 equiv.) dropwise over 5 min at room temperature. The resulting mixture was stirred for additional 2 h at room temperature. The reaction was monitored by LCMS. The resulting mixture was concentrated under reduced pressure. The residue was dissolved in EtOAc (500 mL). The resulting mixture was washed with water (3×500 mL). The resulting mixture was concentrated under reduced pressure. The residue was purified by silica gel column chromatography to afford (2E)-N-(3-bromo-2-fluorophenyl)-3-ethoxyprop-2-enamide (24.6 g, 81.1%). LC-MS: (ES+H, m/z): $[M+H]^+$=288.0/290.0.

Step 2: Preparation of 7-bromo-8-fluoro-1H-quinolin-2-one

A mixture of (2E)-N-(3-bromo-2-fluorophenyl)-3-ethoxyprop-2-enamide (17.00 g, 59.00 mmol, 1.00 equiv.) in $H_2SO_4$ (85 mL) was stirred for 3 h at room temperature under nitrogen atmosphere. The resulting mixture was added to ice water (1 L) dropwise and stirred for 1 h. The precipitated solids were collected by filtration and washed with water (3×200 mL). The resulting mixture was concentrated under reduced pressure to afford 7-bromo-8-fluoro-1H-quinolin-2-one (14.30 g, crude). LC-MS: (ES+H, m/z): $[M+H]^+$=242.0/244.0.

Step 3: Preparation of 7-bromo-3-chloro-8-fluoro-1H-quinolin-2-one

To a stirred mixture of 7-bromo-8-fluoro-1H-quinolin-2-one (3.00 g, 12.39 mmol, 1.00 equiv.) and NCS (2.65 g, 19.83 mmol, 1.60 equiv.) in $CH_3COOH$ (50 mL) was added 2,2-dichloroacetic acid (0.32 g, 2.47 mmol, 0.20 equiv.) dropwise at room temperature under nitrogen atmosphere. The resulting mixture was stirred overnight at 100° C. under nitrogen atmosphere. The reaction was monitored by LCMS. The mixture was allowed to cool down to room temperature. The resulting mixture was concentrated under reduced pressure. The residue was purified by silica gel column chromatography to afford 7-bromo-3-chloro-8-fluoro-1H-quinolin-2-one (2.48 g, crude). LC-MS: (ES+H, m/z): $[M+H]^+$=275.9/277.9. $^1$H NMR (400 MHz, DMSO-$d_6$) δ 12.52 (s, 1H), 8.38 (d, J=1.6 Hz, 1H), 7.52-7.42 (m, 2H).

Step 4: Preparation of 3-chloro-7-ethenyl-8-fluoro-1H-quinolin-2-one

To a stirred mixture of 7-bromo-3-chloro-8-fluoro-1H-quinolin-2-one (2.48 g, 8.97 mmol, 1.00 equiv.), CsF (4.09 g, 26.91 mmol, 3.00 equiv.), Pd(dppf)Cl$_2$ (0.33 g, 0.44 mmol, 0.05 equiv.) and 2-ethenyl-4,4,5,5-tetramethyl-1,3,2-dioxaborolane (1.38 g, 8.97 mmol, 1.00 equiv.) in dioxane (50 mL) was added $H_2O$ (5 mL) dropwise at room temperature under nitrogen atmosphere. The resulting mixture was stirred for 2 h at 100° C. under nitrogen atmosphere. The reaction was monitored by LCMS. The mixture was allowed to cool down to room temperature. The resulting mixture was concentrated under reduced pressure. The residue was purified by silica gel column chromatography to afford 3-chloro-7-ethenyl-8-fluoro-1H-quinolin-2-one (750 mg, 37.3%). LC-MS: (ES+H, m/z): $[M+H]^+$=224.0. $^1$H NMR (300 MHz, DMSO-$d_6$) δ 12.38 (s, 1H), 8.34 (d, J=1.6 Hz, 1H), 7.53-7.46 (m, 2H), 6.95 (dd, J=17.7, 11.2 Hz, 1H), 6.07 (dd, J=17.7, 1.0 Hz, 1H), 5.57 (dd, J=11.2, 1.0 Hz, 1H).

Step 5: Preparation of 3-chloro-8-fluoro-2-oxo-1H-quinoline-7-carbaldehyde

To a stirred mixture of 3-chloro-7-ethenyl-8-fluoro-1H-quinolin-2-one (750 mg, 3.35 mmol, 1.00 equiv.), $K_2OsO_2(OH)_4$ (123 mg, 0.33 mmol, 0.10 equiv.), $NaIO_4$ (2.87 g, 13.41 mmol, 4.00 equiv.) and 2,6-dimethylpyridine (718 mg, 6.70 mmol, 2.00 equiv.) in THF (15 mL) was added $H_2O$ (1.5 mL) dropwise at room temperature under nitrogen atmosphere. The resulting mixture was stirred overnight at room temperature under nitrogen atmosphere. The reaction was monitored by LCMS. The resulting mixture was concentrated under reduced pressure. The residue was purified by silica gel column chromatography to afford 3-chloro-8-fluoro-2-oxo-1H-quinoline-7-carbaldehyde (630 mg, 83.2%). LC-MS: (ES–H, m/z): [M−H]⁻=224.1.

Step 6: Preparation of 5-{[(2R,3S)-1-[(3-chloro-8-fluoro-2-oxo-1H-quinolin-7-yl)methyl]-2-methylazetidin-3-yl]oxy}-N-methylpyridine-2-carboxamide A mixture of 3-chloro-8-fluoro-2-oxo-1H-quinoline-7-carbaldehyde (100 mg, 0.44 mmol, 1.00 equiv.) and N-methyl-5-{[(2R,3S)-2-methylazetidin-3-yl]oxy}pyridine-2-carboxamide (98 mg, 0.44 mmol, 1.00 equiv.) in DCM (10 mL) was stirred for 10 min at room temperature under nitrogen atmosphere. The resulting mixture was concentrated under reduced pressure. To the above mixture was added $CH_3COOH$ (13 mg, 0.22 mmol, 0.50 equiv.) and EtOH (10 mL) at room temperature. The resulting mixture was stirred for additional 4 h at 50° C. under nitrogen atmosphere. The reaction was monitored by LCMS. To the above mixture was added $NaBH_3CN$ (56 mg, 0.88 mmol, 2.00 equiv.) at room temperature. The resulting mixture was stirred for additional overnight at room temperature. The reaction was monitored by LCMS. The reaction was quenched with Water (3 mL) at 0° C. The resulting mixture was concentrated under reduced pressure. The residue was purified by silica gel column chromatography to afford 5-{[(2R,3S)-1-[(3-chloro-8-fluoro-2-oxo-1H-quinolin-7-yl)methyl]-2-methylazetidin-3-yl]oxy}-N-methylpyridine-2-carboxamide (180 mg, crude). The crude product was purified by Prep-HPLC to afford 5-{[(2R,3S)-1-[(3-chloro-8-fluoro-2-oxo-1H-quinolin-7-yl)methyl]-2-methylazetidin-3-yl]oxy}-N-methylpyridine-2-carboxamide (97.2 mg, 50.8%). LC-MS: (ES+H, m/z): [M+H]⁺=431.05. Optical rotation $[\alpha]^{25}_D$ (c=0.27, MeOH): +38.5°; ¹H NMR (400 MHz, DMSO-$d_6$) δ 12.36 (s, 1H), 8.57 (q, J=4.7 Hz, 1H), 8.35 (d, J=1.3 Hz, 1H), 8.22 (d, J=2.9 Hz, 1H), 7.94 (d, J=8.7 Hz, 1H), 7.47 (d, J=8.1 Hz, 1H), 7.42 (dd, J=8.7, 2.9 Hz, 1H), 7.24 (dd, J=8.1, 6.3 Hz, 1H), 4.58 (q, J=5.9 Hz, 1H), 3.96-3.87 (m, 1H), 3.81 (t, J=6.4 Hz, 1H), 3.73-3.64 (m, 1H), 3.39-3.34 (m, 1H), 2.79 (dd, J=8.1, 5.7 Hz, 4H), 1.20 (d, J=6.2 Hz, 3H). ¹⁹F NMR (377 MHz, DMSO-$d_6$) δ−135.11.

The following examples were made using similar procedures as shown for example 106:

| Ex | NMR | LCMS (ESI) m/z |
|---|---|---|
| 99 | ¹H NMR (400 MHz, DMSO-$d_6$) δ 12.33 (s, 1H), 8.50 (d, J = 5.0 Hz, 1H), 8.34 (d, J = 1.4 Hz, 1H), 8.19 (d, J = 2.8 Hz, 1H), 7.93 (d, J = 8.7 Hz, 1H), 7.50-7.39 (m, 2H), 7.24 (dd, J = 8.1, 6.3 Hz, 1H), 4.57 (q, J = 5.9 Hz, 1H), 3.94-3.86 (m, 1H), 3.81 (t, J = 6.4 Hz, 1H), 3.72-3.64 (m, 1H), 3.36 (p, J = 6.1 Hz, 1H), 2.86 (tt, J = 7.1, 3.7 Hz, 1H), 2.79 (t, J = 6.7 Hz, 1H), 1.20 (d, J = 6.1 Hz, 3H), 0.72-0.58 (m, 4H). ¹⁹F NMR (377 MHz, DMSO-$d_6$) δ-135.12. | [M + H]⁺ = 457.05 |

Example 110

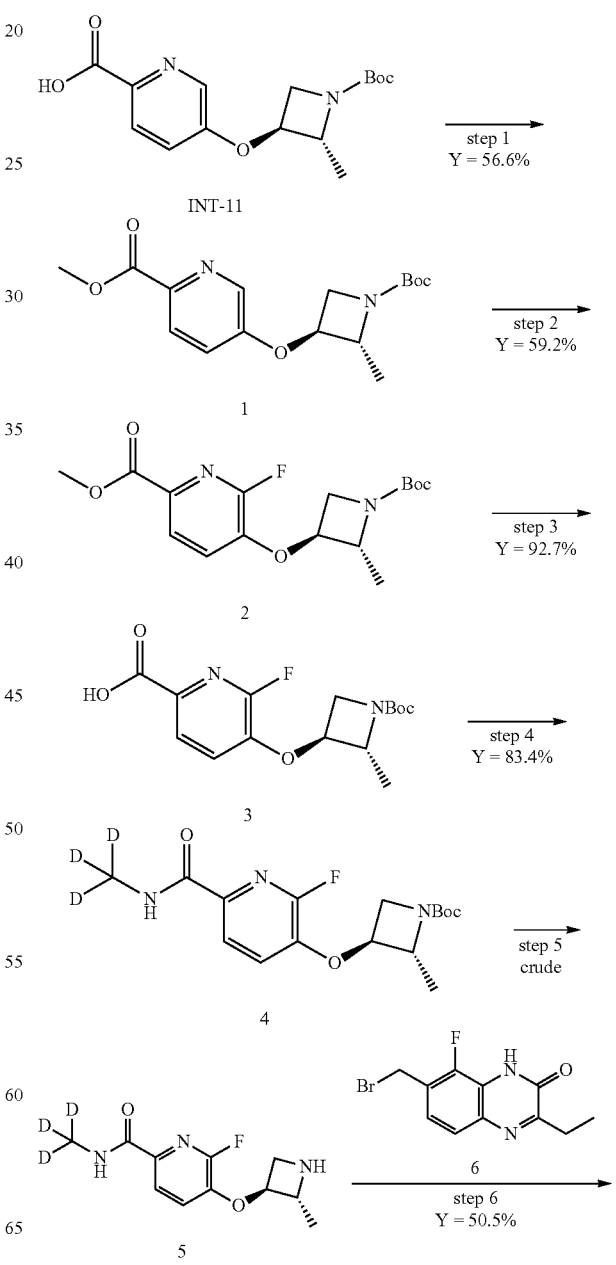

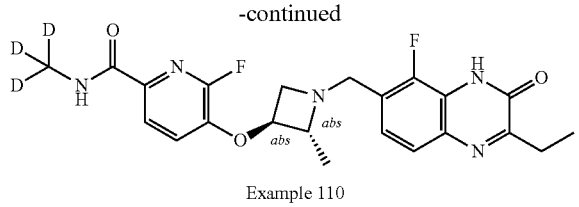

Example 110

Step 1: Preparation of methyl 5-{[(2R,3S)-1-(tert-butoxycarbonyl)-2-methylazetidin-3-yl]oxy}-6-fluoropyridine-2-carboxylate To a stirred mixture of 5-{[(2R,3S)-1-(tert-butoxycarbonyl)-2-methylazetidin-3-yl]oxy}pyridine-2-carboxylic acid (800 mg, 2.59 mmol, 1.00 equiv) in DMF (10 mL) were added DIEA (1.00 g, 10.38 mmol, 4.00 equiv) and $CH_3I$ (320 μL, 5.19 mmol, 2.00 equiv) at 0° C. under nitrogen atmosphere. The resulting mixture was stirred overnight at room temperature under nitrogen atmosphere. The reaction was monitored by LCMS. The resulting mixture was diluted with ethyl acetate (100 mL) and washed with brine (50×2 mL). The organic layers were concentrated under vacuum. The residue was purified by silica gel column chromatography to afford methyl 5-{[(2R,3S)-1-(tert-butoxycarbonyl)-2-methylazetidin-3-yl]oxy}-6-fluoropyridine-2-carboxylate (500 mg, 56.6%). LC-MS: (ES+H, m/z): $[M+H]^+=323.1$.

Step 2: Preparation of methyl 5-{[(2R,3S)-1-(tert-butoxycarbonyl)-2-methylazetidin-3-yl]oxy}-6-fluoropyridine-2-carboxylate To a stirred mixture of methyl 5-{[(2R,3S)-1-(tert-butoxycarbonyl)-2-methylazetidin-3-yl]oxy}pyridine-2-carboxylate (400 mg, 1.24 mmol, 1.00 equiv) in MeCN (10 mL) was added difluorosilver (904 mg, 6.20 mmol, 5.00 equiv) at room temperature under nitrogen atmosphere. The resulting mixture was stirred overnight at 40° C. under nitrogen atmosphere. The reaction was monitored by LCMS. Desired product could be detected by LCMS. The resulting mixture was filtered, the filter cake was washed with $CH_2Cl_2$ (250 mL). The filtrate was concentrated under reduced pressure. The residue was purified by silica gel column chromatography to afford methyl 5-{[(2R,3S)-1-(tert-butoxycarbonyl)-2-methylazetidin-3-yl]oxy}-6-fluoropyridine-2-carboxylate (250 mg, 59.2%). LC-MS: (ES+H, m/z): $[M+H]^+=341.1$. $^1H$ NMR (400 MHz, DMSO-$d_6$) δ 7.99 (d, J=8.2 Hz, 1H), 7.53 (dd, J=10.1, 8.2 Hz, 1H), 4.89-4.79 (m, 1H), 4.37-4.19 (m, 2H), 3.85 (s, 3H), 3.73-3.67 (m, 1H), 1.45 (d, J=6.5 Hz, 3H), 1.39 (s, 9H). $^{19}F$ NMR (400 MHz, DMSO-$d_6$) δ−82.91.

Step 3: Preparation of 5-{[(2R,3S)-1-(tert-butoxycarbonyl)-2-methylazetidin-3-yl]oxy}-6-fluoropyridine-2-carboxylic Acid To a stirred mixture of methyl 5-{[(2R,3S)-1-(tert-butoxycarbonyl)-2-methylazetidin-3-yl]oxy}-6-fluoropyridine-2-carboxylate (900 mg, 2.64 mmol, 1.00 equiv) in THF (5 mL) was added LiOH·$H_2O$ (222 mg, 5.28 mmol, 2.00 equiv) (in 1 mL water) at room temperature under nitrogen atmosphere. The resulting mixture was stirred for 3 h at 50° C. under nitrogen atmosphere. The reaction was monitored by LCMS. Desired product could be detected by LCMS. The mixture was allowed to cool down to room temperature. The resulting mixture was diluted with water (100 mL). The aqueous layer was acidified to pH 3 with HCl (aq. 1N). The aqueous layer was extracted with EA (2×100 mL). The combined organic layers were washed with brine (2×100 mL), dried over anhydrous $Na_2SO_4$. After filtration, the filtrate was concentrated under reduced pressure to afford 5-{[(2R,3S)-1-(tert-butoxycarbonyl)-2-methylazetidin-3-yl]oxy}-6-fluoropyridine-2-carboxylic acid (800 mg, 92.7%). LC-MS: (ES−H, m/z): $[M-H]^-=325.3$.

Step 4: Preparation of tert-butyl(3S)-3-({2-fluoro-6-(methyl-d3carbamoyl)pyridin-3-yl}oxy)-2-methylazetidine-1-carboxylate To a stirred mixture of 5-{[(2S,3S)-1-(tert-butoxycarbonyl)-2-methylazetidin-3-yl]oxy}-6-fluoropyridine-2-carboxylic acid (400 mg, 1.22 mmol, 1.00 equiv) and Methan-d3-amine, hydrochloride (259 mg, 3.67 mmol, 3.00 equiv) in $CH_2Cl_2$ (5 mL) were added DIEA (792 mg, 6.13 mmol, 5.00 equiv) and T3P (1 g, 3.67 mmol, 3.00 equiv, 50% in $CH_2Cl_2$) at room temperature under nitrogen atmosphere. The resulting mixture was stirred for 2 h at room temperature under nitrogen atmosphere. The reaction was monitored by LCMS. Desired product could be detected by LCMS. The resulting mixture was diluted with ethyl acetate (100 mL) and was washed with brine (2×100 mL). The resulting mixture was concentrated under reduced pressure. The residue was purified by Prep-TLC (PE/EA 1:1) to afford tert-butyl(3S)-3-({2-fluoro-6-(methyl-d3carbamoyl)pyridin-3-yl}oxy)-2-methylazetidine-1-carboxylate (350 mg, 83.4%). LC-MS: (ES+H, m/z): $[M+H-tBu]^+=287.1$.

Step 5: Preparation of 6-fluoro-N-methyl-d3-5-{[(2R,3S)-2-methylazetidin-3-yl]oxy}pyridine-2-carboxamide Hydrochloride To a stirred mixture of tert-butyl(3S)-3-({2-fluoro-6-[(2H3)methylcarbamoyl]pyridin-3-yl}oxy)-2-methylazetidine-1-carboxylate (350 mg, 1.02 mmol, 1.00 equiv) in $CH_2Cl_2$ (5 mL) was added HCl (gas) in 1,4-dioxane (5 mL, 4M in dioxane) at room temperature under nitrogen atmosphere. The resulting mixture was stirred for 1 h at room temperature under nitrogen atmosphere. The reaction was monitored by LCMS. Desired product could be detected by LCMS. The resulting mixture was concentrated under reduced pressure to afford 6-fluoro-N-methyl-d3-5-{[(2R,3S)-2-methylazetidin-3-yl]oxy}pyridine-2-carboxamide hydrochloride (300 mg, crude). The crude product was used in the next step directly without further purification. LC-MS: (ES+H, m/z): $[M+H]^+=243.2$.

Step 6: Preparation of 5-{[(2R,3S)-1-[(2-ethyl-5-fluoro-3-oxo-4H-quinoxalin-6-yl)methyl]-2-methylazetidin-3-yl]oxy}-6-fluoro-N-methyl-d3 pyridine-2-carboxamide To a stirred mixture of 6-fluoro-N-methyl-d3-5-{[(2R,3S)-2-methylazetidin-3-yl]oxy}pyridine-2-carboxamide hydrochloride (200 mg, 0.71 mmol, assumed 100% yield, 1.00 equiv) and 7-(bromomethyl)-3-ethyl-8-fluoro-1H-quinoxalin-2-one (204 mg, 0.71 mmol, 1.00 equiv) in MeCN (5 mL) were added KI (23 mg, 0.14 mmol, 0.20 equiv) and DIEA (463 mg, 3.59 mmol, 5.00 equiv) at room temperature under nitrogen atmosphere. The resulting mixture was stirred for 2 h at 80° C. under nitrogen atmosphere. The reaction was monitored by LCMS. Desired product could be detected by LCMS. The mixture was allowed to cool down to room temperature. The resulting mixture was filtered, the filter cake was washed with CH$_2$Cl$_2$/MeOH (10:1, 200 mL). The filtrate was concentrated under reduced pressure. The crude product (400 mg) was purified by HP-FLASH, the pure fraction was concentrated under vacuum and lyophilized to afford 5-{[(2R,3S)-1-[(2-ethyl-5-fluoro-3-oxo-4H-quinoxalin-6-yl)methyl]-2-methylazetidin-3-yl]oxy}-6-fluoro-N-methyl-d3 pyridine-2-carboxamide (163.8 mg, 50.5%). LC-MS: (ES+H, m/z): [M+H]$^+$=447.15. $^1$H NMR (400 MHz, DMSO-d$_6$) δ 12.40 (s, 1H), 8.44 (s, 1H), 7.85 (d, J=8.2 Hz, 1H), 7.61 (dd, J=10.2, 8.2 Hz, 1H), 7.53 (d, J=8.3 Hz, 1H), 7.26 (t, J=7.3 Hz, 1H), 4.60 (q, J=5.9 Hz, 1H), 3.90 (d, 1H), 3.81 (t, J=6.4 Hz, 1H), 3.69 (d, 1H), 3.40 (q, J=6.0 Hz, 1H), 2.81 (q, J=7.3 Hz, 3H), 1.23-1.19 (m, 6H). $^{19}$F NMR (400 MHz, DMSO-d$_6$) δ−84.70, 136.09.

EXAMPLE

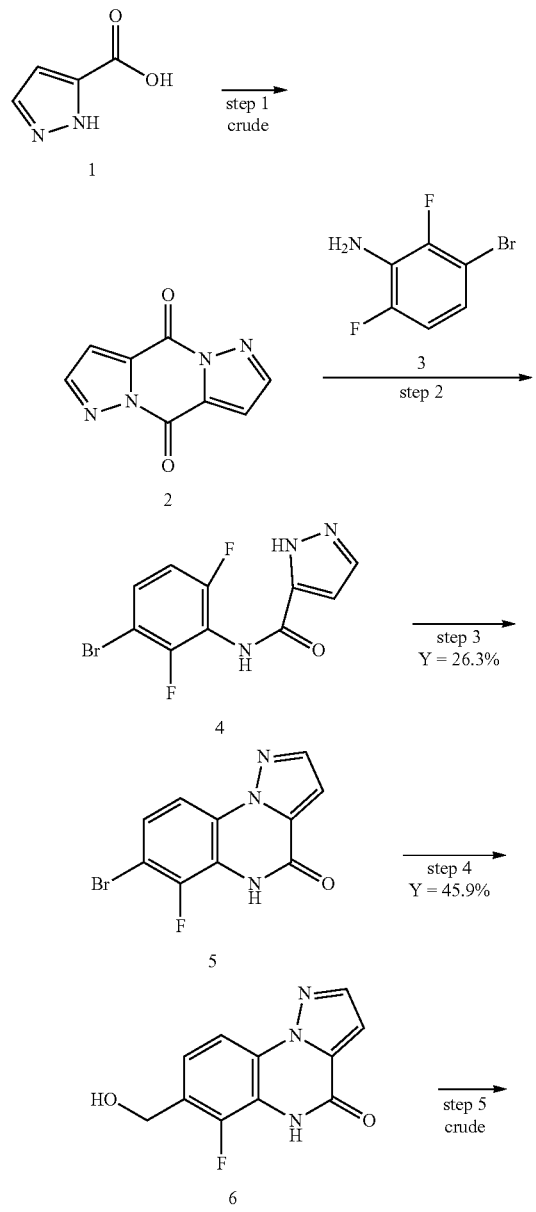

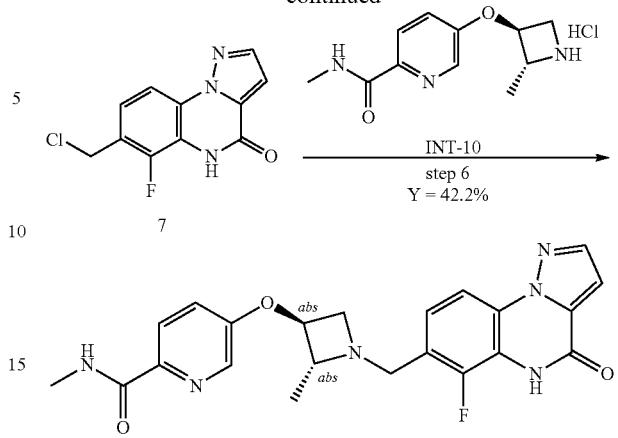

Example 113

Step 1-Step 2: Preparation of N-(3-bromo-2,6-difluorophenyl)-2H-pyrazole-3-carboxamide To a stirred solution of 2H-pyrazole-3-carboxylic acid (3.00 g, 26.76 mmol, 1.00 equiv.) in SOCl$_2$ (30 mL) was stirred overnight at 90° C. under nitrogen atmosphere. The reaction was monitored by LCMS. The mixture was allowed to cool down to room temperature. The precipitated solids were collected by filtration and washed with toluene (3×50 mL). The resulting mixture was concentrated under reduced pressure. The crude product 1,6,7,12-tetraazatricyclo[7.3.0.0^{3,7}]dodeca-3,5,9,11-tetraene-2,8-dione (2.3 g) was used in the next step directly without further purification.

To a stirred solution of 1,6,7,12-tetraazatricyclo[7.3.0.0^{3,7}]dodeca-3,5,9,11-tetraene-2,8-dione (2.30 g, 12.22 mmol, 1.00 equiv.) and 3-bromo-2,6-difluoroaniline (5.09 g, 24.45 mmol, 2.00 equiv.) in THF (100 mL,) was added NaHMDS (2 mol/L, 30.56 mL, 61.12 mmol, 5.00 equiv.) dropwise at −10° C. The resulting mixture was stirred for additional 2 h at −10° C. The reaction was monitored by LCMS. The mixture was neutralized to pH 7 with CH$_3$COOH. The resulting mixture was concentrated under reduced pressure. The residue was dissolved in H$_2$O (100 mL). The resulting mixture was extracted with EtOAc (3×100 mL). The combined organic layers were washed with brine (3×100 mL), dried over anhydrous Na$_2$SO$_4$. After filtration, the filtrate was concentrated under reduced pressure. The residue was purified by silica gel column chromatography to afford N-(3-bromo-2,6-difluorophenyl)-2H-pyrazole-3-carboxamide (6 g, 74.4%). LC-MS: (ES+H, m/z): [M+H]$^+$=301.9. $^1$H NMR (300 MHz, DMSO-d$_6$) δ 13.49 (s, 1H), 10.01 (s, 1H), 7.92 (d, J=2.4 Hz, 1H), 7.78-7.66 (m, 1H), 7.25 (td, J=9.1, 1.9 Hz, 1H), 6.77 (d, J=2.2 Hz, 1H). $^{19}$F NMR (282 MHz, DMSO-d$_6$) δ−109.45, −117.16.

Step 3: Preparation of 7-bromo-6-fluoro-5H-pyrazolo[1,5-a]quinoxalin-4-one

To a stirred solution of N-(3-bromo-2,6-difluorophenyl)-2H-pyrazole-3-carboxamide (5.80 g, 19.20 mmol, 1.00 equiv.) in DMA (2 mL) was added NaH (1.15 g, 28.80 mmol, 1.50 equiv, 60%) in portions at room temperature under nitrogen atmosphere. The resulting mixture was stirred overnight at 120° C. under nitrogen atmosphere. The reaction was monitored by LCMS. The mixture was allowed to cool down to room temperature. The reaction was quenched with water (50 mL) at 0° C. The resulting mixture was diluted with water (100 mL). The resulting mixture was extracted with EtOAc (3×300 mL). The combined organic layers were washed with brine (3×100 mL), dried over anhydrous $Na_2SO_4$. After filtration, the filtrate was concentrated under reduced pressure. The residue was dissolved in DMSO (20 mL). The residue was purified by reverse flash chromatography to afford 7-bromo-6-fluoro-5H-pyrazolo[1,5-a]quinoxalin-4-one (1.5 g, 26.3%). LC-MS: (ES+H, m/z): $[M+H]^+=281.9$. $^1H$ NMR (400 MHz, DMSO-$d_6$) δ 12.14 (s, 1H), 8.13 (s, 1H), 7.89 (d, J=8.9 Hz, 1H), 7.58 (t, J=7.7 Hz, 1H), 7.21 (s, 1H).

Step 4: Preparation of 6-fluoro-7-(hydroxymethyl)-5H-pyrazolo[1,5-a]quinoxalin-4-one To a stirred solution of 7-bromo-6-fluoro-5H-pyrazolo[1,5-a]quinoxalin-4-one (1.00 g, 3.54 mmol, 1.00 equiv.) and (tributylstannyl)methanol (1366 mg, 4.25 mmol, 1.20 equiv.) in dioxane (16 mL) was added 2nd Generation XPhos Precatalyst (279 mg, 0.35 mmol, 0.10 equiv.) at RT under nitrogen atmosphere. The resulting mixture was stirred for 2 h at 80° C. under nitrogen atmosphere. The reaction was monitored by LCMS. The resulting mixture was filtered, the filter cake was washed with DCM/MeOH=(1:5) (3×150 mL). The filtrate was concentrated under reduced pressure. The residue was purified by silica gel column chromatography to afford 6-fluoro-7-(hydroxymethyl)-5H-pyrazolo[1,5-a]quinoxalin-4-one (400 mg, 45.9%). LC-MS: (ES+H, m/z): $[M+H]^+=234.0$. $^1H$ NMR (300 MHz, DMSO-$d_6$) δ 11.95 (s, 1H), 8.10 (d, J=2.1 Hz, 1H), 7.93 (dd, J=8.5, 1.4 Hz, 1H), 7.38 (dd, J=8.5, 7.0 Hz, 1H), 7.19 (d, J=2.1 Hz, 1H), 5.42 (t, J=5.8 Hz, 1H), 4.63 (dd, J=5.8, 1.5 Hz, 2H).

Step 5: Preparation of 7-(chloromethyl)-6-fluoro-5H-pyrazolo[1,5-a]quinoxalin-4-one To a stirred solution of 6-fluoro-7-(hydroxymethyl)-5H-pyrazolo[1,5-a]quinoxalin-4-one (300 mg 1.28 mmol, 1.00 equiv.) in DCM (8 mL) were added $SOCl_2$ (765 mg, 6.43 mmol, 5.00 equiv.) and DMF (5 mg, 0.07 mmol, 0.05 equiv.) dropwise at RT. The resulting mixture was stirred overnight at RT. The reaction was monitored by LCMS. The precipitated solids were collected by filtration and washed with DCM (3×30 mL). The crude product (7-(chloromethyl)-6-fluoro-5H-pyrazolo[1,5-a]quinoxalin-4-one) was used in the next step directly without further purification. LC-MS: (ES+H, m/z): $[M+H]^+=252.0$

Step 6: Preparation of 5-{[(2R,3S)-1-({6-fluoro-4-oxo-5H-pyrazolo[1,5-a]quinoxalin-7-yl}methyl)-2-methylazetidin-3-yl]oxy}-N-methylpyridine-2-carboxamide To a stirred solution of 7-(chloromethyl)-6-fluoro-5H-pyrazolo[1,5-a]quinoxalin-4-one (120 mg, 0.47 mmol, 1.00 equiv) and N-methyl-5-{[(2R,3S)-2-methylazetidin-3-yl]oxy}pyridine-2-carboxamide hydrochloride (147 mg, 0.57 mmol, 1.20 equiv) in MeCN (6 mL) were added KI (15 mg, 0.09 mmol, 0.20 equiv) and DIEA (246 mg, 1.90 mmol, 4.00 equiv) at RT under nitrogen atmosphere. The resulting mixture was stirred for 2 h at 80° C. under nitrogen atmosphere. The mixture was allowed to cool down to RT. The resulting mixture was concentrated under reduced pressure. The residue was purified by silica gel column chromatography to afford 5-{[(2R,3S)-1-({6-fluoro-4-oxo-5H-pyrazolo[1,5-a]quinoxalin-7-yl}methyl)-2-methylazetidin-3-yl]oxy}-N-methylpyridine-2-carboxamide (88 mg, 42.2%). LC-MS: (ES+H, m/z): $[M+H]^+=437.1$. $^1H$ NMR (300 MHz, DMSO-$d_6$) δ 11.97 (s, 1H), 8.57 (d, J=5.0 Hz, 1H), 8.23 (d, J=2.8 Hz, 1H), 8.11 (d, J=2.1 Hz, 1H), 7.99-7.88 (m, 2H), 7.43 (dd, J=8.7, 2.9 Hz, 1H), 7.34 (t, J=7.7 Hz, 1H), 7.20 (d, J=2.1 Hz, 1H), 4.59 (d, J=5.9 Hz, 1H), 3.91 (d, J=13.2 Hz, 1H), 3.83 (t, J=6.3 Hz, 1H), 3.69 (d, J=13.3 Hz, 1H), 3.41-3.38 (m, 1H), 2.85-2.75 (m, 4H), 1.22 (d, J=6.1 Hz, 3H). $^{19}F$ NMR (282 MHz, DMSO-$d_6$) δ−131.63.

The following examples were made using similar procedures as shown for example 113:

| Ex | NMR | LCMS (ESI) m/z |
|---|---|---|
| 114 | $^1H$ NMR (300 MHz, DMSO-$d_6$) δ 11.88 (s, 1H), 8.52 (s, 1H), 8.20 (s, 1H), 7.99-7.76 (m, 2H), 7.49-7.25 (m, 2H), 6.98 (s, 1H), 4.58 (s, 1H), 3.94-3.77 (m, 2H), 3.72-3.63 (m, 1H), 3.43-3.33 (m, 1H), 2.93-2.73 (m, 2H), 2.43 (s, 3H), 1.22 (s, 3H), 0.76-0.56 (m, 4H). 19F NMR (300 MHz, DMSO-$d_6$) δ-131.923. | $[M + Na]^+ =$ 499.10 |
| 119 | $^1H$ NMR (400 MHz, DMSO-$d_6$) δ 11.98 (s, 1H), 8.89 (t, J = 6.3 Hz, 1H), 8.27 (d, J = 2.8 Hz, 1H), 8.11 (d, J = 2.1 Hz, 1H), 7.98 (d, J = 8.7 Hz, 1H), 7.93 (dd, J = 8.4, 1.2 Hz, 1H), 7.46 (dd, J = 8.7, 2.9 Hz, 1H), 7.33 (dd, J = 8.5, 6.8 Hz, 1H), 7.20 (d, J = 2.0 Hz, 1H), 6.12 (tt, J = 56.2, 4.1 Hz, 1H), 4.61 (q, J = 5.9 Hz, 1H), 3.91 (d, J = 13.2 Hz, 1H), 3.83 (t, J = 6.3 Hz, 1H), 3.74-3.60 (m, 3H), 3.39 (q, J = 6.1 Hz, 1H), 2.81 (t, J = 6.7 Hz, 1H), 1.22 (d, J = 6.1 Hz, 3H). $^{19}F$ NMR (377 MHz, DMSO-$d_6$) δ-122.05, −131.62. | $[M + H]^+ =$ 487.20 |

Example 115

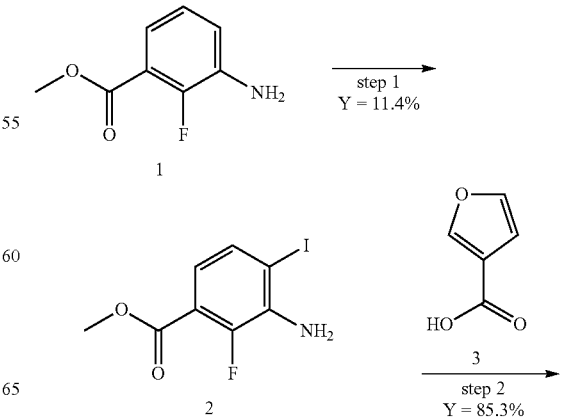

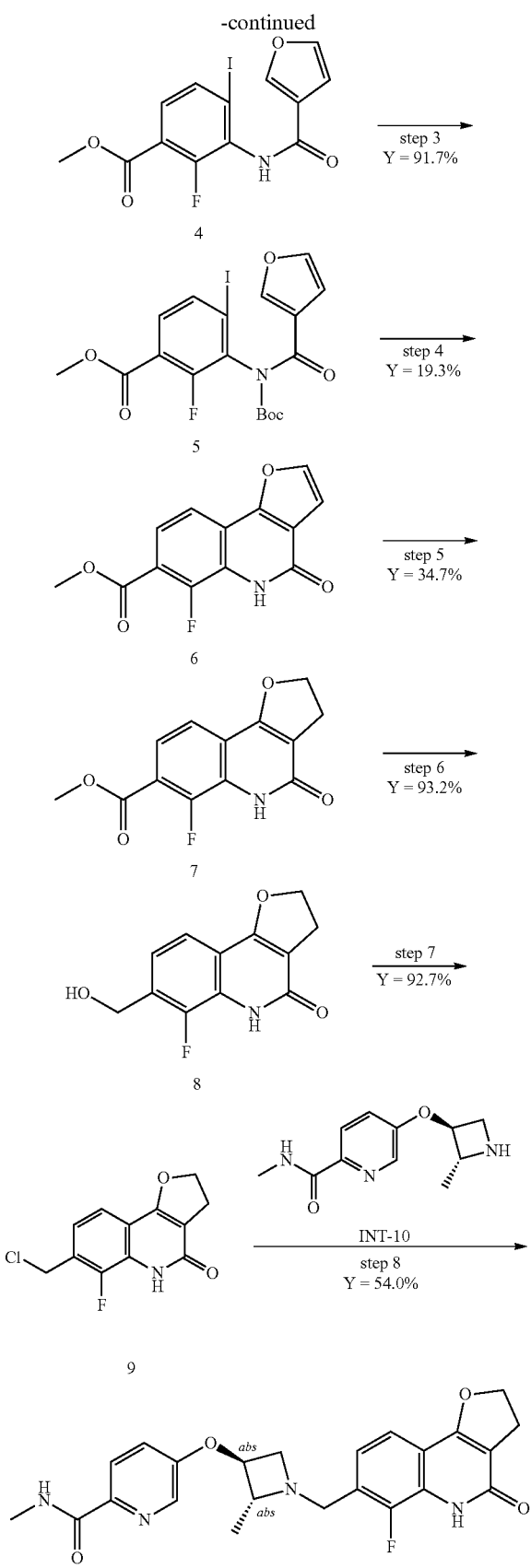

Example 115

Step 1: Preparation of methyl 3-amino-2-fluoro-4-iodobenzoate

A solution of methyl 3-amino-2-fluorobenzoate (20.00 g, 118.23 mmol, 1.00 equiv) and NIS (23.94 g, 106.41 mmol, 0.90 equiv) in AcOH (250 mL) was stirred for 1 h at room temperature under nitrogen atmosphere. The reaction was monitored by LCMS. The resulting mixture was concentrated under reduced pressure. The resulting mixture was diluted with water (200 mL). The resulting mixture was extracted with EtOAc (3×200 mL). The combined organic layers were washed with brine (2×100 mL), dried over anhydrous $Na_2SO_4$. After filtration, the filtrate was concentrated under reduced pressure. The residue was purified by reversed combi-flash chromatography to afford methyl 3-amino-2-fluoro-4-iodobenzoate (4.00 g, 11.4%). LC-MS: (ES+H, m/z): $[M+H]^+$=295.80. $^1$H NMR (300 MHz, DMSO-$d_6$) δ 7.52 (dd, J=8.4, 1.5 Hz, 1H), 6.81 (dd, J=8.3, 6.7 Hz, 1H), 5.43 (s, 2H), 3.83 (s, 3H).

Step 2: Preparation of methyl 2-fluoro-3-(furan-3-amido)-4-iodobenzoate

Into a 250 mL round-bottom flask were added methyl 3-amino-2-fluoro-4-iodobenzoate (4.00 g, 13.55 mmol, 1.00 equiv), 3-furoic acid (1.52 g, 13.55 mmol, 1.00 equiv), $T_3P$ (43.14 g, 67.78 mmol, 5.00 equiv, 50% in EA) and DIEA (2.08 g, 16.10 mmol, 5.00 equiv) at room temperature. The resulting mixture was stirred overnight at 100° C. under nitrogen atmosphere. The reaction was monitored by LCMS. The mixture was allowed to cool down to room temperature. The resulting mixture was diluted with water (100 mL). The resulting mixture was extracted with EtOAc (3×100 mL). The combined organic layers were washed with brine (2×100 mL), dried over anhydrous $Na_2SO_4$. After filtration, the filtrate was concentrated under reduced pressure. The residue was purified by silica gel column chromatography to afford methyl 2-fluoro-3-(furan-3-amido)-4-iodobenzoate (4.50 g, 85.3%). LC-MS: (ES+H, m/z): $[M+H]^+$=389.85. $^1$H NMR (300 MHz, DMSO-$d_6$) δ 9.99 (s, 1H), 8.40 (s, 1H), 7.91 (dd, J=8.4, 1.2 Hz, 1H), 7.83 (t, J=1.7 Hz, 1H), 7.61 (dd, J=8.4, 7.0 Hz, 1H), 7.02-6.96 (m, 1H), 3.86 (s, 3H).

Step 3: Preparation of methyl 3-[N-(tert-butoxycarbonyl)furan-3-amido]-2-fluoro-4-iodobenzoate To a stirred mixture of methyl 2-fluoro-3-(furan-3-amido)-4-iodobenzoate (2.60 g, 6.68 mmol, 1.00 equiv) and (Boc)$_2$O (2.92 g, 13.36 mmol, 2.00 equiv) in DCE (50 mL) was added DMAP (0.82 g, 6.68 mmol, 1.00 equiv) in portions at room temperature under nitrogen atmosphere. The resulting mixture was stirred overnight at room temperature under nitrogen atmosphere. The reaction was monitored by TLC (PE:EA=5:1). The resulting mixture was concentrated under reduced pressure. The residue was purified by silica gel column chromatography to afford methyl 3-[N-(tert-butoxycarbonyl)furan-3-amido]-2-fluoro-4-iodobenzoate (3.00 g, 91.7%).

Step 4: Preparation of methyl 6-fluoro-4-oxo-5H-furo[3,2-c]quinoline-7-carboxylate To a stirred solution of methyl 3-[N-(tert-butoxycarbonyl)furan-3-amido]-2-fluoro-4-iodobenzoate (3.00 g, 6.13 mmol, 1.00 equiv) in DMF (30 mL) was added PCy$_3$ (344 mg, 1.22 mmol, 0.20 equiv), Pd(OAc)$_2$ (275 mg, 1.22 mmol, 0.20 equiv), $K_2CO_3$ (1.69 g, 12.26 mmol, 2.00 equiv) at room temperature under nitrogen atmosphere. The final reaction mixture was irradiated with microwave radiation for 2 h at 120° C. The reaction was monitored by LCMS. The resulting mixture was diluted with water (50 mL). The resulting mixture was extracted with EtOAc (3×100 mL). The combined organic layers were washed with brine (2×50 mL), dried over anhydrous $Na_2SO_4$. After filtration, the filtrate was concentrated under reduced pressure. The residue was purified by silica gel column chromatography to afford methyl 6-fluoro-4-oxo-5H-furo[3,2-c]quinoline-7-carboxylate (310 mg, 19.3%). LC-MS: (ES+H, m/z): $[M+H+MeCN]^+$=302.95.

Step 5: Preparation of methyl 6-fluoro-4-oxo-2H,3H,5H-furo[3,2-c]quinoline-7-carboxylate To a stirred solution of methyl 6-fluoro-4-oxo-5H-furo[3,2-c]quinoline-7-carboxylate (200 mg, 0.76 mmol, 1.00 equiv) in $CF_3CH_2OH$ (50 mL) was added Pd/C (163 mg, 10%) at room temperature. The resulting mixture was stirred overnight at room temperature under hydrogen atmosphere. The reaction was monitored by LCMS. The resulting mixture was filtered; the filter cake was washed with $CH_2Cl_2$/MeOH (10:1, 3×50 mL). The filtrate was concentrated under reduced pressure. The residue was purified by silica gel column chromatography to afford methyl 6-fluoro-4-oxo-2H,3H,5H-furo[3,2-c]quinoline-7-carboxylate (70 mg, 34.7%). LC-MS: (ES+H, m/z): $[M+H]^+$=263.95. $^1$H NMR (300 MHz, DMSO-$d_6$) δ 11.68 (s, 1H), 7.58 (dd, J=8.4, 6.1 Hz, 1H), 7.49 (d, J=8.5 Hz, 1H), 4.85 (t, J=9.4 Hz, 2H), 3.89 (s, 3H), 3.10 (t, J=9.4 Hz, 2H). $^{19}$F NMR (377 MHz, DMSO-$d_6$) δ−124.45.

Step 6: Preparation of 6-fluoro-7-(hydroxymethyl)-2H,3H,5H-furo[3,2-c]quinolin-4-one To a stirred solution of methyl 6-fluoro-4-oxo-2H,3H,5H-furo[3,2-c]quinoline-7-carboxylate (60 mg, 0.22 mmol, 1.00 equiv) in THF (5 mL) was added $LiAlH_4$ (0.18 mL, 0.45 mmol, 2.00 equiv, 2.5M in THF) dropwise at 0° C. under nitrogen atmosphere. The resulting mixture was stirred for 2 h at 0° C. under nitrogen atmosphere. The reaction was monitored by LCMS. The reaction was quenched by the addition of HCl. aq. (1M, 0.5 mL) at 0° C. The resulting mixture was concentrated under reduced pressure. The residue was purified by silica gel column chromatography to afford 6-fluoro-7-(hydroxymethyl)-2H,3H,5H-furo[3,2-c]quinolin-4-one (50 mg, 93.2%). LC-MS: (ES+H, m/z): $[M+H]^+$=236.0

Step 7: Preparation of 7-(chloromethyl)-6-fluoro-2H,3H,5H-furo[3,2-c]quinolin-4-one To a stirred solution of 6-fluoro-7-(hydroxymethyl)-2H,3H,5H-furo[3,2-c]quinolin-4-one (50 mg, 0.21 mmol, 1.00 equiv) and DMF (2 mg, 0.02 mmol, 0.10 equiv) in DCM (10 mL) was added $SOCl_2$ (253 mg, 2.13 mmol, 10.00 equiv) dropwise at room temperature under nitrogen atmosphere. The resulting mixture was stirred overnight at room temperature under nitrogen atmosphere. The reaction was monitored by LCMS. The resulting mixture was concentrated under reduced pressure to afford 7-(chloromethyl)fluoro-2H,3H,5H-furo[3,2-c]quinolin-4-one (50 mg, 92.7%). LC-MS: (ES+H, m/z): $[M+H]^+$=254.0

Step 8: Preparation of 5-{[(2R,3S)-1-({6-fluoro-4-oxo-2H,3H,5H-furo[3,2-c]quinolin-7-yl}methyl)-2-methylazetidin-3-yl]oxy}-N-methylpyridine-2-carboxamide A solution of N-methyl-5-{[(2R,3S)-2-methylazetidin-3-yl]oxy}pyridine-2-carboxamide (62 mg, 0.28 mmol, 1.10 equiv) in MeCN (3 mL) was treated with DIEA (132 mg, 1.02 mmol, 4.00 equiv) for 5 min at room temperature under nitrogen atmosphere followed by the addition of KI (4 mg, 0.02 mmol, 0.10 equiv) and 7-(chloromethyl)-6-fluoro-2H,3H,5H-furo[3,2-c]quinolin-4-one (65 mg, 0.25 mmol, 1.00 equiv). The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography to afford 5-{[(2R,3S)-1-(6-fluoro-4-oxo-2H,3H,5H-furo[3,2-c]quinolin-7-yl)methyl)-2-methylazetidin-3-yl]oxy}-N-methylpyridine-2-carboxamide (62.0 mg, 54.0%). LC-MS: (ES+H, m/z): $[M+H]^+$=439.10. $^1$H NMR (300 MHz, DMSO-$d_6$) δ 11.40 (s, 1H), 8.57 (d, J=4.9 Hz, 1H), 8.22 (d, J=2.8 Hz, 1H), 7.94 (d, J=8.7 Hz, 1H), 7.46-7.34 (m, 2H), 7.24-7.15 (m, 1H), 4.82 (t, J=9.3 Hz, 2H), 4.58 (q, J=5.9 Hz, 1H), 3.96-3.76 (m, 2H), 3.69 (d, J=13.3 Hz, 1H), 3.40-3.36 (m, 1H), 3.07 (t, J=9.2 Hz, 2H), 2.81-2.74 (m, 4H), 1.19 (d, J=6.2 Hz, 3H). $^{19}$F NMR (282 MHz, DMSO-$d_6$) δ−133.55.

The following examples were made using similar procedures as shown for example 113:

| Ex | NMR | LCMS (ESI) m/z |
|---|---|---|
| 116 | $^1$H NMR (300 MHz, DMSO-$d_6$) δ 11.40 (s, 1H), 8.53 (d, J = 5.0 Hz, 1H), 8.20 (d, J = 2.8 Hz, 1H), 7.93 (d, J = 8.7 Hz, 1H), 7.46-7.33 (m, 2H), 7.19 (dd, J = 8.2, 6.2 Hz, 1H), 4.82 (t, J = 9.3 Hz, 2H), 4.57 (q, J = 6.0 Hz, 1H), 3.90 (d, J = 13.3 Hz, 1H), 3.81 (t, J = 6.5 Hz, 1H), 3.69 (d, J = 13.3 Hz, 1H), 3.37-3.33 (m, 1H), 3.07 (t, J = 9.3 Hz, 2H), 2.93-2.71 (m, 2H), 1.19 (d, J = 6.1 Hz, 3H), 0.71-0.58 (m, 4H). $^{19}$F NMR (282 MHz, DMSO-$d_6$) δ-133.55. | $[M + H]^+$ = 465.20 |
| 120 | $^1$H NMR (300 MHz, DMSO-$d_6$) δ 11.40 (s, 1H), 8.88 (t, J = 6.3 Hz, 1H), 8.27 (d, J = 2.8 Hz, 1H), 8.01-7.95 (m, 1H), 7.50-7.34 (m, 2H), 7.23-7.16 (m, 1H), 6.35-5.91 (m, 1H), 4.82 (t, J = 9.3 Hz, 2H), 4.59-4.55 (m, 1H), 4.00-3.77 (m, 2H), 3.76-3.57 (m, 3H), 3.38 (d, J = 6.0 Hz, 1H), 3.07 (t, J = 9.3 Hz, 2H), 2.80 (t, J = 6.7 Hz, 1H), 1.20 (d, J = 6.1 Hz, 3H). $^{19}$F NMR (282 MHz, DMSO-$d_6$) δ-122.05, −133.56. | $[M + H]^+$ = 489.25 |

Example 121
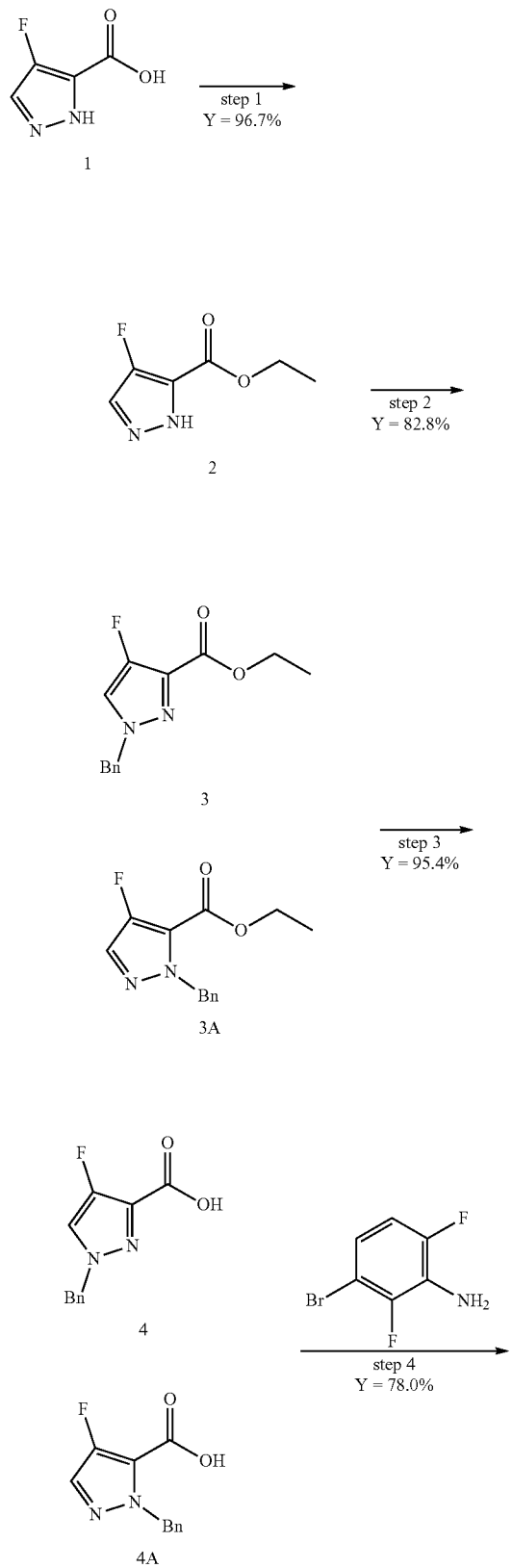
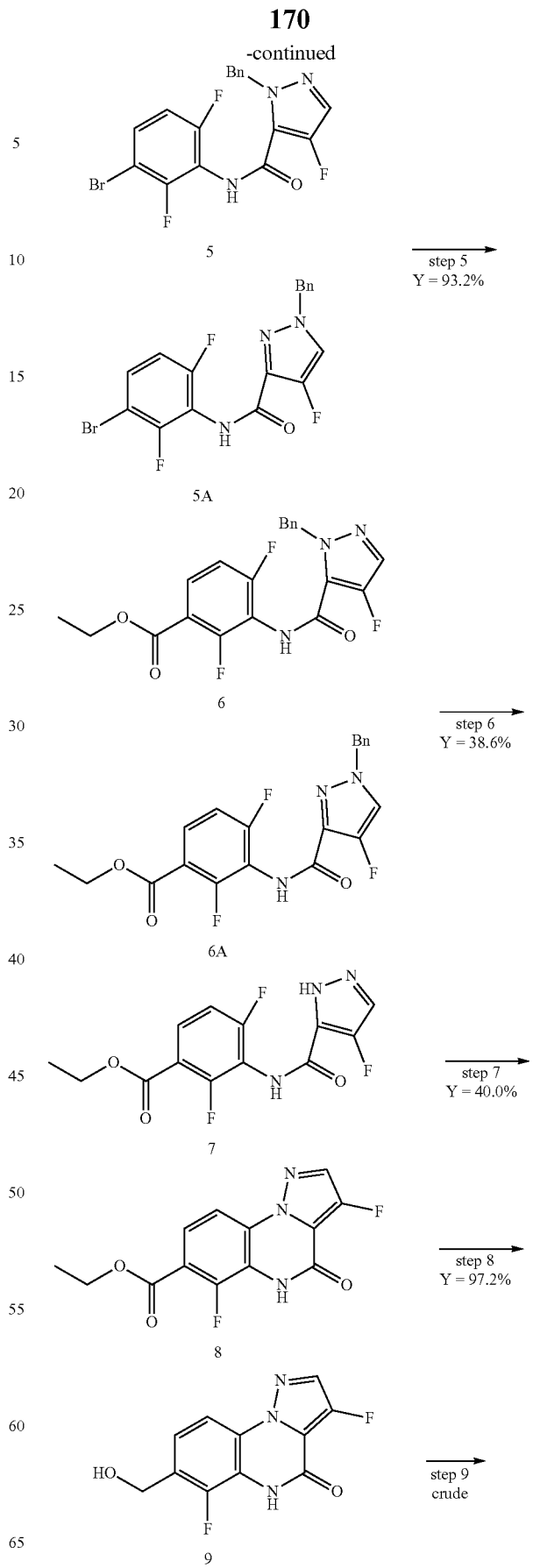

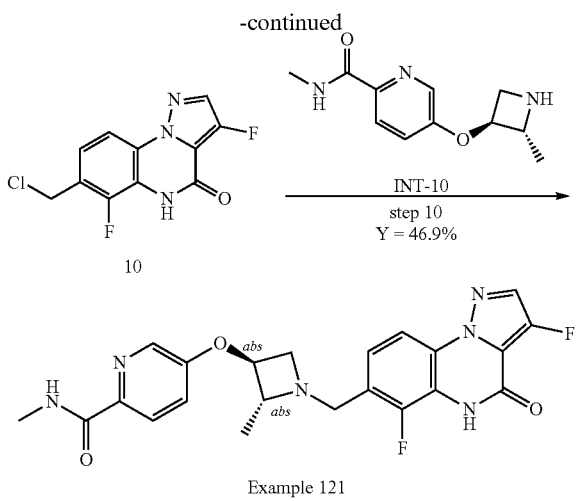

Example 121

Step 1: Preparation of ethyl 4-fluoro-2H-pyrazole-3-carboxylate

To a stirred solution of 4-fluoro-2H-pyrazole-3-carboxylic acid (850 mg, 6.53 mmol, 1.00 equiv) in EtOH (15 mL) was added $SOCl_2$ (4.66 g, 39.21 mmol, 6.00 equiv) at room temperature under nitrogen atmosphere. The resulting mixture was stirred for 1 h at 70° C. under nitrogen atmosphere. The reaction was monitored by LCMS. Desired product could be detected by LCMS. The resulting mixture was concentrated under reduced pressure to afford ethyl 4-fluoro-2H-pyrazole-3-carboxylate (1.00 g, Y=96.7%). LC-MS: (ES–H, m/z): [M–H]$^-$=157.1. $^1$H NMR (300 MHz, DMSO-d$_6$) δ 7.60 (d, J=4.5 Hz, 1H), 4.38 (q, J=7.1 Hz, 2H), 1.35 (t, J=7.1 Hz, 3H).

Step 2: Preparation of ethyl 1-benzyl-4-fluoro-1H-pyrazole-3-carboxylateðyl 1-benzyl-4-fluoro-1H-pyrazole-5-carboxylate & ethyl 1-benzyl-4-fluoro-1H-pyrazole-5-carboxylate To a stirred solution of ethyl 4-fluoro-2H-pyrazole-3-carboxylate (1.00 g, 6.32 mmol, 1.00 equiv) and $K_2CO_3$ (2.62 g, 18.97 mmol, 3.00 equiv) in DMF (30 mL) was added (bromomethyl)benzene (2.16 g, 12.64 mmol, 2.00 equiv) at room temperature under nitrogen atmosphere. The resulting mixture was stirred for 1 h at room temperature under nitrogen atmosphere. The reaction was monitored by LCMS. The resulting mixture was diluted with EtOAc (150 mL). The resulting mixture was washed with 2×100 mL of water, dried over anhydrous $Na_2SO_4$. After filtration, the filtrate was concentrated under reduced pressure. The residue was purified by silica gel column chromatography to afford a mixture of ethyl 1-benzyl-4-fluoro-1H-pyrazole-3-carboxylate & ethyl 1-benzyl-4-fluoro-1H-pyrazole-5-carboxylate (1.30 g, Y=82.8%). LC-MS: (ES+H, m/z): [M+H]$^+$=249.0. $^1$H NMR (300 MHz, DMSO-d$_6$) δ 7.50-7.29 (m, 6H), 7.28-7.20 (m, 4H), 5.69 (s, 1H), 5.32 (s, 2H), 4.46 (q, J=7.2 Hz, 2H), 4.36 (q, J=7.1 Hz, 1H), 1.43 (t, J=7.1 Hz, 3H), 1.36 (t, J=7.1 Hz, 2H).

Step 3: Preparation of 1-benzyl-4-fluoro-1H-pyrazole-3-carboxylic acid & 1-benzyl-4-fluoro-1H-pyrazole-5-carboxylic Acid To a stirred solution of ethyl 1-benzyl-4-fluoro-1H-pyrazole-3-carboxylate & ethyl 1-benzyl-4-fluoro-1H-pyrazole-5-carboxylate (1.30 g, 5.23 mmol, 1.00 equiv) in THF (15 mL) was added LiOH (15 mL, 30.00 mmol, 5.73 equiv, 2M in water) at room temperature under nitrogen atmosphere. The resulting mixture was stirred for 1 h at room temperature under nitrogen atmosphere. The reaction was monitored by LCMS. The resulting mixture was diluted with water (100 mL). The aqueous layer was extracted with EtOAc (1×80 mL). The aqueous layer was acidified to pH 6 with citric acid. The aqueous layer was extracted with EtOAc (3×100 mL). The organic layers were dried $Na_2SO_4$. The resulting mixture was concentrated under reduced pressure to afford 1-benzyl-4-fluoro-1H-pyrazole-3-carboxylic acid & 1-benzyl-4-fluoro-1H-pyrazole-5-carboxylic acid (1.10 g, Y=95.4%). LC-MS: (ES–H, m/z): [M–H]$^-$=219.1.

Step 4: Preparation of 2-benzyl-N-(3-bromo-2,6-difluorophenyl)-5-fluoropyrazole-3-carboxamide & 1-benzyl-N-(3-bromo-2,6-difluorophenyl)-4-fluoro-1H-pyrazole-3-carboxamide To a stirred solution of 1-benzyl-4-fluoro-1H-pyrazole-3-carboxylic acid & 1-benzyl-4-fluoro-1H-pyrazole-5-carboxylic acid (1.10 g, 4.99 mmol, 1.00 equiv) in T3P (40 mL, 50% in EA) were added DIEA (1.94 g, 14.98 mmol, 3.00 equiv) and 3-bromo-2,6-difluoroaniline (1.25 g, 5.99 mmol, 1.20 equiv) at room temperature under nitrogen atmosphere. The resulting mixture was stirred for overnight at 100° C. under nitrogen atmosphere. The reaction was monitored by LCMS. The mixture was allowed to cool down to room temperature. The resulting mixture was diluted with EtOAc (120 mL). The resulting mixture was washed with 2×100 mL of water, dried over anhydrous $Na_2SO_4$. After filtration, the filtrate was concentrated under reduced pressure. The residue was purified by silica gel column chromatography to afford a mixture of 2-benzyl-N-(3-bromo-2,6-difluorophenyl)-5-fluoropyrazole-3-carboxamide & 1-benzyl-N-(3-bromo-2,6-difluorophenyl)-4-fluoro-1H-pyrazole-3-carboxamide (1.60 g, Y=78.0%). LC-MS: (ES+H, m/z): [M+H]$^+$=410.0/412.0. $^1$H NMR (300 MHz, DMSO-d$_6$) δ 10.25 (s, 1H), 10.06 (s, 1H), 8.22 (d, J=4.4 Hz, 1H), 7.84-7.67 (m, 2H), 7.45-7.28 (m, 7H), 7.28-7.15 (m, 3H), 5.56 (s, 1H), 5.40 (s, 2H).

Step 5: Preparation of ethyl 3-(2-benzyl-4-fluoropyrazole-3-amido)-2,4-difluorobenzoate & ethyl 3-(1-benzyl-4-fluoro-1H-pyrazole-3-carboxamido)-2,4-difluorobenzoate To a solution of 2-benzyl-N-(3-bromo-2,6-difluorophenyl)-5-fluoropyrazole-3-carboxamide & 1-benzyl-N-(3-bromo-2,6-difluorophenyl)-4-fluoro-1H-pyrazole-3-carboxamide (1.20 g, 2.92 mmol, 1.00 equiv) in EtOH (8 mL) was added Pd(dppf)Cl$_2$ (214 mg, 0.29 mmol, 0.10 equiv) in a pressure tank. The mixture was purged with nitrogen for 10 min and then was pressurized to 50 atm with carbon monoxide at 120° C. for overnight. The reaction mixture was cooled to room temperature and filtered to remove insoluble solids. The resulting mixture was concentrated under reduced pressure. The residue was purified by silica gel column chromatography to afford a mixture of ethyl 3-(2-benzyl-4-fluoropyrazole-3-amido)-2,4-difluorobenzoate & ethyl 3-(1-benzyl-4-fluoro-1H-pyrazole-3-carboxamido)-2,4-difluorobenzoate (1.10 g, Y=93.2%). LC-MS: (ES+H, m/z): [M+H]$^+$=404.1. $^1$H NMR (400 MHz, DMSO-d6) δ 10.18 (s, 1H), 10.00 (s, 2H), 8.21 (d, J=4.4 Hz, 2H), 7.99-7.86 (m, 3H), 7.78 (d, J=4.3 Hz, 1H), 7.46-7.25 (m, 16H), 7.23-7.16 (m, 2H), 5.56 (s, 2H), 5.40 (s, 4H), 4.38-4.3 (m, 6H), 1.35-1.28 (m, 9H).

Step 6: Preparation of ethyl 2,4-difluoro-3-(4-fluoro-2H-pyrazole-3-amido)benzoate To a solution of ethyl 3-(2-benzyl-4-fluoropyrazole-3-amido)-2,4-difluorobenzoate & ethyl 3-(1-benzyl-4-fluoro-1H-pyrazole-3-carboxamido)-2,4-difluorobenzoate (500 mg, 1.24 mmol, 1.00 equiv) in 20 mL MeOH/HCl=10:1 was added Pd(OH)$_2$/C (1.04 g, 1.49 mmol, 1.20 equiv, 20%) in a pressure tank. The mixture was hydrogenated at room temperature under 30 psi of hydrogen pressure for overnight, filtered through a Celite pad, washed with DCM:MeOH=10:1(3×50 mL). The reaction was monitored by LCMS. The resulting mixture was concentrated under reduced pressure. The residue was purified by silica gel column chromatography to afford ethyl 2,4-difluoro-3-(4-fluoro-2H-pyrazole-3-amido)benzoate (150 mg, Y=38.6%). LC-MS: (ES+H, m/z): [M+H]$^+$=314.1.

Step 7: Preparation of ethyl 3,6-difluoro-4-oxo-5H-pyrazolo[1,5-a]quinoxaline-7-carboxylate To a stirred solution of ethyl 2,4-difluoro-3-(4-fluoro-2H-pyrazole-3-amido)benzoate (160 mg, 0.51 mmol, 1.00 equiv) in DMF (10 mL) was added Cs$_2$CO$_3$ (499 mg, 1.53 mmol, 3.00 equiv) at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was diluted with water (40 mL). The resulting mixture was extracted with CH$_2$Cl$_2$:IPA=10:1 (3×30 mL). The combined organic layers were washed with water (2×40 mL), dried over anhydrous Na$_2$SO$_4$. After filtration, the filtrate was concentrated under reduced pressure. The residue was purified by silica gel column chromatography to afford ethyl 3,6-difluoro-4-oxo-5H-pyrazolo[1,5-a]quinoxaline-7-carboxylate (60 mg, Y=40.0%). LC-MS: (ES-H, m/z): [M-H]$^-$=292.0. $^1$H NMR (300 MHz, DMSO-d$_6$) δ 12.11 (s, 1H), 8.32 (d, J=3.8 Hz, 1H), 7.99 (dd, J=8.8, 1.3 Hz, 1H), 7.77 (dd, J=8.8, 6.9 Hz, 1H), 4.37 (q, J=7.1 Hz, 2H), 1.34 (t, J=7.1 Hz, 3H).

Step 8: Preparation of 3,6-difluoro-7-(hydroxymethyl)-5H-pyrazolo[1,5-a]quinoxalin-4-one To a stirred solution of ethyl 3,6-difluoro-4-oxo-5H-pyrazolo[1,5-a]quinoxaline-7-carboxylate (60 mg, 0.20 mmol, 1.00 equiv) in THF (4 mL) was added LiEt$_3$BH (0.61 mL, 0.61 mmol, 3.00 equiv, 1M in THF) dropwise at 0° C. under nitrogen atmosphere. The resulting mixture was stirred for 2 h at 0° C. under nitrogen atmosphere. The reaction was monitored by LCMS. The reaction was quenched by the addition of Water (0.2 mL) at 0° C. The resulting mixture was concentrated under reduced pressure. The residue was purified by silica gel column chromatography to afford 3,6-difluoro-7-(hydroxymethyl)-5H-pyrazolo[1,5-a]quinoxalin-4-one (50 mg, Y=97.2%). LC-MS: (ES-H, m/z): [M-H]$^-$=249.9.

Step 9: Preparation of 7-(chloromethyl)-3,6-difluoro-5H-pyrazolo[1,5-a]quinoxalin-4-one To a stirred solution of 3,6-difluoro-7-(hydroxymethyl)-5H-pyrazolo[1,5-a]quinoxalin-4-one (50 mg, 0.19 mmol, 1.00 equiv) and DMF (1 mg, 0.02 mmol, 0.10 equiv) in DCM (1 mL) were added SOCl$_2$ (118 mg, 0.99 mmol, 5.00 equiv) at room temperature under nitrogen atmosphere. The resulting mixture was stirred for 2 h at room temperature under nitrogen atmosphere. The reaction was monitored by LCMS. The resulting mixture was concentrated under reduced pressure to afford 7-(chloromethyl)-3,6-difluoro-5H-pyrazolo[1,5-a]quinoxalin-4-one (50 mg, crude). LC-MS: (ES-H, m/z): [M-H]$^-$=268.0.

Step 10: Preparation of 5-{[(2R,3S)-1-({3,6-difluoro-4-oxo-5H-pyrazolo[1,5-a]quinoxalin-7-yl}methyl)-2-methylazetidin-3-yl]oxy}-N-methylpyridine-2-carboxamide To a stirred mixture of 7-(chloromethyl)-3,6-difluoro-5H-pyrazolo[1,5-a]quinoxalin-4-one (120 mg, 0.44 mmol, 1.00 equiv) and N-methyl-5-{[(2R,3S)-2-methylazetidin-3-yl]oxy}pyridine-2-carboxamide hydrochloride (126 mg, 0.49 mmol, 1.10 equiv) in MeCN (5 mL) were added KI (15 mg, 0.09 mmol, 0.20 equiv) and DIEA (115 mg, 0.89 mmol, 2.00 equiv) at room temperature under nitrogen atmosphere. The resulting mixture was stirred for 2 h at 80° C. under nitrogen atmosphere. The reaction was monitored by LCMS. The precipitated solids were collected by filtration and washed with MeCN (3×5 mL). The resulting mixture was concentrated under reduced pressure. The residue was purified by trituration with MeCN (10 mL). The precipitated solids were collected by filtration and washed with MeCN (3×5 mL) to afford 5-{[(2R,3S)-1-({3,6-difluoro-4-oxo-5H-pyrazolo[1,5-a]quinoxalin-7-yl}methyl)-2-methylazetidin-3-yl]oxy}-N-methylpyridine-2-carboxamide (87 mg, 43.0%). LC-MS: (ES+H, m/z): [M+H]$^+$=455.10. $^1$H NMR (300 MHz, DMSO-d$_6$) δ 11.97 (s, 1H), 8.58 (d, J=4.9 Hz, 1H), 8.25-8.19 (m, 2H), 7.98-7.86 (m, 2H), 7.43 (dd, J=8.7, 2.9 Hz, 1H), 7.33 (dd, J=8.5, 6.8 Hz, 1H), 4.59 (q, J=5.9 Hz, 1H), 3.90 (d, J=13.2 Hz, 1H), 3.82 (t, J=6.4 Hz, 1H), 3.68 (d, J=13.0 Hz, 1H), 3.38 (d, J=6.0 Hz, 1H), 2.82-2.78 (m, 4H), 1.22 (d, J=6.2 Hz, 3H). $^{19}$F NMR (282 MHz, DMSO-d$_6$) δ −131.38, −168.36.

Example A: Cell Growth Inhibition Assay

The objective of this study is to evaluate the effect of invention compounds on cell proliferation through the cell viability assay in DLD-1 BRCA2(−/−) and parental isogenic pair and MDA-MB-436 (mutated BRCA1) cell lines. The CellTiter-Glo (CTG) based cell viability assay is designed to determine the number of viable cells in the culture because of compound effect, by quantifying ATP, which indicates the presence of metabolically active cells.

DLD-1 BRCA2(−/−) and parental isogenic pair were cultured in RPMI 1640 supplemented with 10% fetal bovine serum (FBS), and MDA-MB-436 cells were cultured in DMEM supplemented with 10% FBS. Both are culture at 37° C. with 5% CO$_2$. Invention compounds were distributed to the 384 well plate (Corning, 3764) using Echo acoustic liquid handler to form a 1:3 serially diluted final concentration with top dose of 10 or 30 µM. The cells were seeded into the plate in the density of 50 cells/well (DLD-1 parental), 200 cells/well (DLD-1 BRCA2−/−), or 500 cells/well (MDA-MB-436). After a short spun, the cells were cultured in a well moisturized incubator at 37° C. with 5% CO$_2$ for 7 days without disturbance. The cell viability was measured by CellTiter Glo 2.0 assay kit (Promega, G9243), and growth inhibition rate was calculated and plotted against final compound concentration, and the data were fitted in Xfit to generate $IC_{50}$.

Example B: Biochemical (FP) Assay

Assays based on fluorescent polarization (FP) have been widely utilized in drug discovery due to the homogenous format, robust performance and lack of interference seen in other assays. To characterize our compounds, we utilized an assay measuring the displacement of a commercially available fluorescently labeled PARP 1/2 inhibitor (PARPi-FL, Tocris Biosciences, #6461) as exemplified in assays performed in WO2014/064149 and WO2021/013735A1. The assay was performed utilizing the following method:

Compounds were dissolved in DMSO an Echo550 liquid handler was utilized to make serial dilations in the desired concentration range in Optiplate-384F plates. 100% DMSO was used for the high (with protein) and low (without protein) control samples. 20 nL of compound or DMSO alone was added to individual assay plate wells.

PARP1 and PARP2 protein were expressed, purified, and diluted in assay buffer containing 50 mM Tris pH 8.0, 0.001% Triton X-100, 10 mM $MgCl_2$, 150 mM NaCl to a final concentration of 20 nM. The PARPi-FL was then added at a final concentration of 3 nM.

The assay plate is centrifuged at 1000 rpm for 1 min and incubated for 4 h at room temperature.

The fluorescent polarization is read using an Envision plate reader using the following settings:
Excitation filter—FITC FP 480-Ex Slot 3
Emission filter—FITC FP P-pol 535-Em Slot 4
2nd Emission filter—FITC FP S-pol 535-Em Slot 3
Mirror module—FITC FP Dual Enh-Slot 1

The inhibition rate is calculated using the percentage of permuted Mahalanobis distances greater than the control samples (mP value) following the equation below:

$mP_C$: the mP value of compounds
$mP_L$: the mP value of Low controls
$mP_H$: the mP value of High controls $$\text{Inhibition (\%)} = \left(1 - \frac{mP_C - mP_L}{mP_H - mP_L}\right) \times 100\%$$

XLFit (equation 201) is used to calculate a reported $IC_{50}$ for each compound.

The data from examples A and B are provided in Table 2.

TABLE 2

| Ex. | EC50 DLD-1 BRCA2 (−/−) μM | EC50 DLD-1 parental μM | EC50 MDA-MB-436 μM | IC50 FP PARP1 μM | IC50 FP PARP2 μM |
|---|---|---|---|---|---|
| 1 | >1 | | >1 | | |
| 2 | 0.0033 | >30 | 0.0016 | 0.0042 | >10 |
| 3 | 0.013 | | 0.0045 | 0.0064 | >100 |
| 4 | 0.002 | | 0.0011 | 0.0058 | 11 |
| 5 | >1 | | >1 | | |
| 6 | 0.073 | | 0.042 | | |
| 7 | 0.013 | | 0.0083 | 0.0074 | 66 |
| 8 | >1 | | | | |
| 9 | 0.072 | | 0.025 | | |
| 10 | 0.0088 | | 0.0068 | 0.0068 | >100 |
| 11 | 0.028 | | 0.019 | | |
| 12 | 0.083 | | 0.036 | 0.0066 | 62 |
| 13 | 0.038 | | 0.012 | | |
| 14 | 0.0098 | | 0.0041 | 0.0052 | 14 |
| 15 | >1 | | | | |
| 16 | 0.049 | | 0.018 | | |
| 17 | 0.0012 | | 0.00079 | 0.0073 | 21 |
| 18 | >1 | | >1 | | |
| 19 | >1 | | >1 | | |
| 20 | 0.04 | | 0.035 | 0.0056 | 19 |
| 21 | 0.0018 | | 0.0012 | 0.0066 | 14 |
| 22 | 0.037 | | 0.027 | 0.0051 | 16 |
| 23 | 0.063 | | 0.014 | 0.013 | 13 |
| 24 | 0.013 | | 0.024 | 0.0091 | 17 |
| 25 | 0.036 | | 0.041 | 0.011 | 25 |
| 26 | 0.055 | | 0.06 | 0.012 | >100 |
| 27 | 0.019 | | 0.018 | 0.0067 | 9.1 |
| 28 | 0.015 | | 0.0033 | 0.0039 | >100 |
| 29 | 0.078 | | 0.14 | 0.011 | 72 |
| 30 | 0.015 | | 0.047 | 0.0077 | >100 |
| 31 | 0.013 | | 0.031 | 0.037 | >100 |
| 32 | 0.0064 | | 0.016 | 0.0068 | >100 |
| 33 | 0.0042 | | 0.0037 | 0.0055 | 33 |
| 34 | 0.15 | | 0.084 | 0.013 | 12 |
| 35 | 0.0099 | | 0.032 | 0.0036 | >100 |
| 36 | 0.012 | | 0.0037 | 0.005 | 15 |
| 37 | 0.08 | | 0.066 | 0.0045 | >100 |
| 38 | 0.0029 | | 0.0023 | 0.0061 | 10 |
| 39 | 0.0013 | | 0.0011 | 0.0043 | 5.9 |
| 40 | 0.18 | | 0.13 | 0.0055 | 32 |
| 41 | 0.0032 | | 0.003 | 0.0076 | 8.3 |
| 42 | 0.0021 | | 0.0011 | 0.0058 | 6.3 |
| 43 | 0.0011 | | 0.00046 | 0.0066 | 2.9 |
| 44 | 0.0035 | | 0.0013 | 0.0067 | 11 |
| 45 | 0.0015 | | 0.00087 | 0.005 | 6.9 |
| 46 | 0.09 | | 0.1 | 0.0099 | >100 |
| 47 | 0.1 | | 0.1 | 0.0058 | 88 |
| 48 | 0.0057 | | 0.0032 | 0.0062 | 3.5 |
| 49 | 0.0092 | | 0.0095 | 0.0063 | >100 |
| 50 | 0.0053 | | 0.0087 | 0.011 | 83 |
| 51 | 0.0044 | | 0.0079 | 0.0041 | 4.2 |
| 52 | 0.012 | | 0.0098 | 0.0063 | 76 |
| 53 | 0.0022 | | 0.0013 | 0.008 | 61 |
| 54 | 0.0012 | | 0.00062 | 0.0045 | 0.9 |
| 55 | 0.038 | | 0.012 | 0.0064 | >100 |
| 56 | 0.045 | | 0.012 | 0.0062 | 76 |
| 57 | 0.012 | | 0.0068 | 0.0094 | 47 |
| 58 | 0.0033 | | 0.0017 | 0.006 | 8.3 |
| 59 | 0.0098 | | 0.0047 | 0.0055 | >100 |
| 60 | >1 | | >1 | >0.1 | >100 |
| 61 | 0.01 | | 0.0088 | 0.018 | 23 |
| 62 | 0.086 | | 0.14 | 0.018 | 52 |
| 63 | 0.0048 | | 0.0036 | 0.0066 | 9.6 |
| 64 | 0.096 | | 0.043 | >0.1 | 2.6 |
| 65 | 0.093 | | 0.091 | | |
| 66 | 0.0021 | | 0.001 | 0.0033 | 6.4 |
| 67 | 0.00097 | | 0.00065 | | |
| 68 | 0.015 | | 0.018 | | |
| 69 | 0.011 | | 0.0056 | | |
| 70 | 0.0013 | | 0.0011 | 0.0041 | 2.4 |
| 71 | 0.00089 | | 0.00049 | | |
| 72 | 0.033 | | 0.05 | | |
| 73 | 0.0048 | | 0.0021 | 0.0036 | 1.7 |
| 74 | 0.0039 | | 0.0026 | 0.0089 | 25 |
| 75 | 0.0012 | | 0.00072 | 0.004 | 5.2 |
| 76 | 0.0014 | | 0.0011 | 0.0028 | 8.7 |
| 77 | 0.0038 | | 0.0018 | 0.0038 | >100 |
| 78 | 0.032 | | 0.035 | | |
| 79 | 0.0063 | | 0.0019 | | |
| 80 | 0.0043 | | 0.0018 | 0.0038 | 5.3 |
| 81 | 0.003 | | 0.0017 | | |
| 82 | 0.0031 | | 0.0021 | 0.0045 | 6.8 |
| 83 | 0.022 | | 0.011 | | |
| 84 | 0.003 | | 0.0014 | 0.0088 | 48 |
| 85 | 0.0018 | | 0.0013 | | |

TABLE 2-continued

| Ex. | EC50 DLD-1 BRCA2 (−/−)µM | EC50 DLD-1 parental µM | EC50 MDA-MB-436 µM | IC50 FP PARP1 µM | IC50 FP PARP2 µM |
|---|---|---|---|---|---|
| 86 | 0.0034 | | 0.0018 | | |
| 87 | 0.02 | | 0.012 | | |
| 88 | 0.0063 | | 0.0034 | | |
| 89 | 0.0018 | | 0.0011 | 0.0072 | 9.6 |
| 90 | 0.0028 | | 0.0018 | 0.0085 | 3.1 |
| 91 | 0.023 | | 0.027 | 0.011 | >100 |
| 92 | 0.0016 | | 0.0011 | | |
| 93 | 0.0072 | | 0.005 | | |
| 94 | 0.043 | | 0.011 | | |
| 95 | 0.0035 | | 0.0032 | | |
| 96 | >1 | | >1 | | |
| 97 | 0.034 | | 0.021 | | |
| 98 | 0.061 | | 0.029 | | |
| 99 | 0.004 | | 0.0017 | | |
| 100 | 0.011 | | 0.0059 | | |
| 101 | 0.0054 | | 0.0031 | | |
| 102 | 0.049 | | 0.11 | | |
| 103 | 0.027 | | 0.03 | | |
| 104 | 0.0019 | | 0.00085 | | |
| 105 | 0.0022 | | 0.00093 | | |
| 106 | 0.0083 | | 0.005 | | |
| 107 | 0.03 | | 0.017 | | |
| 108 | 0.012 | | 0.012 | | |
| 109 | 0.0074 | | 0.0042 | | |
| 110 | 0.014 | | 0.0094 | | |
| 111 | 0.015 | | 0.013 | | |
| 112 | 0.0047 | | 0.0026 | | |
| 113 | 0.016 | | 0.0087 | | |
| 114 | 0.0059 | | 0.0036 | | |
| 115 | 0.17 | | 0.17 | | |
| 116 | 0.013 | | 0.0033 | | |
| 117 | 0.013 | | 0.013 | | |
| 118 | 0.024 | | 0.022 | | |
| 119 | 0.0068 | | 0.0044 | | |
| 120 | 0.021 | | 0.0087 | | |
| 121 | 0.0012 | | 0.0018 | | |

What is claimed is:

1. A compound that is:

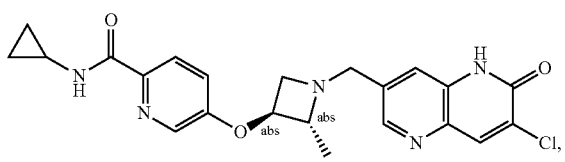 [SMILES: C[C@@H]1[C@@H](Oc2ccc(C(=O)NC3CC3)nc2)CN1Cc1cnc2cc(Cl)c(=O)[nH]c2c1]

or a pharmaceutically acceptable salt, solvate, or stereoisomer thereof.

2. A compound that is:

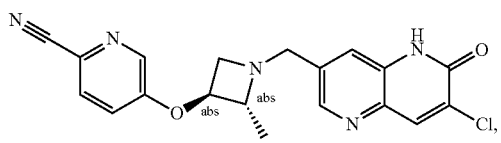 [SMILES: C[C@@H]1[C@@H](Oc2ccc(C#N)nc2)CN1Cc1cnc2cc(Cl)c(=O)[nH]c2c1]

or a pharmaceutically acceptable salt, solvate, or stereoisomer thereof.

3. A compound that is:

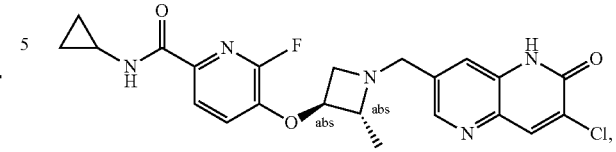

or a pharmaceutically acceptable salt, solvate, or stereoisomer thereof.

4. The compound of claim 1, that is:

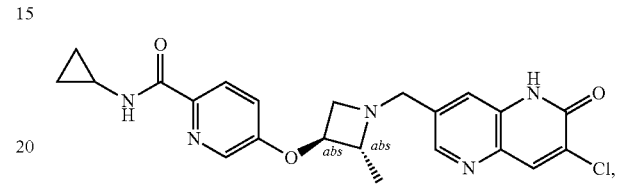

or a pharmaceutically acceptable salt thereof.

5. The compound of claim 1, that is:

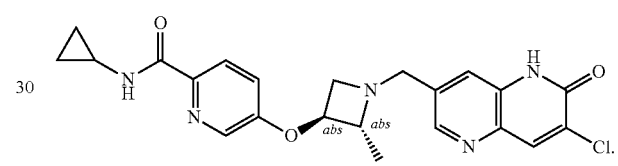

6. The compound of claim 2, that is:

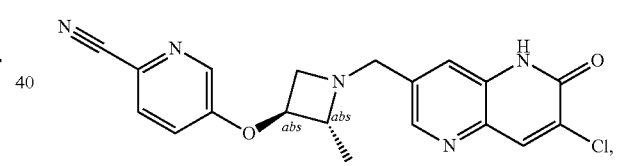

or a pharmaceutically acceptable salt thereof.

7. The compound of claim 2, that is:

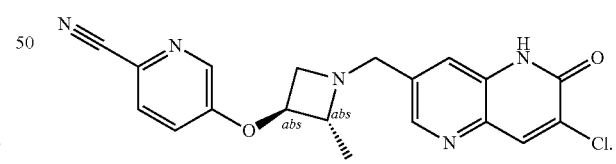

8. The compound of claim 3, that is:

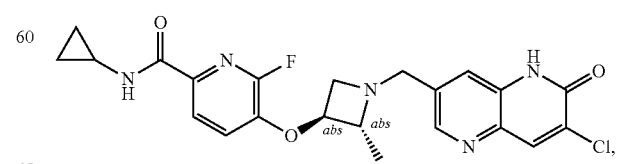

or a pharmaceutically acceptable salt thereof.

9. The compound of claim 3, that is:

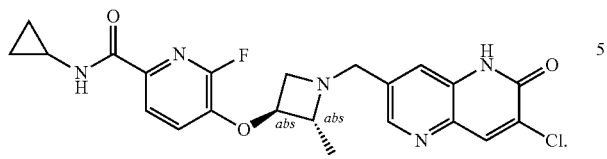

10. A pharmaceutical composition comprising a compound of claim 4, or a pharmaceutically acceptable salt thereof, and a pharmaceutically acceptable excipient.

11. A pharmaceutical composition comprising a compound of claim 5 and a pharmaceutically acceptable excipient.

12. A pharmaceutical composition comprising a compound of claim 6, or a pharmaceutically acceptable salt thereof, and a pharmaceutically acceptable excipient.

13. A pharmaceutical composition comprising a compound of claim 7 and a pharmaceutically acceptable excipient.

14. A pharmaceutical composition comprising a compound of claim 8, or a pharmaceutically acceptable salt thereof, and a pharmaceutically acceptable excipient.

15. A pharmaceutical composition comprising a compound of claim 9 and a pharmaceutically acceptable excipient.

* * * * *